United States Patent
Sebastian

(10) Patent No.: US 8,987,548 B2
(45) Date of Patent: *Mar. 24, 2015

(54) SOYBEAN PLANTS HAVING SUPERIOR AGRONOMIC PERFORMANCE AND METHOD FOR THEIR PRODUCTION

(75) Inventor: Scott Sebastian, Polk City, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 350 days.

This patent is subject to a terminal disclaimer.

(21) Appl. No.: 13/104,432

(22) Filed: May 10, 2011

(65) Prior Publication Data

US 2011/0258733 A1     Oct. 20, 2011

Related U.S. Application Data

(63) Continuation of application No. 10/901,425, filed on Jul. 27, 2004, now Pat. No. 7,973,212.

(60) Provisional application No. 60/492,074, filed on Aug. 1, 2003, provisional application No. 60/547,811, filed on Feb. 25, 2004, provisional application No. 60/582,241, filed on Jun. 22, 2004.

(51) Int. Cl.
*A01H 1/04*     (2006.01)
*C12Q 1/68*     (2006.01)
*A01H 5/10*     (2006.01)
*A01H 1/02*     (2006.01)

(52) U.S. Cl.
CPC .. *A01H 1/04* (2013.01); *A01H 5/10* (2013.01); *C12Q 1/6895* (2013.01); *A01H 1/02* (2013.01)
USPC .......................................... 800/267; 800/312

(58) Field of Classification Search
None
See application file for complete search history.

(56) References Cited

U.S. PATENT DOCUMENTS

| | | | |
|---|---|---|---|
| 5,437,697 | A | 8/1995 | Sebastian et al. |
| 7,973,212 | B2 * | 7/2011 | Sebastian .................. 800/267 |
| 2002/0129402 | A1 | 9/2002 | Lightfoot et al. |
| 2002/0133852 | A1 | 9/2002 | Hauge et al. |
| 2002/0144310 | A1 | 10/2002 | Lightfoot et al. |
| 2003/0150016 | A1 | 8/2003 | Han et al. |

FOREIGN PATENT DOCUMENTS

| | | |
|---|---|---|
| WO | WO 98/49887 | 11/1998 |
| WO | WO 99/31964 | 7/1999 |
| WO | WO 00/18963 | 4/2000 |

OTHER PUBLICATIONS

Orf et al (Crop Sci. 39: 1642-1651, 1999).*
United States of America, Secretary of Agriculture, Plant Variety Protection Certificate No. 200400078 for Soybean 93M50 dated Aug. 16, 2004.
United States of America, Secretary of Agriculture, Plant Variety Protection Certificate No. 200400077 for Soybean 93M92 dated Aug. 19, 2004.
United States of America, Secretary of Agriculture, Plant Variety Protection Certificate No. 200400076 for Soybean 93M93 dated Aug. 19, 2004.
United States of America, Secretary of Agriculture, Plant Variety Protection Certificate No. 200000037 for Soybean 91B53 dated Apr. 24, 2001.
United States of America, Secretary of Agriculture, Plant Variety Protection Certificate No. 200400083 for Soybean 92M91 dated Aug. 16, 2004.
United States of America, Secretary of Agriculture, Plant Variety Protection Certificate No. 200400081 for Soybean 93M10 dated Aug. 16, 2004.
United States of America, Secretary of Agriculture, Plant Variety Protection Certificate No. 200400079 for Soybean 93M30 dated Aug. 16, 2004.
Arahana et al., "Identification of QTL's for Resistance to *Sclerotinia sclerotiorum* in Soybean". Crop Science, vol. 41, pp. 180-188 (2001).
Burnham et al. "Quantitative Trait Loci for Partial Resistance to *Phytophthora sojae* in Soybean", Crop Sci., vol. 43, pp. 1610-1617 (2003).
Chapman et al., "Quantitative trait loci for agronomic and seed quality traits in an F.sub.2 and F.sub.4:6 soybean population", Euphytica, vol. 129, pp. 387-393 (2003).
Charlson et al., "Associating SSR Markers with Soybean Resistance to Iron Deficiency Chlorosis", J. Plant Nutr., vol. 26, pp. 2267-2276 (2003).
Cregan et al., "An intergrated genetic linkage map of the soybean", Crop Sci., vol. 39, pp. 1464-1490 (1999).
Delanney et al., "Relative contribution among ancestral lines to North American soybean cultivars", Crop Sci., vol. 23, pp. 944-949 (1983).
Hartwell et al., "Genetics From Gents to Genomes", The McGraw-Hill Companies, Inc., ISBN 0-07-540923-2 two pages and pp. 311-325 (2000).
Kim et al., "inheritance of Partial Resistance to Sclerotinia Stem Rot in Soybean," Crop Sci., vol. 40, pp. 55-61 (2000).
Li et al., "Molecular Mapping Genes Conditioning Reduced Palmitic Acid Content in N87-2122-4 Soybean," Crop Sci., vol. 42, pp. 373-378 (2002).
Narvel et al., "Development of multiplex sets of simple sequences repeat DNA markers covering the soybean genome", Molecular Breeding, vol. 6, pp. 175-183 (2000).
Narvel et al., "Simple Sequence Repeat Diversity Among Soybean Plant Introductions and Elite Genotypes," Crop Sci., vol. 40, pp. 1452-1458 (2000).
Njiiti el al., "Resistance to Soybean Sudden Death Syndrome and Root Colonization by *Fusarium solani* l. sp. Glycine in Near-Isogenic Lines", Crop Sci., 38, pp. 472-477 (1998).
Orf et al., "Genetics of soybean agronomic traits l: comparison of three related recombinant inbred populations", Crop Sci., vol. 39, pp. 1642-1651 (1999).
Reyna et al., "Evaluation of Marker-Assisted Introgression of Yeild QTL Alleles into Adapted Soybean", Crop Sci., vol. 41, pp. 1317-1321 (2001).

(Continued)

*Primary Examiner* — David T Fox
*Assistant Examiner* — Keith Robinson

(57) ABSTRACT

This invention provides compositions including favorable alleles of marker loci associated with genetic elements contributing to superior agronomic performance. Also provided are markers for identifying favorable alleles of marker loci associated with genetic elements involved in superior agronomic performance, as well as methods employing the markers.

24 Claims, 6 Drawing Sheets

(56) References Cited

OTHER PUBLICATIONS

Specht et al., "Soybean Yield Potential—A Genetic and Physiological Perspective", Crop Sci., vol. 39, pp. 1560-1570 (1999).
Various seed catalogs, pp. 1-53, 1999.
Wang et al., "Identification of putative QTL that underlie yeild in interspecific soybean backcross populations", Theor. Appl. Genet., vol. 108, pp. 458-467 (2004).
Yuan et al., "Quantitative trail loci in Two Soybean Recombinant Inbred Line Populations Segregation for Yield and Disease Resistance", Crop Sci., vol. 42, pp. 271-277 (2002).
Zhang et al., "QTL mapping of ten agronomic traits on the soybean (Glycine max L. Merr.) genetic map and their . . . ", Theor. Appl. Genet., vol. 108, pp. 1131-1139 (2004).
Zhu et al., "Molecular breeding for grain yield in barley: an evaluation of QTL effects in a spring barley cross", Theor. Appl. Genet., vol. 68, pp. 772-779 (1999).

* cited by examiner

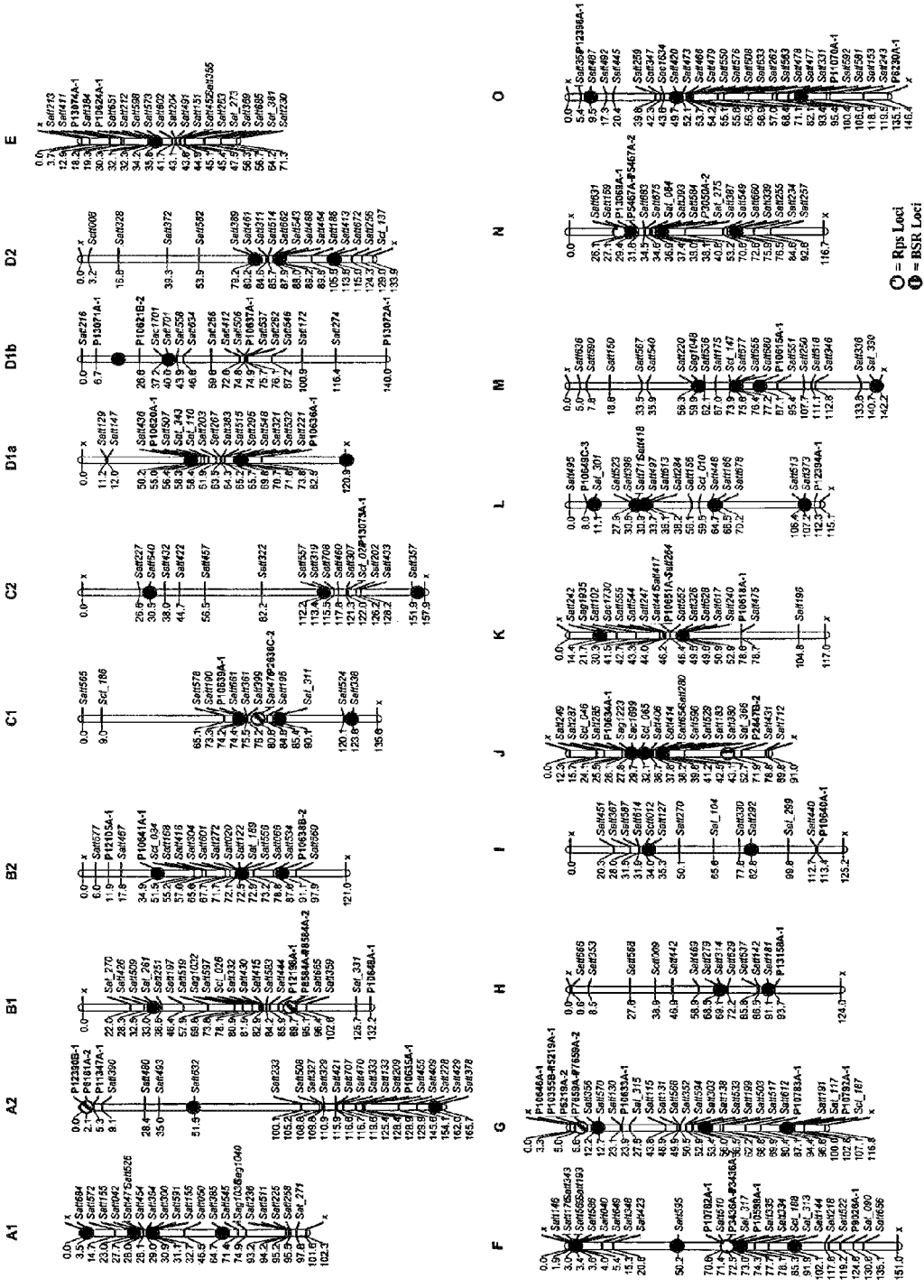
Fig. 2   All Soybean ASH and SSR Pioneer Markers

SOYBEAN PLANTS HAVING SUPERIOR AGRONOMIC PERFORMANCE AND METHOD FOR THEIR PRODUCTION

CROSS REFERENCE TO RELATED APPLICATIONS

This application is a continuation of U.S. Patent Application Ser. No. 10/901,425, filed on Jul. 27, 2004, which claims the benefit of U.S. Provisional Patent Application Ser. No. 60/582, 241, filed Jun. 22, 2004, U.S. Provisional Patent Application Ser. No. 60/547,811, filed Feb. 25, 2004, and U.S. Provisional Patent Application Ser. No. 60/492,074, filed Aug. 1, 2003, the disclosures of which are incorporated herein by reference in their entirety for all purposes.

FIELD OF THE INVENTION

The invention relates to the field of agricultural biotechnology and, more specifically, to molecular marker assisted selection and breeding of soybean plants.

BACKGROUND OF THE INVENTION

One of the most challenging aspects of plant breeding is to identify plant varieties that are superior to the currently available varieties used in commerce. Herein, the term "variety" and "genotype" will be used interchangeably since genetic differences are what make each variety unique and what make one variety superior to another in terms of commercial value.

For commodity crops like soybeans and corn, the most universal measure of commercial value is grain productivity per unit area or "yield". Since a farmer is paid according to the quantity (weight) of grain he delivers to an elevator, a farmer typically wants to plant a variety that produces the most grain per acre.

Although yield is arguably the most important trait that a plant breeder is concerned with, it is also the least understood genetically. There are many different plant traits that control the efficiency of converting nutrients and light into grain. Yield is therefore the final culmination of many different traits that contribute to productivity over the growing season. These would include seedling emergence vigor, photosynthetic ability, disease resistance, ability to mine nutrients from the soil, ability to produce flowers, and ability to shuttle photosynthate into grain, etc. The genetic bases of these individual traits that contribute to yield are largely unknown. Each trait that contributes to "yield" could be controlled by several or many genetic loci. Therefore, the overall genetic basis for yield is undoubtedly very complex. This is just one reason why traditional methods of determining the genetic basis of yield have not been very successful. To make incremental improvements in yield potential, for the most part, plant breeders are still using the same resource-intensive methods that have been in use for the last 80 or more years. Existing varieties are crossed to produce an array of new genotypes which are then exhaustively tested over many locations and replications in order to get enough yield data to differentiate the few consistently superior genotypes. This is one of the most expensive and time-consuming aspects of plant breeding.

During the 1990's, genetic markers linked to genes that contribute to yield emerged as a means to improve efficiency in certain aspects of the breeding process. These success stories have been limited to traits that are controlled by relatively few genes that are highly heritable. In this case, it is fairly routine to make a reliable association between a DNA sequence and a phenotype that can be confirmed with a greenhouse or field assay. However, until very recently, it has been extremely difficult to make reliable associations between specific DNA sequences and a very complex quantitative trait such as yield.

"Breeding bias," described in U.S. Pat. No. 5,437,697, which is incorporated herein in its entirety for all purposes, is a unique way to determine which genetic loci have been affected by extended periods of recurrent selection for yield. By comparing the genetic marker profiles of modern high yielding varieties to their most distant ancestors, breeding bias can quickly leverage an entire century of yield data to determine which specific alleles of which genetic markers have increased in frequency over time due to selection. Since increased yield has been the main criteria for selection, these markers are those most likely to be associated with yield progress over time. The present invention provides genetic markers that are associated with yield performance in a variety of geographic regions, as well as methods for utilizing these markers to efficiently identify soybean fines and sublines with increased yield.

SUMMARY OF THE INVENTION

The present invention provides representative markers that correspond to, and identify, chromosome segments important for superior agronomic performance in a variety of geographic regions and growing conditions. The markers described herein are shown to be associated with genetic elements contributing to increased yield in soybean. The markers, and methods for their use, described herein provide the means for defining and identifying soybean plants with improved yield relative to existing elite lines. Using the markers and methods described herein, identification of residual allelic variation among segregating lines of soybeans derived from elite strains can be used to increase the efficiency of the breeding program to develop novel sublines of soybean with increased yield relative to existing elite strains.

In a first aspect, the invention provides methods for identifying soybean sublines with increased yield relative to existing elite lines of soybeans. The methods of the invention involve detecting at least one allelic form of a plurality of chromosome segments, each of which a) includes a genetic element contributing to increased yield; and, b) includes or is proximal to a marker locus shown to be associated with increased yield in soybean.

For example, detecting an allelic form involves identifying at least one favorable allelic form of a chromosome segment, where the identified chromosome segment includes a genetic element contributing to increased yield and either includes or is proximal to (linked to) a marker selected from the specified set of markers which have been shown to be associated with yield. The favorable allelic form of a chromosome segment can be confirmed by identifying a polymorphic marker locus selected from the set, which is segregating in various sublines of progeny derived from a progenitor soybean. Yield is assessed in at least two sublimes of progeny with different allelic forms of the marker locus, and a subline of progeny with increased yield relative to the progenitor soybean is identified.

Exemplary marker loci shown by Breeding Bias analysis to be associated with genetic elements that contribute to increased yield in one or more geographic growing region are included in the following set of markers: Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_110, P10620A-1, Satt129, Satt147, Satt216, SAT_351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Satt280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P13561A-1, P2481A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-T13, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512. As such, marker loci of the set identify chromosome segments contributing to increased yield. Any number of additional marker loci linked to a marker locus selected from the set can be identified and will function as equivalents in the methods of the invention.

For example, in some embodiments the favorable allelic form of at least one chromosome segment, i.e., the allelic form associated with increased yield, is determined by a) identifying at least one polymorphic marker locus selected from the set in a plurality of sublines of progeny of a progenitor soybean, and b) assessing yield in at least two sublines of progeny having different allelic forms of the marker locus.

In other embodiments, the methods of identifying a soybean subline with increased yield involve detecting at least one allele of a marker locus segregating among progeny of a progenitor soybean. The marker locus includes at least two alleles, one of which correlates with increased yield whereas the other allele(s) does not correlate with increased yield. Increase in yield is measured relative to the mean yield of the progeny. Optionally, more than one marker locus is evaluated.

The marker loci are selected from the set of loci consisting of Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_110, P10620A-1, Satt129, Satt147, Satt216, SAT_351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Satt280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P13561A-1, P2481A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512.

In some embodiments, the allelic form of between about 10% and about 100% of chromosome segments in the set, or in a specified subset of the markers relevant in a particular geographic region, as enumerated in Tables 3 through 12, are detected. Usually the allelic form of between about 10% and about 90% of the chromosome segments relevant in a particular geographic region are determined. Commonly, a majority of the allelic forms are determined. In an embodiment, the allelic forms of essentially all of the chromosome segments are determined.

For example, in a breeding program aimed at developing soybeans with increased yield in the central growing region (e.g., Iowa) allelic forms of between about 10% and about 100% of the chromosome segments including or proximal to the markers from the set including Satt642, Satt042, Satt364, Satt454, Satt526, Satt300, Satt591, Satt155, Satt385, Satt511, P12390B-1, Satt632-TB, Satt429, SAT_261, Satt197, P10641A-1, Satt556, Satt534, P10638B-2, Satt399. Satt361, P10639A-1, Satt661-TB, Satt190, SAT_311-DB, Satt338, Satt640-TB, Satt557, Satt319, SAT_142-DB, Satt460, Satt433, Satt357, Satt321, Satt295, Satt203, Satt507, Satt129, Satt147, SAT_351, P10621B-2, Satt558, Satt701, Satt634, Satt582, Satt389, Satt464, Satt662, Satt672, Satt573, Satt598, Satt263, Satt602, Satt151, SAT_273-DB, Satt146, Satt193, Satt569, Satt176, Satt343, Satt586, Satt040, Satt595, P10782A-1, Satt334, Satt144, Satt522, Satt570, Satt356, Satt533, Satt199, Satt517, Satt191, SAT_117, Satt279, Satt181, Satt127, Satt270, Satt292, SAG1223, SAC1699, SAT_065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, Satt346, Satt336, SAT_330-DB, P13069A-1, P5467A-1, P5467A-2, SAT_084, SAT_275-DB, Satt660, Satt339, P12396A-1, Satt358, Satt487, Satt259, Satt420, Satt576, Satt633, Satt477, Satt581, Satt153, Satt243, P10793A-1, P12391A-1, P12392A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt111, Satt176, Satt219 and Satt299 are determined. In an embodiment, the set of markers includes Satt684, Satt042, Satt364, Satt454, Satt526, Satt300, Satt591, Satt155, Satt385, Satt632-TB, Satt429, SAT-_261, P10641A-1, Satt556, P10638B-2, Satt399, Satt361, Satt661-TB, Satt190, SAT_311-DB, Satt338, Satt640-TB, Satt557, Satt319, SAT_142-DB, Satt321, Satt203, Satt129, Satt147, SAT_351, P10621B-2, Satt701, Satt634, Satt582, Satt389, Satt464, Satt662, Satt672, Satt573, Satt598, Satt263, Satt151, SAT_273-DB, Satt146, Satt193, Satt569, Satt343, Satt586, Satt040, Satt595, Satt334, Satt144, Satt522, Satt570, Satt356, Satt199, Satt517, Satt191, Sat 117, Satt279, Satt181, Satt127, Satt270, Satt292, SAG1223, SAC1699, Sat 065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, SAT_330-DB, P13069A-1, P5467A-1, P5467A-2, SAT_084, SAT_275-DB, Satt660, Satt339, Satt358, Satt487, Satt487, Satt420, Satt576, Satt633, Satt581, Satt153, Satt243, P10793A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt111, Satt219 and Satt299 are determined. In an embodiment, the set of markers includes Satt684, Satt526, Satt591, Satt385, Satt632-TB, Satt429, SAT-261, P10641A-1, Satt556, P106388-2, Satt190, SAT_311-DB, Satt338, Satt640-TB, Satt557, SAT_142-DB, Satt321, Satt203, Satt129, SAT_351, Satt701, Satt582, Satt389, Satt464, Satt672, Satt598, Satt343, Satt595, Satt334, Satt144, Satt522, Satt570, Satt356, Satt199, Sat 117, Satt279, Satt181, Satt127, Satt270, Satt292, SAG1223, Sat_065, Satt529, Satt242, Satt617, SAT_301, Satt398, Satt497, Satt166, Satt373, SAG1048, Satt680, P10615A-1, SAT_330-DB, P13069A-1, SAT_275-DB, Satt339, Satt487, Satt420, Satt581 and Satt153.

In other embodiments, the methods of identifying a soybean subline with increased yield involve detecting at least one allele of a marker locus segregating among progeny of a progenitor soybean. The marker locus includes at least two alleles, one of which correlates with increased yield whereas the other allele(s) does not correlate with increased yield. Increase in yield is measured relative to the mean yield of the progeny. Optionally, more than one marker locus is evaluated. The marker loci are selected from the set of loci consisting of: Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_110, P10620A-1, Satt129, Satt147, Satt216, SAT_351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Satt280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-I, P10793A-1, P12391A-1, P13560A-1, P13561A-1, P13561A-1, P2481A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512.

In some embodiments, at least one allele of between about 10% and about 100% of the markers in the set, or in a specified subset of the markers relevant in a particular geographic region, as enumerated in Tables 3 through 12, are detected. Usually at least one allele of between about 10% and about 90% of the marker loci relevant in a particular geographic region are determined. Commonly, a majority of the marker loci are evaluated. In an embodiment, essentially all of the marker loci are evaluated.

For example, in a breeding program aimed at developing soybeans with increased yield in the central growing region (e.g., Iowa) at least one allele of between about 10% and about 100% of the marker loci from the set including Satt642, Satt042, Satt364, Satt454, Satt526, Satt300, Satt591, Satt155, Satt385, Satt511, P12390B-1, Satt632-TB, Satt429, SAT_261, Satt197, P10641A-1, Satt556, Satt534, P10638B-2, Satt399, Satt361, P10639A-1, Satt661-TB, Satt190, SAT_311-DB, Satt338, Satt640-TB, Satt557, Satt319, SAT_142-DB, Satt460, Satt433, Satt357, Satt321, Satt295, Satt203, Satt507, Satt129, Satt147, SAT_351, P10621B-2, Satt558, Satt701, Satt634, Satt582, Satt389, Satt464, Satt662, Satt672, Satt573, Satt598, Satt263, Satt602, Satt151, SAT_273-DB, Satt146, Satt193, Satt569, Satt176, Satt343, Satt586, Satt040, Satt595, P10782A-1, Satt334, Satt144, Satt522, Satt570, Satt356, Satt533, Satt199, Satt517, Satt191, SAT_117, Satt279, Satt181, Satt127, Satt270, Satt292, SAG1223, SAC1699, SAT_065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, Satt346, Satt336, SAT_330-DB, P13069A-1, P5467A-1, P5467A-2, SAT_084, SAT_275-DB, Satt660, Satt339, P12396A-1, Satt358, Satt487, Satt259, Satt420, Satt576, Satt633, Satt477, Satt581, Satt153, Satt243, P10793A-1, P12391A-1, P12392A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt111, Satt176, Satt219 and Satt299 are determined. In an embodiment, the set of markers includes Satt684, Satt042, Satt364, Satt454, Satt526, Satt300, Satt591, Satt155, Satt385, Satt632-TB, Satt429, SAT-261, P10641A-1, Satt556, P10638B-2, Satt399, Satt361, Satt661-TB, Satt190, SAT_311-DB, Satt338, Satt640-TB, Satt557, Satt319, SAT_142-DB, Satt321, Satt203, Satt129, Satt147, SAT_351, P10621B-2, Satt701, Satt634, Satt582, Satt389, Satt464, Satt662, Satt672, Satt573, Satt598, Satt263, Satt151, SAT_273-DB, Satt146, Satt193, Satt569, Satt343, Satt586, Satt040, Satt595, Satt334, Satt144, Satt522, Satt570, Satt356, Satt199, Satt517, Satt191, Sat 117, Satt279, Satt181, Satt127, Satt270, Satt292, SAG1223, SAC1699, Sat_065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, SAT_330-DB, P13069A-1, P5467A-1, P5467A-2, SAT_084, SAT_275-DB, Satt660, Satt339, Satt358, Satt487, Satt487, Satt420, Satt576, Satt633, Satt581, Satt153, Satt243, P10793A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt111, Satt219 and Satt299 are determined. In an embodiment, the set of markers includes Satt684, Satt526, Satt591, Satt385, Satt632-TB, Satt429, SAT-261, P10641A-1, Satt556, P10638B-2, Satt190, SAT_311-DB, Satt338, Satt640-TB, Satt557, SAT_142-DB, Satt321, Satt203, Satt129, SAT_351, Satt701, Satt582, Satt389, Satt464, Satt672, Satt598, Satt343, Satt595, Satt334, Satt144, Satt522, Satt570, Satt356, Satt199, Sat_117, Satt279, Satt181, Satt127, Satt270, Satt292, SAG1223, Sat 065, Satt529, Satt242, Satt617, SAT_301, Satt398, Satt497, Satt166, Satt373, SAG1048, Satt680, P10615A-1, SAT_330-DB, P13069A-1, SAT_275-DB, Satt339, Satt487, Satt420, Satt581 and Satt153.

In some embodiments, the allele correlated with increased yield, and conversely, the allele not correlated with increased yield, are determined as follows. At least one polymorphic marker locus having at least two segregating alleles in a plurality of sublines of progeny soybean plants is selected. The yield is assessed in at least two sublines of progeny with different alleles of the marker. A subline with increased yield relative to the mean yield of the sublimes is then identified confirming a correlation between one of the segregating alleles and increased yield.

ed yield, and conversely, the allele not correlated with increased yield, are determined as follows. At least one polymorphic marker locus having at least two segregating alleles in a plurality of sublines of progeny soybean plants is selected. The yield is assessed in at least two sublines of progeny with different alleles of the marker. A subline with increased yield relative to the mean yield of the sublines is then identified confirming a correlation between one of the segregating alleles and increased yield.

The methods for identifying soybean sublines with increased yield involve detecting at least one allelic form of multiple marker loci. Typically, the number of marker loci is greater than two, and typically is between 10% and 100% of the set of marker loci including: Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_11.0, P10620A-1, Satt129, Satt147, Satt216, SAT_351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Satt280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-

DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P13561A-1, P2481A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512, or a geographically relevant subset thereof as indicated in Tables 3 through 12. Usually, the methods involve detecting between about 10% and about 90% of the markers in the set. Frequently, at least 50% of the markers are detected, i.e., a majority of the markers in the set. In some instances essentially all of the markers are detected. Each of the detected marker loci identifies a chromosome segment shown to include a genetic element which contributes to increased yield in at least one geographic growing region. Thus, by identifying alleles of the markers associated with increased yield, sublines of soybeans with increased yield are identified.

The population of progeny soybeans utilized can be obtained by crossing a first progenitor soybean with a second progenitor soybean. Alternatively, the population of progeny can be obtained by selfing a single progenitor soybean. In some embodiments, the sublines of progeny evaluated include random sublines. In some embodiments, the sublines include near isogenic sublines.

Typically, the progenitor soybean is selected from an elite strain of germplasm. Such a progenitor can be self-fertilized to generate progeny. More commonly, in the methods of the invention, the progenitor soybean is crossed to a second soybean selected from a different elite strain of germplasm. Alternatively, the progenitor soybean can be crossed to a soybean with an exotic strain of germplasm.

The elite strain of germplasm is typically selected from among the following strains of germplasm: 90A07, 90B11, 90B31, 90B43, 90B72, 90B73, 91B01, 91B12, 91B33, 91B52, 91B53, 91B64, 91B91, 91B92, 92B05, 92B12, 92B23, 92B38, 92B52, 92B63, 92B74, 92B75, 92B84, 92B95, 92M30, 92M31, 92M70, 92M71, 92M72, 92M80, 92M91, 93B01, 93B09, 93B11, 93B15, 93B25, 93B26, 93B36, 93B41, 93B45, 93B46, 93B66, 93B67, 93B68, 93B72, 93B82, 93B84, 93B85, 93B86, 93B87, 93M10, 93M30, 93M40, 93M50, 93M60, 93M80, 93M90, 93M92, 93M93, 94B01, 94B23, 94B24, 94B53, 94B54, 94B73, 95B32, 95B33, 95B34, 95B53, 95B95, 95B96, 95B97, 96B21, 96B51, 97B52, 97B61, A1395, A2722, A2835, A2943, A3127, A3237, A3242, A3322, A3431, A4009, A4138, A4415, A4595, A4715, A5403, A5560, A5843, A5885, A5979, A5980, A6297, BEDFORD, CM428, CX105, CX232, CX253, CX289, CX394C, CX469C, D00566D362, ESSEX, EX04C00, EX06A00, EX10F01, EX13P01, EX13Q01, EX15N01, EX16N00, EX16P01, EX22Y01, EX22Z01, EX23B03, EX34T03, EX35F03, EX36Y01, EX39E00, EX40T03, EX44V03, FORREST, G3362, HS93-4118, HUTCHESON, JIM, KORADA, MO15733, M0400644-02, M0413735-11-52, M0501577-27-23, M0505469-61-89, MP39009, P1677, P9007, P9008, P9041, P9042, P9061, P9062, P9063, P9071, P9092, P9132, P9141, P9151, P9163, P9182, P9203, P9233, P9244, P9273, P9281, P9305, P9306, P9321, P9341, P9392, P9395, P9481, P9482, P9492, P9521, P9552, P9561, P9584, P9591, P9592, P9594, P9631, P9641, PHARAOH, RA451, R01154R002, S0066, S03W4, S0880, S1550, S1990, S19T9, S20F8, S22C3, S24L2, S25J5, S32Z3, S33N1, S38T8, S3911, S4260, S42H1, S43B5, S5960, S6189, S6262, ST0653, ST1073, ST1090, ST1570, ST1690, ST1970, ST2250, ST2488, ST2660, ST2686, ST2688, ST2788, ST2870, ST3171, ST3380, ST3630, ST3660, ST3870, ST3883, TRACY, TRAILL, X9916, YB03E00, XB03F01, XB07E01, XB10D01, XB15M01, XB19U04, XB20M01, XB22C04, XB22R01, XB23W03, XB23Y02, XB25E02, XB25L04, XB25×04, XB25W01, XB26L04, XB27P04, XB29A04, XB29D01, XB29K04, XB29L04, XB30E04, XB31C01, XB31R04, XB33B, XB34D04, XB34F01, XB35D, XB35L04, XB35W00, XB38A01, XB41M01, XB42J00, XB42M01, XB48H01, XB54K01, XB55J01, XB58P99, XB63D00, XB67A00, YB03G01, YB08D01, YB09F01, YB09G01, YB10E01, YB11D01, YB14H01, YB15K99, YB21F01, YB21G01, YB22S00, YB22V01, YB22W01, YB22×01, YB24Z01, YB25R03, YB25R99, YB25X00, YB25Y01, YB25Z01, YB27L03, YB27S00, YB27×01, YB27Y01, YB28A03, YB28N01, YB29H01, YB29J01, YB29T04, YB30J01, YB30N01, YB30P01, YB31E01, YB32K01, YB33K01, YB34H01, YB34R03, YB34S03, YB35C01, YB36E03, YB36V00, YB38E03, YB38G03, YB39M01, YB39V03, YB40M01, YB40N01, YB41Q01, YB48L01, YB52J00, YB53E00, YB54H00, YB54J00, YB54L00, YB55H00, YB56E00, YB60N01, and YOUNG.

In some embodiments, the methods include electronically transmitting or electronically storing data representing the determined marker alleles or allelic forms or chromosome segments in a computer readable medium. Accordingly, another aspect of the invention includes computer systems including a data input device for inputting genotyping data, and a computer readable medium incorporating the genotyping data corresponding to the markers of the invention. Computer readable medium including the genotyping data are also a feature of the invention.

In some embodiments, the methods further include selecting at least one plant of the identified soybean subline. The selected plant can be a whole plant, a plant organ, a plant seed, a plant cell, a plant tissue culture, or the like. Optionally, the selected soybean plant, or a progeny thereof is crossed with a second soybean plant. Typically the second soybean plant lacks the determined allele of the marker locus (or allelic form of the chromosome segment).

In some embodiments, the second soybean plant is from an elite strain of germplasm. In other embodiments, the second soybean plant is from an exotic strain of germplasm.

Soybean plants with increased yield produced according to the methods of the invention are also a feature of the invention.

In another aspect, the invention includes sets of markers useful for identifying soybean plants with increased yield. The marker sets include markers selected from the set of markers including Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_110, P10620A-1, Satt129, Satt147, Satt216, SAT_351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Satt280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P13561A-1, P2481A-1, S60021-TB, S60048-TB, S60076-T13, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512. Typically a subset of markers shown to be relevant in a geographic growing region is selected, as indicated in Tables 3 through 12. For example, in a breeding program designed to develop strains of soybean with increased yield in the Central (e.g., Iowa) region, a set of markers selected from among the following marker set is preferred: Satt642, Satt042, Satt364, Satt454, Satt526, Satt300, Satt591, Satt155, Satt385, Satt511, P12390B-1, Satt632-TB, Satt429, SAT_261, Satt197, P10641A-1, Satt556, Satt534, P106388-2, Satt399. Satt361, P10639A-1, Satt661-TB, Satt190, SAT_311-DB, Satt338, Satt640-TB, Satt557, Satt319, SAT_142-DB, Satt460, Satt433, Satt357, Satt321, Satt295, Satt203, Satt507, Satt129, Satt147, SAT_351, P10621B-2, Satt558, Satt701, Satt634, Satt582, Satt389, Satt464, Satt662, Satt672, Satt573, Satt598, Satt263, Satt602, Satt151, SAT_273-DB, Satt146, Satt193, Satt569, Satt176, Satt343, Satt586, Satt040, Satt595, P10782A-1, Satt334, Satt144, Satt522, Satt570, Satt356, Satt533, Satt199, Satt517, Satt191, SAT_117, Satt279, Satt181, Satt127, Satt270, Satt292, SAG1223, SAC1699, SAT_065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, Satt346, SAT_330-DB, P13069A-1, P5467A-1, P5467A-2, SAT_084, SAT_275-DB, Satt660, Satt339, P12396A-1, Satt358, Satt487, Satt259, Satt420, Satt576, Satt633, Satt477, Satt581, Satt153, Satt243, P10793A-1, P12391A-1, P12392A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt111, Satt176, Satt219 and Satt299. In some embodiments the markers of the set are selected from among: Satt684, Satt042, Satt364, Satt454, Satt526, Satt300, Satt591, Satt155, Satt385, Satt632-TB, Satt429, SAT-261, P10641A-1, Satt556, P10638B-2, Satt399, Satt361, Satt661-TB, Satt190, SAT_311-DB, Satt338, Satt640-TB, Satt557, Satt319, SAT_142-DB, Satt321, Satt203, Satt129, Satt147, SAT_351, P10621B-2, Satt701, Satt634, Satt582, Satt389, Satt464, Satt662, Satt672, Satt573, Satt598, Satt263, Satt151, SAT_273-DB, Satt146, Satt193, Satt569, Satt343, Satt586, Satt040, Satt595, Satt334, Satt144, Satt522, Satt570, Satt356, Satt199, Satt517, Satt191, Sat 117, Satt279, Satt181, Satt127, Satt270, Satt292, SAG1223, SAC1699, Sat 065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, SAT_330-DB, P13069A-1, P5467A-1, P5467A-2, SAT_084, SAT_275-DB, Satt660, Satt339, Satt358, Satt487, Satt487, Satt420, Satt576, Satt633, Satt581, Satt153, Satt243, P10793A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt111, Satt219 and Satt299. In certain embodiments the markers are selected from the set including: Satt684, Satt526, Satt591, Satt385, Satt632-TB, Satt429, SAT-261, P10641A-1, Satt556, P10638B-2, Satt190, SAT_311-DB, Satt338, Satt640-TB, Satt557, SAT_142-DB, Satt321, Satt203, Satt129, SAT_351, Satt701, Satt582, Satt389, Satt464, Satt672, Satt598, Satt343, Satt595, Satt334, Satt144, Satt522, Satt570, Satt356, Satt199, Sat 117, Satt279, Satt181, Satt127, Satt270, Satt292, SAG1223, Sat 065, Satt529, Satt242, Satt617, SAT_301, Satt398, Satt497, Satt166, Satt373, SAG1048, Satt680, P10615A-1, SAT_330-DB, P13069A-1, SAT_275-DB, Satt339, Satt487, Satt420, Satt581 and Satt153.

Typically the set of markers includes between about 10% and about 100% of the markers shown to be relevant in a selected geographic region. Usually, the set includes between about 10% and about 90% of the relevant markers. Frequently, the set includes a majority of the relevant markers. In some embodiments, the set includes essentially all of the markers shown to be relevant in a particular geographic region.

BRIEF DESCRIPTION OF THE DRAWINGS

FIG. 2. Genetic map indicating position of marker loci associated with yield in Iowa.

DETAILED DESCRIPTION

Figure 1A:
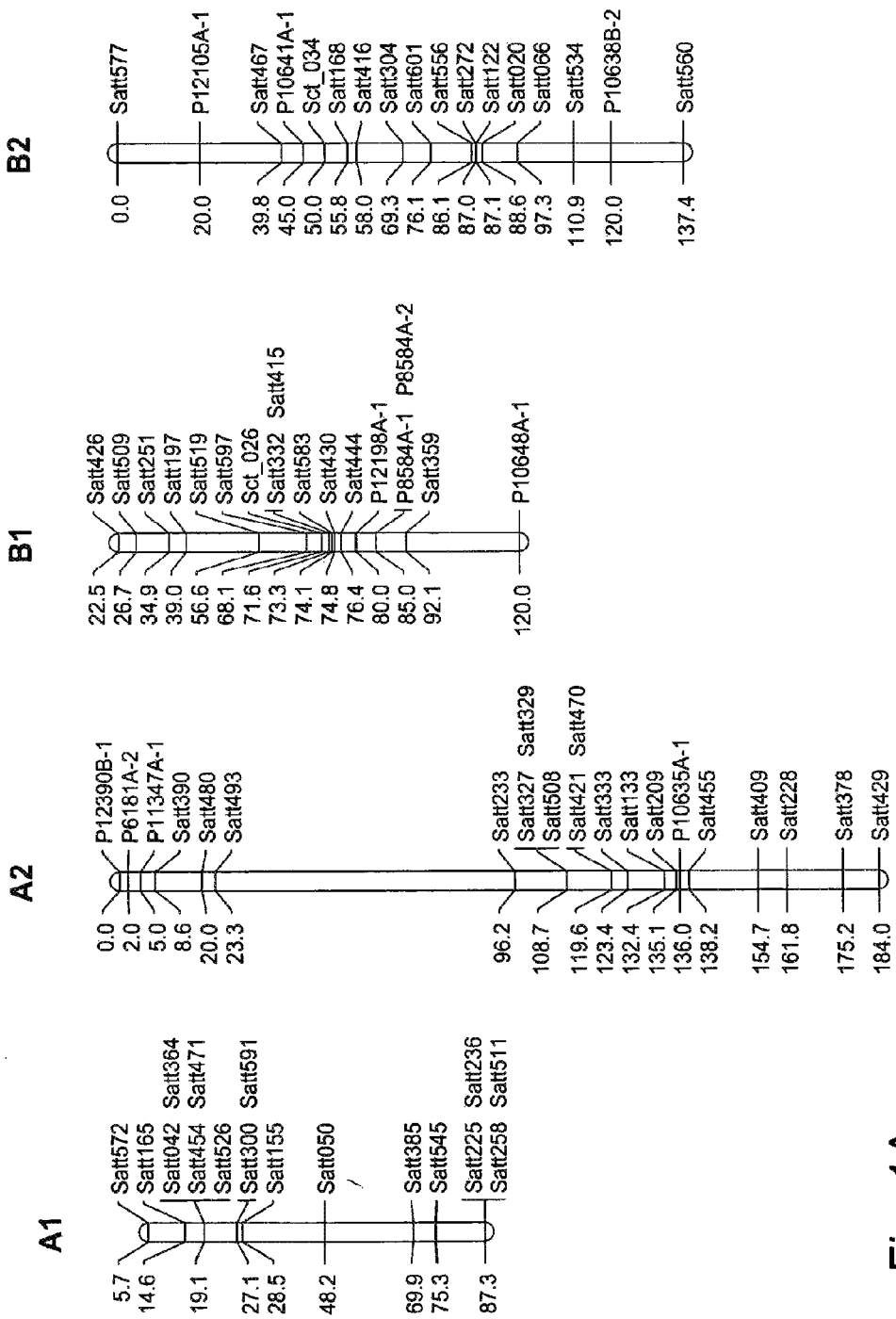
FIGS. 1A-E. Schematic illustration of genetic map indicating positions of markers.
Figure 1B:
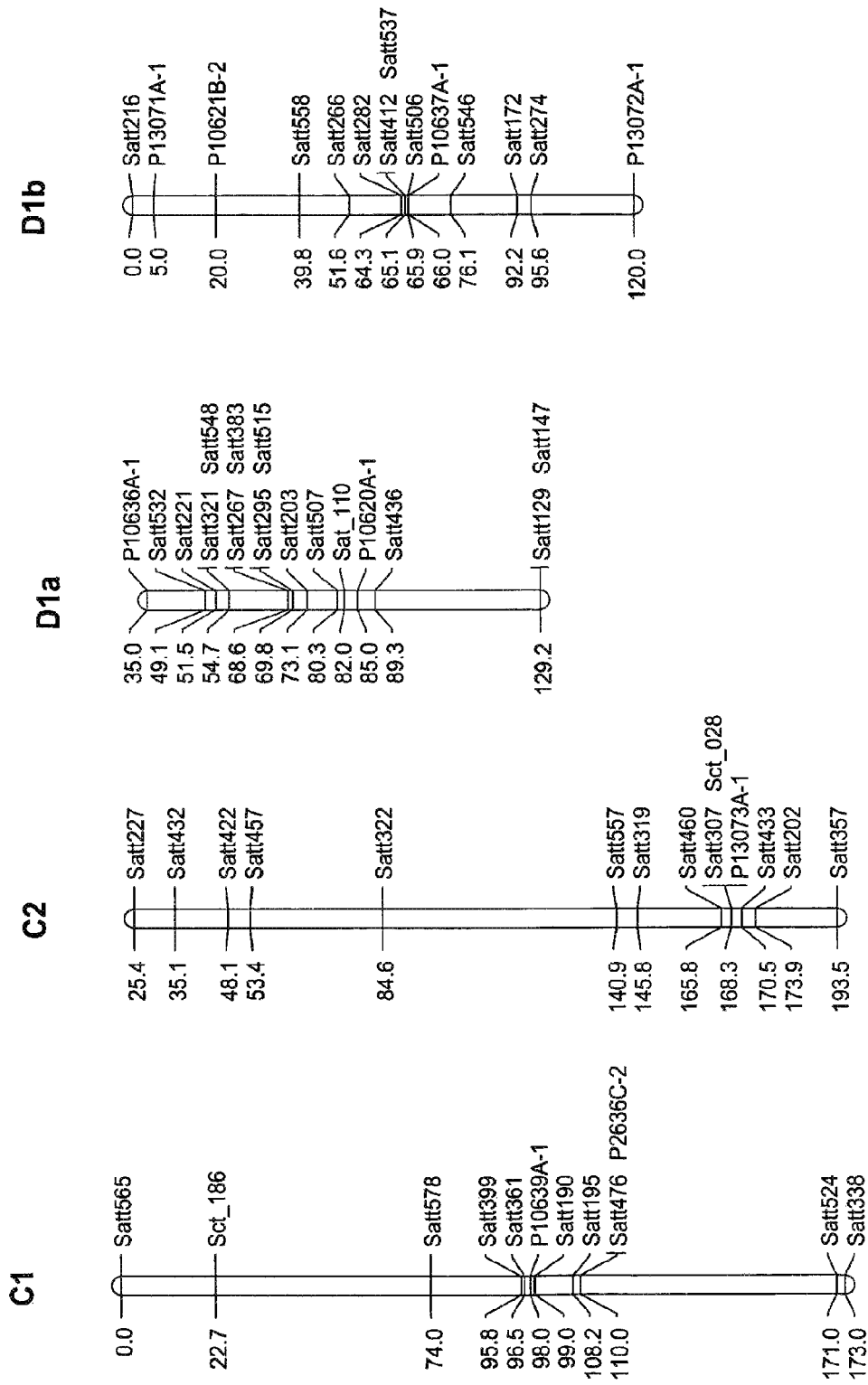
Figure 1C:
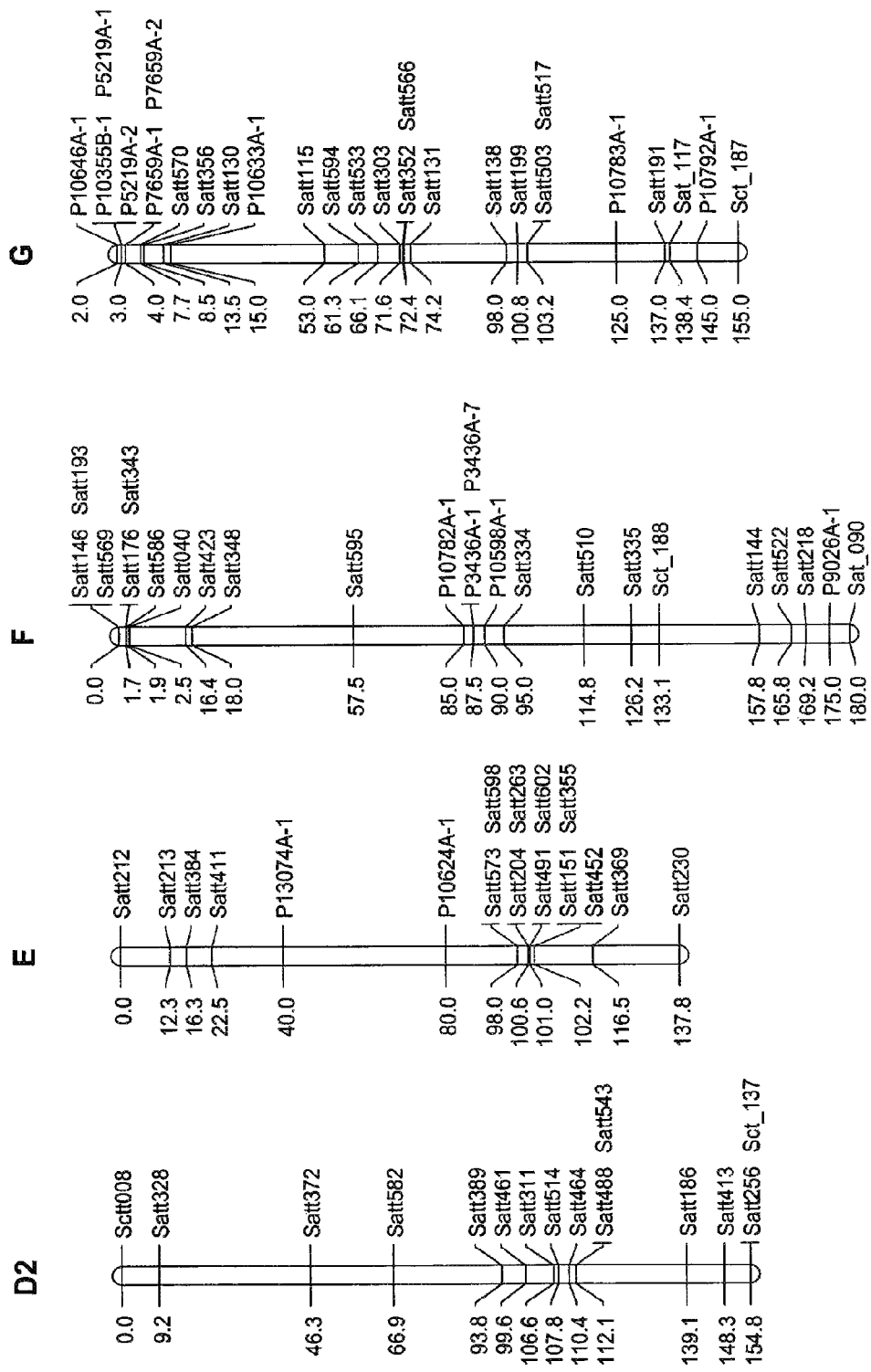
Figure 1D:
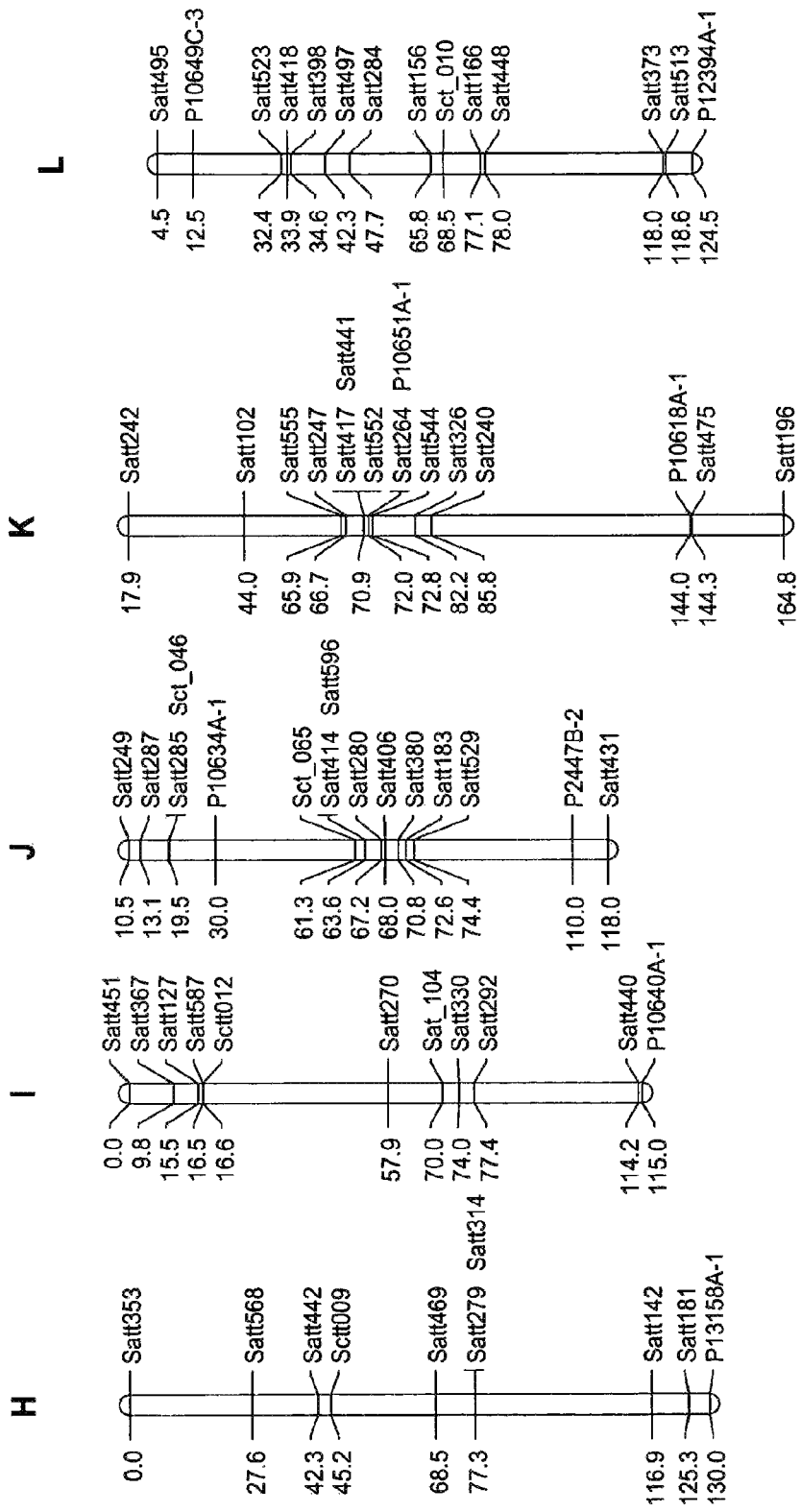
Figure 1E:
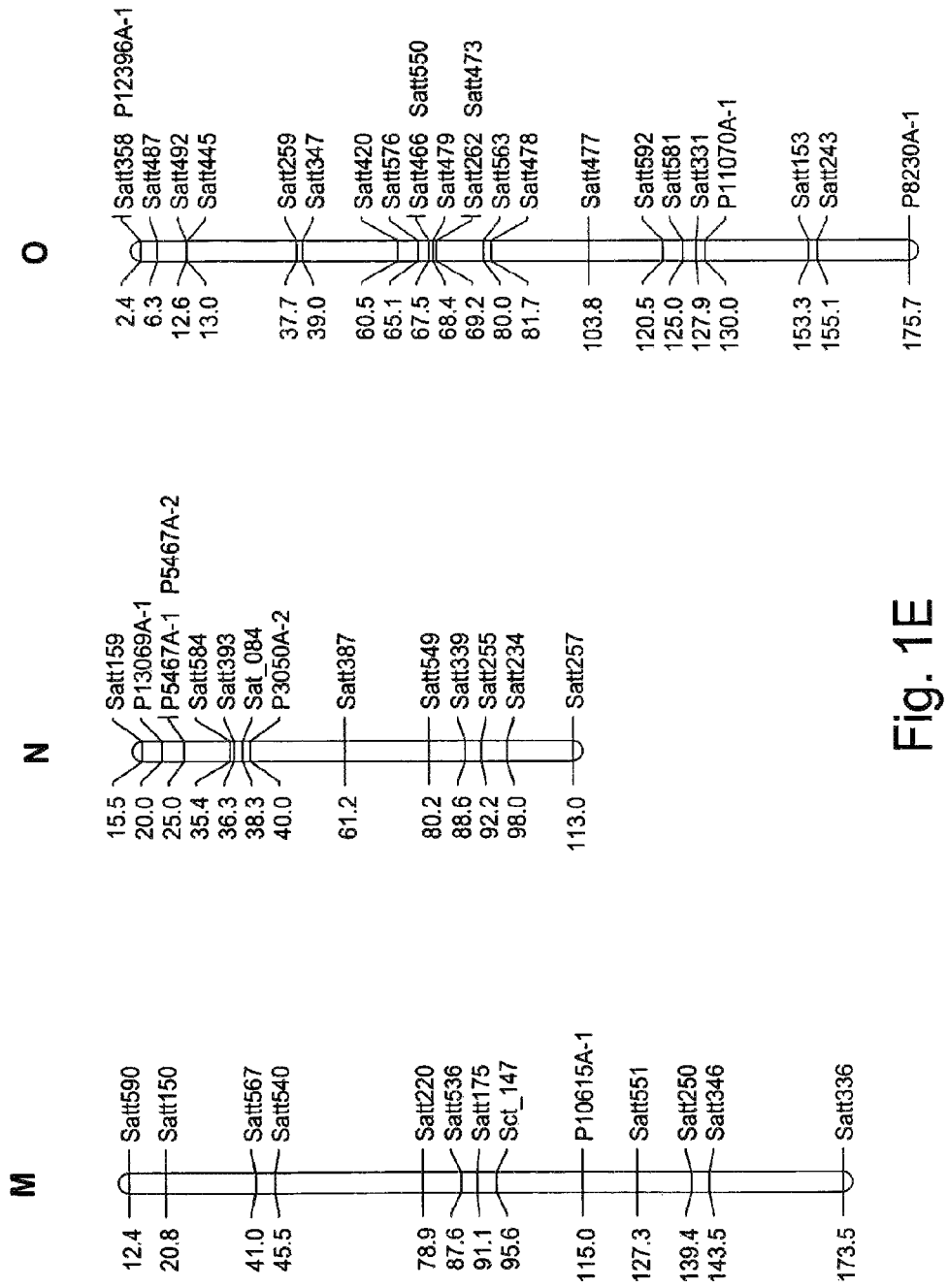

The present invention provides soybean markers associated with loci important for soybean yield. Using methods described in U.S. Pat. No. 5,437,697, which is incorporated in its entirety for all purposes, a series of breeding bias analyses were conducted to identify genetic markers that define regions of the soybean genome that are important for yield. Each analysis identified loci that were affected by selection in one of seven different soybean growing regions in North America. For each geographic region, an "elite population" of between 38 and 86 representative elite lines was chosen by an experienced soybean breeder. Each elite line was evaluated for up to 309 molecular markers to determine its allelic genotype at each of 309 different genetic loci spanning the soybean genome.

In addition to determining the marker genotypes for these elite lines, the most relevant leaf ancestors for each representative elite line were genotyped with the same 309 genetic markers. A "leaf ancestor" is an ancestor for whom the previous parents are unknown, representing an endpoint in the pedigree of each elite line. The breeding bias analysis uses computer simulation and the known pedigree structure between the elite lines and the leaf ancestors to determine the "expected" frequency of each marker allele within the elite population assuming no bias due to selection. The expected frequency is merely the average frequency with which a given allele would be expected in the elite population due to the rules of random Mendelian segregation. The simulation uses the actual pedigrees of each elite line to determine the path that each allele must take during the simulated inheritance process. For example, for any diploid biparental cross within a pedigree, the simulation assumes a 50-50 chance that a given parent allele will be passed on to a given progeny from that cross. By knowing the genotypes of the ancestors and the pedigree of a given elite line, one can simulate the inheritance of each allele through a pedigree structure to determine how often that allele would be expected in the elite line according to a purely random process.

However, plant breeding is not a random process; breeders purposely select for characteristics that provide adaptation and high grain yield in specific geographic regions. By practicing many cycles of genetic recombination and selection of the best genotypes for a given region, breeders indirectly "bias" the gene pool towards the alleles that provide the best grain yield in that locale. Using this logic, any marker allele that was inherited significantly more frequently than expected by random simulation, must reside in a genomic region (chromosome segment) that contributes either directly or indirectly to high grain yield.

Following identification of regions of the soybean genome important for yield using the Breeding Bias analysis, specific marker alleles associated with increased yield can be identified in lines and sublines of soybeans within a breeding program. Since favorable allelic forms of chromosome segments are linked to and defined by genetic markers, accurate selection based on genotype can then replace inefficient selection based solely on phenotype. The end result is more efficient progress towards a genotype with the favorable allelic forms with respect to yield being fixed within the elite gene pool.

Definitions

Before describing the present invention in detail, it is to be understood that this invention is not limited to particular biological systems, e.g., soybean lines, or reagents, such as particular markers, which can, of course, vary. It is also to be understood that the terminology used herein is for the purpose of describing particular embodiments only, and is not intended to be limiting. As used in this specification and the appended claims, the singular forms "a," "an" and "the" include plural referents unless the content clearly dictates otherwise. The term "plurality" is used to mean "two or more." Thus, for example, reference to "a marker" includes a single marker as well as a plurality of markers, such as two or more markers; and the like.

Unless defined otherwise, all technical and scientific terms used herein have the same meaning as commonly understood by one of ordinary skill in the art to which the invention pertains. Exemplary methods and materials are described herein, however, any methods and materials similar or equivalent to those described herein, such as additional or alternative markers physically and genetically linked to the markers (and alleles) described herein, can be used in the practice of the present invention. In describing and claiming the present invention, the following terminology will be used in accordance with the definitions set out below.

The term "germplasm" refers to an individual, a group of individuals, or a clone representing a genotype, variety, species or culture, or the genetic material thereof.

In the context of this disclosure, the term "yield" refers to the productivity per unit area of a particular plant product of commercial significance. For example, yield of soybean is commonly measured in bushels of seed per acre or metric tons of seed per hectare per season. Yield is affected by both genetic and environmental factors. "Agronomics," "agronomic traits," and "agronomic performance" refer to the traits (and underlying genetic elements) of a given plant variety that contribute to yield over the course of growing season. Individual agronomic traits include emergence vigor, vegetative vigor, stress tolerance, disease resistance, herbicide resistance, branching, flowering, seed set, seed size, seed density, standability, threshability and the like. Yield is, therefore, the final culmination of all agronomic traits.

The term "genetic element" or "gene" refers to a heritable sequence of DNA, i.e., a genomic sequence, with functional significance. The term "gene" can be used to refer to, e.g., a cDNA and/or an mRNA encoded by a genomic sequence, as well as to that genomic sequence.

"Locus" refers to a specific chromosome location in the genome of a species where a specific gene can be found. The term "quantitative trait locus" or "QTL" refers to a genetic locus with at least two alleles that differentially affect the expression of a phenotypic trait on at least one genetic background, e.g., in at least one breeding population or sample of progeny.

The term "chromosome segment" designates a contiguous linear span of genomic DNA that resides in planta on a single chromosome. The genetic elements or genes located on a single chromosome segment are physically linked. In the context of the present invention the genetic elements located within a chromosome segment are also genetically linked, typically within a genetic recombination distance of less than or equal to 10 centimorgan (CM). That is, two genetic elements within a single chromosome segment undergo recombination during meiosis with each other at a frequency of less than or equal to about 10%.

"Allele" refers to one of two or more different DNA sequences at a specific locus. In the example of a specific locus where a gene for growth habit is located, one allele is a specific DNA sequence that, e.g., codes for determinate growth habit while another allele is a different DNA sequence that codes for indeterminate growth habit. A "favorable allele" is the allele at a particular locus that confers, or contributes to, an agronomically desirable phenotype, e.g., increased yield. A favorable allele of a marker is an allele associated with a favorable allele at a linked locus which confers or contributes to an agronomically desirable phenotype, e.g., increased yield. A favorable allelic form of a chromosome segment is a chromosome segment including a DNA sequence that contributes to superior agronomic performance at one or more genetic loci physically located on the chromosome segment.

"Allele frequency" refers to the frequency (proportion or percentage) at which an allele is present at a locus within an individual, within a line, or within a population of lines. For example, regarding the allele "A," diploid individuals of genotype "AA," "Aa," or "aa" have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines containing the allele.

A "genetic marker" is any qualitatively (discretely) inherited phenotype that can be used to monitor the segregation of alleles at loci that are genetically linked to the marker. Genetic markers include visible traits such as flower color; enzyme variants such as isozymes and molecular markers such as simple sequence repeats (SSRs), single nucleotide polymorphisms (SNPs), e.g., allele specific hybridization (ASH) markers, restriction fragment length polymorphisms (RFLPs) or randomly amplified polymorphic DNA (RAPDs), etc. Thus, a "marker allele," alternatively an "allele of a marker locus" is one of a plurality of polymorphic nucleotide sequences at a marker locus.

"Codominant markers" reveal the presence of each allele (two per diploid individual) at a locus, e.g., SSR, SNP (e.g., ASH), RFLP, AFLP markers. "Dominant markers" reveal the presence of only a single allele per locus, e.g., RAPD markers. The presence of the dominant marker phenotype (e.g., a band of DNA) is an indication that one allele is present in either the homozygous or heterozygous condition. The absence of the dominant marker phenotype (e.g., absence of a DNA band) is merely evidence that some other, undefined, allele is present. In the case of populations where individuals are predominantly homozygous and loci are predominantly dimorphic, dominant and codominant markers are equally valuable. As individuals within populations become more heterozygous and multi-allelic, codominant markers become more informative of genotype than dominant markers.

A "set" of markers refers to a collection or group of markers, or the data derived therefrom, used for a common purpose, e.g., identifying soybean plants with increased yield. Frequently, the data is stored in an electronic medium. While each of the members of the set has been shown to possess utility with respect to the specified purpose: individual markers selected from the set as well as subsets including some, but not all of the markers, are also effective in achieving the specified purpose.

A "genetic map" is a description of the genetic linkage relationships among loci on one or more chromosomes (or linkage groups) within a given species, generally depicted in a diagrammatic or tabular form. "Mapping" is the process of defining the linkage relationships of loci through the use of genetic markers, populations segregating for the markers, and standard genetic principles of recombination frequency. A "map location" is an assigned location on a genetic map relative to linked genetic markers where a specified marker can be found within a given species.

A "genotype" is the genetic constitution of an individual (or group of individuals) at one or more genetic loci. Genotype is defined by the allele(s) of one or more known loci that the individual has inherited from its parents. A "haplotype" is the genotype of an individual at a plurality of genetic loci. Typically, the genetic loci described by a haplotype are physically and genetically linked, i.e., on the same chromosome segment.

An individual is "homozygous" if the individual has only one type of allele at a given locus (e.g., a diploid individual with two copies of the same allele at a locus). An individual is "Heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

A "line" or "strain" is a group of individuals of identical parentage that are generally inbred to some degree and are generally homozygous and homogeneous at most loci.

An "elite line" or "elite strain" is a genetically superior line that has resulted from many cycles of breeding and selection for superior agronomic performance. Numerous elite lines are available and known to those of skill in the art of soybean breeding. An "elite population" is an assortment of elite lines that can be used to represent the state of the art in terms of agronomically superior genotypes of a given crop species, such as soybean. Similarly, an "elite germplasm" or elite strain of germplasm is a genetically superior germplasm, typically derived from and/or capable of giving rise to a plant with superior agronomic performance, such as an existing or newly developed elite line of soybean.

In contrast, an "exotic germplasm" is a germplasm derived from a soybean not belonging to an available elite soybean line or strain of germplasm. In the context of a cross between two soybean plants or strains of germplasm, an exotic germplasm is unrelated by descent to the elite germplasm with which it is crossed. Most commonly, the exotic germplasm is not derived from any known elite line of soybean, but rather is selected to introduce novel genetic elements (novel alleles) into a breeding program.

An "ancestral line" is a parent used as a source of genes for the development of elite lines. An "ancestral population" is a group of ancestors that have contributed the bulk of the genetic variation that was used to develop elite lines. "Descendants" are the progeny of ancestors, and may be separated from their ancestors by many generations of breeding. For example, elite lines are the descendants of their ancestors. A "pedigree structure" defines the relationship between a descendant and each ancestor that gave rise to that descendant. A pedigree structure can span one or more generations, describing relationships between the descendant and it's parents, grand parents, great-grand parents, etc.

The term "subline" refers to a an inbred subset of descendents that genetically distinct from other similarly inbred subsets descended from the same progenitor. Traditionally, a "subline" has been derived by inbreeding the seed from an individual soybean plant selected and at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. In the context of the invention, marker-based sublines, that differ from each other based on qualitative polymorphism at the DNA level at one or more specific marker loci, are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for increased yield.

The term "near-isogenic" lines refers to lines that are genetically similar to each other except at one or a small number of genetic loci (e.g., at 1, 2, or about 5 to about 10 specified genetic loci). These can be created as described for marker-based sublines or based on differences for any qualitative trait that can serve as an effective genetic marker. Percent similarity between near-isogenic lines is a function of the similarity of the parents of the original cross and the generation at which self-pollination is performed. On average, the relatedness between members of a given inbred line increases 50% with each cycle of inbreeding, due to a 50% increase in homozygosity at each cycle of inbreeding. Percent similarity can be more accurately determined with genetic markers that span the genome. In some cases, near-isogenic lines differ from each other at one defined genetic locus.

"Transgressive segregation" is an inheritance pattern that results in a phenotype (e.g., agronomic performance) of an individual that is more extreme than either parent. For example, with respect to agronomic performance, transgressive segregation results in a progeny with yield that is greater than a best parent or less than a worst parent. Desirable transgressive segregation is the case where the progeny are better than either parent. Transgressive segregation can also be measured in terms of the number of favorable alleles that an individual inherits in relation to the number of favorable alleles of each of its parents. A "target segregant" is a progeny from a specific cross that includes only favorable alleles at each defined locus segregating in the cross. The target segregant therefore, has the best possible genotype that can result from a cross between parents that differ in genotype at known loci. "Target genotype" refers to an individual containing the favorable allelic forms at all chromosome segments or loci known to affect a particular trait or phenotype, such as agronomic performance. With respect to agronomic performance, the target genotype is that of the target segregant from a cross between parents that complement in terms of favorable alleles at all defined loci affecting agronomic performance.

A "survey" or "genetic survey" or "genetic marker survey" is the process of determining and recording the genotype of individuals or lines (e.g., ancestral and elite lines), at any number of defined loci, with the use of genetic markers.

The term "associated with" or "associated," when referring to a nucleic acid (e.g., a genetic marker) and a phenotype in the context of the present invention, refers to a nucleic acid and a phenotypic trait that are in linkage phase disequilibrium. The term "linkage phase disequilibrium" or "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci (including genetic marker loci) that are physically close enough to each other on the same chromosome such that they have a recombination frequency of less than 0.5. When referring to the relationship between two genetic elements, such as a genetic element contributing to yield and a proximal marker, "Coupling" phase linkage indicates the state where the "favorable" allele at the yield locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the yield locus is physically linked with an "unfavorable" allele at the proximal marker locus, and the two "favorable" alleles are not inherited together (i.e., the two loci are "out of phase" with each other).

The term "physically linked" is used to indicate that two genetic loci, e.g., two marker loci, a marker locus and a locus contributing to variation in a phenotype, are physically present on the same chromosome. Typically, the two loci are located in close proximity, such that recombination between homologous chromosome pairs does not occur between the two loci with high frequency. That is, recombination between two physically linked loci typically occurs with a frequency of less than about 10%, favorably with a frequency of less than 5%, more favorably with a frequency of 2% or less or a frequency of 1% or less. Thus, two loci that are localized to the same chromosome, and at such a distance that recombination between the two loci occurs at a frequency of less than 10% are said to be "proximal to" each other.

"Marker Assisted Selection" or "MAS" refers to the practice of selecting for desired phenotypes among members of a breeding population using genetic markers.

The phrase "hybrid plants" refers to plants which result from a cross between genetically different individuals.

The term "crossed" or "cross" in the context of this invention means the fusion of gametes, e.g., via pollination to produce progeny (i.e., cells, seeds, or plants) in the case of plants. The term encompasses both sexual crosses (the pollination of one plant by another) and, in the case of plants, selfing (self-pollination, i.e., when the pollen and ovule are from the same plant).

"Random mating" is the mating of individuals within a population in a way that insures the equal probability of any two individuals mating regardless of genotype. "Non-random mating" is any deviation from random mating in which specific crosses between individuals occur with greater frequency than others.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker or QTL or a transgene.

The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 80% sequence identity, preferably at least 90% sequence identity, and most preferably 95%, 97%, 99%, or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is partially or substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

The term "recombinant" when referring to a molecular species, such as a nucleic acid or protein, indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention, e.g., performed on the cell from which it originates. When the term "recombinant" is used in the classical genetic sense, it refers to an individual with one of the many possible rearrangements of genes due to natural sexual recombination. For example, "recombinant inbred lines" or "RILs" are merely the variety of inbred progeny from specific crosses of divergent parents. The manner in which the term recombinant is employed will be self evident from the context of its use.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The teen includes such nucleic acid introduction means as "transfection," "transformation" and "transduction."

The term "host cell" means a cell that contains a heterologous nucleic acid, such as a vector, and supports the replication and/or expression of the nucleic acid. Host cells may be prokaryotic cells such as E. coli, or eukaryotic cells such as yeast, insect, amphibian, or mammalian cells. In the context of the present invention, a eukaryotic host cell is most commonly a soybean cell.

The term "transgenic" plant (or animal) refers to a plant (or animal) which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, tissue, part or organisms, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional breeding methods (i.e., crosses) or by naturally occurring events such as random cross-fertilization, viral infection with non-recombinant nucleic acids, bacterial transformation with non-recombinant nucleic acids, transposition with non-recombinant nucleic acids, or spontaneous mutation. Examples of processes by which a transgenic organism can be produced are described below, and include electroporation, microinjection, Agrobacterium-mediated transformation, biolistic methods, in planta techniques, and the like.

The term "plant" includes any of: whole plants, plant organs (e.g., leaves, stems, roots, etc.), tissues, seeds, plant cells, and/or progeny of the same. Similarly, "plant cell," as used herein includes, without limitation, seeds, suspension cultures, embryos, meristematic regions, callus tissue, leaves, roots, shoots, gametophytes, sporophytes, pollen, and microspores. In addition, the term "plant" encompasses in silico representations of part or all of a plant's genetic constitution.

Introduction

The present invention addresses the need in the field of agriculture to more efficiently develop soybean plants having superior agronomic performance. Superior agronomic performance, as measured by increased yields of soybeans, is a function of such diverse factors as seedling emergence vigor, resistance to environmental stress, pest resistance, insect resistance, disease resistance, ability to mine nutrients from the soil, ability to produce flowers, photosynthetic ability, and ability to shuttle photosynthate into grain, etc. As disclosed herein, genetic loci associated with superior agronomic performance have been identified by analysis of a plurality of soybean breeding programs (some of which extend back more than 70 years) in a variety of geographic zones in the United States and Canada.

Soybean germplasm having superior agronomic performance (relative to their parents and sibs developed in these same breeding programs) show a statistically significant retention of particular allelic forms (alternatively, "alleles") encompassed within the chromosome segments of the present invention. This highly significant statistical association demonstrates that loci within these chromosome segments are linked (genetically and physically) to genetic elements associated with the various traits involved in determining soybean yield in the context of modern agricultural practices. Collectively, favorable attributes corresponding to such traits are descriptively referred to as "superior agronomic performance," and contribute to increased yield. Consequently, molecular markers localized within these chromosome segments can be used to define (and identify) soybean plants with superior agronomic performance, and in marker assisted selection ("MAS") and marker assisted breeding strategies (alternatively referred to as "molecular breeding") to create soybean plants with superior agronomic performance. Furthermore, chromosome segments encompassing the genetic elements associated with the phenotype of superior agronomic performance can be isolated and transformed into soybean or other monocot or dicot plant species.

The methodology used to identify these chromosome segments, referred to as "Breeding Bias" is disclosed in U.S. Pat. No. 5,437,697 to Sebastian et al., incorporated herein in its entirety for all purposes.

Briefly, loci (e.g., markers and chromosome segments encompassing genetic elements contributing to superior agronomic performance) that have been affected by selection for agronomic performance, are identified by comparing the genotype of modern elite lines with that of their ancestors. Because domesticated soybeans are known to have a fairly narrow gene pool and have been selected to fairly stringent standards, a relatively small number of elite lines is adequate to identify relevant chromosome regions associated with superior agronomic performance. The identity of elite lines used for each geographical region is indicated in Table 1.

Based on the selection of elite lines, the relevant ancestral population, e.g., ancestors that were used most frequently by breeders to develop the elite population is identified. A pedigree tracing the relationship between each elite line and its earliest known ancestors is obtained, and the genetic contribution of each ancestor is converted into a proportional or percentage representation, assuming that on average 50% of each parent's genome is passed on to each progeny as a result of a two-way cross with another parent. By tracing the pedigree back until no more branch points are found, the earliest known ancestors can be identified and their contribution to each elite line calculated. Calculations are performed, generally in a computerized format, for each of the elite lines included in the genetic survey.

Once the appropriate elite and ancestral lines have been chosen, the genotype of each line is determined through the use of genetic markers. Genetic markers include any qualitative phenotype that can be used as a direct measure of genotype at a specific locus. Markers include visual traits such as flower color, enzyme variants such as isozymes, and molecular markers, which can be detected by a variety of means such as simple sequence repeats (SSR), single nucleotide polymorphism (SNP), allele specific hybridization (ASH), restriction fragment length polymorphism (RFLP), amplified variable sequences, single strand conformation polymorphism (SSCP), amplified fragment length polymorphism (AFLP) and randomly amplified polymorphic DNA (RAPD).

Regardless of which genetic markers are used to monitor genotype, the end result is a marker genotype for each of the elite and ancestral lines. The genotype of each line is merely an indication of which allele the line possesses at any number of loci defined by the genetic markers.

Once one has determined the genotypes of ancestral and elite lines, statistical analyses are used to determine whether selection for superior agronomic performance has favored particular alleles at certain loci. The first statistic to calculate is the probability of finding each allele within the elite population with the assumption that selection had no effect on allele frequency. This expected allele frequency within the elite population serves as a basis for comparison to the observed allele frequency.

Expected allele frequency within the elite population is a function of the genotype of each ancestor and the pedigrees of elite lines representing the elite population. In a random mating population, the allele frequency among descendants should be similar to allele frequency among ancestors unless breeding and selection has favored particular alleles. However, since breeding of many crops (including soybeans) is not done through random mating, one can use the pedigree of each descendant (e.g., elite line) to calculate the probability of inheriting a given allele from its ancestors. Within non-random mating populations, expected allele frequency can be obtained by averaging the individual probabilities of inheriting an allele over any number of descendants (that may differ greatly in pedigree).

By comparing the observed frequency of a given allele in the elite population to the average probability of inheriting that allele (i.e., comparing observed count to expected count), one can determine which loci have been affected by historical selection for agronomic traits. Favorable alleles are identified as the ones that have been inherited more frequently than expected (i.e., have been favored by selection). Unfavorable alleles are those inherited less frequently than expected (i.e., selected against). A statistical test is then used, e.g., as described in detail in U.S. Pat. No. 5,437,697, to determine the significance of a difference between observed and expected allele frequency.

According to these methods, loci and alleles with significant deviations from expected allele frequency correlating with superior agronomic performance in different growing environments have been identified. These loci can be used to define and identify, as well as select for soybeans with superior agronomic performance. For example, the markers disclosed herein can be used to 1) identify soybean germplasm with superior and/or improved agronomic performance, e.g., relative to presently existing or parental soybean lines; 2) identify parents that will produce superior transgressive segregants; 3) select superior lines from crosses that are segregating at loci (e.g., QTL loci) which contribute to superior agronomic performance; 4) select parents that will produce the best hybrids; 5) purify heterogeneous lines, i.e., by selecting only those individuals that include the favorable allele(s) at loci that are still segregating within the line; 6) select for and maintain desirable heterogeneity; 7) maintain favorable alleles at multiple loci that have been assembled by many years of selection while incorporating exotic alleles from new germplasm at other loci; 8) to test the effects of exotic allele substitution at loci that have proven important for domestication, e.g., in the event that an exotic allele provides better agronomic performance at the loci identified by breeding bias; and, 9) in any process where it is important to prioritize which loci are more important for agronomic fitness than random loci within the genome.

Markers and Alleles Correlating with Superior Agronomic Performance in Soybeans

In one aspect, the present invention provides marker loci correlated with superior agronomic performance in soybean. Each of the identified markers is expected to be in close physical and genetic proximity (i.e., physically and genetically linked) to a genetic element, e.g., a quantitative trait locus or QTL, that contributes to superior agronomic performance. If a particular marker were not in proximity to an important QTL, the extended period of recurrent selection (70+ years for soybean) would have provided many opportunities for crossing over between the marker and QTL. This would result in disassociation between the marker allele and the QTL allele resulting in "linkage equilibrium" and statistically non-significant estimates of correlation between the marker and yield, i.e., LOD or probability scores. Breeding bias does not detect poorly-linked markers, that is, markers that are distant from important loci, even if both the marker and the genetic element (e.g., QTL) contributing to yield are found on the same chromosome. In addition, since thousands of different environments have been sampled to test performance during each cycle of selection, alleles that provide adaptation to a wide range of environments will be most readily identified. Alleles that are only favorable under rare environmental conditions will not consistently increase in frequency due to selection in different environments and will, therefore, not be detected by breeding bias analysis. Furthermore, the narrow gene pool and high relatedness among elite soybean germplasm shared by both public and private institutions (Delanney et al, 1983, Crop Science 23:944-949) act to homogenize the gene pool and make marker-QTL associations more reliable. Taken together, these features in combination with the large body of data analyzed by breeding bias, ensure that QTL with a substantial contribution to yield are located in close proximity to the markers disclosed herein.

Accordingly, each of the disclosed markers defines a chromosome segment associated with a genetic element, e.g., a QTL contributing to superior agronomic performance. One of skill in the art will recognize that for each of the chromosome segments encompassing QTL related to yield, identification of and/or selection for the QTL is optimized by using a genetic marker that is as close as possible to the actual QTL locus that is responsible for the phenotype in question. Thus, a "perfect" marker would be one that is localized within the genetic element or QTL itself, and corresponds to the DNA polymorphism that is responsible for the superior phenotype. That is, the marker polymorphism is the mutation underlying the improvement in yield. However, since most of the genetic markers available for soybean consist of RFLPs, SSRs, RAPDs and SNPs of unknown function, it would be highly unlikely that a given marker from those currently available was already "perfect." Nevertheless, the markers described herein constitute a set of tools for detecting important chromosome segments comprising QTL associated with yield. These markers are sufficiently close to their respective linked QTL to detect a statistically significant shift in allele frequency (due to selection) over 70 years of recurrent selection for yield, thus, are useful for the purposes of identifying desirable germplasm and for MAS. In addition, these markers are useful for identifying additional markers, e.g., including a "perfect" marker within the QTL gene of interest.

Tables 3 through 12 disclose exemplary molecular, which define the chromosome segments that are embodiments of the present invention. Each of Tables 3 through 12 provides marker loci and favorable alleles, identified by Breeding Bias, relevant in a specified growing environment distinguished by geographic region.

The exemplary markers provided in Tables 3 through 12 identify chromosome segments including genetic elements (genes) important for yield in soybean. The chromosome segments of the present invention are contiguous lengths of chromosome delimited by a specified crossover frequency or map distance (centimorgans or CM) from a molecular marker of the present invention. The chromosome segments of the present invention are delimited by a crossover frequency of up to about 10%, i.e., 10 CM, from a marker locus known to be associated with superior agronomic performance, e.g., Satt165; Satt042; Satt364; Satt454; Satt526; Satt300; Satt591; Satt155; Satt385; Satt511; P12390B-1; Satt327; Satt329; Satt508; P10635A-1; Satt409; Satt228; Satt429; Satt509; Satt197; SCT_026; Satt415; Satt583; Satt430; P12198A-1; P8584A-1; Satt359; P10648A-1; P10641A-1; Satt168; Satt556; Satt272; Satt020; Satt534; P1063813-2; Satt399; Satt361; P10639A-1; Satt190; Satt338; Satt227; Satt457; Satt557; Satt319; Sat_1460; Satt307; SCT_028; Satt433; Satt357; Satt321; Satt267; Satt295; Satt203; Satt507; SAT_110; P10620A-1; Satt129; Satt147; Satt216; P10621B-2; Satt558; Satt266; Satt282; Satt537; Satt506; P13072A-1; Satt582; Satt389; Satt461; Satt514; Satt464; Satt543; P13074A-1; P10624A-1; Satt573; Satt598; Satt204; Satt263; Satt491; Satt602; Satt151; Satt355; Satt452; Satt146; Satt193; Satt569; Satt343; Satt586; Satt423; Satt348; Satt595; P10782A-1; P3436A-1; Satt334; Satt510; Satt144; Satt522; P9026A-1; P10646A-1; P5219A-1; P7659A-2; Satt570; Satt356; Satt130; Satt115; Satt594; Satt533; Satt303; Satt352; Satt566; Satt199; Satt503; Satt517; Satt191; SAT_117; Satt353; Satt442; Satt279; Satt314; Satt181; Satt367; Satt127; Satt270; Satt440; P10640A-1; Satt249; SCT_065; Satt596; Satt280; Satt406; Satt380; Satt183; Satt529; Satt431; Satt242; Satt102; Satt240; P10618A-1; Satt523; Satt398; Satt497; Satt166; Satt448; Satt373; Satt513; P12394A-1; Satt590; Satt220; Satt536; Satt175; P10615A-1; Satt250; Satt346; Satt336; P13069A-1; P5467A-1; Satt584; SAT_084; Satt387; Satt339; P12396A-1; Satt487; Satt259; Satt347; Satt420; Satt576; Satt550; Satt262; Satt473; Satt477; Satt581; P11070A-1; Satt153; Satt243; P8230A-1; P10623A-1; P10632A-1; P12391A-1; P12392A-1; P13560A-1; P13561A-1; p2481A-1; SAC1677; Satt040; Satt109; Satt111; Satt176; Satt219; Satt299; and Satt512. The genetic element contributing to yield can be localized to any portion of the chromosome segment defined by these molecular markers. For example, a gene encoding a function leading to improved yield can reside within the chromosome segment at a distance of less than 1 CM (at a distance resulting in recombination in fewer than 1% of mitotic events), or at any distance between about 1 CM and 10 CM, e.g., values of approximately 2 CM, 3 CM, 4 CM, 5 CM, 6 CM, 7 CM, 8 CM, or 9 CM, or any value between about 0 CM and about 10 CM. Thus, a chromosome segment is defined as a contiguous length of chromosome extending up to 10 CM in either direction from a designated marker, and including the portion of the chromosome that undergoes crossover with the marker locus at a frequency of no greater than 10%. In many cases, the chromosome segment of interest, is in fact a continuous length extending less than 10 CM, i.e., a length of chromosome that undergoes crossover with the marker at a frequency of less than 10%, e.g., 9%, 8%, 7%, 6%, 5%, 4%, 3%, 2%, 1% or less, or any value therebetween. Alternatively, physical distances may be utilized to determine the aforementioned chromosome segments using a conversion factor of 1 (one) Mbp (one million base pairs) for 1 (one) CM of map distance or 1% (one percent) crossover frequency. The actual conversion factor in soybean ranges from about 100 Kbp to close to 1 Mbp depending on the chromosome region. Accordingly, the arbitrary but reasonable conversion factor of 1 Mbp is to be understood in the context of the present invention.

The exemplary favorable alleles of marker loci enumerated herein have been shown, e.g., by breeding bias analysis, to be associated with genetic elements contributing to improved yield in various lines of soybeans. One of skill will appreciate, that this is an empirical association, and that a particular marker locus (and the designated favorable alleles thereof) are used to identify a corresponding chromosome segment having a genetic element that contributes to yield. However, because a marker locus is not necessarily, or even typically, identical to the genetic element which results in enhanced yield, in some percentage of crosses, genetic recombination will occur between the enumerated favorable allele and the genetic element contributing to yield. This does not negate the importance of either the genetic element or the identification of the marker locus and exemplary favorable alleles. Any such recombination events can be detected and subsequent marker assisted selection can be performed using the allele determined to be in coupling linkage phase with the favorable genetic element as discussed in more detail in EXAMPLE 4: SEGREGATION FOR YIELD IN NEAR ISO-GENIC SUB-LINES, in the context of detecting residual polymorphisms associated with yield in near iso-genic sublines, and in EXAMPLE 5: ALLELE CONFIRMATION USING RANDOM CROSSES.

In the context of the present invention, the allelic form of multiple chromosome segments is determined, whether the purpose is to define the genotype of a soybean or for marker assisted selection (MAS). In most circumstances, it is desirable to ascertain the allelic form for a large proportion, e.g., all, of the chromosome segments known to contribute to yield in a particular geographic region. However, in some circumstances, particularly when the parents are known to share particular favorable alleles, a subset of the chromosome segments can be employed, reducing time and cost, without losing efficiency. Thus, in the context of the present invention it is common to assess at least 10%, typically between at least 10% and about 90% of the relevant chromosome segments, e.g., by determining the allelic form of the marker loci specified in Tables 3 through 12. Commonly, at least about 25%, frequently at least about 50%, often at least about 75% or more of the allelic forms are determined. For example, at least about 80%, 85%, 90%, 95%, 97%, 98%, 99%. Accordingly, it is generally desirable to determine the allele at a majority of the loci shown to be relevant to agronomic performance in a particular geographic region or growing environment. In one favorable embodiment, the allelic form of a set of markers defining a set of chromosome segments consisting essentially of the markers shown to be relevant to agronomic performance in a particular region are determined. A set of markers is deemed to consist essentially of the markers relevant in a particular region if it includes a sufficient number of markers to prevent a diminishing yield phenotype or to prevent a decrease in efficiency of selection when the set of markers is used for marker assisted selection. Typically such a set will include at least about 90%, 95%, 97%, 98%, 99% or more of the markers. That is, no more than 10% of the markers shown to be relevant in a particular region will be omitted, e.g., no more than 5%, 3%, 2%, or 1% of the allelic forms of the relevant markers will be left undetermined.

Typically, the marker loci evaluated are shown to correlate with superior agronomic performance with a significance of greater that 95%. Often the marker loci are selected that exhibit a significance of greater than 99% within a geographic region of interest. If desired, the allelic form of multiple marker loci within the same chromosome segment can be determined. Frequently, the allelic form of a single marker representing the chromosome segment is determined.

Identification of Residual Polymorphism

The marker loci identified by Breeding Bias are associated with genetic elements contributing to increased yield in soybean. Although particular alleles of the marker loci have been found to be statistically correlated with increased yield according to the Breeding Bias analysis, alleles at one or more marker loci are typically not fixed within an elite line or among progeny derived from a progenitor soybean selected from an elite strain of germplasm. Indeed, such residual polymorphisms provide valuable genetic variation from which improved sublines can be selected. By identifying particular marker loci from among the set of loci shown to be associated with genetic elements contributing to yield, the efficiency of selection can be improved.

To this end, marker loci with one or more segregating alleles in a population of progeny derived from an elite progenitor are evaluated to identify the specific allele correlating with increased yield in the population of progeny. Detailed descriptions of exemplary methods for confirming the favorable allele in a population of progeny are provided in EXAMPLES 4 and 5.

Definition and Identification of Target Germplasm

The marker loci of the present invention can be used as proxies for loci contributing to improved yield to define the theoretically optimal or "target" soybean genotype. Accordingly, alleles of marker loci identified by Breeding Bias, and confirmed to correlate with increased yield in a given environmental or geographic context can be used to define or identify a soybean plant with superior agronomic performance. While existing elite lines include favorable alleles at numerous marker loci (and corresponding functional loci contributing to yield), none of the existing elite lines yet incorporates all of the genetic elements contributing to the ideal soybean genotype. Indeed, prior to the markers of the present invention, it would not have been possible to predict the ideal soybean genotype (or define a target genotype) with respect to yield. Thus, a feature of the invention is the definition of a target soybean genotype for superior agronomic performance. Any soybean plant having an increased number of favorable allelic forms of chromosome segments defined according to the markers of the invention, i.e., that more closely approximates the target soybean genotype than existing elite lines, constitutes a feature of the present invention.

The markers and methods described herein provide the means for identifying and developing soybean plants having the target soybean genotype for superior agronomic performance and genomes having increased numbers of favorable allelic forms of the relevant chromosome segments relative to existing elite lines, and or relative to either parent giving rise to the soybean plant genome. Accordingly, the methods of the invention can be used to produce compositions, including whole plants, plant organs, seeds, and isolated genetic constituents, e.g., including the entire chromosomal complement of the genome, or a subset thereof, such as an individual chromosome or chromosome fragment (all of which are collectively described by the term "soybean plant genome") with an increased number of genetic elements contributing to yield. Methods for separating and isolating genomes or individual chromosomes are well known in the art and include, e.g., flow cytometry and pulse field gel electrophoresis. Replicates of the soybean plant genome are also encompassed within the meaning of the term soybean plant genome. Replicates are identical or substantially identical (i.e., a mutant arising from mitotic division from the same progenitor cell) to the initial soybean plant genome. Replicates can be created, for example, by yeast or bacterial artificial chromosomes or any of a variety of nucleic acid vectors or replication methods such as PCR (polymerase chain reaction).

A soybean plant genome(s) of the present invention can be from an individual soybean plant. As used herein, the term "plant" includes whole plants, plant organs (e.g., leaves, stems, roots, etc.), seeds, suspension cultures, embryos, meristematic regions, callus tissue, leaves, roots, shoots, gametophytes, sporophytes, pollen, and microspores.

Marker Assisted Selection and Breeding

The ultimate goal of any breeding program is to combine as many favorable alleles as possible into elite varieties of germplasm that are genetically superior (with respect to one or more agronomic traits) to their ancestors. The markers provided herein identify chromosome segments, i.e., genomic regions, and alleles (allelic forms) that have been favored by long-term selection for yield. Accordingly, these markers can be used for marker assisted selection of soybean plants with superior agronomic performance. For example, in a cross between parents that complement favorable alleles at the target loci, progeny can be selected that include more favorable alleles than either parent. Such progeny are predicted to be phenotypically superior to either parent as illustrated in Table 2.

Marker assisted selection (MAS), employing the markers of the present invention, and the chromosome segments they identify are useful in the context of a soybean breeding program to increase efficiency in yield improvements. Phenotypic screening for a trait of interest, such as yield, for large numbers of samples can be expensive, as well as time consuming. In addition, phenotypic screening alone is often unreliable due to the effects of epistasis and non-genetic (e.g., environmental) contributions to the phenotype. MAS offers the advantage over field evaluation that it can be performed at any time of year regardless of the growing season or developmental stage. In addition, MAS facilitates evaluation of organisms grown in disparate regions or under different conditions.

A breeder of ordinary skill, desiring to breed soybean plants with increased yield, can apply the methods for MAS described herein, using, e.g., the exemplary markers provided herein or linked markers localized to the chromosome segments identified by markers provided in Tables 3 through 12, to derive soybean lines with superior agronomic performance.

Genetic marker alleles, e.g., the exemplary markers provided Tables 3 through 12, linked markers, QTL, identifying the chromosome segments encompassing genetic elements that are important for yield, are used to identify plants that contain a desired genotype at one or more loci, and that are expected to transfer the desired genotype, along with a desired phenotype to their progeny. Marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. Similarly, by identifying plants lacking the desired allele, plants with an undesirable phenotype, e.g., plants with poor yield, can be identified, and, e.g., eliminated from subsequent crosses. It will be appreciated that for the purposes of MAS, the term marker can encompass both marker and QTL loci as both can be used to identify plants with a desired phenotype.

For example, MAS can be used to develop lines or strains of soybean and soybean germplasm with superior agronomic performance by identifying favorable allelic forms of chromosome segments shown to be important, e.g., that include a genetic element, for yield. Favorable alleles of markers defining the chromosome segments of interest, e.g., Satt684, Satt165, Satt042, Satt364, Satt454, Satt526, Satt300, Satt591, Satt155, Satt385, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT_261, Satt197, Satt519, Satt597, SCT_026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT_311-DB, Satt338, Satt227, Satt640-TB, Satt422, Satt457, Satt457, Satt557, Satt319, SAT_142-DB, Satt460, P13073A-1, Satt307, SCT_028, Satt433, Satt357, Satt321, Satt267, Satt383, Satt295, Satt203, Satt507, SAT_110, P10620A-1, Satt129, Satt147, Satt216, SAT_351, P1062113-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT_273-DB, Satt146, Satt193, Satt569, Satt343, Satt586, Satt040, Satt423, Satt348, Satt595, P10782A-1, P3436A-1, P10598A-1, Satt334, Satt510, Satt510, Satt144, Satt522, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT_117, Satt353, Satt442, Satt279, Satt314, Satt142, Satt181, Satt367, Satt127, SCTT012, Satt270, Satt292, Satt440, P10640A-1, Satt249, SAG1223, SAC1699, SCT_065, Satt596, Sat_1280, Satt406, Satt380, Satt183, Satt529, Satt431, Satt242, Satt102, Satt441, Satt544, Satt617, Satt240, P10618A-1, Satt475, Satt196, SAT_301, Satt523, Satt418, Satt418, Satt398, Satt497, Satt284, Satt166, Satt448, Satt373, Satt513, P12394A-1, Satt590, Satt567, Satt220, SAG1048, Satt536, Satt175, Satt677, Satt680, P10615A-1, Satt551, Satt250, Satt346, Satt336, SAT_330-DB, P13069A-1, P5467A-1, P5467A-2, Satt584, SAT_084, P3050A-2, SAT_275-DB, Satt387, Satt549, Satt660, Satt339, Satt255, Satt257, Satt358, P12396A-1, Satt487, Satt259, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P2481A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt108, Satt109, Satt111, Satt176, Satt176, Satt219, Satt299, and Satt512 as enumerated Tables 3 through 12 are detected in a genomic sample of a soybean plant.

For example, in a breeding program designed to produce soybeans with increased yield in the Central United States growing region (e.g., exemplified by the growing conditions in Iowa), markers can be selected from the following set of markers: Satt642, Satt042, Satt364, Satt454, Satt526, Satt300, Satt591, Satt155, Satt385, Satt511, P12390B-1, Satt632-TB, Satt429, SAT_261, Satt197, P10641A-1, Satt556, Satt534, P10638B-2, Satt399. Satt361, P10639A-1, Satt661-TB, Satt190, SAT_311-DB, Satt338, Satt640-TB, Satt557, Satt319, SAT_142-DB, Satt460, Satt433, Satt357, Satt321, Satt295, Satt203, Satt507, Satt129, Satt147, SAT_351, P10621B-2, Satt558, Satt701, Satt634, Satt582, Satt389, Satt464, Satt662, Satt672, Satt573, Satt598, Satt263, Satt602, Satt151, SAT_273-DB, Satt146, Satt193, Satt569, Satt176, Satt343, Satt586, Satt040, Satt595, P10782A-1, Satt334, Satt144, Satt522, Satt570, Satt356, Satt533, Satt199, Satt517, Satt191, SAT_117, Satt279, Satt181, Satt127, Satt270, Satt292, SAG1223, SAC1699, SAT_065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, Satt346, Satt336, SAT_330-DB, P13069A-1, P5467A-1, P5467A-2, SAT_084, SAT_275-DB, Satt660, Satt339, P12396A-1, Satt358, Satt487, Satt259, Satt420, Satt576, Satt633, Satt477, Satt581, Satt153, Satt243, P10793A-1, P12391A-1, P12392A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt040, Satt111, Satt176, Satt219 and Satt299, such as: Satt684, Satt042, Satt364, Satt454, Satt526, Satt300, Satt591, Satt155, Satt385, Satt632-TB, Satt429, SAT-261, P10641A-1, Satt556, P1063813-2, Satt399, Satt361, Satt661-TB, Satt190, SAT_311-DB, Satt338, Satt640-TB, Satt557, Satt319, SAT_142-DB, Satt321, Satt203, Satt129, Satt147, SAT_351, P10621B-2, Satt701, Satt634, Satt582, Satt389, Satt464, Satt662, Satt672, Satt573, Satt598, Satt263, Satt151, SAT_273-DB, Satt146, Satt193, Satt569, Satt343, Satt586, Satt040, Satt595, Satt334, Satt144, Satt522, Satt570, Satt356, Satt199, Satt517, Satt191, Sat 117, Satt279, Satt181, Satt127, Satt270, Satt292, SAG1223, SAC1699, Sat 065, Satt596, Satt406, Satt380, Satt183, Satt529, Satt242, Satt617, Satt240, SAT_301, Satt418, Satt398, Satt497, Satt166, Satt448, Satt373, Satt513, P12394A-1, SAG1048, Satt536, Satt175, Satt677, Satt680, P10615A-1, Satt551, SAT_330-DB, P13069A-1, P5467A-1, P5467A-2, SAT_084, SAT_275-DB, Satt660, Satt339, Satt358, Satt487, Satt487, Satt420, Satt576, Satt633, Satt581, Satt153, Satt243, P10793A-1, P13560A-1, P13561A-1, S60021-TB, S60048-TB, S60076-TB, S60148-TB, S60149-TB, S60201-TB, S60243-TB, S60326-TB, S60338-TB, S60350-TB, S60361-TB, S60422-TB, S60440-TB, S60446-TB, S60505-TB, S60513-TB, S60519-TB, S60536-TB, S60552-TB, S60585-TB, S60630-TB, S60728-TB, S60812-TB, SAC1677, SAC1724, SAG1055, Satt111, Satt219 and Satt299. The following exemplary markers represent the best markers for selection for yield in the Central Region in each chromosome region: Satt684, Satt526, Satt591, Satt385, Satt632-TB, Satt429, SAT-261, P10641A-1, Satt556, P10638B-2, Satt190, SAT_31'-DB, Satt338, Satt640-TB, Satt557, SAT_142-DB, Satt321, Satt203, Satt129, SAT_351, Satt701, Satt582, Satt389, Satt464, Satt672, Satt598, Satt343, Satt595, Satt334, Satt144, Satt522, Satt570, Satt356, Satt199, Sat 117, Satt279, Satt181, Satt127, Satt270, Satt292, SAG1223, Sat 065, Satt529, Satt242, Satt617, SAT_301, Satt398, Satt497, Satt166, Satt373, SAG1048, Satt680, P10615A-1, SAT_330-DB, P13069A-1, SAT_275-DB, Satt339, Satt487, Satt420, Satt581 and Satt153. Comparable lists of markers can be compiled from Tables 3 through 12 at the discretion of the practitioner based on the desired growing region.

A soybean plant so identified can be utilized in a plant breeding program to develop lines with improved yield. Similarly, the detection of favorable (or conversely, non-favorable) allelic forms of the chromosome segments can be used to trace the flow of alleles in a soybean plant pedigree to ensure that the desired complement of alleles are included or excluded in the resulting soybean plant(s).

After a desired phenotype and a polymorphic chromosomal locus, e.g., a marker locus or QTL, are determined to segregate together (i.e., are determined to be in linkage disequilibrium), alleles corresponding to the desired phenotype are selected. In brief, a nucleic acid corresponding to the marker nucleic acid is detected in a biological sample from a plant to be selected. This detection can take the from of hybridization of a probe nucleic acid to a marker, e.g., using allele-specific hybridization, Southern analysis, northern analysis, in situ hybridization, hybridization of primers followed by PCR amplification of a product including the marker, or the like. A variety of procedures for detecting markers are described herein, e.g., in the section entitled "DETECTION OF MARKER LOCI." After the presence (or absence) of a particular marker in the biological sample is verified, the plant is selected and, optionally, crossed to produce progeny plants.

When a population is segregating for multiple loci affecting one or multiple traits, e.g., multiple loci involved in resistance to single disease, or multiple loci each involved in resistance to different diseases, the efficiency of MAS compared to phenotypic screening becomes even greater because all the loci can be processed in the lab together from a single sample of DNA. Thus, use of marker information for each of the traits in the breeding process is facilitated.

It will be appreciated that plants positive for a marker of the invention can be selected and crossed according to any breeding protocol relevant to the particular breeding program. Accordingly, progeny can be generated from a selected plant by crossing the selected plant to one or more additional plants selected on the basis of the same marker or a different marker, e.g., a different marker correlating with superior agronomic performance, or a different phentoype of interest, e.g., resistance to a particular disease. Alternatively, a selected plant can be back crossed to one or both parents. Backcrossing is usually done for the purpose of introgressing one or a few loci from a donor parent, e.g., a donor parent comprising exotic germplasm, into an otherwise desirable genetic background from the recurrent (typically, an elite) parent. The more cycles of backcrossing that are performed, the greater the genetic contribution of the recurrent parent to the resulting variety. A selected plant can also be outcrossed, e.g., to a plant or line not present in its genealogy. Such a plant can be selected from among a population subject to a prior round of analysis, or may be introduced into the breeding program de novo. A plant positive for a desired marker can also be self-crossed ("selfed") to create a true breeding line with the same genotype.

In some instances, even if a marker is close enough to a QTL to detect breeding bias, the marker may not be close enough for reliable MAS. If such a marker is far enough away from the QTL of interest, there may be crossing over between the marker and the QTL leading to repulsion phase linkages (in the elite population) between the marker allele that was originally linked in coupling to the favorable QTL allele. With time, the marker locus and the linked QTL locus could reach "linkage equilibrium" and this will prevent the use of that marker for reliable selection of the favorable QTL allele. For highly heritable traits, linkage phase between marker and QTL in any given parent can be easily determined through MAS followed by phenotypic characterization. However, linkage phase determination for traits of low heritability (e.g., yield) is much more difficult. In fact, the effects of single loci on yield may be extremely difficult to measure even with highly replicated field tests. In addition, if yield genes were highly heritable, the continuous selection for this trait would have "fixed" all of the favorable alleles quickly and yield progress would have previously reached a plateau. Since steady yield progress continues in soybean, it does not appear that a "yield plateau" has been reached yet (Specht et al., 1999, Crop Science 39:1560-1570). Therefore, many of the favorable alleles at the major yield loci in soybean are not yet fixed within the elite population. The question remains whether the existing marker loci are still in original linkage phase with the QTL loci. Fortunately, the results of breeding bias disclosed here can be used to solve the problem of "imperfect" yield gene markers several ways: a) linkage phase and QTL effect determination within specific crosses prior to MAS, b) use of flanking markers to predict which markers are still linked in coupling, and c) alternating cycles of MAS and phenotypic selection.

Linkage Phase and QTL Effect Determination within Specific Crosses:

Because elite soybean lines are highly related, a relatively small set of elite lines contains most of the favorable alleles that exist within the entire elite population. Therefore, determining the linkage phase between marker and QTL alleles at the loci identified as important for yield can be accomplished to further increase efficiency of MAS in the context of a soybean breeding program. Progeny from parents that are both high yielding and polymorphic for many of the target marker loci are assessed for yield in a small number of field locations. Using orthoganol comparisons, one locus at a time, predictions concerning correlations between marker alleles and phenotype can be made. For example if 40 random homozygous progeny from a cross that is segregating at 10 of the target loci are field tested, on average, 20 of the progeny will be homozygous for one of the parental alleles and 20 will be homozygous for the other parental allele. One can then pool the replicated yield data for lines containing the same marker allele and determine if the yield of said group is statistically different from the yield of lines containing the alternate marker allele. If so, then this marker should be effective for selection within that cross. This comparison is then done separately for each of the 10 segregating marker loci to determine which set of those 10 markers should be effective for selection within that cross.

Optionally, flanking markers can be used to predict which markers are linked in coupling. By comparing the genotype of flanking markers that are linked to the target marker in both elite lines and ancestors, one can predict which haplotypes have been most conserved during selection over many cycles. In the event that recombination has occurred between the target marker and the genetic element contributing to yield, such that the desired genetic element and the linked target marker locus are no longer in coupling linkage phase, flanking markers can be utilized to identify progeny with superior agronomic performance.

In addition, MAS and phenotypic selection can be alternated to insure that the allele in coupling phase is detected. Markers identified by breeding bias are employed for MAS as described above (with or without the advantages of linkage phase determination within specific crosses) and replicated yield testing is performed on selected progeny. If enough replicates and environments are sampled, a reasonable measure of yield phenotype can be obtained. Progeny that are confirmed as high yielding can be used as parents in the next cycle of MAS selection. By screening related populations according to this method, the population will move toward fixation of the favorable QTL alleles even if the favorable marker allele is not always in coupling with the QTL allele. Alternatively, residual polymorphisms at the marker loci described herein can be detected in near iso-genic lines, and the marker allele in corresponding to increased yield can be validated.

Introgression of Favorable Alleles
More Efficient Backcrossing of Specific Genes into Elite Lines One application of MAS, in the context of the present invention is to use the "yield gene" markers to increase the efficiency of a introgression or backcrossing effort. In typical marker assisted backcrossing of a specific gene(s) from a donor source to an elite genetic background, one selects among backcross progeny for the donor trait and then uses markers to reconstitute as much of the elite background's genome as possible. Prior to the present invention, the markers used to identify the elite background were of unknown function, and many of the markers commonly used may be selecting for parts of the elite genome that do not actually contribute to high yield. Similarly, prior to the present invention, the major loci that contribute to yield were largely unknown, so the entire elite genome of the recurrent parent was selected for with the hopes of including all of the favorable alleles that it contained. However, the markers identified by breeding bias can be used to identify only those parts of the elite genome that are most significant with respect to yield. These markers can be used to concentrate backcrossing efforts on the most important parts of the elite genome. The fewer markers needed, the higher the probability of recapturing the elite phenotype quickly.

Thus, the markers and methods of the present invention can be utilized to guide marker assisted selection or breeding of soybean varieties with the desired complement (i.e., set) of allelic forms of chromosome segments associated with superior agronomic performance. Each of the disclosed alleles can be introduced into a soybean line via introgression, i.e., by means of traditional breeding (or introduced via transformation, or both) to yield a soybean plant with superior agronomic performance. The number of alleles associated with superior agronomic performance that can be introduced or be present in a soybean plant of the present invention ranges from 1 to the number of alleles disclosed herein, each integer of which is incorporated herein as if explicitly recited.

Exemplary soybean lines including at least one (and typically several or many) of the favorable allelic forms of the relevant chromosome segments are provided in Table 1. Without intent to limit the invention, these include the elite soybean lines: 90A07, 90B11, 90B31, 90B43, 90B72, 90B73, 91B01, 91B12, 91B33, 91B52, 91B53, 91B64, 91B91, 91B92, 92B05, 92B12, 92B23, 92B38, 92B63, 92B74, 92B75, 92B84, 92B95, 93B01, 93B11, 93B15, 93B25, 93B26, 93B41, 93B45, 93B46, 93B66, 93B67, 93B72, 93B82, 93B84, 93B85, 93B86, 93B87, 94B01, 94B23, 94B24, 94B53, 94B54, 94B73, 95B32, 95B33, 95B34, 95B53, 95B95, 95B96, 95B97, 96B21, 96B51, 97B52, 97B61, A1395, A2835, A2943, A3127, A3242, A3431, A4009, A4138, A4415, A4595, A4715, A5403, A5560, A5843, A5885, A5979, A5980, A6297, BEDFORD, CM428, CX105, CX232, CX253, CX289, CX394C, CX469C, D00566D362, ESSEX, EX04C00, EX06A00, EX10F01, EX13P01, EX13Q01, EX15N01, EX16N00, EX16P01, EX22Y01, EX22Z01, EX39E00, FORREST, G3362, HS93-4118, HUTCHESON, JIM, KORADA, M015733, M0400644-02, M0413735-11-52, M0501577-27-23, M0505469-61-89, MP39009, P1677, P9007, P9008, P9041, P9042, P9061, P9062, P9063, P9071, P9092, P9132, P9141, P9151, P9163, P9182, P9203, P9233, P9244, P9273, P9281, P9305, P9306, P9321, P9341, P9392, P9395, P9481, P9482, P9492, P9521, P9552, P9561, P9584, P9591, P9592, P9594, P9631, P9641, PHARAOH, RA451, R01154R002, S0066, S03W4, S0880, S1550, S1990, S19T9, S20F8, S22C3, S24L2, S25J5, S32Z3, S33N1, S38T8, S3911, S4260, S42H1, S43B5, S5960, S6189, S6262, ST0653, ST1073, ST1090, ST1970, ST2250, ST2488, ST2660, ST2688, ST2870, ST3171, ST3380, ST3630, ST3870, ST3883, TRACY, TRAILL, X9916, YB03E00, XB03F01, XB07E01, XB10D01, XB15M01, XB20M01, XB22R01, XB25W01, XB31C01, XB33B, XB34F01, XB35D, XB35W00, XB38A01, XB41M01, X842.100, XB42M01, XB48H01, XB54K01, XB55J01, XB58P99, XB63D00, XB67A00, YB03G01, YB08D01, YB09F01, YB09G01, YB10E01, YB11D01, YB14H01, YB15K99, YB21F01, YB21G01, YB22S00, YB22V01, YB22W01, YB22×01, YB24Z01, YB25R99, YB25×00, YB25Y01, YB25Z01, YB27×01, YB27Y01, YB28N01, YB29H01, YB29J01, YB30J01, YB30N01, YB30P01, YB31E01, YB32K01, YB33K01, YB34H01, YB35C01, YB36V00, YB39M01, YB40M01, YB40N01, YB41Q01, YB48L01, YB52J00, YB53E00, YB54H00, YB54J00, YB54L00, YB55H00, YB56E00, YB60N01, and YOUNG. These lines and progeny derived therefrom, as well as numerous additional elite lines, are conveniently utilized as breeding material to develop novel lines with increased numbers of favorable allelic forms of chromosome segments involved in yield.

The present invention also extends to a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for the alleles associated with superior agronomic performance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant of the present invention in that it comprises at least one of the allelic forms of the present invention such that the progeny are capable of inheriting the allele. Conveniently, the first or second soybean plant line can be one of the elite lines of Table 1, or a derivative of such a line (i.e., a descendant or progenitor in that line's pedigree), or any relative of these elite lines (such as any elite line that was derived from the ancestors of these elite lines) that retains the same allelic form as that associated with superior agronomic performance. However, it will readily be recognized by one of skill in the art that following characterization essentially any elite line of soybean can be utilized.

Often, a method of the present invention is applied to at least one related soybean plant such as from progenitor or descendant lines in the subject soybean plants pedigree such that inheritance of the desired allele can be traced. The number of generations separating the soybean plants being subject to the method of the present invention will generally be from 1 to 20, commonly 1 to 5, and typically 1, 2, or 3 generations of separation, and quite often a direct descendant or parent of the soybean plant will be subject to the method (i.e., 1 generation of separation).

Incorporation of "Exotic" Germplasm while Maintaining Historical Progress

Genetic diversity is important for long term genetic gain in any breeding program. With limited diversity, genetic gain will eventually plateau when all of the favorable alleles have been fixed within the elite population. The challenge is to incorporate diversity into the elite pool without losing the genetic gain that has already been made and with the minimum possible investment. Breeding bias results provide an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers of the present invention can be used for MAS in crosses involving elite x exotic soybean lines by subjecting the segregating progeny to MAS to maintain the major yield alleles that have already been "fixed" by decades of selection and leave the rest of the genome open for contribution from the exotic sources. This would be a much more efficient system than conventional selection or MAS selection of elite alleles for which we have no prior information.

If the donor parent has polymorphic alleles at the elite target loci as well, the breeder can also relax the backcrossing selection intensity to allow variation at these loci to slip through. This provides the opportunity to see if an exotic line has something even more favorable than what was in the elite gene pool at the elite target loci.

The methods of the present invention also address another limitation of conventional backcrossing: that is, as the recurrent parent is reconstituted with increased cycles of backcrossing, potentially favorable alleles from the donor parent are excluded along with the unfavorable alleles from the donor parent. By selectively reconstituting the recurrent parent's genotype at the loci that have been shown by breeding bias to be important, one allows favorable alleles to be introduced from the donor parent at other loci. This allows for the donor parent to contribute exotic favorable alleles at loci that are not part of the elite "target genotype." This increases the chances of transgressive segregation while still retaining the most critical parts of the recurrent parent's genome. If the donor parent has polymorphic alleles at the elite target loci as well, the breeder can also relax the backcrossing selection intensity to allow variation at these loci to slip through and be tested in the context of a genome that is representative of the elite gene pool.

Detection of Marker Loci

Tables 3 through 12 provide a set of markers and favorable alleles associated with superior agronomic performance in a variety of geographic regions with a range of different growing environments. Each of the markers identifies a chromosome segment that includes one or more genetic elements, i.e., genes, that influences yield in soybeans. One of skill in the art will appreciate that the markers provided and discussed herein are merely exemplary and that numerous other linked markers can be identified based on genetic linkage and/or physical proximity on a chromosome to the markers provided herein. Thus, the compositions and methods of the present invention described herein are not intended to be limited only to the markers provided in Tables 3 through 12, but also include additional markers linked thereto. Additionally, while favorable alleles of the exemplary marker loci are disclosed herein, it will be readily appreciated by those of skill in the art, that favorable alleles of additional loci linked to the marker loci described herein can be determined without undue experimentation and employed in the compositions and methods of the present invention. Accordingly, any marker locus linked to the markers described herein, and localized to a chromosome segment identified by the markers of the invention, can also be used to identify that chromosome segment, and to define the genotype of a soybean plant, or to select for favorable allelic forms of a chromosome segment correlated with superior agronomic performance.

Although the specific DNA sequences which encode proteins are generally well-conserved across a species, regions of DNA which are non-coding, or which encode proteins or portions of proteins which lack critical function, tend to accumulate mutations, and therefore, are variable between members of the same species. Such regions provide the basis for numerous molecular genetic markers. Markers identify alterations in the genome, which can be insertions, deletions, point mutations, recombination events, or the presence and sequence of transposable elements. Many molecular or genetic markers have been characterized in plant species of interest, including soybean, and are known to those of skill in the art. For example, a collection of genetic markers for soybean is publicly available from Linkage Genetics (151 West 2200 South, Suite C, Salt Lake City, Utah 84119, 801-975-1188).

Molecular markers can be detected by numerous methods, well-established in the art (e.g., allele specific hybridization (ASH) or other methods for detecting single nucleotide polymorphisms (SNP), amplified fragment length polymorphisms (AFLP), amplified variable sequences, randomly amplified polymorphic DNA (RAPD), restriction fragment length polymorphisms (RFLP), self-sustained sequence replication, simple sequence repeat (SSR), single-strand conformation polymorphisms (SSCP), and isozyme markers). While the exemplary markers provided in Tables 3 through 12 are either SSR or SNP (ASH) markers, any of the aforementioned marker types can be employed in the context of the invention to identify chromosome segments encompassing genetic element that contribute to superior agronomic performance.

The majority of genetic markers rely on one or more property of nucleic acids for their detection. For example, some techniques for detecting genetic markers utilize hybridization of a probe nucleic acid to nucleic acids corresponding to the genetic marker. Hybridization formats including but not limited to, solution phase, solid phase, mixed phase, or in situ hybridization assays. Among the earliest markers detected, restriction fragment length polymorphisms (RFLP), are detected by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, well known in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Detectable labels suitable for use with nucleic acid probes include any composition detectable by spectroscopic, radioisotopic, photochemical, biochemical, immunochemical, electrical, optical or chemical means. Useful labels include biotin for staining with labeled streptavidin conjugate, magnetic beads, fluorescent dyes, radiolabels, enzymes, and colorimetric labels. Other labels include ligands that bind to antibodies labeled with fluorophores, chemiluminescent agents, and enzymes. Labeling markers is readily achieved such as by the use of labeled PCR primers to marker loci.

The hybridized probe is then detected using, most typically by autoradiography or other similar detection technique (e.g., fluorography, liquid scintillation counter, etc.). Examples of specific hybridization protocols are widely available in the art, see, e.g., Berger, Sambrook, Ausubel, cited in the section entitled "GENERAL MOLECULAR BIOLOGY REFERENCES."

More specifically with respect to certain of the exemplary markers of the present invention, Allele-specific hybridization (ASH) technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides of markers comprising a single nucleotide polymorphism (SNP). Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described in U.S. Pat. No. 5,468,613, which is incorporated by reference herein in its entirety for all purposes, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Other of the exemplary molecular markers provided herein are Simple sequence repeats (SSR). SSR markers take advantage of high levels of di-, tri-, or tetra-nucleotide tandem repeats within a genome. Dinucleotide repeats have been reported to occur in the human genome as many as 50,000 times with n varying from 10 to 60 or more (Jacob et al. (1991) Cell 67:213. Dinucleotide repeats have also been found in higher plants (Condit and Hubbell (1991) Genome 34:66).

Briefly, SSR data is generated by hybridizing primers to conserved regions of the plant genome which flank the SSR sequence. PCR is then used to amplify the dinucleotide repeats between the primers. The amplified sequences are then electorphoresed to determine the size and therefore the number of di-, tri-, and tetra-nucleotide repeats.

Amplified variable sequences refer to amplified sequences of the plant genome which exhibit high nucleic acid residue variability between members of the same species, e.g., microsatellite sequences. All organisms have variable genomic sequences and each organism (with the exception of a clone) has a different set of variable sequences. Once identified, the presence of specific variable sequences can be used to predict phenotypic traits. Preferably, DNA from the plant serves as a template for amplification with primers that flank a variable sequence of DNA. The variable sequence is amplified and then sequenced.

Randomly amplified polymorphic DNA (RAPD) markers are genomic sequences amplified by PCR using a single short primer of arbitrary sequence at low stringency. During amplification at low stringency a number of PCR products, some of which differ in length (and sequence) between individuals, are generated from random locations throughout the genome. Unlike amplified variable sequences, no prior sequence information is required to identify RAPD markers.

In vitro amplification techniques are well known in the art. Examples of techniques sufficient to direct persons of skill through such in vitro methods, including the polymerase chain reaction (PCR), the ligase chain reaction (LCR), Qβ-replicase amplification and other RNA polymerase mediated techniques (e.g., NASBA), are found in Berger, Sambrook and Ausubel as well as Mullis et al. (1987) U.S. Pat. No. 4,683,202, which is incorporated by reference herein in its entirety for all purposes; *PCR Protocols, A Guide to Methods and Applications* (Innis et al., eds.) Academic Press Inc., San Diego Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci.* USA 86, 1173; Guatelli et al. (1990) *Proc. Nat!. Acad. Sci.* USA 87, 1874; Lomeli et al. (1989) *J. Clin. Chem.* 35, 1826; Landegren et al., (1988) Science 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039, which is incorporated by reference herein in its entirety for all purposes. Improved methods of amplifying large nucleic acids by PCR are summarized in Cheng et al. (1994)*Nature* 369: 684, and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger.

Oligonucleotides for use as primers, e.g., in amplification reactions and for use as nucleic acid sequence probes are typically synthesized chemically according to the solid phase phosphoramidite triester method described by Beaucage and Caruthers (1981) *Tetrahedron Lett.* 22:1859, or can simply be ordered commercially.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) Rnase H, and (3) a DNA-dependent RNA polymerase (Guatelli et al. (1990) Proc Natl Acad Sci USA 87:1874). By mimicking the retroviral strategy of RNA replication by means of cDNA intermediates, this reaction accumulates cDNA and RNA copies of the original target.

Amplified restriction fragment polymorphisms or amplified fragment length polymorphisms (AFLP) can also be used as genetic markers (Vos et al. (1995) *Nucl Acids Res* 23:4407. The phrase "amplified restriction fragment polymorphism" refers to selected restriction fragments, which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) *Mol Gen Genet* 249:65; and Meksem et al. (1995) *Mol Gen Genet* 249:74.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. In such cases the marker may also be referred to as a single-strand conformation polymorphism or SSCP. However, alternative modes of detection, such as hybridization, e.g., ASH, or RFLP analysis are not excluded.

Alternatively, isozyme markers are employed as genetic markers. Isozymes are multiple forms of enzymes that differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes that differ at the nucleic acid level can be determined. In such cases any of the nucleic acid based methods described herein can be used to analyze isozyme markers.

In alternative embodiments, in silica methods can be used to detect the marker loci. For example, the sequence of a nucleic acid comprising the marker can be stored in a computer. The desired marker locus sequence or its homolog can be identified using an appropriate nucleic acid search algorithm as provided by, for example, in such readily available programs as BLAST.

Integrated Systems/Computer Assisted Methods

In some embodiments, the present invention includes an "integrated system" including an electronic means of storing or transmitting computer readable data representing or designating the allelic forms determined by the method of the present invention. The computer readable media includes cache, main, and storage memory and other electronic data storage means for storage of computer code. Data representing the allelic forms determined by the method of the present invention can also be electronically transmitted in a computer data signal embodied in a transmission medium over a network such as an intranet or interact or combinations thereof.

The phrase "integrated system" in the context of this invention refers to a system in which data entering a computer corresponds to physical objects or processes external to the computer, e.g., a marker allele, and a process that, within a computer, causes a physical transformation of the input signals to different output signals. In other words, the input data, e.g., amplification of a particular marker allele is transformed to output data, e.g., the identification of the allelic form of a chromosome segment. The process within the computer is a set of instructions, or "program," by which positive amplification or hybridization signals are recognized by the integrated system and attributed to individual samples as a genotype. Additional programs correlate the identity of individual samples with phenotypic values or marker alleles, e.g., statistical methods. In addition there are numerous e.g., C/C++ programs for computing, Delphi and/or Java programs for GUI interfaces, and productivity tools (e.g., Microsoft Excel and/or SigmaPlot) for charting. Other useful software tools in the context of the integrated systems of the invention include statistical packages such as SAS, Genstat, Matlab, Mathematica, and S-Plus and genetic modeling packages such as QU-GENE. Furthermore additional programming languages such as Fortran and the like are also suitably employed in the integrated systems of the invention.

For example, marker allele values assigned to a population of progeny descending from crosses between elite lines are recorded in a computer readable medium, thereby establishing a database corresponding allelic forms with unique identifiers for each member of the population of progeny. Any file or folder, whether custom-made or commercially available (e.g., from Oracle or Sybase) suitable for recording data in a computer readable medium is acceptable as a database in the context of the present invention. Data regarding genotype for one or more molecular markers, e.g., ASH, SSR, RFLP, RAPD, AFLP, SNP, isozyme markers or other markers as described herein, are similarly recorded in a computer accessible database. Optionally, marker data is obtained using an integrated system that automates one or more aspects of the assay (or assays) used to determine marker(s) genotype. In such a system, input data corresponding to genotypes for molecular markers are relayed from a device, e.g., an array, a scanner, a CCD, or other detection device directly to files in a computer readable medium accessible to the central processing unit. A set of instructions (embodied in one or more programs) encoding the statistical models of the invention is then executed by the computational device to identify correlations between yield data and marker genotypes. Typically, the integrated system also includes a user input device, such as a keyboard, a mouse, a touchscreen, or the like, for, e.g., selecting files, retrieving data, etc., and an output device (e.g., a monitor, a printer, etc.) for viewing or recovering the product of the statistical analysis.

Thus, in one aspect, the invention provides an integrated system comprising a computer or computer readable medium comprising set of files and/or a database with at least one data set that corresponds to genotypes for genetic markers. The system also includes a user interface allowing a user to selectively view one or more databases. In addition, standard text manipulation software such as word processing software (e.g., MICROSOFT® Word or COREL® WORDPERFECT®) and database or spreadsheet software (e.g., spreadsheet software such as MICROSOFT EXCEL™, COREL® QUATTRO PRO®, or database programs such as MICROSOFT® ACCESS® or PARADOX®) can be used in conjunction with a user interface (e.g., a GUI in a standard operating system such as a WINDOWS®, MACINTOSH®, Unix or Linux system) to manipulate strings of characters.

The invention also provides integrated systems for sample manipulation incorporating robotic devices as previously described. A robotic liquid control armature for transferring solutions (e.g., plant cell extracts) from a source to a destination, e.g., from a microtiter plate to an array substrate, is optionally operably linked to the digital computer (or to an additional computer in the integrated system). An input device for entering data to the digital computer to control high throughput liquid transfer by the robotic liquid control armature and, optionally, to control transfer by the armature to the solid support is commonly a feature of the integrated system.

Integrated systems for molecular marker analysis of the present invention typically include a digital computer with one or more of high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled probes hybridized, e.g., to expression products on a solid support operably linked to the digital computer. The image scanner interfaces with the image analysis software to provide a measurement of, e.g., differentiating nucleic acid probe label intensity upon hybridization to an arrayed sample nucleic acid population, where the probe label intensity measurement is interpreted by the data interpretation software to show whether, and to what degree, the labeled probe hybridizes to a label. The data so derived is then correlated with sample identity, to determine the identity of a plant with a particular genotype(s) for genetic markers, e.g., to facilitate marker assisted selection of soybean plants with favorable allelic forms of chromosome segments involved in agronomic performance.

Optical images, e.g., hybridization patterns viewed (and, optionally, recorded) by a camera or other recording device (e.g., a photodiode and data storage device) are optionally further processed in any of the embodiments herein, e.g., by digitizing the image and/or storing and analyzing the image on a computer. A variety of commercially available peripheral equipment and software is available for digitizing, storing and analyzing a digitized video or digitized optical image, e.g., using PC (INTEL®x86 or PENTIUM® chip-compatible MS-DOS®, OS2™, WINDOWS®, WINDOWS® NT or WINDOWS®95 based machines), MACINTOSH®, LINUX, or UNIX based (e.g., SUN™ work station) computers.

Identification of Additional Markers and QTL Associated with Yield

Nucleic acids isolated from the chromosome segments of the present invention, e.g., nucleic acids corresponding to additional marker loci, nucleic acids corresponding to genetic elements contributing to superior agronomic performance, are within the scope of the present invention. For example, in the rare instance in which the markers and alleles of the present invention are not well suited for MAS, the markers can, nonetheless, be used to identify additional linked markers that are, e.g., closer to, or within, the QTL of interest. Based on the markers disclosed herein, improvement in the efficiency of MAS can be obtained by saturating the relevant chromosome segments with numerous linked markers. The breeding bias analysis can be repeated on all markers within the region to identify those having the highest statistical significance. MAS can be practiced with all markers in the region followed by phenotypic characterization (i.e., of yield) to determine which markers are most efficient.

Additional markers can be identified in a variety of ways. For example, additional markers can be identified by evaluating publicly or privately available markers that have been mapped to the genomic region(s) of interest, including candidate markers known to encode proteins that are, at least theoretically, likely to be related to yield. Alternatively, unmapped markers can be evaluated to determine which markers map to the same genomic region via independent mapping studies.

A theoretically optimal marker can be obtained by isolating genetic elements contributing to superior agronomic performance, such as coding regions giving rise to expression products that influence yield. Identification of a QTL underlying superior agronomic performance can be accomplished by anchoring the marker to a physical DNA map and then progressing upstream and downstream to identify coding sequences, i.e., by "positional gene cloning."

Positional gene cloning uses the physical proximity of a genetic marker (such as a marker provided in Tables 3 through 12) to identify a cloned chromosomal fragment that includes a nucleic acid of interest, e.g., a QTL contributing to superior agronomic performance. Clones of nucleic acids linked to the markers of the invention have a variety of uses, including as additional genetic markers to define the chromosome segments of the invention and for use in marker assisted selection (MAS). Markers which are adjacent to an open reading frame (ORF) can hybridize to a DNA clone, thereby identifying a clone on which an ORE associated with a trait contributing to yield is located. If the marker is more distant, a fragment containing the open reading frame is identified by successive rounds of screening and isolation of clones which together comprise a contiguous sequence of DNA, a "contig." Protocols sufficient to guide one of skill through the isolation of clones associated with linked markers are found in, e.g., in the references cited in the section entitled "GENERAL MOLECULAR BIOLOGY REFERENCES" below.

An isolated chromosome fragment can be produced by such well known methods as digesting chromosomal DNA with one or more restriction enzymes, or by amplifying a chromosomal region in a polymerase chain reaction (PCR), or alternative amplification reaction. The digested or amplified fragment is typically ligated into a vector suitable for replication, e.g., a plasmid, a cosmid, a phage, an artificial chromosome, or the like, and, optionally expression, of the inserted fragment.

Such chromosome segments can be utilized to identify homologous nucleic acids, e.g., in other lines or species, and/or can be used in the production of transgenic plants with desirable phenotypic attributes related to agronomic performance. A chromosome segment comprising a nucleic acid contributing to increased yield is isolated, e.g., cloned via positional cloning methods outlined above. A chromosome segment can contain one or more ORFs associated with the desired phenotypic trait, and can be cloned on one or more individual vectors, e.g., depending on the size of the chromosome interval.

It will be appreciated that numerous vectors are available in the art for the isolation and replication of the nucleic acids of the invention. For example, plasmids, cosmids and phage vectors are well known in the art, and are sufficient for many applications (e.g., in applications involving insertion of nucleic acids ranging from less than 1 to about 20 kilobases (kb). In certain applications, it is advantageous to make or clone large nucleic acids to identify nucleic acids more distantly linked to a given marker, or to isolate nucleic acids in excess of 10-20 kb, e.g., up to several hundred kilobases or more, such as the entire interval between two linked markers, i.e., up to and including one or more centimorgans (CM), linked to markers as identified herein. In such cases, a number of vectors capable of accommodating large nucleic acids are available in the art, these include, yeast artificial chromosomes (YACs), bacterial artificial chromosomes (BACs), plant artificial chromosomes (PACs) and the like. For a general introduction to YACs, BACs, PACs and MACs as artificial chromosomes, see, e.g., Monaco and Larin (1994) *Trends Biotechnol* 12:280. In addition, methods for the in vitro amplification of large nucleic acids linked to genetic markers are widely available (e.g., Cheng et al. (1994) *Nature* 369: 684, and references therein). Cloning systems can be created or obtained from commercially; see, for example, Stratagene (La Jolla, Calif.).

Vectors, Promoters and Expression Systems

The present invention includes recombinant constructs incorporating one or more of the nucleic acid sequences described above. Such constructs include a vector, for example, a plasmid, a cosmid, a phage, a virus, a bacterial artificial chromosome (BAC), a yeast artificial chromosome (YAC), etc., into which one or more polynucleotide sequences of interest (e.g., a marker or genetic element contributing to yield) has been inserted, in a forward or reverse orientation. For example, the inserted nucleic acid can include a chromosomal sequence or cDNA including a all or part of at least one genetic element or open reading frame ("ORF") associated with yield. In a preferred embodiment, the construct further comprises regulatory sequences, including, for example, a promoter, operably linked to the sequence. Large numbers of suitable vectors and promoters are known to those of skill in the art, and are commercially available.

As desired, the polynucleotides of the present invention, e.g., a genetic element contributing to superior agronomic performance identified according to the methods described herein, can be included in any one of a variety of vectors suitable for generating sense or antisense RNA, and optionally, polypeptide expression products. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that is capable of introducing genetic material into a cell, and, if replication is desired, which is replicable in the relevant host can be used.

In an expression vector or expression cassette, the polynucleotide sequence of interest is physically arranged in proximity and orientation to an appropriate transcription control sequence (promoter, and optionally, one or more enhancers) to direct mRNA synthesis. That is, the polynucleotide sequence of interest is "operably linked" to an appropriate transcription control sequence. Examples of such promoters include: LTR or SV40 promoter, *E. coli* lac or trp promoter, phage lambda $P_L$ promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

Additional Expression Elements

Where translation of polypeptide encoded by a nucleic acid comprising a polynucleotide sequence of the invention is desired, additional translation specific initiation signals can improve the efficiency of translation. These signals can include, e.g., an ATG initiation codon and adjacent sequences. In some cases, for example, full-length cDNA molecules or chromosomal segments including a coding sequence incorporating, e.g., a QTL or an ORF associated with a QTL or QTL marker, a translation initiation codon and associated sequence elements are inserted into the appropriate expression vector simultaneously with the polynucleotide sequence of interest. In such cases, additional translational control signals frequently are not required. However, in cases where only a polypeptide coding sequence, or a portion thereof, is inserted, exogenous translational control signals, including an ATG initiation codon must be provided. Furthermore, the initiation codon must be in the correct reading frame to ensure transcription of the polynucleotide sequence of interest. Exogenous transcriptional elements and initiation codons can be of various origins, both natural and synthetic. The efficiency of expression can be enhanced by the inclusion of enhancers appropriate to the cell system in use (Scharf D et al. (1994) *Results Probl Cell Differ* 20:125-62; Bittner et al. (1987) *Methods in Enzymol* 153:516-544).

Generation of Transgenic Plants and Cells

The present invention also relates to host cells and organisms which are transformed with nucleic acids corresponding to genetic elements contributing to superior agronomic performance and other genes identified according to the methods of the invention. For example, such nucleic acids include chromosome segments, ORFs, and/or cDNAs or corresponding to a sequence or subsequence included within the identified chromosome segment or ORF. Additionally, the invention provides for the production of polypeptides corresponding to such genetic elements by recombinant nucleic acid (and expression) techniques. Host cells are genetically engineered (i.e., transduced, transfected or transformed) with the vectors of this invention (i.e., vectors incorporating genetic elements contributing to increased yield, or other nucleic acids identified according to the methods of the invention and as described above) which are, for example, a cloning vector or an expression vector. Such vectors include, in addition to those described above, e.g., an *agrobacterium*, a virus (such as a plant virus), a naked polynucleotide, or a conjugated polynucleotide. The vectors are introduced into plant tissues, cultured plant cells or plant protoplasts by a variety of standard methods including electroporation (From et al. (1985) *Proc. Natl. Acad. Sci. USA* 82; 5824), infection by viral vectors such as cauliflower mosaic virus (CaMV) (Hohn et al. (1982) *Molecular Biology of Plant Tumors* (Academic Press, New York, pp. 549-560; Howell U.S. Pat. No. 4,407,956), high velocity ballistic penetration by small particles with the nucleic acid either within the matrix of small beads or particles, or on the surface (Klein et al. (1987) *Nature* 327; 70), use of pollen as vector (WO 85/01856), or use of *Agrobacterium tumefaciens* or *A. rhizogenes* carrying a T-DNA plasmid in which DNA fragments are cloned. The T-DNA plasmid is transmitted to plant cells upon infection by *Agrobacterium tumefaciens*, and a portion is stably integrated into the plant genome (Horsch et al. (1984) *Science* 233; 496; Fraley et al. (1983) *Proc. Natl. Acad. Sci. USA* 80; 4803). The method of introducing a nucleic acid of the present invention into a host cell is not critical to the instant invention. Thus, any method, e.g., including but not limited to the above examples, which provides for effective introduction of a nucleic acid into a cell or protoplast can be employed.

The engineered host cells can be cultured in conventional nutrient media modified as appropriate for such activities as, for example, activating promoters or selecting transformants. These cells can optionally be cultured into transgenic plants. Plant regeneration from cultured protoplasts is described in Evans et al. (1983) "Protoplast Isolation and Culture," *Handbook of Plant Cell Cultures* 1, 124-176 (MacMillan Publishing Co., New York; Davey (1983) "Recent Developments in the Culture and Regeneration of Plant Protoplasts," *Protoplasts*, pp. 12-29, (Birkhauser, Basel); Dale (1983) "Protoplast Culture and Plant Regeneration of Cereals and Other Recalcitrant Crops," *Protoplasts* pp. 31-41, (Birkhauser, Basel); Binding (1985) "Regeneration of Plants," *Plant Protoplasts*, pp. 21-73, (CRC Press, Boca Raton,).

The present invention also relates to the production of transgenic organisms, which may be bacteria, yeast, fungi, or plants, transduced with the nucleic acids, e.g., cloned QTL of the invention. A thorough discussion of techniques relevant to bacteria, unicellular eukaryotes and cell culture may be found in references enumerated above and are briefly outlined as follows. Several well-known methods of introducing target nucleic acids into bacterial cells are available, any of which may be used in the present invention. These include: fusion of the recipient cells with bacterial protoplasts containing the DNA, treatment of the cells with liposomes containing the DNA, electroporation, projectile bombardment (biolistics), carbon fiber delivery, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, numerous kits are commercially available and can be employed according to the manufacturers instructions for the purification of plasmids from bacteria (and other cells). For their proper use, follow the manufacturer's instructions (see, for example, EASYPREP™, FLEXIPREP®, both from Pharmacia Biotech; STRATACLEAN®, from Stratagene; and, QIAPREP® from Qiagen). The isolated and purified plasmids are then further manipulated to produce other plasmids, used to transfect plant cells or incorporated into *Agrobacterium tumefaciens* related vectors to infect plants. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or preferably both. See, Gillman & Smith (1979) Gene 8:81; Roberts et al. (1987) *Nature* 328:731; Schneider et al. (1995) *Protein Expr. Purif* 6435; 10; Ausubel, Sambrook, Berger (all supra). A catalogue of Bacteria and Bacteriophages useful for cloning is provided, e.g., by the ATCC, e.g., *The ATCC Catalogue of Bacteria and Bacteriophage* (1992) Gherna et al. (eds) published by the ATCC. Additional basic procedures for sequencing, cloning and other aspects of molecular biology and underlying theoretical considerations are also found in Watson at al. (1992). *Recombinant DNA*, Second Edition, Scientific American Books, NY.

Transforming Nucleic Acids into Plants.

Embodiments of the present invention pertain to the production of transgenic plants comprising the cloned nucleic acids, e.g., chromosome segments, isolated ORFs, and cDNAs associated with genetic elements identified by their proximity to the markers of the invention. Techniques for transforming plant cells with nucleic acids are generally available and can be adapted to the invention by the use of nucleic acids encoding or corresponding to chromosome segments, subsequences, e.g., ORFs, and the like. In addition to Berger, Ausubel and Sambrook (infra), useful general references for plant cell cloning, culture and regeneration include Jones (ed) (1995) *Plant Gene Transfer and Expression Protocols—Methods in Molecular Biology, Volume* 49 Humana Press Towata N.J.; Payne et al. (1992) *Plant Cell and Tissue Culture in Liquid Systems* John Wiley & Sons, Inc. New York, N.Y. (Payne); and Gamborg and Phillips (eds) (1995) *Plant Cell, Tissue and Organ Culture; Fundamental Methods* Springer Lab Manual, Springer-Verlag (Berlin Heidelberg New York) (Gamborg). A variety of cell culture media are described in Atlas and Parks (eds) *The Handbook of Microbiological Media* (1993) CRC Press, Boca Raton, Fla. (Atlas). Additional information for plant cell culture is found in available commercial literature such as the *Life Science Research Cell Culture Catalogue* (1998) from Sigma-Aldrich, Inc (St Louis, Mo.) (Sigma-LSRCCC) and, e.g., the *Plant Culture Catalogue* and supplement (1997) also from Sigma-Aldrich, Inc (St. Louis, Mo.) (Sigma-PCCS). Additional details regarding plant cell culture are found in Croy, (ed.) (1993) *Plant Molecular Biology* Bios Scientific Publishers, Oxford, U.K.

The nucleic acid constructs of the invention, e.g., plasmids, cosmids, artificial chromosomes, DNA and RNA polynucleotides, are introduced into plant cells, either in culture or in the organs of a plant by a variety of conventional techniques. Where the sequence is expressed, the sequence is optionally combined with transcriptional and translational initiation regulatory sequences which direct the transcription or translation of the sequence from the exogenous DNA in the intended tissues of the transformed plant.

Isolated nucleic acids can be introduced into plants according to any of a variety of techniques known in the art. Techniques for transforming a wide variety of higher plant species are well known and described in the technical, scientific, and patent literature. See, for example, Weising et al. (1988) *Ann. Rev. Genet.* 22:421-477.

For example plasmids, cosmids, phage, naked or variously conjugated-DNA polynucleotides, (e.g., polylysine-conjugated DNA, peptide-conjugated DNA, liposome-conjugated DNA, etc.), or artificial chromosomes, can be introduced directly into the genomic DNA of the plant cell using techniques such as electroporation and microinjection of plant cell protoplasts, or the DNA constructs can be introduced directly to plant cells using ballistic methods, such as DNA particle bombardment.

Microinjection techniques for injecting e.g., cells, embryos, callus and protoplasts, are known in the art and well described in the scientific and patent literature. For example, a number of methods are described in Jones (ed) (1995) *Plant Gene Transfer and Expression Protocols—Methods in Molecular Biology, Volume* 49 Humana Press Towata N.J., as well as in the other references noted herein and available in the literature.

For example, the introduction of DNA constructs using polyethylene glycol precipitation is described in Paszkowski, et al., EMBO J. 3:2717 (1984). Electroporation techniques are described in Fromm, et al., *Proc. Nat'l. Acad. Sci.* USA 82:5824 (1985). Ballistic transformation techniques are described in Klein, et al., *Nature* 327:70-73 (1987). Additional details are found in Jones (1995) and Gamborg and Phillips (1995), *supra*, and in U.S. Pat. No. 5,990,387, which is incorporated by reference herein in its entirety for all purposes.

Alternatively, and in some cases preferably, *Agrobacterium* mediated transformation is employed to generate transgenic plants. *Agrobacterium*-mediated transformation techniques, including disarming and use of binary vectors, are also well described in the scientific literature. See, for example Horsch, et al. (1984) *Science* 233:496; and Fraley et al. (1984) *Proc. Nat'l. Acad. Sci.* USA 80:4803 and recently reviewed in Hansen and Chilton (1998) *Current Topics in Microbiology* 240:22 and Das (1998) *Subcellular Biochemistry* 29: *Plant Microbe Interactions* pp 343-363.

The DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616, which is incorporated by reference herein in its entirety for all purposes. Although *Agrobacterium* is useful primarily in dicots, certain monocots can be transformed by *Agrobacterium*. For instance, *Agrobacterium* transformation of maize is described in U.S. Pat. No. 5,550,318, which is incorporated by reference herein in its entirety for all purposes.

Other methods of transfection or transformation include (I) *Agrobacterium rhizogenes*-mediated transformation (see, e.g., Lichtenstein and Fuller (1987) In: *Genetic Engineering*, vol. 6, P W J Rigby, Ed., London, Academic Press; and Lichtenstein; C. P., and Draper (1985) In: *DNA Cloning*, Vol. II, D. M. Glover, Ed., Oxford, IRI Press; WO 88/02405, published Apr. 7, 1988, describes the use of *A. rhizogenes* strain A4 and its Ri plasmid along with *A. tumefaciens* vectors pARC8 or pARC16 (2) liposome-mediated DNA uptake (see, e.g., Freeman et al. (1984) *Plant Cell Physiol.* 25:1353), (3) the vortexing method (see, e.g., Kindle (1990) *Proc. Natl. Acad. Sci.*, (*USA*) 87:1228.

DNA can also be introduced into plants by direct DNA transfer into pollen as described by Zhou et al. (1983) *Methods in Enzymology*, 101:433; D. Hess (1987) *Intern Rev. Cytol.* 107:367; Luo et al. (1988) *Plant Mol. Biol. Reporter* 6:165. Expression of polypeptide coding genes can be obtained by injection of the DNA into reproductive organs of a plant as described by Pena et al. (1987) *Nature* 325:274. DNA can also be injected directly into the cells of immature embryos and the desiccated embryos rehydrated as described by Neuhaus et al. (1987) *Theor. Appl. Genet.* 75:30; and Benbrook et al. (1986) in *Proceedings Bio Expo* Butterworth, Stoneham, Mass., pp. 27-54. Additionally, a variety of plant viruses that can be employed as vectors are known in the art and include cauliflower mosaic virus (CaMV), geminivirus, brome mosaic virus, and tobacco mosaic virus.

Regeneration of Transgenic Plants

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al. (1983) *Protoplasts Isolation and Culture, Handbook of Plant Cell Culture* pp. 124-176, Macmillian Publishing Company, New York; and Binding (1985) *Regeneration of Plants, Plant Protoplasts* pp. 21-73, CRC Press, Boca Raton. Regeneration can also be obtained from plant callus, explants, somatic embryos (Dandekar et al. (1989) *J. Tissue Cult. Meth.* 12:145; McGranahan, et al. (1990) *Plant Cell Rep.* 8:512) organs, or parts thereof. Such regeneration techniques are described generally in Klee et al. (1987)., *Ann. Rev. of Plant Phys.* 38:467-486. Additional details are found in Payne (1992) and Jones (1995), both supra, and Weissbach and Weissbach, eds. (1988) *Methods for Plant Molecular Biology* Academic Press, Inc., San Diego, Calif. This regeneration and growth process includes the steps of selection of transformant cells and shoots, rooting the transformant shoots and growth of the plantlets in soil. These methods are adapted to the invention to produce transgenic plants bearing QTLs and other genes isolated according to the methods of the invention.

In addition, the regeneration of plants containing the polynucleotide of the present invention and introduced by *Agrobacterium* into cells of leaf explants can be achieved as described by Horsch et al. (1985) *Science* 227:1229-1231. In this procedure, transformants are grown in the presence of a selection agent and in a medium that induces the regeneration of shoots in the plant species being transformed as described by Fraley et al. (1983) *Proc. Natl. Acad. Sci.* (*U.S.A.*) 80:4803. This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

In construction of recombinant expression cassettes of the invention, which include, for example, an ORF associated with a marker or genetic element contributing to yield, a plant promoter fragment is optionally employed which directs expression of a nucleic acid in any or all tissues of a regenerated plant. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers.

Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from native Ti plasmids. See, Herrara-Estrella et al. (1983), *Nature,* 303:209. Viral promoters include the 35S and 19S RNA promoters of cauliflower mosaic virus. See, Odell et al. (1985) *Nature,* 313:810. Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315. Many other promoters are in current use and can be coupled to an exogenous DNA sequence to direct expression of the nucleic acid.

If expression of a polypeptide, including those encoded by QTL or other nucleic acid, is desired, a polyadenylation region at the 3'-end of the coding region is typically included. The polyadenylation region can be derived from the natural gene, from a variety of other plant genes, or from, e.g., T-DNA.

The vector comprising the sequences (e.g., promoters or coding regions) from genes encoding expression products and transgenes of the invention will typically include a nucleic acid subsequence, a marker gene which confers a selectable, or alternatively, a screenable, phenotype on plant cells. For example, the marker may encode biocide tolerance, particularly antibiotic tolerance, such as tolerance to kanamycin, G418, bleomycin, hygromycin, or herbicide tolerance, such as tolerance to chlorosluforon, or phosphinothricin (the active ingredient in the herbicides bialaphos or Basta). See, e.g., Padgette et al. (1996) In: *Herbicide-Resistant Crops* (Duke, ed.), pp 53-84, CRC Lewis Publishers, Boca Raton ("Padgette, 1996"). For example, crop selectivity to specific herbicides can be conferred by engineering genes into crops which encode appropriate herbicide metabolizing enzymes from other organisms, such as microbes. See, Vasil (1996) In: *Herbicide-Resistant Crops* (Duke, ed.), pp 85-91, CRC Lewis Publishers, Boca Raton) ("Vasil", 1996).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed. In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype. Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing a polynucleotide of the present invention can be screened for transmission of the nucleic acid of the present invention by, for example, standard immunoblot and DNA detection techniques. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

General Molecular Biology References

In the context of the invention, e.g., identifying, monitoring and/or cloning molecular markers and/or other loci, nucleic acids and/or proteins are manipulated according to well known molecular biology techniques. Detailed protocols for numerous such procedures are described in, e.g., in Ausubel et al. *Current Protocols in Molecular Biology* (supplemented through 2000) John Wiley & Sons, New York ("Ausubel"); Sambrook et al. *Molecular Cloning—A Laboratory Manual* (2nd Ed.), Vol. 1-3, Cold Spring Harbor Laboratory, Cold Spring Harbor, N.Y., 1989 ("Sambrook"), and Berger and Kimmel *Guide to Molecular Cloning Techniques, Methods in Enzymology* volume 152 Academic Press, Inc., San Diego, Calif. ("Berger").

In addition to the above references, protocols for in vitro amplification techniques, such as the polymerase chain reaction (PCR), the ligase chain reaction (LCR), Qβ-replicase amplification, and other RNA polymerase mediated techniques (e.g., NASBA), useful e.g., for amplifying cDNA probes of the invention, are found in Mullis et al. (1987) U.S. Pat. No. 4,683,202; *PCR Protocols A Guide to Methods and Applications* (Innis et al. eds) Academic Press Inc. San Diego, Calif. (1990) ("Innis"); Arnheim and Levinson (1990) *C&EN* 36; *The Journal Of NIH Research* (1991) 3:81; Kwoh et al. (1989) *Proc Natl Acad Sci USA* 86, 1173; Guatelli et al. (1990) *Proc Natl Acad Sci USA* 87:1874; Lomeli et al. (1989) *J Clin Chem* 35:1826; Landegren et al. (1988) *Science* 241: 1077; Van Brunt (1990) *Biotechnology* 8:291; Wu and Wallace (1989) *Gene* 4: 560; Barringer et al. (1990) *Gene* 89:117, and Sooknanan and Malek (1995) *Biotechnology* 13:563.

Additional methods, useful for cloning nucleic acids in the context of the present invention, include Wallace et al. U.S. Pat. No. 5,426,039. Improved methods of amplifying large nucleic acids by PCR are summarized in Cheng et al. (1994) *Nature* 369:684 and the references therein.

Certain polynucleotides of the invention, e.g., oligonucleotides can be synthesized utilizing various solid-phase strategies involving mononucleotide- and/or trinucleotide-based phosphoramidite coupling chemistry. For example, nucleic acid sequences can be synthesized by the sequential addition of activated monomers and/or trimers to an elongating polynucleotide chain. See e.g., Caruthers, M. H. et al. (1992) *Meth Enzymol* 211:3.

In lieu of synthesizing the desired sequences, essentially any nucleic acid can be custom ordered from any of a variety of commercial sources, such as The Midland Certified Reagent Company, The Great American Gene Company, ExpressGen, Inc., Operon Technologies, Inc., and many others.

Similarly, commercial sources for nucleic acid and protein microarrays are available, and include, e.g., Affymetrix, Santa Clara, Calif.; and Incyte, Palo Alto, Calif.; and Ciphergen Biosciences, Fremont, Calif.

High Throughput Screening

In one aspect of the invention, the determination of genetic marker alleles is performed by high throughput screening. High throughput screening involves providing a library of genetic markers, e.g., SSR primers, ASH primers and probes, RFLPs, AFLPs, isozymes, specific alleles and variable sequences, including SSR, RAPD and the like. Such libraries are then screened against plant genomes to generate a "fingerprint" for each plant under consideration. In some cases a partial fingerprint comprising a sub-portion of the markers is generated in an area of interest. Once the genetic marker alleles of a plant have been identified, the correspondence between one or several of the marker alleles and a desired phenotypic trait is determined through statistical associations based on the methods of this invention.

High throughput screening can be performed in many different formats. Hybridization can take place in a 96-, 324-, or a 1524-well format or in a matrix on a silicon chip or other format.

A number of well-known robotic systems have been developed for high throughput screening, particularly in a 96 well format. These systems include automated work stations like the automated synthesis apparatus developed by Takeda Chemical Industries, LTD. (Osaka, Japan) and many robotic systems utilizing robotic arms (Zymate II, Zymark Corporation, Hopkinton, Mass.; ORCA™, Beckman Coulter, Fullerton Calif.). Any of the above devices are suitable for use with the present invention. The nature and implementation of modifications to these devices (if any) so that they can operate as discussed herein will be apparent to persons skilled in the relevant art.

In addition, high throughput screening systems themselves are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate or membrane in detector(s) appropriate for the assay. These configurable systems provide high throughput and rapid start up as well as a high degree of flexibility and customization. The manufacturers of such systems provide detailed protocols for the use of their products in high throughput applications.

In one variation of the invention, solid phase arrays are adapted for the rapid and specific detection of multiple polymorphic nucleotides. Typically, a nucleic acid probe is linked to a solid support and a target nucleic acid is hybridized to the probe. Either the probe, or the target, or both, can be labeled, typically with a fluorophore. If the target is labeled, hybridization is evaluated by detecting bound fluorescence. If the probe is labeled, hybridization is typically detected by quenching of the label by the bound nucleic acid. If both the probe and the target are labeled, detection of hybridization is typically performed by monitoring a color shift resulting from proximity of the two bound labels.

In one embodiment, an array of probes are synthesized on a solid support. Using chip masking technologies and photoprotective chemistry, it is possible to generate ordered arrays of nucleic acid probes. These arrays, which are known, e.g., as "DNA chips" or as very large scale immobilized polymer arrays (VLSIPS™ arrays) can include millions of defined probe regions on a substrate having an area of about 1 cm$^2$ to several cm$^2$.

In another embodiment, capillary electrophoresis is used to analyze polymorphism. This technique works best when the polymorphism is based on size, for example, SSR and AFLP. This technique is described in detail in U.S. Pat. Nos. 5,534,123 and 5,728,282. Briefly, capillary electrophoresis tubes are filled with the separation matrix. The separation matrix contains hydroxyethyl cellulose, urea and optionally formamide. The SSR and AFLP samples are loaded onto the capillary tube and electrophoresed. Because of the small amount of sample and separation matrix required by capillary electrophoresis, the run times are very short. The molecular sizes and therefore, the number of nucleotides present in the nucleic acid sample is determined by techniques described herein. In a high throughput format, many capillary tubes are placed in a capillary electrophoresis apparatus. The samples are loaded onto the tubes and electrophoresis of the samples is run simultaneously. See, Mathies and Huang, (1992) *Nature* 359:167.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1

Summary of Breeding Bias Data-Favorable Allelic Forms by Geographic Region

Tables 3 through 9 enumerate favorable allelic forms of chromosome segments contributing to superior agronomic performance in different geographic regions and growing environments. * 95% significance level. ** 99% significance level. UM indicates an unmapped locus. Details regarding SSR and ASH markers and alleles are provided in Appendices I through IV. The geographic regions are defined with respect to the following reference points.

Central Region: Central Midwest United States centered around Des Moines, Iowa.

Canada Region Eastern Canada centered around Chatham, Ontario.

North Region Northern Midwest United States centered around Redwood Falls, Minn.

Illinois Region Northern and central Illinois centered around Champaign, Ill.

East Region: Eastern Midwest United States centered around Napoleon, Ohio.

Mid South Region: Mid Southern United States centered around Hamil, Ill.

South Region Southern United States centered around Memphis, Tenn.

Example 2

Favorable Soybean Alleles and "Target Genotype(s)" for Adaptation to Environments Similar to Those Found in Iowa USA (Central Region)

Three separate breeding bias analyses were conducted to identify favorable alleles that have provided adaptation to geographic regions that are typical of Iowa, USA. The first analysis used 41 elite lines as the "elite population" adapted to Iowa, the second analysis included a larger sample of 71 elite lines (Table 1, Central Region) and the third analysis, performed following the 2003 growing season, used 86 elite lines (Table 1, Central Region 2003). In all cases, the elite population was chosen as a representative sample of elite lines that yield well in Iowa and/or are good parents for developing elite lines adapted to Iowa. Each successive analysis was run after more elite line marker data was available and was therefore considered more rigorous. Despite this fact, the results of the first analysis were very similar and demonstrated that the breeding bias method is useful even with smaller datasets. Herein, results of the second (A) and third (B) analyses are reported due to the larger sample size of the elite population.

A computer program described in U.S. Pat. No. 5,437,697 that simulates the flow of alleles from ancestors to elite lines at each marker locus was used to determine what percent of the elite lines would be expected to inherit each marker allele by chance alone. By doing multiple iterations of the simulation process (10,000 iterations in this case), a statistical measure of random result variation was obtained. The average frequency of each allele in the simulated elite population (from the 10,000 iterations) is herein referred to as the "expected frequency" (EXP) of each marker allele. The expected frequency was then compared to the "observed frequency" (OBS) which is simply a count of how many lines within the elite population actually contain a given allele divided by the total number of elite lines examined. By comparing the observed results to the results of the simulation process, one can determine how often the observed results would be expected to occur by chance alone. If the observed results would only be expected 5% of the time or less due to chance (i.e. a LOD score of 1.3 or greater), it is safe to assume that the observed results did not occur by chance alone. In this case, selection for grain yield must have biased selection towards one or more alleles at the locus in question. The allele(s) that occurred at higher frequency than expected were therefore labeled as "favorable alleles" and those occurring at a lower frequency than expected were labeled as "unfavorable alleles." Favorable alleles are those that must have contributed either directly or indirectly to higher grain yield.

The statistically significant results of the Iowa (A) analysis are shown in Table 10. Since only the major ancestors were genotyped in the analysis, occasionally an allele that was detected in the elite population was not always found in the ancestral population. This resulted in an unusually high LOD score since the frequency of the allele in the ancestral population was assumed to be zero. It is also reasonable to assume that a favorable allele should have increased in frequency by some threshold percentage before that allele should be considered generally "favorable" over the wide range of environments encountered by soybean breeders over the past century. For these reasons, an allele with a LOD score of greater than or equal to 1.3 (95% confidence) AND an observed frequency of at least 25% higher than expected was considered to be "favorable" and "significant" from both a practical and statistical view. Alleles with these criteria plus a LOD score of 2.0 or greater (99% confidence), were considered to be "favorable" and "highly significant." Alleles with a LOD scores of greater than 1.3 but that did not increase in frequency by at least 25% over the past century were considered statistically significant but not enough to be considered generally favorable over most environments.

The term "LOD" score refers to the negative inverse log (base 10) probability that the observed frequency of an allele in the elite population could be attributed to chance alone. More specifically, the LOD score is a measure of the number of rounds that the breeding bias simulation generated an allele frequency at least as extreme as that observed in the actual elite population of soybean lines. The formula for a LOD score of a "favorable" allele is: $-1.0 \times \log 10$ (f) where: f=(the number of rounds of simulation where the observed allele frequency in the elite population was greater than that generated by the simulated allele frequency) divided by (the total number of rounds of simulation).

For example, a LOD score of >1.30 is analogous to a probability of <0.05 that the observed allele frequency in the elite population was due to chance alone; a LOD score of >2.00 is analogous to a probability of <0.01 that the observed allele frequency in the elite population was due to chance alone; a LOD score of >3.00 is analogous to a probability of <0.001 that the observed allele frequency in the elite population was due to chance alone; a LOD score of 4.00 is analogous to a probability of 0.0001 that the observed allele frequency in the elite population was due to chance alone. Since only 10,000 rounds of simulation were conducted, the maximum LOD score observed did not go any higher than 4.00.

Based on the Iowa analysis, out of 1540 alleles over 309 genetic marker loci, a total of 94 alleles showed evidence of being favorable by the aforementioned definition: a LOD score of at least 1.30 (95% confidence level) and an increase in allele frequency of at least 25% more than expected by random inheritance. Since some of these favorable alleles are closely linked (i.e., less than 10 CM apart according to independent mapping studies), not all 94 alleles are diagnostic of unique QTL loci. Therefore, the markers were divided into genomic regions with the assumption that markers on the same chromosome that are approximately 10 CM or greater apart are probably diagnostic of different QTL loci.

In addition to listing the favorable alleles that span the genome, Table 10 indicates the favorable allele with the best statistical score and/or the most marker data within each predefined genomic region. The "best" marker allele to use for each region can also be chosen based on which marker works best in the laboratory. In most cases, the marker with the highest LOD score and highest % difference of expected and observed allele frequency was considered to "best" marker in its genomic region. For example, on chromosome C1, there are 4 markers that map to positions 95.8 through 99.0—Satt399, Satt361, P10639A-1, and Satt190. These are all within 10 CM of each other and therefore were assigned to the same genomic region #29. Among these 4 markers, markers Satt399 and Satt190 had the highest possible LOD score of 4.0 when 10,000 iterations of a simulation were done. This means that even after 10,000 iterations were done, there was not even 1 iteration where the simulation produced results more extreme than that observed in the actual elite population. A LOD score of 4.0 is merely the inverse log of the probability (1 in 10,000) that the results obtained at these loci was due to chance alone. From there, one can decide which of these 2 loci would be the best marker to identify the favorable allele in that region. In this case, Satt190 was chosen as the best marker in that region because the results were based on data from 65 as opposed to 61 elite lines. Although a total of 71 elite lines were genotyped for this marker, 6 elite lines had missing data for this locus.

Once a desirable marker is identified and the favorable allele of that marker is determined, selection for that favorable allele in a lab assay can then be used for MAS to identify plants that have the favorable allele. The MAS process can be done at multiple loci simultaneously to select for plants that contain the maximum number of favorable alleles that span the genome. This genome-wide group of favorable alleles upon which selection is based is herein referred to as the "Target Genotype." Table 11 shows the genome-wide Target Genotype for the best locus from each genomic region that meets the criteria of "significant"—i.e. LOD score of at least 1.3 and an increase in allele frequency of at least 25% greater than expected by chance alone. A total of 57 favorable alleles, each representing what was favored by selection in a different genomic region, fit these criteria to make the Target Genotype at LOD1.3 (Table 11, *). If one raises the statistical cutoff to a LOD of 2.0, the Target Genotype focuses in on 30 favorable alleles (Table 11, **). For purposes of MAS, one would want to select for the favorable alleles with the highest statistical significance first. Hence, the logical path for breeding purposes would be to select among segregating progeny for the 30 locus Target Genotype first. Once these loci are fixed for the favorable alleles, the other 27 loci in the 57-locus Target Genotype could be the focus of selection. If resources are unlimited, one could conceivably work with all 57 loci. Loci can also be weighted based on their statistical significance for selection purposes.

Following the 2003 growing season, an additional analysis (13) was performed increasing the number of elite parental lines from 71 to 86, and evaluating an additional 265 SSR markers. The elite lines used in this analysis are given in Table 1.

Significant favorable alleles are given in Table 12. Because more elite lines were used to define the population, and because some previously absent data was obtained for the previously employed markers, some differences in the statistical LOD scores were observed for the markers in Analysis B as compared to prior Analysis A. Almost all of the previously identified markers were confirmed in the expanded analysis, and several new markers in the same genomic regions were found to have higher LOD scores. Accordingly, these new markers are also deemed to be useful in defining the target genotype and identifying and tracking favorable alleles in soybean germplasm.

The Target Genotype is actually a consensus marker genotype that the elite population has been moving towards as the result of selection. Since this genotype is now defined by specific markers and specific favorable alleles, it is possible to practice selection by genotype instead of the inefficient and slow process of selection based on phenotype. The resolution of the consensus genotype is limited only by the genomic coverage provided by the genetic markers that are available for MAS.

Example 3

Status of Favorable Alleles in Soybean Variety A3127

The following example is given to illustrate how the favorable alleles identified in the previous example came together in the most famous transgressive segregant in soybean breeding history. Most new soybean varieties are a small improvement over either of their parents in terms of yield. Yield progress per cycle (5 to 6 years) of breeding is commonly a few percent better than either parent. However, in the early 1980's a variety called A3127 was developed that was much better than either parent (~10% better than either parent). In fact, A3127 is probably one of the few lines that all soybean breeders are familiar with because it was famous for being the highest yielding variety of it's time (early 1980's). Prior to commercialization A3127 proved to be much higher yielding than either of its two parents Williams and Essex. A3127 was so popular, that it became the most frequently used parent in soybean breeding history. Since A3127 is adapted to Iowa, we studied the marker profiles of Williams, Essex, and A3127 at the 30 preferred "yield gene" loci identified for the Iowa geographic zone. We found that Williams and Essex differ at 23 out of 30 of these loci (Table 13). Out of the 23 segregating loci, Williams supplied 13 of the favorable alleles and Essex supplied the other 10 favorable alleles. If these really are the major yield loci, one would expect that A3127 would have significantly more favorable alleles than either parent. Amazingly, A3127 had all 23 favorable alleles. Such a segregant would only be expected to happen by chance in 1 out of >8 million progeny ($0.5^{23}$) unless these loci really are diagnostic of yield and A3127 is truly a unique segregant. The marker genotype of A3127 is therefore consistent with the hypothesis that these 30 marker loci are diagnostic of yield.

Example 4

Segregation for Yield in Near-Isogenic Sublines

Typically, modern soybean varieties originate from a single plant selected from a partially inbred (commonly F3) population that was generated from a controlled mating between genetically different parents. Seed of the new variety is then multiplied by subsequent pooling (or "bulking") of seed from the self-pollinating progeny of the selected F3 plant. For any locus in the original F3 plant that was heterozygous, the resulting inbred variety will eventually become a mixture of the two homozygotes at said locus. For commercial purposes, soybean varieties are purified for obvious visual traits (e.g., flower color, hilum color, maturity, and other visual traits that are highly heritable and controlled by one or a few genes) but often harbor residual genetic variation that is not obvious to the naked eye. Genetic markers can be used to detect loci contributing to that variation that are still segregating within a so-called "pure line." Since the breeding bias analysis identifies which marker loci have been affected by selection for seed yield, these markers are ideal tools to identify genetic differences among plants within the original heterogeneous variety that may translate into seed yield improvement. These markers can be used to separate the original heterogeneous variety into "near-isogenic" sublines that differ at specific genetic loci.

For example, samples of seed from individual self-pollinated progeny selected from the variety are genotyped, and seed sharing a common allele at one or more identified marker loci is pooled to produce a subline. Such sublines are genetically distinct from one another. In "blind" sublining (i.e., sublining unassisted by marker data) there is no guarantee that the generated sublines are genetically distinct. By pooling seed of many plants with a homogenous marker genotype, enough seed for controlled replicate trials can be obtained in one generation. This is preferable to blind sublining in several ways. First, the only way to attempt genetic homogeneity without markers is to pool the seed of a single plant that may or may not be genetically distinct from the seed of other single plants. Second, a single plant can only supply enough seed for a short row yield test in one environment. Therefore, blind sublining requires subsequent generations of seed increase to obtain enough seed for highly replicated yield trials that are necessary for reliable yield comparisons. Third, even if phenotypic differences are observed with blind sublining, no genomic information is gained for future use. By comparing the field performance of such marker-based sublines in controlled experiments, one can determine the phenotypic effect (e.g., with respect to yield) of each allele (and the corresponding genomic region, if the marker is mapped) in a given genetic background. This is particularly useful for traits, such as yield, in which gene-by-gene and gene-by-environment interactions play a substantial role in phenotype. If one subline performs significantly better than the other, the better subline can be multiplied and released as an improved version of the original variety.

Because selection that is based on genotype (e.g., qualitative DNA polymorphism) and then confirmed with a phenotypic difference is more reliable and heritable than selection based on phenotype alone (i.e., blind sublining), the improvement in phenotype in a blind subline is less likely to be heritable, and unlikely to be repeated in subsequent generations. In contrast, marker-based sublining not only provides useful genomic information, but it also improves the heritability and reproducibility of selected traits. Thus, marker-based "sublining" can be a powerful tool for both product development and to determine the phenotypic effect of individual loci in a given genetic background.

In accordance with this method, the genetic markers identified through breeding bias were shown to be effective tools to select within elite lines for residual yield gain. When genotyping elite lines with genetic markers, 8 random plants from each elite line are routinely sampled and bulked. If the elite line is a 50:50 mixture of two homozygotes at a given locus, a random 8-plant sample will detect both alleles >99% of the time. Using this sampling procedure, segregation within commercial soybean lines is detected at an average of about 4% of the marker loci assayed (e.g., when assaying the "best" marker loci for each chromosomal region).

In the following exemplary trial, six elite lines were examined. Two of the elite lines (91B91 and 92M70) were shown to be segregating at two marker loci each while the other 4 elite lines (92B05, 93B01, 93M80, and 93M90) were segregating at one marker locus as indicated in Table 14.

To develop the sublines, leaf tissue from individual plants of each of the above elite lines was genotyped with the marker(s) segregating in the originating line. Progeny seed from individual homozygous plants of the same marker genotype were then pooled to obtain enough seed of each subline to conduct replicated yield trials. The number of plant used to create each sublime is shown in Table 15.

To determine the relative seed yield, sublines derived from the same elite line were planted in a split plot field design at between 5 and 14 locations, treating each location as an individual replication. Locations were chosen to span the soybean growing region of appropriate maturity zone for the lines being tested in the Midwestern United States. Sublines derived from a given elite line were randomly assigned to split plots within each main plot. Each split plot consisted of two 12-foot long rows of a given subline that were spaced 30 inches apart. Seed yield was measured at maturity and converted to bushels per acre (1 bushel-60 pounds).

Significant yield differences between isolines were detected in 3 of the 6 isoline tests. Since the isolines tested above were derived from pooling many plants of similar genotype, one can reasonably assume that the possibility of residual segregation at other independent loci was randomized and not the source of the yield difference between isolines. The magnitude of the significant yield differences (5.4 to 6.2% between sublines or 2.7 to 3.1% better than the original mixed variety) is of similar magnitude as yield improvements that can typically be obtained using much more exhaustive breeding efforts. New soybean varieties developed without the aid of yield gene markers can easily require hundreds to thousands of yield plots to identify a new variety that is 2 or 3% better than it's best parent. This method can be used to identify yield gains of similar magnitude with very limited resources (2 isolines×14 replications=28 plots per test). In addition, by basing selection on a real genetic difference at a locus showing historical breeding bias, the confidence that the yield differences detected are genetically based (as opposed to environmental or experimental error) is substantially increased.

Additionally, these results confirm that the effects of epistasis, gene-by-environment interactions and/or recombination between the marker allele identified by breeding bias and the genetic element underlying yield improvements, while prevalent, do not impair selection of improved soybean varieties, especially if care is taken to identify residual variation and select appropriate sublines. For example, Satt591 was used to select sublines from two different elite lines (93B01 and 93M90). Breeding Bias analysis alone indicated that Satt591 allele 3 was the one favored by breeders over time. In the case of 93B01, allele 3 was the favorable allele since it was the genotype of the better-yielding subline. In contrast, in the case of 93M90, marker allele 1 was the favorable allele.

For example, while the Breeding Bias analysis identifies marker loci linked to genetic elements which have been favorable on most genetic backgrounds in a variety of growing environments, epistatis and other non-additive interactions influence which allele is "favorable" within specific populations, or for particular environments. In addition, disease resistance genes, which contribute to higher relative yield when the disease is prevalent, have been documented to result in lower yield in the absence of disease pressure.

Recombination between a marker locus and the linked genetic element contributing to improved yield can also reduce efficiency of marker assisted. An accepted and proven genetic principle is that the frequency of crossing over between two genetic loci, e.g., a marker locus and a quantitative trait locus, is a function of genetic distance between the two loci. The only way to avoid such phase reversals is to develop "perfect" markers that are diagnostic of the DNA polymorphism that is responsible for the phenotypic difference controlled by the QTL. That is, recombination can only be eliminated by cloning the QTL, and identifying the mutation causally determining the difference in phenotype. Development of perfect markers is possible but is not a trivial exercise. It requires DNA sequencing of the surrounding genomic region and exhaustive sequence-phenotype association to determine conclusively which DNA polymorphism is always associated with the desired phenotype. This is an expensive and time-consuming endeavor, the benefits of which can, in large part, be achieved using the methods and marker loci of the present invention, without the expense and delay of cloning each significant yield QTL associated with a marker locus identified using breeding bias. By periodically confirming marker and phenotype association, using the methods of the present invention, breeders can still reap the benefits of linked (but non-perfect) markers.

Breeding Bias is an effective method for identifying genomic regions that have undergone directional selection. If a marker is close enough (typically within about 10 CM) to an important QTL in a given ancestor, the marker allele originally linked in coupling to the favorable QTL allele will remain in coupling phase for a sufficient period of selection under standard breeding procedures to detect that selection is occurring in the genomic region including the marker. Thus, the marker loci enumerated herein are associated with, and stand as proxies for, QTL contributing to increased yield. Although, with repeated cycles of recombination among members of a given gene pool, genetic crossovers between the marker locus and the QTL will tend to accumulate and eventually result in a state of "linkage equilibrium" between the marker alleles and the QTL, periodic reassessment using the near isogenic subline procedures described herein can insure that selection proceeds for the allele in linkage phase with the desired QTL allele, despite the potential for recombination.

The above subline experiments indicate that marker-based sublining is an effective method for purification and improvement of elite soybean lines. If the number of markers segregating within a given line or population is small, non-additive effects and linkage phase (coupling or repulsion) do not pose a problem, as it is fairly inexpensive to field test all possible recombinants and identify those with the optimal phenotype.

Example 5

Allele Confirmation Using Random Crosses

To increase efficiency of marker assisted selection for improved yield using, e.g., the marker loci enumerated herein, the allele of the marker locus segregating with yield can be confirmed. Following identification of marker loci by Breeding Bias, a limited number of crosses is performed between the highest yielding elite parents for a particular geographic zone or growing environment. Preferably, the parents should be as polymorphic as possible at the identified marker loci. Progeny (F1) from these elite by elite crosses is inbred to generate a large population (e.g., between about 200-5000, typically at least about 1000) F3-derived lines. If desired, inbreeding to later generations can also be done to increase genetic variation among lines.

A subset of "tester lines" is randomly selected from among the inbred lines derived from each cross. For example, between about 10 and 500 lines can be selected. Typically, between about 50 and 100 inbred lines are randomly selected, and enough seed to conduct a reliable yield trial is produced. Several (i.e., between at least 5 and 12, e.g., 8) plants from each inbred line are genotyped at marker loci segregating in the elite parents from which the line was founded, to determine whether the line is segregating or fixed (homozygous) with respect to the relevant marker. The remaining lines ("remnant population") can be stored under conditions that preserve seed viability. If desired, additional lines can be selected for testing, or genotyped for presence of the alleles confirmed to be in coupling linkage phase.

For each cross, a replicated yield trial of each tester line is performed. The test is replicated in enough environments to adequately sample the geographic region of interest and to gain a reliable measure of phenotype. The effect on yield for each marker locus within each cross is determined by comparing the mean yield of lines with a first allele to the mean yield of lines with the alternate allele. If the difference in yield is not significant, the marker can be eliminated in that cross. In contrast, if the difference in yield is significant, the "favorable" allele is confirmed and the locus is used for subsequent marker assisted selection for yield.

Confirmation of the favorable alleles also permits identification of a "target genotype" including all of the favorable alleles across all segregating loci in a particular elite by elite cross. As indicated above, the entire remnant population can be screened with the subset of confirmed markers to identify those segregants that have the highest number of favorable alleles. Typically, at least 5% of the remnant lines that most closely approach the target genotype will be selected, although additional lines can be included at the breeder's discretion. The selected lines can then be evaluated in highly replicated yield tests to identify which crosses perform better than either elite parent under a variety of environments and growing conditions.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations.

TABLE 1

Elite Soybean Lines by Geographic Region

| Central (Iowa) | Iowa (2003) | Canada | RF (North) | SJ (Illinois) | NP (East) | HL (MidSouth) | ME (South) |
|---|---|---|---|---|---|---|---|
| 91B91 | 92B05 | 90A07 | 90B73 | 92B38 | 92B52 | 93B66 | 94B73 |
| 92B05 | 92B12 | 90B11 | 91B12 | 92B63 | 91B91 | 93B67 | 94B74 |
| 92B38 | 92B38 | 90B31 | 91B33 | 92B74 | 92B05 | 93B82 | 94M70 |
| 92B52 | 92B52 | 90B43 | 91B53 | 93B01 | 92B38 | 93B84 | 94M90 |
| 92B63 | 92B63 | 90B72 | 91B91 | 93B11 | 92B63 | 93B85 | 95B32 |
| 92B74 | 92B74 | 90B73 | 91B92 | 93B15 | 92B74 | 93B86 | 95B33 |
| 92B75 | 92M30 | 91B01 | 92B05 | 93B41 | 93B01 | 93B87 | 95B34 |
| 92B84 | 92M31 | 91B12 | 92B12 | 93B66 | 93B46 | 94B01 | 95B42 |
| 93B01 | 92M70 | 91B33 | 92B23 | 93B67 | 93B67 | 94B23 | 95B43 |
| 93B41 | 92M71 | 91B52 | 92B38 | 93B82 | 93B82 | 94B24 | 95B53 |
| 93B45 | 92M72 | 91B53 | 92B63 | 93B85 | 93B86 | 94B53 | 95B95 |
| 93B47 | 92M80 | 91B64 | 92B74 | 93B86 | 93B87 | 94B54 | 95B96 |
| 93B66 | 92M91 | 92B95 | A1395 | 93B87 | A3431 | 94B73 | 95B97 |
| 93B67 | 93B09 | 93B25 | CX105 | 94B53 | CX289 | A4009 | 95M80 |
| 93B72 | 93B36 | 93B26 | D00566D362 | 94B54 | CX394C | A4138 | 96B21 |
| 93B82 | 93B41 | A1395 | EX04C00 | 94B73 | EX39E00 | A4415 | 96B32 |
| 93B85 | 93B45 | CX105 | EX06A00 | CM428 | G3362 | A4595 | 96B51 |
| 93B86 | 93B66 | EX10F01 | EX10F01 | MO15733 | MO15733 | A4715 | 96M20 |
| 93B87 | 93B67 | P1677 | EX13P01 | MP39009 | P9273 | CM428 | 97B52 |
| 94B23 | 93B68 | P9007 | EX13Q01 | P9306 | P9281 | CX469C | 97B61 |
| 94B54 | 93B82 | P9008 | EX15N01 | P9395 | P9306 | P9395 | A5403 |
| A2835 | 93B85 | P9041 | EX16N00 | S32Z3 | P9392 | P9481 | A5560 |

TABLE 1-continued

Elite Soybean Lines by Geographic Region

| Central (Iowa) | Iowa (2003) | Canada | RF (North) | SJ (Illinois) | NP (East) | HL (MidSouth) | ME (South) |
|---|---|---|---|---|---|---|---|
| A2943 | 93B86 | P9042 | EX16P01 | S33N1 | P9395 | P9482 | A5843 |
| A3127 | 93B87 | P9061 | EX22Y01 | S38T8 | S3911 | P9492 | A5885 |
| A3242 | 93M10 | P9062 | BX22Z01 | S42H1 | ST2660 | S3911 | A5979 |
| CX232 | 93M30 | P9063 | JTM | ST2660 | ST3380 | S4260 | A5980 |
| CX253 | 93M40 | P9071 | KORADA | ST2870 | ST3883 | S42H1 | A6297 |
| HS93-4118 | 93M50 | P9092 | MO400644-02 | ST3171 | XB31C01 | S43B5 | BEDFORD |
| P9273 | 93M60 | P9132 | MO413735-11-52 | ST3630 | XB33B | ST3870 | CLIFFORD |
| P9281 | 93M80 | P9141 | MO501577-27-23 | ST3883 | XB34F01 | ST3883 | CM428 |
| P9305 | 93M90 | P9163 | MO505469-61-89 | XB31C01 | XB35D | XB41M01 | DAVIS |
| P9306 | 93M92 | P9182 | P9007 | XB34F01 | XB35W00 | XB42J00 | ESSEX |
| P9321 | 93M93 | P9203 | P9151 | XB38A01 | XB38A01 | XB42M01 | EX53F03 |
| P9341 | A2722 | P9244 | P9233 | XB42M01 | YB25Y01 | XB48H01 | EX56H03 |
| P9395 | A3237 | R01154R002 | S03W4 | XB48H01 | YB25Z01 | YB40M01 | EX61E03 |
| S22C3 | A3322 | S0066 | S0880 | YB28N01 | YB27X01 | YB40N01 | FORREST |
| ST1970 | A3431 | S0880 | S19T9 | YB29H01 | YB27Y01 | YB41Q01 | FOWLER |
| ST2250 | A4138 | S1550 | S20F8 | YB29J01 | YB28N01 | YB48L01 | HARTWIG |
| ST2488 | EX23B03 | S1990 | S24L2 | YB30J01 | Y829H01 | | HOLLADAY |
| ST2688 | EX34T03 | S19T9 | S25J5 | YB30N01 | YB29J01 | | HOOD |
| ST2870 | EX35F03 | ST1073 | ST0653 | YB35C01 | YB30J01 | | HUTCHESON |
| ST3171 | EX36Y01 | XB03F01 | ST1090 | YB36V00 | YB30P01 | | LEE |
| ST3380 | EX40T03 | XB07E01 | ST1970 | YB39M01 | YB33K01 | | MANOKIN |
| ST3630 | EX44V03 | | TRAILL | YB40M01 | YB35C01 | | P9481 |
| ST3870 | S25J5 | | X9916 | YB40N01 | YB36V00 | | P9482 |
| ST3883 | S32Z3 | | XB03F01 | YB48L01 | YB40N01 | | P9492 |
| XB22R01 | ST1570 | | XB10D01 | | | | P9521 |
| XB25W01 | ST1690 | | XB15M01 | | | | P9552 |
| XB31C01 | ST1970 | | XB20M01 | | | | P9561 |
| XB34F01 | ST2488 | | XB22R01 | | | | P9584 |
| XB35W00 | ST2686 | | XB25W01 | | | | P9591 |
| XB38A01 | ST2788 | | YB03E00 | | | | P9592 |
| XB42M01 | ST2870 | | YB03G01 | | | | P9593 |
| YB22W01 | ST3171 | | YB08D01 | | | | P9594 |
| YB25R99 | ST3630 | | YB09F01 | | | | P9611 |
| YB25Y01 | ST3660 | | YB09G01 | | | | P9631 |
| YB27X01 | ST3870 | | YB10E01 | | | | P9641 |
| YB28N01 | ST3883 | | YB11D01 | | | | P5960 |
| YB29H01 | XB19U04 | | YB14H01 | | | | PHARAOH |
| YB29J01 | XB22C04 | | YB15K99 | | | | RA451 |
| YB30J01 | XB23W03 | | YB21F01 | | | | S5960 |
| YB30P01 | XB23Y02 | | YB21G01 | | | | S6189 |
| YB31E01 | XB25E02 | | YB22S00 | | | | S6262 |
| YB32K01 | XB25L04 | | YB22V01 | | | | TRACY |
| YB33K01 | XB25X04 | | YB22W01 | | | | XB48H01 |
| YB34H01 | XB26L04 | | YB22X01 | | | | XB48T04 |
| YB37A01 | XB27P04 | | YB24Z01 | | | | XB53J04 |
| YB39M01 | XB29A04 | | YB25R99 | | | | XB54K01 |
| YB40M01 | XB29D01 | | YB25X00 | | | | XB55J01 |
| YB40N01 | XB29K04 | | YB25Y01 | | | | XB55K04 |
| YB41Q01 | XB29L04 | | YB25Z01 | | | | XB57M04 |
| | XB30E04 | | YB27Y01 | | | | XB58P99 |
| | XB31R04 | | | | | | XB58Y02 |
| | XB34D04 | | | | | | XB58Z04 |
| | XB35L04 | | | | | | XB59U04 |
| | YB25R03 | | | | | | XB63D00 |
| | YB27L03 | | | | | | XB64C04 |
| | YB27S00 | | | | | | XB67A00 |
| | YB28A03 | | | | | | YB48L01 |
| | YB29T04 | | | | | | YB51D00 |
| | YB34R03 | | | | | | YB52J00 |
| | YB34S03 | | | | | | YB53C00 |
| | YB36E03 | | | | | | YB53D00 |
| | YB38E03 | | | | | | YB53E00 |
| | YB38G03 | | | | | | YB53G03 |
| | YB39V03 | | | | | | YB53H03 |
| | | | | | | | YB53K03 |
| | | | | | | | YB54H00 |
| | | | | | | | YB54J00 |
| | | | | | | | YB54L00 |
| | | | | | | | YB55G00 |
| | | | | | | | YB55H00 |
| | | | | | | | YB56E00 |
| | | | | | | | YB56G03 |

TABLE 1-continued

Elite Soybean Lines by Geographic Region

| Central (Iowa) | Iowa (2003) | Canada | RF (North) | SJ (Illinois) | NP (East) | HL (MidSouth) | ME (South) |
|---|---|---|---|---|---|---|---|
| | | | | | | | YB57L03 |
| | | | | | | | YB58B04 |
| | | | | | | | YB59T03 |
| | | | | | | | YB59V03 |
| | | | | | | | YB60N01 |
| | | | | | | | YB60P03 |
| | | | | | | | YB63E00 |
| | | | | | | | YB65C00 |
| | | | | | | | YOUNG |

TABLE 2

Exemplary Target Progeny from Segregating Cross.

| Marker | Parent 1 | Parent 2 | Target Progeny |
|---|---|---|---|
| 1 | + | − | + |
| 2 | − | + | + |
| 3 | + | − | + |
| 4 | − | + | + |
| 5 | + | − | + |
| 6 | − | + | + |
| 7 | + | − | + |
| 8 | − | + | + |
| 9 | + | − | + |
| 10 | − | + | + | where + = contains the most favorable allele
− = contains some other allele

TABLE 3

Favorable Allelic Forms: Central Region

| Region | Chromosome | Position | Locus | Allele | Sig. |
|---|---|---|---|---|---|
| 2 | A1 | 19.1 | SATT042 | 3 | ** |
| 2 | A1 | 19.1 | SATT364 | 3 | ** |
| 2 | A1 | 19.1 | SATT454 | 1 | ** |
| 2 | A1 | 19.1 | SATT526 | 1 | ** |
| 3 | A1 | 27.1 | SATT300 | 3 | ** |
| 3 | A1 | 27.1 | SATT591 | 3 | ** |
| 3 | A1 | 28.5 | SATT155 | 2 | ** |
| 4 | A1 | 69.9 | SATT385 | 1 | * |
| 5 | A1 | 87.3 | SATT236 | 1 | * |
| 5 | A1 | 87.3 | SATT511 | 1 | * |
| 6 | A2 | 0.0 | P12390B-1 | 1 | ** |
| 13 | A2 | 184.0 | SATT429 | 4 | ** |
| 15 | B1 | 39.0 | SATT197 | 5 | * |
| 17 | B1 | 74.1 | SATT583 | 1 | * |
| 20 | B2 | 20.0 | P12105A-1 | 1 | * |
| 21 | B2 | 45.0 | P10641A-1 | 2 | ** |
| 23 | B2 | 86.1 | SATT556 | 2 | * |
| 23 | B2 | 88.6 | SATT020 | 2 | * |
| 25 | B2 | 110.9 | SATT534 | 7 | * |
| 26 | B2 | 120.0 | P10638B-2 | 1 | * |
| 29 | C1 | 95.8 | SATT399 | 3 | ** |
| 29 | C1 | 96.5 | SATT361 | 2 | ** |
| 29 | C1 | 98.0 | P10639A-1 | 1 | ** |
| 29 | C1 | 99.0 | SATT190 | 4 | ** |
| 31 | C1 | 173.0 | SATT338 | 3 | * |
| 36 | C2 | 140.9 | SATT557 | 5 | ** |
| 36 | C2 | 145.8 | SATT319 | 1 | * |
| 37 | C2 | 165.8 | SATT460 | 5 | * |
| 37 | C2 | 170.5 | SATT433 | 3 | * |
| 38 | C2 | 193.5 | SATT357 | 1 | * |
| 40 | D1a | 54.7 | SATT321 | 2 | * |
| 41 | D1a | 68.6 | SATT383 | 3 | * |
| 41 | D1a | 69.8 | SATT295 | 2 | * |
| 42 | D1a | 80.3 | SATT507 | 3 | * |

TABLE 3-continued

Favorable Allelic Forms: Central Region

| Region | Chromosome | Position | Locus | Allele | Sig. |
|---|---|---|---|---|---|
| 43 | D1a | 129.2 | SATT129 | 5 | ** |
| 43 | D1a | 129.2 | SATT147 | 1 | * |
| 44 | D1b | 0.0 | SATT216 | 4 | * |
| 45 | D1b | 20.0 | P10621B-2 | 2 | * |
| 46 | D1b | 39.8 | SATT558 | 3 | * |
| 49 | D1b | 76.1 | SATT546 | 4 | * |
| 51 | D1b | 120.0 | P13072A-1 | 2 | * |
| 53 | D2 | 66.9 | SATT582 | 2 | ** |
| 54 | D2 | 93.8 | SATT389 | 6 | ** |
| 55 | D2 | 110.4 | SATT464 | 1 | ** |
| 57 | D2 | 148.3 | SATT413 | 3 | * |
| 60 | E | 40.0 | P13074A-1 | 1 | * |
| 62 | E | 98.0 | SATT573 | 2 | * |
| 62 | E | 98.0 | SATT598 | 1 | ** |
| 62 | E | 100.6 | SATT263 | 2 | * |
| 62 | E | 101.0 | SATT602 | 4 | * |
| 62 | E | 102.2 | SATT151 | 4 | * |
| 62 | E | 102.2 | SATT355 | 3 | * |
| 62 | E | 102.2 | SATT452 | 2 | * |
| 64 | F | 0.0 | SATT146 | 1 | ** |
| 64 | F | 0.0 | SATT193 | 3 | ** |
| 64 | F | 0.0 | SATT569 | 3 | ** |
| 64 | F | 1.7 | SATT343 | 3 | ** |
| 64 | F | 1.9 | SATT586 | 5 | ** |
| 66 | F | 57.5 | SATT595 | 1 | * |
| 67 | F | 85.0 | P10782A-1 | 1 | ** |
| 67 | F | 95.0 | SATT334 | 3 | * |
| 70 | F | 157.8 | SATT144 | 1 | * |
| 71 | F | 165.8 | SATT522 | 5 | * |
| 73 | G | 8.5 | SATT356 | 2 | * |
| 75 | G | 66.1 | SATT533 | 1 | * |
| 77 | G | 100.8 | SATT199 | 1 | ** |
| 77 | G | 103.2 | SATT503 | 3 | * |
| 77 | G | 103.2 | SATT517 | 4 | * |
| 79 | G | 137.0 | SATT191 | 2 | * |
| 79 | G | 138.4 | SAT_117 | 1 | * |
| 81 | H | 0.0 | SATT353 | 2 | * |
| 85 | H | 125.3 | SATT181 | 5 | ** |
| 86 | I | 15.5 | SATT127 | 2 | * |
| 87 | I | 57.9 | SATT270 | 5 | * |
| 92 | J | 61.3 | SCT_065 | 2 | ** |
| 92 | J | 63.6 | SATT596 | 4 | ** |
| 92 | J | 68.0 | SATT406 | 2 | ** |
| 92 | J | 70.8 | SATT380 | 3 | ** |
| 92 | J | 72.6 | SATT183 | 1 | ** |
| 92 | J | 74.4 | SATT529 | 1 | ** |
| 94 | K | 17.9 | SATT242 | 4 | ** |
| 96 | K | 70.9 | SATT441 | 2 | * |
| 96 | K | 72.8 | SATT544 | 2 | * |
| 97 | K | 85.8 | SATT240 | 2 | * |
| 101 | L | 34.6 | SATT398 | 4 | ** |
| 102 | L | 42.3 | SATT497 | 3 | * |
| 102 | L | 47.7 | SATT284 | 2 | * |
| 103 | L | 77.1 | SATT166 | 3 | ** |
| 103 | L | 78.0 | SATT448 | 4 | * |
| 104 | L | 118.0 | SATT373 | 3 | ** |

TABLE 3-continued

Favorable Allelic Forms: Central Region

| Region | Chromosome | Position | Locus | Allele | Sig. |
|---|---|---|---|---|---|
| 104 | L | 118.6 | SATT513 | 11 | * |
| 104 | L | 124.5 | P12394A-1 | 2 | ** |
| 108 | M | 87.6 | SATT536 | 4 | ** |
| 108 | M | 91.1 | SATT175 | 5 | * |
| 109 | M | 115.0 | P10615A-1 | 1 | * |
| 110 | M | 143.5 | SATT346 | 3 | * |
| 111 | M | 173.5 | SATT336 | 4 | * |
| 112 | N | 20.0 | P13069A-1 | 3 | ** |
| 112 | N | 25.0 | P5467A-1 | 2 | ** |
| 115 | N | 88.6 | SATT339 | 5 | * |
| 118 | O | 2.4 | P12396A-1 | 1 | * |
| 118 | O | 6.3 | SATT487 | 4 | ** |
| 119 | O | 37.7 | SATT259 | 4 | ** |
| 120 | O | 60.5 | SATT420 | 2 | ** |
| 120 | O | 65.1 | SATT576 | 4 | * |
| 122 | O | 103.8 | SATT477 | 3 | * |
| 123 | O | 125.0 | SATT581 | 2 | ** |
| 124 | O | 153.3 | SATT153 | 3 | ** |
| 124 | O | 155.1 | SATT243 | 1 | ** |
| 128 | UM | # | P10793A-1 | 2 | * |
| 129 | UM | # | P12391A-1 | 1 | * |
| 129 | UM | # | P12392A-1 | 1 | * |
| 131 | UM | # | P13560A-1 | 1 | * |
| 131 | UM | # | P13561A-1 | 2 | ** |
| 133 | UM | # | SAC1677 | 3 | ** |
| 134 | UM | # | SATT040 | 4 | ** |
| 139 | UM | # | SATT111 | 3 | ** |
| 140 | UM | # | SATT176 | 3 | ** |
| 143 | UM | # | SATT299 | 5 | * |

TABLE 4

Favorable Allelic Forms: Canada

| Region | Chromosome | Position | Locus | Allele | Sig. |
|---|---|---|---|---|---|
| 4 | A1 | 69.9 | SATT385 | 6 | * |
| 5 | A1 | 87.3 | SATT225 | 1 | * |
| 9 | A2 | 108.7 | SATT508 | 2 | ** |
| 11 | A2 | 136.0 | P10635A-1 | 1 | * |
| 15 | B1 | 39.0 | SATT197 | 5 | * |
| 17 | B1 | 68.1 | SATT597 | 3 | * |
| 17 | B1 | 71.6 | SCT_026 | 1 | * |
| 17 | B1 | 73.3 | SATT415 | 3 | * |
| 17 | B1 | 74.1 | SATT583 | 1 | * |
| 18 | B1 | 80.0 | P12198A-1 | 1 | * |
| 18 | B1 | 92.1 | SATT359 | 1 | * |
| 23 | B2 | 86.1 | SATT556 | 2 | * |
| 29 | C1 | 95.8 | SATT399 | 3 | ** |
| 29 | C1 | 96.5 | SATT361 | 2 | * |
| 29 | C1 | 98.0 | P10639A-1 | 1 | ** |
| 29 | C1 | 99.0 | SATT190 | 4 | ** |
| 31 | C1 | 173.0 | SATT338 | 3 | ** |
| 32 | C2 | 25.4 | SATT227 | 1 | * |
| 33 | C2 | 48.1 | SATT422 | 4 | * |
| 36 | C2 | 145.8 | SATT319 | 3 | * |
| 41 | D1a | 68.6 | SATT267 | 1 | ** |
| 42 | D1a | 80.3 | SATT507 | 3 | ** |
| 42 | D1a | 85.0 | P10620A-1 | 1 | * |
| 43 | D1a | 129.2 | SATT129 | 2 | * |
| 46 | D1b | 39.8 | SATT558 | 3 | * |
| 48 | D1b | 65.9 | SATT506 | 3 | * |
| 53 | D2 | 66.9 | SATT582 | 2 | ** |
| 55 | D2 | 110.4 | SATT464 | 1 | ** |
| 62 | E | 100.6 | SATT204 | 4 | * |
| 62 | E | 100.6 | SATT263 | 2 | * |
| 62 | E | 101.0 | SATT491 | 3 | ** |
| 62 | E | 102.2 | SATT151 | 4 | * |
| 62 | E | 102.2 | SATT355 | 3 | * |
| 62 | E | 102.2 | SATT452 | 2 | * |
| 64 | F | 0.0 | SATT146 | 1 | ** |
| 64 | F | 0.0 | SATT193 | 3 | * |
| 64 | F | 0.0 | SATT569 | 3 | * |

TABLE 4-continued

Favorable Allelic Forms: Canada

| Region | Chromosome | Position | Locus | Allele | Sig. |
|---|---|---|---|---|---|
| 64 | F | 1.7 | SATT343 | 3 | * |
| 64 | F | 1.7 | SATT343 | 5 | * |
| 64 | F | 1.9 | SATT586 | 5 | ** |
| 67 | F | 85.0 | P10782A-1 | 1 | ** |
| 67 | F | 90.0 | P10598A-1 | 1 | * |
| 67 | F | 95.0 | SATT334 | 3 | ** |
| 68 | F | 114.8 | SATT510 | 3 | * |
| 72 | F | 175.0 | P9026A-1 | 2 | * |
| 75 | G | 53.0 | SATT115 | 1 | * |
| 85 | H | 125.3 | SATT181 | 5 | ** |
| 86 | I | 9.8 | SATT367 | 2 | * |
| 86 | I | 15.5 | SATT127 | 2 | ** |
| 86 | I | 16.6 | SCTT012 | 2 | * |
| 87 | I | 57.9 | SATT270 | 5 | * |
| 89 | I | 114.2 | SATT440 | 2 | * |
| 92 | J | 68.0 | SATT406 | 2 | * |
| 92 | J | 70.8 | SATT380 | 3 | * |
| 92 | J | 72.6 | SATT183 | 1 | ** |
| 92 | J | 74.4 | SATT529 | 1 | * |
| 96 | K | 70.9 | SATT441 | 3 | * |
| 97 | K | 85.8 | SATT240 | 2 | * |
| 101 | L | 32.4 | SATT523 | 1 | * |
| 103 | L | 77.1 | SATT166 | 3 | * |
| 103 | L | 78.0 | SATT448 | 1 | * |
| 104 | L | 124.5 | P12394A-1 | 2 | ** |
| 108 | M | 87.6 | SATT536 | 4 | * |
| 110 | M | 143.5 | SATT346 | 3 | * |
| 112 | N | 20.0 | P13069A-1 | 2 | ** |
| 113 | N | 35.4 | SATT584 | 3 | * |
| 113 | N | 40.0 | P3050A-2 | 2 | * |
| 114 | N | 61.2 | SATT387 | 4 | * |
| 118 | O | 2.4 | P12396A-1 | 1 | * |
| 118 | O | 6.3 | SATT487 | 4 | ** |
| 119 | O | 37.7 | SATT259 | 4 | * |
| 119 | O | 39.0 | SATT347 | 2 | * |
| 120 | O | 69.2 | SATT262 | 5 | * |
| 123 | O | 130.0 | P11070A-1 | 1 | ** |
| 131 | UM | # | P13560A-1 | 1 | ** |
| 131 | UM | # | P13561A-1 | 2 | ** |
| 133 | UM | # | SAC1677 | 3 | * |
| 134 | UM | # | SATT040 | 4 | * |
| 138 | UM | # | SATT109 | 3 | ** |
| 139 | UM | # | SATT111 | 3 | ** |
| 140 | UM | # | SATT176 | 3 | * |
| 140 | UM | # | SATT176 | 5 | * |
| 145 | UM | # | SATT512 | 5 | ** |

TABLE 5

Favorable Allelic Forms: North Region

| Region | Chromosome | Position | Locus | Allele | Sig. |
|---|---|---|---|---|---|
| 2 | A1 | 19.1 | SATT454 | 1 | * |
| 2 | A1 | 19.1 | SATT526 | 1 | * |
| 3 | A1 | 27.1 | SATT300 | 3 | * |
| 3 | A1 | 27.1 | SATT591 | 3 | * |
| 6 | A2 | 0.0 | P12390B-1 | 1 | * |
| 9 | A2 | 108.7 | SATT327 | 2 | * |
| 9 | A2 | 108.7 | SATT508 | 2 | * |
| 12 | A2 | 154.7 | SATT409 | 5 | ** |
| 13 | A2 | 184.0 | SATT429 | 4 | ** |
| 14 | B1 | 22.5 | SATT426 | 5 | * |
| 14 | B1 | 26.7 | SATT509 | 1 | ** |
| 15 | B1 | 39.0 | SATT197 | 5 | ** |
| 17 | B1 | 73.3 | SATT415 | 3 | * |
| 17 | B1 | 74.1 | SATT583 | 1 | * |
| 18 | B1 | 80.0 | P12198A-1 | 1 | ** |
| 18 | B1 | 85.0 | P8584A-1 | 1 | * |
| 18 | B1 | 92.1 | SATT359 | 1 | * |
| 21 | B2 | 45.0 | P10641A-1 | 2 | * |
| 23 | B2 | 86.1 | SATT556 | 2 | * |
| 23 | B2 | 86.1 | SATT556 | 4 | * |

TABLE 5-continued

Favorable Allelic Forms: North Region

| Region | Chromosome | Position | Locus | Allele | Sig. |
|---|---|---|---|---|---|
| 23 | B2 | 88.6 | SATT020 | 2 | * |
| 25 | B2 | 110.9 | SATT534 | 7 | * |
| 29 | C1 | 95.8 | SATT399 | 3 | ** |
| 29 | C1 | 96.5 | SATT361 | 2 | ** |
| 29 | C1 | 98.0 | P10639A-1 | 1 | ** |
| 29 | C1 | 99.0 | SATT190 | 4 | ** |
| 31 | C1 | 173.0 | SATT338 | 3 | ** |
| 32 | C2 | 25.4 | SATT227 | 1 | ** |
| 33 | C2 | 53.4 | SATT457 | 1 | * |
| 36 | C2 | 140.9 | SATT557 | 5 | * |
| 37 | C2 | 168.3 | P13073A-1 | 2 | * |
| 37 | C2 | 170.5 | SATT433 | 3 | * |
| 41 | D1a | 68.6 | SATT267 | 1 | * |
| 42 | D1a | 80.3 | SATT507 | 3 | ** |
| 42 | D1a | 82.0 | SAT_110 | 3 | * |
| 43 | D1a | 129.2 | SATT129 | 5 | * |
| 46 | D1b | 39.8 | SATT558 | 3 | * |
| 48 | D1b | 65.9 | SATT506 | 3 | ** |
| 51 | D1b | 120.0 | P13072A-1 | 2 | * |
| 53 | D2 | 66.9 | SATT582 | 2 | ** |
| 54 | D2 | 93.8 | SATT389 | 6 | ** |
| 54 | D2 | 99.6 | SATT461 | 1 | * |
| 55 | D2 | 110.4 | SATT464 | 1 | ** |
| 62 | E | 98.0 | SATT573 | 2 | * |
| 62 | E | 98.0 | SATT598 | 1 | * |
| 62 | E | 100.6 | SATT204 | 3 | * |
| 64 | F | 0.0 | SATT146 | 1 | ** |
| 64 | F | 0.0 | SATT193 | 3 | ** |
| 64 | F | 0.0 | SATT569 | 3 | ** |
| 64 | F | 1.7 | SATT343 | 3 | ** |
| 64 | F | 1.9 | SATT586 | 5 | ** |
| 65 | F | 18.0 | SATT348 | 2 | * |
| 67 | F | 85.0 | P10782A-1 | 1 | ** |
| 67 | F | 90.0 | P10598A-1 | 1 | * |
| 67 | F | 95.0 | SATT334 | 3 | * |
| 70 | F | 157.8 | SATT144 | 1 | * |
| 71 | F | 165.8 | SATT522 | 4 | * |
| 75 | G | 53.0 | SATT115 | 3 | * |
| 75 | G | 61.3 | SATT594 | 5 | * |
| 76 | G | 71.6 | SATT303 | 6 | * |
| 76 | G | 72.4 | SATT566 | 1 | * |
| 77 | G | 100.8 | SATT199 | 1 | * |
| 77 | G | 103.2 | SATT517 | 2 | * |
| 81 | H | 0.0 | SATT353 | 2 | * |
| 85 | H | 125.3 | SATT181 | 5 | ** |
| 86 | I | 15.5 | SATT127 | 2 | ** |
| 87 | I | 57.9 | SATT270 | 5 | ** |
| 89 | I | 114.2 | SATT440 | 2 | ** |
| 90 | J | 10.5 | SATT249 | 4 | * |
| 92 | J | 61.3 | SCT_065 | 2 | * |
| 92 | J | 63.6 | SATT596 | 4 | * |
| 92 | J | 68.0 | SATT406 | 2 | ** |
| 92 | J | 70.8 | SATT380 | 3 | ** |
| 92 | J | 72.6 | SATT183 | 1 | ** |
| 92 | J | 74.4 | SATT529 | 1 | ** |
| 94 | K | 17.9 | SATT242 | 4 | * |
| 101 | L | 32.4 | SATT523 | 1 | * |
| 101 | L | 34.6 | SATT398 | 4 | ** |
| 102 | L | 42.3 | SATT497 | 3 | ** |
| 103 | L | 77.1 | SATT166 | 3 | ** |
| 103 | L | 78.0 | SATT448 | 4 | * |
| 104 | L | 118.6 | SATT513 | 11 | * |
| 104 | L | 124.5 | P12394A-1 | 2 | ** |
| 108 | M | 87.6 | SATT536 | 4 | ** |
| 108 | M | 91.1 | SATT175 | 5 | * |
| 110 | M | 143.5 | SATT346 | 3 | * |
| 111 | M | 173.5 | SATT336 | 4 | * |
| 112 | N | 20.0 | P13069A-1 | 3 | ** |
| 113 | N | 38.3 | SAT_084 | 2 | * |
| 115 | N | 88.6 | SATT339 | 5 | * |
| 116 | N | 92.2 | SATT255 | 3 | * |
| 118 | O | 2.4 | P12396A-1 | 1 | ** |
| 118 | O | 6.3 | SATT487 | 4 | ** |
| 119 | O | 37.7 | SATT259 | 4 | ** |
| 120 | O | 60.5 | SATT420 | 2 | * |
| 120 | O | 65.1 | SATT576 | 4 | * |
| 123 | O | 130.0 | P11070A-1 | 1 | * |
| 129 | UM | # | P12391A-1 | 1 | * |
| 131 | UM | # | P13560A-1 | 1 | ** |
| 131 | UM | # | P13561A-1 | 2 | ** |
| 133 | UM | # | SAC1677 | 3 | ** |
| 134 | UM | # | SATT040 | 4 | ** |
| 138 | UM | # | SATT109 | 3 | * |
| 139 | UM | # | SATT111 | 3 | ** |
| 140 | UM | # | SATT176 | 3 | ** |

TABLE 6

Favorable Allelic Forms: Illinois

| Region | Chromosome | Position | Locus | Allele | Sig. |
|---|---|---|---|---|---|
| 2 | A1 | 19.1 | SATT042 | 3 | ** |
| 2 | A1 | 19.1 | SATT364 | 3 | ** |
| 2 | A1 | 19.1 | SATT454 | 1 | ** |
| 2 | A1 | 19.1 | SATT526 | 1 | ** |
| 3 | A1 | 27.1 | SATT300 | 3 | ** |
| 3 | A1 | 27.1 | SATT591 | 3 | ** |
| 3 | A1 | 28.5 | SATT155 | 2 | ** |
| 4 | A1 | 69.9 | SATT385 | 1 | * |
| 5 | A1 | 87.3 | SATT511 | 1 | * |
| 6 | A2 | 0.0 | P12390B-1 | 1 | ** |
| 13 | A2 | 184.0 | SATT429 | 4 | ** |
| 15 | B1 | 39.0 | SATT197 | 5 | * |
| 16 | B1 | 56.6 | SATT519 | 1 | * |
| 21 | B2 | 45.0 | P10641A-1 | 2 | ** |
| 23 | B2 | 86.1 | SATT556 | 2 | * |
| 23 | B2 | 87.0 | SATT272 | 1 | * |
| 23 | B2 | 88.6 | SATT020 | 2 | * |
| 24 | B2 | 97.3 | SATT066 | 3 | * |
| 26 | B2 | 120.0 | P10638B-2 | 1 | * |
| 29 | C1 | 95.8 | SATT399 | 3 | ** |
| 29 | C1 | 96.5 | SATT361 | 2 | ** |
| 29 | C1 | 98.0 | P10639A-1 | 1 | ** |
| 29 | C1 | 99.0 | SATT190 | 4 | ** |
| 31 | C1 | 173.0 | SATT338 | 3 | * |
| 36 | C2 | 140.9 | SATT557 | 5 | ** |
| 36 | C2 | 145.8 | SATT319 | 1 | * |
| 37 | C2 | 165.8 | SATT460 | 5 | * |
| 37 | C2 | 170.5 | SATT433 | 3 | * |
| 38 | C2 | 193.5 | SATT357 | 1 | * |
| 40 | D1a | 54.7 | SATT321 | 2 | * |
| 42 | D1a | 73.1 | SATT203 | 4 | * |
| 43 | D1a | 129.2 | SATT129 | 5 | ** |
| 43 | D1a | 129.2 | SATT147 | 1 | * |
| 44 | D1b | 0.0 | SATT216 | 4 | * |
| 45 | D1b | 20.0 | P10621B-2 | 2 | * |
| 46 | D1b | 39.8 | SATT558 | 3 | * |
| 54 | D2 | 93.8 | SATT389 | 6 | * |
| 55 | D2 | 110.4 | SATT464 | 1 | ** |
| 60 | E | 40.0 | P13074A-1 | 1 | * |
| 62 | E | 98.0 | SATT573 | 2 | * |
| 62 | E | 98.0 | SATT598 | 1 | * |
| 62 | E | 100.6 | SATT263 | 2 | * |
| 62 | E | 101.0 | SATT602 | 4 | * |
| 62 | E | 102.2 | SATT151 | 4 | * |
| 62 | E | 102.2 | SATT355 | 3 | * |
| 62 | E | 102.2 | SATT452 | 2 | * |
| 64 | F | 0.0 | SATT146 | 1 | * |
| 64 | F | 0.0 | SATT193 | 3 | ** |
| 64 | F | 0.0 | SATT569 | 3 | ** |
| 64 | F | 1.7 | SATT343 | 3 | ** |
| 64 | F | 1.9 | SATT586 | 5 | ** |
| 66 | F | 57.5 | SATT595 | 1 | ** |
| 67 | F | 85.0 | P10782A-1 | 1 | * |
| 67 | F | 95.0 | SATT334 | 3 | * |
| 70 | F | 157.8 | SATT144 | 1 | * |
| 71 | F | 165.8 | SAFT522 | 5 | * |
| 73 | G | 4.0 | P7659A-2 | 2 | * |

TABLE 6-continued

Favorable Allelic Forms: Illinois

| Region | Chromosome | Position | Locus | Allele | Sig. |
|---|---|---|---|---|---|
| 73 | G | 7.7 | SATT570 | 3 | ** |
| 73 | G | 8.5 | SATT356 | 2 | * |
| 75 | G | 53.0 | SATT115 | 1 | ** |
| 75 | G | 66.1 | SATT533 | 1 | * |
| 77 | G | 100.8 | SATT199 | 1 | ** |
| 77 | G | 103.2 | SATT503 | 3 | * |
| 77 | G | 103.2 | SATT517 | 4 | * |
| 79 | G | 137.0 | SATT191 | 2 | ** |
| 79 | G | 138.4 | SAT_117 | 1 | ** |
| 83 | H | 77.3 | SATT279 | 6 | * |
| 85 | H | 125.3 | SATT181 | 5 | ** |
| 86 | I | 15.5 | SATT127 | 2 | * |
| 92 | J | 61.3 | SCT_065 | 2 | ** |
| 92 | J | 63.6 | SATT596 | 4 | * |
| 92 | J | 68.0 | SATT406 | 2 | ** |
| 92 | J | 70.8 | SATT380 | 3 | ** |
| 92 | J | 72.6 | SATT183 | 1 | ** |
| 92 | J | 74.4 | SATT529 | 1 | ** |
| 94 | K | 17.9 | SATT242 | 4 | ** |
| 97 | K | 85.8 | SATT240 | 2 | * |
| 101 | L | 34.6 | SATT398 | 4 | ** |
| 102 | L | 42.3 | SATT497 | 3 | * |
| 103 | L | 77.1 | SATT166 | 3 | ** |
| 103 | L | 78.0 | SATT448 | 4 | * |
| 104 | L | 118.0 | SATT373 | 3 | ** |
| 104 | L | 124.5 | P12394A-1 | 2 | ** |
| 105 | M | 12.4 | SATT590 | 17 | * |
| 106 | M | 41.0 | SATT567 | 3 | * |
| 107 | M | 78.9 | SATT220 | 3 | * |
| 108 | M | 87.6 | SATT536 | 4 | * |
| 108 | M | 91.1 | SATT175 | 5 | * |
| 109 | M | 115.0 | P10615A-1 | 1 | * |
| 112 | N | 20.0 | P13069A-1 | 3 | ** |
| 112 | N | 25.0 | P5467A-1 | 2 | ** |
| 112 | N | 25.0 | P5467A-2 | 1 | * |
| 113 | N | 38.3 | SAT_084 | 2 | * |
| 115 | N | 88.6 | SATT339 | 5 | * |
| 118 | O | 2.4 | P12396A-1 | 1 | * |
| 118 | O | 6.3 | SATT487 | 4 | ** |
| 119 | O | 37.7 | SATT259 | 4 | * |
| 120 | O | 60.5 | SATT420 | 2 | ** |
| 120 | O | 65.1 | SATT576 | 4 | * |
| 122 | O | 103.8 | SATT477 | 3 | * |
| 123 | O | 125.0 | SATT581 | 2 | ** |
| 123 | O | 130.0 | P11070A-1 | 1 | * |
| 124 | O | 153.3 | SATT153 | 3 | ** |
| 124 | O | 155.1 | SATT243 | 1 | * |
| 127 | UM | # | P10632A-1 | 2 | * |
| 128 | UM | # | P10793A-1 | 2 | * |
| 129 | UM | # | P12391A-1 | 1 | * |
| 129 | UM | # | P12392A-1 | 1 | * |
| 131 | UM | # | P13560A-1 | 1 | * |
| 131 | UM | # | P13561A-1 | 2 | ** |
| 133 | UM | # | SAC1677 | 3 | ** |
| 134 | UM | # | SATT040 | 4 | ** |
| 139 | UM | # | SATT111 | 3 | ** |
| 140 | UM | # | SATT176 | 3 | ** |
| 141 | UM | # | SATT219 | 1 | * |
| 143 | UM | # | SATT299 | 5 | * |

TABLE 7

Favorable Allelic Forms: East Region

| Region | Chromosome | Position | Locus | Allele | Sig. |
|---|---|---|---|---|---|
| 2 | A1 | 19.1 | SATT042 | 3 | ** |
| 2 | A1 | 19.1 | SATT364 | 3 | ** |
| 2 | A1 | 19.1 | SATT454 | 1 | ** |
| 2 | A1 | 19.1 | SATT526 | 1 | ** |
| 3 | A1 | 27.1 | SATT300 | 3 | ** |
| 3 | A1 | 27.1 | SATT591 | 3 | ** |
| 3 | A1 | 28.5 | SATT155 | 2 | ** |

TABLE 7-continued

Favorable Allelic Forms: East Region

| Region | Chromosome | Position | Locus | Allele | Sig. |
|---|---|---|---|---|---|
| 4 | A1 | 69.9 | SATT385 | 1 | * |
| 5 | A1 | 87.3 | SATT236 | 1 | * |
| 5 | A1 | 87.3 | SATT511 | 1 | * |
| 6 | A2 | 0.0 | P12390B-1 | 1 | ** |
| 12 | A2 | 154.7 | SATT409 | 5 | * |
| 13 | A2 | 184.0 | SATT429 | 4 | ** |
| 15 | B1 | 39.0 | SATT197 | 5 | * |
| 17 | B1 | 74.1 | SATT583 | 1 | * |
| 21 | B2 | 45.0 | P10641A-1 | 2 | ** |
| 23 | B2 | 86.1 | SATT556 | 2 | * |
| 23 | B2 | 88.6 | SATT020 | 2 | * |
| 26 | B2 | 120.0 | P10638B-2 | 1 | * |
| 29 | C1 | 95.8 | SATT399 | 3 | ** |
| 29 | C1 | 96.5 | SATT361 | 2 | ** |
| 29 | C1 | 98.0 | P10639A-1 | 1 | ** |
| 29 | C1 | 99.0 | SATT190 | 4 | ** |
| 31 | C1 | 173.0 | SATT338 | 3 | * |
| 36 | C2 | 140.9 | SATT557 | 5 | ** |
| 36 | C2 | 145.8 | SATT319 | 1 | * |
| 37 | C2 | 170.5 | SATT433 | 3 | * |
| 38 | C2 | 193.5 | SATT357 | 1 | * |
| 40 | D1a | 54.7 | SATT321 | 2 | * |
| 41 | D1a | 68.6 | SATT383 | 3 | * |
| 43 | D1a | 129.2 | SATT129 | 5 | ** |
| 43 | D1a | 129.2 | SATT147 | 1 | * |
| 45 | D1b | 20.0 | P10621B-2 | 2 | * |
| 46 | D1b | 39.8 | SATT558 | 3 | * |
| 53 | D2 | 66.9 | SATT582 | 2 | * |
| 54 | D2 | 93.8 | SATT389 | 6 | * |
| 55 | D2 | 110.4 | SATT464 | 1 | ** |
| 60 | E | 40.0 | P13074A-1 | 1 | * |
| 62 | E | 98.0 | SATT573 | 2 | * |
| 62 | E | 98.0 | SATT598 | 1 | * |
| 62 | E | 100.6 | SATT263 | 2 | * |
| 62 | E | 101.0 | SATT602 | 4 | * |
| 62 | E | 102.2 | SATT151 | 4 | * |
| 62 | E | 102.2 | SATT355 | 1 | * |
| 62 | E | 102.2 | SATT452 | 2 | * |
| 64 | F | 0.0 | SATT146 | 1 | ** |
| 64 | F | 0.0 | SATT193 | 3 | ** |
| 64 | F | 0.0 | SATT569 | 3 | ** |
| 64 | F | 1.7 | SATT343 | 3 | ** |
| 64 | F | 1.9 | SATT586 | 5 | ** |
| 66 | F | 57.5 | SATT595 | 1 | * |
| 67 | F | 85.0 | P10782A-1 | 1 | ** |
| 67 | F | 95.0 | SATT334 | 3 | * |
| 70 | F | 157.8 | SATT144 | 1 | * |
| 73 | G | 8.5 | SATT356 | 2 | * |
| 75 | G | 53.0 | SATT115 | 1 | ** |
| 75 | G | 66.1 | SATT533 | 1 | * |
| 77 | G | 100.8 | SATT199 | 1 | ** |
| 77 | G | 103.2 | SATT503 | 3 | * |
| 77 | G | 103.2 | SATT517 | 4 | ** |
| 79 | G | 137.0 | SATT191 | 2 | * |
| 79 | G | 138.4 | SAT_117 | 1 | ** |
| 83 | H | 77.3 | SATT279 | 6 | * |
| 85 | H | 125.3 | SATT181 | 5 | ** |
| 86 | I | 15.5 | SATT127 | 2 | * |
| 92 | J | 61.3 | SCT_065 | 2 | ** |
| 92 | J | 63.6 | SATT596 | 4 | ** |
| 92 | J | 68.0 | SATT406 | 2 | ** |
| 92 | J | 70.8 | SATT380 | 3 | ** |
| 92 | J | 72.6 | SATT183 | 1 | ** |
| 92 | J | 74.4 | SATT529 | 1 | ** |
| 94 | K | 17.9 | SATT242 | 4 | ** |
| 97 | K | 85.8 | SATT240 | 2 | * |
| 103 | L | 77.1 | SATT166 | 3 | ** |
| 104 | L | 118.0 | SATT373 | 3 | ** |
| 104 | L | 124.5 | P12394A-1 | 2 | ** |
| 108 | M | 87.6 | SATT536 | 4 | ** |
| 108 | M | 91.1 | SATT175 | 5 | * |
| 109 | M | 115.0 | P10615A-1 | 1 | * |
| 110 | M | 143.5 | SATT346 | 3 | * |
| 111 | M | 173.5 | SATT336 | 4 | * |
| 112 | N | 20.0 | P13069A-1 | 3 | ** |
| 112 | N | 25.0 | P5467A-1 | 2 | ** |

TABLE 7-continued

Favorable Allelic Forms: East Region

| Region | Chromosome | Position | Locus | Allele | Sig. |
|---|---|---|---|---|---|
| 112 | N | 25.0 | P5467A-2 | 1 | * |
| 113 | N | 38.3 | SAT_084 | 2 | * |
| 115 | N | 88.6 | SATT339 | 5 | * |
| 118 | O | 2.4 | P12396A-1 | 1 | * |
| 118 | O | 6.3 | SATT487 | 4 | ** |
| 119 | O | 37.7 | SATT259 | 4 | ** |
| 120 | O | 60.5 | SATT420 | 2 | ** |
| 120 | O | 65.1 | SATT576 | 4 | * |
| 120 | O | 69.2 | SATT473 | 2 | * |
| 122 | O | 103.8 | SATT477 | 3 | * |
| 123 | O | 125.0 | SATT581 | 2 | ** |
| 123 | O | 130.0 | P11070A-1 | 1 | * |
| 124 | O | 153.3 | SATT153 | 3 | ** |
| 124 | O | 155.1 | SATT243 | 1 | ** |
| 128 | UM | # | P10793A-1 | 2 | * |
| 129 | UM | # | P12391A-1 | 1 | * |
| 129 | UM | # | P12392A-1 | 1 | * |
| 131 | UM | # | P13560A-1 | 1 | * |
| 131 | UM | # | P13561A-1 | 2 | ** |
| 133 | UM | # | SAC1677 | 3 | ** |
| 134 | UM | # | SATT040 | 4 | ** |
| 139 | UM | # | SATT111 | 3 | ** |
| 140 | UM | # | SATT176 | 3 | ** |
| 141 | UM | # | SATT219 | 9 | ** |
| 143 | UM | # | SATT299 | 5 | * |

TABLE 8

Favorable Allelic Forms: Mid South Region

| Region | Chromosome | Position | Locus | Allele | Sig. |
|---|---|---|---|---|---|
| 2 | A1 | 19.1 | SATT042 | 3 | * |
| 2 | A1 | 19.1 | SATT364 | 3 | ** |
| 2 | A1 | 19.1 | SATT454 | 1 | ** |
| 2 | A1 | 19.1 | SATT526 | 1 | ** |
| 3 | A1 | 27.1 | SATT300 | 3 | ** |
| 3 | A1 | 27.1 | SATT591 | 3 | ** |
| 3 | A1 | 28.5 | SATT155 | 2 | ** |
| 5 | A1 | 87.3 | SATT511 | 1 | * |
| 6 | A2 | 0.0 | P12390B-1 | 1 | * |
| 8 | A2 | 96.2 | SATT233 | 6 | * |
| 11 | A2 | 136.0 | P10635A-1 | 1 | * |
| 12 | A2 | 154.7 | SATT409 | 2 | * |
| 12 | A2 | 161.8 | SATT228 | 4 | ** |
| 13 | A2 | 184.0 | SATT429 | 4 | ** |
| 15 | B1 | 39.0 | SATT197 | 5 | * |
| 18 | B1 | 92.1 | SATT359 | 3 | ** |
| 20 | B2 | 20.0 | P12105A-1 | 1 | * |
| 21 | B2 | 45.0 | P10641A-1 | 2 | ** |
| 23 | B2 | 86.1 | SATT556 | 2 | * |
| 23 | B2 | 87.0 | SATT272 | 1 | * |
| 23 | B2 | 88.6 | SATT020 | 2 | * |
| 29 | C1 | 95.8 | SATT399 | 3 | ** |
| 29 | C1 | 96.5 | SATT361 | 2 | * |
| 29 | C1 | 98.0 | P10639A-1 | 1 | * |
| 29 | C1 | 99.0 | SATT190 | 4 | ** |
| 31 | C1 | 173.0 | SATT338 | 3 | * |
| 36 | C2 | 140.9 | SATT557 | 5 | ** |
| 36 | C2 | 145.8 | SATT319 | 1 | * |
| 37 | C2 | 165.8 | SATT460 | 5 | * |
| 40 | D1a | 54.7 | SATT321 | 2 | ** |
| 42 | D1a | 73.1 | SATT203 | 4 | * |
| 43 | D1a | 129.2 | SATT129 | 5 | ** |
| 44 | D1b | 0.0 | SATT216 | 4 | * |
| 45 | D1b | 20.0 | P10621B-2 | 2 | ** |
| 46 | D1b | 39.8 | SATT558 | 3 | * |
| 54 | D2 | 93.8 | SATT389 | 6 | * |
| 55 | D2 | 110.4 | SATT464 | 1 | ** |
| 62 | E | 98.0 | SATT598 | 1 | * |
| 62 | E | 100.6 | SATT263 | 2 | * |
| 62 | E | 102.2 | SATT151 | 4 | * |
| 62 | E | 102.2 | SATT355 | 3 | * |
| 62 | E | 102.2 | SATT452 | 2 | * |
| 64 | F | 0.0 | SATT146 | 1 | ** |

TABLE 8-continued

Favorable Allelic Forms: Mid South Region

| Region | Chromosome | Position | Locus | Allele | Sig. |
|---|---|---|---|---|---|
| 64 | F | 0.0 | SATT193 | 3 | ** |
| 64 | F | 0.0 | SATT569 | 3 | ** |
| 64 | F | 1.7 | SATT343 | 3 | ** |
| 64 | F | 1.9 | SATT586 | 5 | ** |
| 65 | F | 16.4 | SATT423 | 3 | * |
| 65 | F | 18.0 | SATT348 | 4 | * |
| 66 | F | 57.5 | SATT595 | 1 | * |
| 67 | F | 85.0 | P10782A-1 | 1 | ** |
| 67 | F | 95.0 | SATT334 | 3 | * |
| 73 | G | 2.0 | P10646A-1 | 2 | ** |
| 73 | G | 3.0 | P5219A-1 | 2 | * |
| 73 | G | 4.0 | P7659A-2 | 2 | ** |
| 73 | G | 7.7 | SATT570 | 3 | ** |
| 73 | G | 8.5 | SATT356 | 2 | * |
| 75 | G | 53.0 | SATT115 | 1 | * |
| 75 | G | 66.1 | SATT533 | 1 | * |
| 77 | G | 100.8 | SATT199 | 1 | * |
| 77 | G | 103.2 | SATT503 | 3 | * |
| 77 | G | 103.2 | SATT517 | 4 | * |
| 79 | G | 137.0 | SATT191 | 2 | * |
| 79 | G | 138.4 | SAT_117 | 1 | ** |
| 84 | H | 116.9 | SATT142 | 3 | * |
| 85 | H | 125.3 | SATT181 | 5 | ** |
| 86 | I | 9.8 | SATT367 | 6 | * |
| 86 | I | 15.5 | SATT127 | 2 | * |
| 89 | I | 114.2 | SATT440 | 3 | * |
| 92 | J | 61.3 | SCT_065 | 2 | ** |
| 92 | J | 63.6 | SATT596 | 4 | * |
| 92 | J | 68.0 | SATT406 | 2 | ** |
| 92 | J | 70.8 | SATT380 | 3 | ** |
| 92 | J | 72.6 | SATT183 | 1 | ** |
| 92 | J | 74.4 | SATT529 | 1 | ** |
| 94 | K | 17.9 | SATT242 | 4 | * |
| 96 | K | 72.8 | SATT544 | 2 | * |
| 97 | K | 85.8 | SATT240 | 2 | * |
| 101 | L | 34.6 | SATT398 | 4 | ** |
| 102 | L | 42.3 | SATT497 | 3 | * |
| 103 | L | 77.1 | SATT166 | 3 | ** |
| 103 | L | 78.0 | SATT448 | 4 | * |
| 104 | L | 124.5 | P12394A-1 | 2 | * |
| 107 | M | 78.9 | SATT220 | 3 | * |
| 108 | M | 87.6 | SATT536 | 4 | * |
| 109 | M | 115.0 | P10615A-1 | 1 | * |
| 110 | M | 143.5 | SATT346 | 3 | * |
| 115 | N | 88.6 | SATT339 | 5 | * |
| 118 | O | 2.4 | P12396A-1 | 1 | * |
| 118 | O | 6.3 | SATT487 | 4 | ** |
| 119 | O | 37.7 | SATT259 | 4 | * |
| 120 | O | 60.5 | SATT420 | 2 | * |
| 120 | O | 65.1 | SATT576 | 4 | * |
| 122 | O | 103.8 | SATT477 | 3 | * |
| 123 | O | 125.0 | SATT581 | 2 | ** |
| 124 | O | 153.3 | SATT153 | 3 | ** |
| 124 | O | 155.1 | SATT243 | 1 | * |
| 129 | UM | # | P12392A-1 | 1 | * |
| 131 | UM | # | P13560A-1 | 1 | * |
| 131 | UM | # | P13561A-1 | 2 | ** |
| 133 | UM | # | SAC1677 | 3 | * |
| 134 | UM | # | SATT040 | 4 | ** |
| 139 | UM | # | SATT111 | 3 | ** |
| 140 | UM | # | SATT176 | 3 | ** |
| 141 | UM | # | SATT219 | 9 | ** |
| 143 | UM | # | SATT299 | 5 | * |

TABLE 9

Favorable Allelic Forms: South Region

| Region | Chromosome | Position | Locus | Allele | Sig. |
|---|---|---|---|---|---|
| 2 | A1 | 14.6 | SATT165 | 2 | * |
| 2 | A1 | 19.1 | SATT042 | 3 | * |
| 2 | A1 | 19.1 | SATT042 | 4 | * |

TABLE 9-continued

Favorable Allelic Forms: South Region

| Region | Chromosome | Position | Locus | Allele | Sig. |
|---|---|---|---|---|---|
| 2 | A1 | 19.1 | SATT364 | 4 | * |
| 2 | A1 | 19.1 | SATT526 | 1 | ** |
| 3 | A1 | 27.1 | SATT300 | 3 | ** |
| 3 | A1 | 27.1 | SATT591 | 3 | * |
| 3 | A1 | 28.5 | SATT155 | 2 | ** |
| 4 | A1 | 69.9 | SATT385 | 1 | * |
| 5 | A1 | 87.3 | SATT236 | 1 | * |
| 5 | A1 | 87.3 | SATT511 | 1 | * |
| 6 | A2 | 0.0 | P12390B-1 | 1 | * |
| 7 | A2 | 20.0 | SATT480 | 1 | * |
| 9 | A2 | 108.7 | SATT329 | 2 | * |
| 14 | B1 | 26.7 | SATT509 | 6 | * |
| 17 | B1 | 71.6 | SCT_026 | 2 | ** |
| 17 | B1 | 74.1 | SATT583 | 3 | * |
| 17 | B1 | 74.8 | SATT430 | 1 | * |
| 18 | B1 | 92.1 | SATT359 | 3 | ** |
| 19 | B1 | 120.0 | P10648A-1 | 2 | * |
| 21 | B2 | 55.8 | SATT168 | 2 | * |
| 23 | B2 | 86.1 | SATT556 | 2 | * |
| 23 | B2 | 87.0 | SATT272 | 2 | * |
| 29 | C1 | 95.8 | SATT399 | 3 | * |
| 29 | C1 | 99.0 | SATT190 | 4 | * |
| 33 | C2 | 53.4 | SATT457 | 2 | * |
| 37 | C2 | 168.3 | SATT307 | 2 | * |
| 37 | C2 | 168.3 | SCT_028 | 2 | * |
| 37 | C2 | 170.5 | SATT433 | 4 | * |
| 38 | C2 | 193.5 | SATT357 | 1 | * |
| 40 | D1a | 54.7 | SATT321 | 2 | * |
| 46 | D1b | 39.8 | SATT558 | 3 | * |
| 47 | D1b | 51.6 | SATT266 | 1 | * |
| 48 | D1b | 64.3 | SATT282 | 4 | * |
| 48 | D1b | 65.1 | SATT537 | 8 | * |
| 54 | D2 | 93.8 | SATT389 | 6 | * |
| 54 | D2 | 99.6 | SATT461 | 1 | * |
| 55 | D2 | 106.6 | SATT311 | 2 | * |
| 55 | D2 | 107.8 | SATT514 | 1 | * |
| 55 | D2 | 110.4 | SATT464 | 1 | ** |
| 55 | D2 | 112.1 | SATT543 | 4 | ** |
| 56 | D2 | 139.1 | SATT186 | 1 | * |
| 60 | E | 40.0 | P13074A-1 | 1 | * |
| 61 | E | 80.0 | P10624A-1 | 2 | * |
| 62 | E | 100.6 | SATT204 | 1 | * |
| 62 | E | 101.0 | SATT491 | 3 | * |
| 62 | E | 102.2 | SATT151 | 3 | * |
| 62 | E | 102.2 | SATT355 | 3 | * |
| 62 | E | 102.2 | SATT452 | 2 | ** |
| 64 | F | 0.0 | SATT146 | 4 | ** |
| 64 | F | 0.0 | SATT569 | 3 | * |
| 64 | F | 1.7 | SATT343 | 5 | * |
| 64 | F | 1.9 | SATT586 | 2 | * |
| 67 | F | 87.5 | P3436A-1 | 2 | ** |
| 67 | F | 95.0 | SATT334 | 3 | * |
| 68 | F | 114.8 | SATT510 | 5 | ** |
| 70 | F | 157.8 | SATT144 | 1 | * |
| 73 | G | 2.0 | P10646A-1 | 2 | ** |
| 73 | G | 3.0 | P5219A-1 | 2 | * |
| 73 | G | 4.0 | P7659A-2 | 2 | * |
| 73 | G | 7.7 | SATT570 | 3 | ** |
| 73 | G | 8.5 | SATT356 | 2 | * |
| 74 | G | 13.5 | SATT130 | 2 | * |
| 75 | G | 61.3 | SATT594 | 6 | ** |
| 75 | G | 66.1 | SATT533 | 1 | * |
| 76 | G | 71.6 | SATT303 | 7 | * |
| 76 | G | 71.6 | SATT303 | 9 | ** |
| 76 | G | 72.4 | SATT352 | 10 | ** |
| 76 | G | 72.4 | SATT566 | 3 | * |
| 77 | G | 100.8 | SATT199 | 1 | ** |
| 77 | G | 103.2 | SATT503 | 3 | ** |
| 77 | G | 103.2 | SATT517 | 4 | * |
| 79 | G | 137.0 | SATT191 | 2 | * |
| 79 | G | 138.4 | SAT_117 | 1 | ** |
| 81 | H | 0.0 | SATT353 | 2 | * |
| 82 | H | 42.3 | SATT442 | 4 | ** |
| 83 | H | 77.3 | SATT279 | 5 | ** |
| 83 | H | 77.3 | SATT314 | 1 | ** |
| 86 | I | 9.8 | SATT367 | 6 | ** |
| 86 | I | 15.5 | SATT127 | 2 | * |
| 87 | I | 57.9 | SATT270 | 5 | * |
| 89 | I | 115.0 | P10640A-1 | 1 | * |
| 92 | J | 67.2 | SATT280 | 5 | ** |
| 92 | J | 70.8 | SATT380 | 3 | ** |
| 92 | J | 72.6 | SATT183 | 2 | ** |
| 93 | J | 118.0 | SATT431 | 3 | ** |
| 94 | K | 17.9 | SATT242 | 1 | ** |
| 95 | K | 44.0 | SATT102 | 2 | * |
| 98 | K | 144.0 | P10618A-1 | 1 | * |
| 98 | K | 144.3 | SATT475 | 1 | * |
| 99 | K | 164.8 | SATT196 | 4 | * |
| 101 | L | 32.4 | SATT523 | 3 | * |
| 101 | L | 33.9 | SATT418 | 4 | * |
| 103 | L | 77.1 | SATT166 | 1 | ** |
| 103 | L | 78.0 | SATT448 | 4 | * |
| 104 | L | 118.0 | SATT373 | 17 | * |
| 104 | L | 118.6 | SATT513 | 1 | ** |
| 104 | L | 124.5 | P12394A-1 | 2 | * |
| 105 | M | 12.4 | SATT590 | 2 | * |
| 108 | M | 87.6 | SATT536 | 4 | * |
| 110 | M | 139.4 | SATT250 | 1 | * |
| 113 | N | 35.4 | SATT584 | 2 | * |
| 114 | N | 61.2 | SATT387 | 5 | ** |
| 115 | N | 80.2 | SATT549 | 5 | * |
| 117 | N | 113.0 | SATT257 | 2 | * |
| 118 | O | 2.4 | P12396A-1 | 1 | * |
| 118 | O | 6.3 | SATT487 | 1 | ** |
| 119 | O | 37.7 | SATT259 | 3 | ** |
| 119 | O | 39.0 | SATT347 | 2 | * |
| 120 | O | 65.1 | SATT576 | 4 | * |
| 120 | O | 67.5 | SATT550 | 1 | * |
| 124 | O | 155.1 | SATT243 | 2 | * |
| 125 | O | 175.7 | P8230A-1 | 2 | ** |
| 126 | UM | # | P10623A-1 | 2 | * |
| 129 | UM | # | P12391A-1 | 2 | * |
| 131 | UM | # | P13561A-1 | 1 | * |
| 132 | UM | # | p2481A-1 | 1 | * |
| 133 | UM | # | SAC1677 | 3 | ** |
| 136 | UM | # | SATT108 | 1 | * |
| 139 | UM | # | SATT111 | 3 | * |
| 140 | UM | # | SATT176 | 8 | ** |
| 141 | UM | # | SATT219 | 4 | ** |
| 143 | UM | # | SATT299 | 5 | * |
| 145 | UM | # | SATT512 | 3 | * |

TABLE 10

Favorable Alleles: Iowa (A)

| Genomic Region | Chromosome | Position | Locus | Allele | Best Marker in Genomic Region | Sig. | LOD Iowa | EXP Iowa | OBS Iowa | CHG Iowa | #ELI Iowa |
|---|---|---|---|---|---|---|---|---|---|---|---|
| 2 | A1 | 19.1 | Satt042 | 3 | | ** | 2.68 | 0.13 | 0.75 | 0.62 | 67 |
| 2 | A1 | 19.1 | Satt364 | 3 | | ** | 3.22 | 0.05 | 0.72 | 0.67 | 68 |
| 2 | A1 | 19.1 | Satt454 | 1 | | ** | 3.70 | 0.05 | 0.74 | 0.69 | 69 |

TABLE 10-continued

Favorable Alleles: Iowa (A)

| Genomic Region | Chromosome | Position | Locus | Allele | Best Marker in Genomic Region | Sig. | LOD Iowa | EXP Iowa | OBS Iowa | CHG Iowa | #ELI Iowa |
|---|---|---|---|---|---|---|---|---|---|---|---|
| 2 | A1 | 19.1 | Satt526 | 1 | Best | ** | 4.00 | 0.06 | 0.79 | 0.72 | 68 |
| 3 | A1 | 27.1 | Satt300 | 3 |  | ** | 3.22 | 0.08 | 0.77 | 0.69 | 64 |
| 3 | A1 | 27.1 | Satt591 | 3 | Best | ** | 3.22 | 0.13 | 0.82 | 0.70 | 67 |
| 3 | A1 | 28.5 | Satt155 | 2 |  | ** | 2.96 | 0.18 | 0.82 | 0.64 | 66 |
| 5 | A1 | 87.3 | Satt511 | 1 | Best | * | 1.40 | 0.14 | 0.57 | 0.44 | 61 |
| 6 | A2 | 0.0 | P12390B-1 | 1 | Best | ** | 2.59 | 0.32 | 0.89 | 0.57 | 66 |
| 13 | A2 | 184.0 | Satt429 | 4 | Best | ** | 4.00 | 0.02 | 0.63 | 0.61 | 53 |
| 15 | B1 | 39.0 | Satt197 | 5 | Best | * | 1.66 | 0.22 | 0.64 | 0.41 | 48 |
| 21 | B2 | 45.0 | P10641A-1 | 2 | Best | ** | 3.22 | 0.34 | 0.94 | 0.60 | 70 |
| 25 | B2 | 110.9 | Satt534 | 7 |  | * | 1.47 | 0.49 | 0.89 | 0.40 | 61 |
| 26 | B2 | 120.0 | P10638B-2 | 1 | Best | * | 1.91 | 0.62 | 0.94 | 0.33 | 70 |
| 29 | C1 | 95.8 | Satt399 | 3 |  | ** | 4.00 | 0.08 | 0.89 | 0.81 | 61 |
| 29 | C1 | 96.5 | Satt361 | 2 |  | ** | 3.05 | 0.15 | 0.80 | 0.65 | 68 |
| 29 | C1 | 98.0 | P10639A-1 | 1 |  | ** | 3.22 | 0.19 | 0.86 | 0.66 | 63 |
| 29 | C1 | 99.0 | Satt190 | 4 | Best | ** | 4.00 | 0.05 | 0.79 | 0.73 | 65 |
| 31 | C1 | 173.0 | Satt338 | 3 | Best | * | 1.55 | 0.25 | 0.71 | 0.46 | 63 |
| 36 | C2 | 140.9 | Satt557 | 5 | Best | ** | 3.52 | 0.58 | 1.00 | 0.42 | 70 |
| 36 | C2 | 145.8 | Satt319 | 1 |  | * | 1.90 | 0.74 | 1.00 | 0.26 | 67 |
| 37 | C2 | 165.8 | Satt460 | 5 |  | * | 1.43 | 0.63 | 0.97 | 0.34 | 44 |
| 37 | C2 | 170.5 | Satt433 | 3 | Best | * | 1.59 | 0.15 | 0.48 | 0.34 | 61 |
| 38 | C2 | 193.5 | Satt357 | 1 | Best | * | 1.52 | 0.68 | 0.97 | 0.29 | 66 |
| 40 | D1a | 54.7 | Satt321 | 2 | Best | * | 1.82 | 0.19 | 0.69 | 0.50 | 66 |
| 41 | D1a | 69.8 | Satt295 | 2 | Best | * | 1.67 | 0.70 | 0.98 | 0.28 | 50 |
| 42 | D1a | 80.3 | Satt507 | 3 | Best | * | 1.37 | 0.20 | 0.63 | 0.43 | 66 |
| 43 | D1a | 129.2 | Satt129 | 5 | Best | ** | 2.89 | 0.31 | 0.93 | 0.61 | 61 |
| 43 | D1a | 129.2 | Satt147 | 1 |  | * | 1.46 | 0.69 | 0.97 | 0.28 | 62 |
| 46 | D1b | 39.8 | Satt558 | 3 | Best | * | 1.76 | 0.29 | 0.81 | 0.52 | 56 |
| 53 | D2 | 66.9 | Satt582 | 2 |  | ** | 2.89 | 0.01 | 0.28 | 0.27 | 50 |
| 54 | D2 | 93.8 | Satt389 | 6 | Best | ** | 2.46 | 0.05 | 0.53 | 0.49 | 63 |
| 55 | D2 | 110.4 | Satt464 | 1 | Best | ** | 3.40 | 0.05 | 0.67 | 0.62 | 66 |
| 62 | E | 98.0 | Satt573 | 2 |  | * | 1.72 | 0.46 | 0.91 | 0.45 | 62 |
| 62 | E | 98.0 | Satt598 | 1 | Best | ** | 2.28 | 0.38 | 0.92 | 0.54 | 66 |
| 62 | E | 100.6 | Satt263 | 2 |  | * | 1.88 | 0.07 | 0.53 | 0.46 | 59 |
| 62 | E | 101.0 | Satt602 | 4 |  | * | 1.36 | 0.12 | 0.43 | 0.31 | 61 |
| 62 | E | 102.2 | Satt151 | 4 |  | * | 1.78 | 0.05 | 0.44 | 0.40 | 60 |
| 64 | F | 0.0 | Satt146 | 1 |  | ** | 2.89 | 0.20 | 0.86 | 0.66 | 50 |
| 64 | F | 0.0 | Satt193 | 3 |  | ** | 3.70 | 0.10 | 0.84 | 0.74 | 62 |
| 64 | F | 0.0 | Satt569 | 3 |  | ** | 3.16 | 0.15 | 0.86 | 0.71 | 69 |
| 64 | F | 1.7 | Satt176 | 3 |  | ** | 4.00 | 0.09 | 0.85 | 0.76 | 71 |
| 64 | F | 1.7 | Satt343 | 3 | Best | ** | 4.00 | 0.09 | 0.89 | 0.80 | 66 |
| 64 | F | 1.9 | Satt586 | 5 |  | ** | 4.00 | 0.09 | 0.84 | 0.75 | 55 |
| 64 | F | 2.5 | Satt040 | 4 |  | ** | 3.52 | 0.09 | 0.81 | 0.73 | 67 |
| 67 | F | 85.0 | P10782A-1 | 1 | Best | ** | 3.16 | 0.27 | 0.90 | 0.64 | 70 |
| 70 | F | 157.8 | Satt144 | 1 | Best | * | 1.79 | 0.45 | 0.90 | 0.45 | 67 |
| 71 | F | 165.8 | Satt522 | 5 | Best | * | 1.48 | 0.04 | 0.32 | 0.27 | 63 |
| 73 | G | 8.5 | Satt356 | 2 | Best | * | 1.42 | 0.69 | 0.97 | 0.28 | 68 |
| 75 | G | 66.1 | Satt533 | 1 | Best | * | 1.94 | 0.43 | 0.90 | 0.46 | 68 |
| 77 | G | 100.8 | Satt199 | 1 | Best | ** | 3.22 | 0.44 | 0.98 | 0.54 | 65 |
| 77 | G | 103.2 | Satt517 | 4 |  | * | 1.54 | 0.10 | 0.54 | 0.44 | 64 |
| 79 | G | 137.0 | Satt191 | 2 |  | * | 1.65 | 0.15 | 0.62 | 0.47 | 65 |
| 79 | G | 138.4 | Sat_117 | 1 | Best | * | 1.70 | 0.20 | 0.68 | 0.48 | 66 |
| 85 | H | 125.3 | Satt181 | 5 | Best | ** | 2.14 | 0.05 | 0.61 | 0.56 | 61 |
| 86 | I | 15.5 | Satt127 | 2 | Best | * | 1.99 | 0.62 | 0.99 | 0.37 | 58 |
| 92 | J | 61.3 | Sct_065 | 2 |  | ** | 3.70 | 0.26 | 0.91 | 0.65 | 58 |
| 92 | J | 63.6 | Satt596 | 4 |  | ** | 2.47 | 0.14 | 0.79 | 0.65 | 65 |
| 92 | J | 68.0 | Satt406 | 2 | Best | ** | 3.52 | 0.18 | 0.87 | 0.69 | 66 |
| 92 | J | 70.8 | Satt380 | 3 |  | ** | 3.70 | 0.28 | 0.94 | 0.66 | 63 |
| 92 | J | 72.6 | Satt183 | 1 |  | ** | 3.30 | 0.45 | 0.97 | 0.53 | 69 |
| 92 | J | 74.4 | Satt529 | 1 |  | ** | 3.52 | 0.38 | 0.97 | 0.59 | 61 |
| 94 | K | 17.9 | Satt242 | 4 | Best | ** | 3.05 | 0.07 | 0.71 | 0.64 | 65 |
| 97 | K | 85.8 | Satt240 | 2 | Best | * | 1.49 | 0.11 | 0.52 | 0.41 | 54 |
| 101 | L | 34.6 | Satt398 | 4 | Best | ** | 2.00 | 0.33 | 0.83 | 0.50 | 51 |
| 103 | L | 77.1 | Satt166 | 3 | Best | ** | 4.00 | 0.10 | 0.90 | 0.80 | 61 |
| 103 | L | 78.0 | Satt448 | 4 |  | * | 1.46 | 0.22 | 0.68 | 0.46 | 67 |
| 104 | L | 118.0 | Satt373 | 3 |  | ** | 3.70 | 0.00 | 0.37 | 0.36 | 52 |
| 104 | L | 118.6 | Satt513 | 11 |  | * | 1.47 | 0.07 | 0.33 | 0.26 | 40 |
| 104 | L | 124.5 | P12394A-1 | 2 | Best | ** | 3.05 | 0.66 | 1.00 | 0.35 | 71 |
| 108 | M | 87.6 | Satt536 | 4 | Best | ** | 3.70 | 0.14 | 0.83 | 0.70 | 66 |
| 108 | M | 91.1 | Satt175 | 5 |  | * | 1.99 | 0.19 | 0.77 | 0.58 | 68 |
| 109 | M | 115.0 | P10615A-1 | 1 | Best | * | 1.75 | 0.10 | 0.54 | 0.44 | 70 |
| 110 | M | 143.5 | Satt346 | 3 | Best | * | 1.30 | 0.16 | 0.61 | 0.45 | 61 |
| 111 | M | 173.5 | Satt336 | 4 | Best | * | 1.63 | 0.25 | 0.71 | 0.46 | 44 |
| 112 | N | 20.0 | P13069A-1 | 3 | Best | ** | 4.00 | 0.00 | 0.31 | 0.31 | 61 |

TABLE 10-continued

Favorable Alleles: Iowa (A)

| Genomic Region | Chromosome | Position | Locus | Allele | Best Marker in Genomic Region | Sig. | LOD Iowa | EXP Iowa | OBS Iowa | CHG Iowa | #ELI Iowa |
|---|---|---|---|---|---|---|---|---|---|---|---|
| 112 | N | 25.0 | P5467A-1 | 2 | | ** | 4.00 | 0.00 | 0.26 | 0.26 | 62 |
| 115 | N | 88.6 | Satt339 | 5 | Best | * | 1.96 | 0.19 | 0.73 | 0.54 | 60 |
| 118 | O | 2.4 | P12396A-1 | 1 | | * | 1.89 | 0.64 | 0.97 | 0.33 | 66 |
| 118 | O | 6.3 | Satt487 | 4 | Best | ** | 4.00 | 0.37 | 0.97 | 0.60 | 64 |
| 119 | O | 37.7 | Satt259 | 4 | Best | ** | 3.30 | 0.37 | 0.92 | 0.55 | 63 |
| 120 | O | 60.5 | Satt420 | 2 | Best | ** | 2.28 | 0.30 | 0.85 | 0.54 | 68 |
| 120 | O | 65.1 | Satt576 | 4 | | * | 1.80 | 0.22 | 0.77 | 0.55 | 44 |
| 122 | O | 103.8 | Satt477 | 3 | Best | * | 1.32 | 0.43 | 0.83 | 0.40 | 53 |
| 123 | O | 125.0 | Satt581 | 2 | Best | ** | 2.70 | 0.35 | 0.88 | 0.53 | 69 |
| 124 | O | 153.3 | Satt153 | 3 | Best | ** | 2.96 | 0.49 | 0.94 | 0.46 | 68 |
| 124 | O | 155.1 | Satt243 | 1 | | ** | 2.17 | 0.60 | 0.96 | 0.36 | 56 |
| 129 | UM | | P12391A-1 | 1 | Best | * | 1.84 | 0.39 | 0.84 | 0.45 | 69 |
| 129 | UM | | P12392A-1 | 1 | Best | * | 1.30 | 0.55 | 0.88 | 0.33 | 69 |
| 131 | UM | | P13560A-1 | 1 | Best | * | 1.71 | 0.23 | 0.64 | 0.41 | 70 |
| 131 | UM | | P13561A-1 | 2 | Best | ** | 3.10 | 0.63 | 1.00 | 0.37 | 67 |
| 133 | UM | | Sac1677 | 3 | Best | ** | 4.00 | 0.15 | 0.90 | 0.75 | 70 |
| 139 | UM | | Satt111 | 3 | Best | ** | 4.00 | 0.08 | 0.81 | 0.74 | 67 |
| 143 | UM | | Satt299 | 5 | Best | * | 1.59 | 0.17 | 0.65 | 0.48 | 61 |

* 95% significance level
** 99% significance level

TABLE 11

Significant Alleles at the "Best" marker locus in each genomic region.

| Region | Chromosome | Position | Locus | Allele | SIGNIF Iowa | LOD Iowa | EXP Iowa | OBS Iowa | CHG Iowa | #ELI Iowa |
|---|---|---|---|---|---|---|---|---|---|---|
| 2 | A1 | 19.1 | Satt526 | 1 | ** | 4.00 | 0.06 | 0.79 | 0.72 | 68 |
| 3 | A1 | 27.1 | Satt591 | 3 | ** | 3.22 | 0.13 | 0.82 | 0.70 | 67 |
| 5 | A1 | 87.3 | Satt511 | 1 | * | 1.40 | 0.14 | 0.57 | 0.44 | 61 |
| 6 | A2 | 0.0 | P12390B-1 | 1 | ** | 2.59 | 0.32 | 0.89 | 0.57 | 66 |
| 13 | A2 | 184.0 | Satt429 | 4 | ** | 4.00 | 0.02 | 0.63 | 0.61 | 53 |
| 15 | B1 | 39.0 | Satt197 | 5 | * | 1.66 | 0.22 | 0.64 | 0.41 | 48 |
| 21 | B2 | 45.0 | P10641A-1 | 2 | ** | 3.22 | 0.34 | 0.94 | 0.60 | 70 |
| 25 | B2 | 110.9 | Satt534 | 7 | * | 1.47 | 0.49 | 0.89 | 0.40 | 61 |
| 26 | B2 | 120.0 | P10638B-2 | 1 | * | 1.91 | 0.62 | 0.94 | 0.33 | 70 |
| 29 | C1 | 99.0 | Satt190 | 4 | ** | 4.00 | 0.05 | 0.79 | 0.73 | 65 |
| 31 | C1 | 173.0 | Satt338 | 3 | * | 1.55 | 0.25 | 0.71 | 0.46 | 63 |
| 36 | C2 | 140.9 | Satt557 | 5 | ** | 3.52 | 0.58 | 1.00 | 0.42 | 70 |
| 37 | C2 | 170.5 | Satt433 | 3 | * | 1.59 | 0.15 | 0.48 | 0.34 | 61 |
| 38 | C2 | 193.5 | Satt357 | 1 | * | 1.52 | 0.68 | 0.97 | 0.29 | 66 |
| 40 | D1a | 54.7 | Satt321 | 2 | * | 1.82 | 0.19 | 0.69 | 0.50 | 66 |
| 41 | D1a | 69.8 | Satt295 | 2 | * | 1.67 | 0.70 | 0.98 | 0.28 | 50 |
| 42 | D1a | 80.3 | Satt507 | 3 | * | 1.37 | 0.20 | 0.63 | 0.43 | 66 |
| 43 | D1a | 129.2 | Satt129 | 5 | ** | 2.89 | 0.31 | 0.93 | 0.61 | 61 |
| 46 | D1b | 39.8 | Satt558 | 3 | * | 1.76 | 0.29 | 0.81 | 0.52 | 56 |
| 54 | D2 | 93.8 | Satt389 | 6 | ** | 2.46 | 0.05 | 0.53 | 0.49 | 63 |
| 55 | D2 | 110.4 | Satt464 | 1 | ** | 3.40 | 0.05 | 0.67 | 0.62 | 66 |
| 62 | E | 98.0 | Satt598 | 1 | ** | 2.28 | 0.38 | 0.92 | 0.54 | 66 |
| 64 | F | 1.7 | Satt343 | 3 | ** | 4.00 | 0.09 | 0.89 | 0.80 | 66 |
| 67 | F | 85.0 | P10782A-1 | 1 | ** | 3.16 | 0.27 | 0.90 | 0.64 | 70 |
| 70 | F | 157.8 | Satt144 | 1 | * | 1.79 | 0.45 | 0.90 | 0.45 | 67 |
| 71 | F | 165.8 | Satt522 | 5 | * | 1.48 | 0.04 | 0.32 | 0.27 | 63 |
| 73 | G | 8.5 | Satt356 | 2 | * | 1.42 | 0.69 | 0.97 | 0.28 | 68 |
| 75 | G | 66.1 | Satt533 | 1 | * | 1.94 | 0.43 | 0.90 | 0.46 | 68 |
| 77 | G | 100.8 | Satt199 | 1 | ** | 3.22 | 0.44 | 0.98 | 0.54 | 65 |
| 79 | G | 138.4 | Sat_117 | 1 | * | 1.70 | 0.20 | 0.68 | 0.48 | 66 |
| 85 | H | 125.3 | Satt181 | 5 | ** | 2.14 | 0.05 | 0.61 | 0.56 | 61 |
| 86 | I | 15.5 | Satt127 | 2 | * | 1.99 | 0.62 | 0.99 | 0.37 | 58 |
| 92 | J | 68.0 | Satt406 | 2 | ** | 3.52 | 0.18 | 0.87 | 0.69 | 66 |
| 94 | K | 17.9 | Satt242 | 4 | ** | 3.05 | 0.07 | 0.71 | 0.64 | 65 |
| 97 | K | 85.8 | Satt240 | 2 | * | 1.49 | 0.11 | 0.52 | 0.41 | 54 |
| 101 | L | 34.6 | Satt398 | 4 | ** | 2.00 | 0.33 | 0.83 | 0.50 | 51 |
| 103 | L | 77.1 | Satt166 | 3 | ** | 4.00 | 0.10 | 0.90 | 0.80 | 61 |
| 104 | L | 124.5 | P12394A-1 | 2 | ** | 3.05 | 0.66 | 1.00 | 0.35 | 71 |
| 108 | M | 87.6 | Satt536 | 4 | ** | 3.70 | 0.14 | 0.83 | 0.70 | 66 |
| 109 | M | 115.0 | P10615A-1 | 1 | * | 1.75 | 0.10 | 0.54 | 0.44 | 70 |
| 110 | M | 143.5 | Satt346 | 3 | * | 1.30 | 0.16 | 0.61 | 0.45 | 61 |
| 111 | M | 173.5 | Satt336 | 4 | * | 1.63 | 0.25 | 0.71 | 0.46 | 44 |

TABLE 11-continued

Significant Alleles at the "Best" marker locus in each genomic region.

| Region | Chromosome | Position | Locus | Allele | SIGNIF Iowa | LOD Iowa | EXP Iowa | OBS Iowa | CHG Iowa | #ELI Iowa |
|---|---|---|---|---|---|---|---|---|---|---|
| 112 | N | 20.0 | P13069A-1 | 3 | ** | 4.00 | 0.00 | 0.31 | 0.31 | 61 |
| 115 | N | 88.6 | Satt339 | 5 | * | 1.96 | 0.19 | 0.73 | 0.54 | 60 |
| 118 | O | 6.3 | Satt487 | 4 | ** | 4.00 | 0.37 | 0.97 | 0.60 | 64 |
| 119 | O | 37.7 | Satt259 | 4 | ** | 3.30 | 0.37 | 0.92 | 0.55 | 63 |
| 120 | O | 60.5 | Satt420 | 2 | ** | 2.28 | 0.30 | 0.85 | 0.54 | 68 |
| 122 | O | 103.8 | Satt477 | 3 | * | 1.32 | 0.43 | 0.83 | 0.40 | 53 |
| 123 | O | 125.0 | Satt581 | 2 | ** | 2.70 | 0.35 | 0.88 | 0.53 | 69 |
| 124 | O | 153.3 | Satt153 | 3 | ** | 2.96 | 0.49 | 0.94 | 0.46 | 68 |
| 129 | UM | | P12391A-1 | 1 | * | 1.84 | 0.39 | 0.84 | 0.45 | 69 |
| 129 | UM | | P12392A-1 | 1 | * | 1.30 | 0.55 | 0.88 | 0.33 | 69 |
| 131 | UM | | P13560A-1 | 1 | * | 1.71 | 0.23 | 0.64 | 0.41 | 70 |
| 131 | UM | | P13561A-1 | 2 | ** | 3.10 | 0.63 | 1.00 | 0.37 | 67 |
| 133 | UM | | Satt677 | 3 | ** | 4.00 | 0.15 | 0.90 | 0.75 | 70 |
| 139 | UM | | Satt111 | 3 | ** | 4.00 | 0.08 | 0.81 | 0.74 | 67 |
| 143 | UM | | Satt299 | 5 | * | 1.59 | 0.17 | 0.65 | 0.48 | 61 |

* 95% significance level
** 99% significance level

TABLE 12

Favorable Alleles: Iowa (B)

| Genomic Region | Chromosome | Position | Locus | Allele | New Marker in Genomic Region | Best Marker in Genomic Region | Sig. | LOD Iowa | EXP Iowa | OBS Iowa | CHG Iowa | #ELI Iowa |
|---|---|---|---|---|---|---|---|---|---|---|---|---|
| 1 | A1 | 1.4 | Satt684 | 3 | NEW | Best | * | 1.84 | 0.03 | 0.36 | 0.36 | 79 |
| 2 | A1 | 19.1 | Satt042 | 3 | | | ** | 2.66 | 0.14 | 0.77 | 0.64 | 82 |
| 2 | A1 | 19.1 | Satt364 | 3 | | | ** | 3.16 | 0.05 | 0.70 | 0.65 | 65 |
| 2 | A1 | 19.1 | Satt454 | 1 | | | ** | 3.40 | 0.06 | 0.71 | 0.64 | 66 |
| 2 | A1 | 19.1 | Satt526 | 1 | | Best | ** | 4.00 | 0.07 | 0.77 | 0.70 | 86 |
| 3 | A1 | 27.1 | Satt300 | 3 | | | ** | 3.30 | 0.11 | 0.79 | 0.68 | 82 |
| 3 | A1 | 27.1 | Satt591 | 3 | | Best | ** | 3.40 | 0.15 | 0.83 | 0.69 | 81 |
| 3 | A1 | 28.5 | Satt155 | 2 | | | ** | 2.89 | 0.18 | 0.83 | 0.65 | 81 |
| 4 | A1 | 69.9 | Satt385 | 1 | | Best | * | 1.99 | 0.44 | 0.91 | 0.48 | 80 |
| 7.5 | A2 | 41.8 | Satt632-TB | 4 | NEW | Best | * | 1.88 | 0.66 | 1.00 | 0.34 | 41 |
| 13 | A2 | 184.0 | Satt429 | 4 | | Best | ** | 4.00 | 0.04 | 0.80 | 0.76 | 76 |
| 14 | B1 | 27.6 | SAT_261 | 1 | NEW | Best | ** | 2.42 | 0.49 | 1.00 | 0.51 | 28 |
| 21 | B2 | 45.0 | P10641A-1 | 2 | | Best | ** | 3.70 | 0.34 | 0.99 | 0.65 | 86 |
| 23 | B2 | 86.1 | Satt556 | 2 | | Best | * | 1.73 | 0.16 | 0.75 | 0.59 | 76 |
| 26 | B2 | 120.0 | P10638B-2 | 1 | | Best | * | 1.30 | 0.63 | 0.93 | 0.30 | 85 |
| 29 | C1 | 95.8 | Satt399 | 3 | | | ** | 4.00 | 0.07 | 0.89 | 0.82 | 77 |
| 29 | C1 | 96.5 | Satt361 | 2 | | | ** | 3.30 | 0.16 | 0.83 | 0.67 | 64 |
| 29 | C1 | 99.0 | SATT661-TB | 2 | NEW | | * | 1.68 | 0.39 | 0.94 | 0.55 | 59 |
| 29 | C1 | 99.0 | Satt190 | 4 | | Best | ** | 4.00 | 0.05 | 0.83 | 0.78 | 79 |
| 30 | C1 | 117.6 | SAT_311-DB | 3 | NEW | Best | * | 1.72 | 0.45 | 0.92 | 0.47 | 56 |
| 31 | C1 | 173.0 | Satt338 | 3 | | Best | * | 1.49 | 0.24 | 0.67 | 0.43 | 47 |
| 32 | C2 | 28.6 | SATT640-TB | 3 | NEW | Best | * | 1.50 | 0.57 | 0.98 | 0.41 | 45 |
| 36 | C2 | 140.9 | Satt557 | 5 | | Best | ** | 2.68 | 0.61 | 1.00 | 0.28 | 84 |
| 36 | C2 | 145.8 | Satt319 | 1 | | | * | 1.66 | 0.72 | 1.00 | 0.28 | 84 |
| 36.5 | C2 | 153.5 | SAT_142-DB | 3 | NEW | Best | ** | 2.44 | 0.58 | 1.00 | 0.42 | 62 |
| 40 | D1a | 54.7 | Satt321 | 2 | | Best | * | 1.52 | 0.17 | 0.64 | 0.47 | 82 |
| 42 | D1a | 73.1 | Satt203 | 4 | | Best | * | 1.54 | 0.07 | 0.42 | 0.35 | 76 |
| 43 | D1a | 129.2 | Satt129 | 5 | | Best | ** | 3.52 | 0.36 | 0.99 | 0.63 | 75 |
| 43 | D1a | 129.2 | Satt147 | 1 | | | * | 1.85 | 0.70 | 1.00 | 0.30 | 63 |
| 45 | D1b | 19.1 | SAT_351 | 3 | NEW | Best | ** | 2.08 | 0.14 | 0.73 | 0.59 | 66 |
| 45 | D1b | 20.0 | P10621B-2 | 2 | NEW | | * | 1.51 | 0.60 | 0.96 | 0.36 | 86 |
| 46 | D1b | 36.7 | Satt701 | 2 | NEW | Best | * | 1.97 | 0.15 | 0.59 | 0.44 | 27 |
| 46 | D1b | 39.8 | Satt634 | 3 | NEW | | * | 1.40 | 0.44 | 0.89 | 0.45 | 27 |
| 53 | D2 | 66.9 | Satt582 | 2 | | Best | * | 1.33 | 0.06 | 0.37 | 0.31 | 78 |
| 54 | D2 | 93.8 | Satt389 | 6 | | Best | * | 1.35 | 0.11 | 0.48 | 0.37 | 81 |
| 55 | D2 | 110.4 | Satt464 | 1 | | Best | ** | 4.00 | 0.05 | 0.75 | 0.70 | 83 |
| 55 | D2 | 111.8 | Satt662 | 1 | NEW | | ** | 2.08 | 0.06 | 0.65 | 0.59 | 27 |
| 57 | D2 | 149.1 | Satt672 | 1 | NEW | Best | * | 1.64 | 0.15 | 0.57 | 0.42 | 27 |
| 62 | E | 98.0 | Satt573 | 2 | | | * | 1.83 | 0.45 | 0.92 | 0.47 | 61 |
| 62 | E | 98.0 | Satt598 | 1 | | Best | * | 1.92 | 0.49 | 0.95 | 0.46 | 73 |
| 62 | E | 100.6 | Satt263 | 2 | | | * | 1.42 | 0.11 | 0.49 | 0.38 | 58 |
| 62 | E | 102.2 | Satt151 | 4 | | | * | 1.39 | 0.08 | 0.44 | 0.36 | 79 |
| 62 | E | 103.7 | SAT_273-DB | 1 | NEW | | * | 1.59 | 0.11 | 0.59 | 0.48 | 62 |
| 64 | F | 0.0 | Satt146 | 1 | | | ** | 3.10 | 0.20 | 0.89 | 0.70 | 75 |
| 64 | F | 0.0 | Satt193 | 3 | | | ** | 3.70 | 0.09 | 0.86 | 0.77 | 62 |

TABLE 12-continued

Favorable Alleles: Iowa (B)

| Genomic Region | Chromosome | Position | Locus | Allele | New Marker in Genomic Region | Best Marker in Genomic Region | Sig. | LOD Iowa | EXP Iowa | OBS Iowa | CHG Iowa | #ELI Iowa |
|---|---|---|---|---|---|---|---|---|---|---|---|---|
| 64 | F | 0.0 | Satt569 | 3 | | | ** | 3.30 | 0.18 | 0.91 | 0.73 | 64 |
| 64 | F | 1.7 | Satt343 | 3 | | Best | ** | 3.70 | 0.08 | 0.89 | 0.81 | 74 |
| 64 | F | 1.9 | Satt586 | 5 | | | ** | 3.10 | 0.08 | 0.82 | 0.74 | 70 |
| 64 | F | 2.5 | Satt040 | 4 | | | ** | 3.16 | 0.08 | 0.81 | 0.73 | 62 |
| 66 | F | 57.5 | Satt595 | 1 | NEW | Best | ** | 2.35 | 0.69 | 1.00 | 0.31 | 75 |
| 67 | F | 95.0 | Satt334 | 3 | NEW | Best | * | 1.55 | 0.15 | 0.63 | 0.48 | 73 |
| 70 | F | 157.8 | Satt144 | 1 | | Best | * | 1.77 | 0.46 | 0.93 | 0.47 | 84 |
| 71 | F | 165.8 | Satt522 | 5 | | Best | * | 1.32 | 0.06 | 0.37 | 0.31 | 77 |
| 73 | G | 7.7 | Satt570 | 3 | NEW | Best | ** | 3.70 | 0.00 | 0.27 | 0.27 | 82 |
| 73 | G | 8.5 | Satt356 | 2 | | Best | * | 1.30 | 0.68 | 0.98 | 0.30 | 62 |
| 77 | G | 100.8 | Satt199 | 1 | | Best | * | 1.61 | 0.45 | 0.89 | 0.44 | 81 |
| 77 | G | 103.2 | Satt517 | 4 | | | * | 1.59 | 0.07 | 0.51 | 0.44 | 58 |
| 79 | G | 137.0 | Satt191 | 2 | | | * | 1.39 | 0.18 | 0.63 | 0.44 | 80 |
| 79 | G | 138.4 | Sat_117 | 1 | | Best | * | 1.89 | 0.23 | 0.77 | 0.54 | 77 |
| 83 | H | 77.3 | Satt279 | 6 | NEW | Best | * | 2.02 | 0.40 | 0.90 | 0.50 | 63 |
| 85 | H | 125.3 | Satt181 | 5 | | Best | ** | 3.06 | 0.05 | 0.72 | 0.66 | 76 |
| 86 | I | 15.5 | Satt127 | 2 | | Best | ** | 2.36 | 0.64 | 1.00 | 0.36 | 77 |
| 87 | I | 57.9 | Satt270 | 12 | NEW | Best | ** | 2.28 | 0.00 | 0.04 | 0.04† | 82 |
| 88 | I | 77.4 | Satt292 | 3 | NEW | Best | * | 1.84 | 0.06 | 0.56 | 0.50 | 64 |
| 90 | J | 19.6 | SAG1223 | 4 | NEW | Best | ** | 2.59 | 0.22 | 0.89 | 0.67 | 27 |
| 90 | J | 26.4 | SAC1699 | 3 | NEW | | ** | 1.96 | 0.04 | 0.62 | 0.58 | 74 |
| 91.5 | J | 61.3 | Sat_065 | 2 | | Best | ** | 4.00 | 0.23 | 0.96 | 0.73 | 65 |
| 91.5 | J | 63.6 | Satt596 | 4 | | | * | 1.77 | 0.24 | 0.80 | 0.56 | 64 |
| 92 | J | 68.0 | Satt406 | 2 | | | ** | 3.05 | 0.19 | 0.89 | 0.70 | 77 |
| 92 | J | 70.8 | Satt380 | 3 | | | ** | 2.80 | 0.29 | 0.91 | 0.63 | 69 |
| 92 | J | 72.6 | Satt183 | 1 | | | ** | 2.52 | 0.43 | 0.96 | 0.53 | 84 |
| 92 | J | 74.4 | Satt529 | 1 | | Best | ** | 3.22 | 0.43 | 0.99 | 0.56 | 73 |
| 94 | K | 17.9 | Satt242 | 4 | | Best | ** | 3.05 | 0.07 | 0.71 | 0.64 | 65 |
| 97 | K | 83.7 | Satt617 | 6 | NEW | Best | * | 1.68 | 0.08 | 0.60 | 0.53 | 24 |
| 97 | K | 85.8 | Satt240 | 2 | | | * | 1.57 | 0.05 | 0.60 | 0.45 | 74 |
| 100 | L | 15.6 | SAT_301 | 5 | NEW | Best | * | 1.97 | 0.22 | 0.83 | 0.61 | 78 |
| 101 | L | 33.9 | Satt418 | 2 | NEW | | * | 1.44 | 0.56 | 0.94 | 0.37 | 63 |
| 101 | L | 34.6 | Satt398 | 4 | | Best | ** | 3.22 | 0.34 | 0.94 | 0.61 | 71 |
| 102 | L | 42.3 | Satt497 | 3 | NEW | Best | * | 1.66 | 0.60 | 0.96 | 0.36 | 78 |
| 103 | L | 77.1 | Satt166 | 3 | | Best | ** | 3.22 | 0.11 | 0.86 | 0.75 | 80 |
| 103 | L | 78.0 | Satt448 | 4 | | | * | 1.80 | 0.22 | 0.74 | 0.52 | 65 |
| 104 | L | 118.0 | Satt373 | 3 | | Best | ** | 4.00 | 0.02 | 0.44 | 0.42 | 79 |
| 104 | L | 118.6 | Satt513 | 5 | | | ** | 2.51 | 0.02 | 0.24 | 0.22† | 64 |
| 104 | L | 124.5 | P12394A-1 | 2 | | | ** | 2.64 | 0.68 | 1.00 | 0.32 | 85 |
| 107 | M | 84.2 | SAG1048 | 2 | NEW | Best | ** | 4.00 | 0.01 | 0.69 | 0.68 | 76 |
| 108 | M | 87.6 | Satt536 | 4 | | | ** | 2.12 | 0.12 | 0.69 | 0.58 | 83 |
| 108 | M | 91.1 | Satt175 | 5 | | | * | 1.76 | 0.18 | 0.75 | 0.57 | 78 |
| 108 | M | 98.1 | Satt677 | 2 | NEW | | * | 1.34 | 0.56 | 0.96 | 0.40 | 28 |
| 108 | M | 100.5 | Satt680 | 2 | NEW | Best | ** | 3.22 | 0.13 | 0.86 | 0.73 | 71 |
| 109 | M | 115.0 | P10615A-1 | 1 | | Best | * | 1.96 | 0.09 | 0.58 | 0.50 | 85 |
| 109 | M | 127.3 | Satt551 | 3 | NEW | | * | 1.62 | 0.04 | 0.49 | 0.45 | 59 |
| 111 | M | 180.5 | SAT_330-DB | 1 | NEW | Best | ** | 3.00 | 0.16 | 0.85 | 0.69 | 61 |
| 112 | N | 20.0 | P13069A-1 | 3 | | Best | ** | 4.00 | 0.00 | 0.44 | 0.44 | 84 |
| 112 | N | 25.0 | P5467A-1 | 2 | NEW | | ** | 4.00 | 0.00 | 0.45 | 0.45 | 83 |
| 112 | N | 25.0 | P5467A-2 | 1 | | | * | 1.72 | 0.21 | 0.63 | 0.42 | 86 |
| 113 | N | 38.3 | SAT_084 | 2 | NEW | | * | 1.37 | 0.13 | 0.55 | 0.42 | 68 |
| 113 | N | 40.2 | SAT_275-DB | 2 | NEW | Best | * | 1.89 | 0.17 | 0.73 | 0.55 | 62 |
| 115 | N | 83.4 | Satt660 | 2 | NEW | | ** | 2.34 | 0.10 | 0.77 | 0.67 | 28 |
| 115 | N | 88.6 | Satt339 | 5 | | Best | ** | 2.44 | 0.17 | 0.77 | 0.60 | 80 |
| 118 | O | 2.4 | Satt358 | 2 | | | ** | 2.35 | 0.03 | 0.44 | 0.41 | 75 |
| 118 | O | 6.3 | Satt487 | 1 | | | ** | 2.33 | 0.00 | 0.02 | 0.02† | 84 |
| 118 | O | 6.3 | Satt487 | 4 | | Best | ** | 2.30 | 0.37 | 0.89 | 0.52 | 84 |
| 120 | O | 60.5 | Satt420 | 2 | | Best | * | 1.95 | 0.33 | 0.85 | 0.52 | 84 |
| 120 | O | 65.1 | Satt576 | 4 | | | * | 1.49 | 0.20 | 0.74 | 0.54 | 54 |
| 120 | O | 68.9 | Satt633 | 1 | NEW | | * | 1.40 | 0.25 | 0.72 | 0.47 | 27 |
| 123 | O | 125.0 | Satt581 | 2 | | Best | ** | 2.31 | 0.35 | 0.89 | 0.54 | 85 |
| 124 | O | 153.3 | Satt153 | 3 | | Best | ** | 2.75 | 0.49 | 0.96 | 0.47 | 84 |
| 124 | O | 155.1 | Satt243 | 1 | | | * | 1.82 | 0.61 | 0.97 | 0.36 | 68 |
| UM | UM | | P10793A-1 | 2 | | | * | 1.40 | 0.10 | 0.52 | 0.43 | 86 |
| UM | UM | | P13560A-1 | 1 | | | * | 1.42 | 0.22 | 0.60 | 0.38 | 86 |
| UM | UM | | P13561A-1 | 2 | | | ** | 2.51 | 0.64 | 1.00 | 0.36 | 82 |
| UM | UM | | S60021-TB | 1 | NEW | | * | 1.32 | 0.53 | 0.95 | 0.41 | 28 |
| UM | UM | | S60048-TB | 2 | NEW | | ** | 2.00 | 0.60 | 1.00 | 0.40 | 28 |
| UM | UM | | S60076-TB | 1 | NEW | | * | 1.35 | 0.59 | 0.93 | 0.34 | 28 |
| UM | UM | | S60148-TB | 2 | NEW | | ** | 2.22 | 0.52 | 0.96 | 0.45 | 28 |
| UM | UM | | S60149-TB | 1 | NEW | | * | 1.46 | 0.36 | 0.86 | 0.50 | 28 |
| UM | UM | | S60201-TB | 1 | NEW | | ** | 2.35 | 0.24 | 0.89 | 0.65 | 28 |

TABLE 12-continued

Favorable Alleles: Iowa (B)

| Genomic Region | Chromosome | Position | Locus | Allele | New Marker in Genomic Region | Best Marker in Genomic Region | Sig. | LOD Iowa | EXP Iowa | OBS Iowa | CHG Iowa | #ELI Iowa |
|---|---|---|---|---|---|---|---|---|---|---|---|---|
| UM | UM |  | S60243-TB | 3 | NEW |  | ** | 2.92 | 0.27 | 0.93 | 0.66 | 28 |
| UM | UM |  | S60326-TB | 2 | NEW |  | ** | 2.11 | 0.43 | 0.96 | 0.54 | 27 |
| UM | UM |  | S60338-TB | 1 | NEW |  | ** | 2.60 | 0.51 | 1.00 | 0.49 | 25 |
| UM | UM |  | S60350-TB | 3 | NEW |  | ** | 2.64 | 0.08 | 0.75 | 0.67 | 26 |
| UM | UM |  | S60361-TB | 2 | NEW |  | ** | 3.22 | 0.14 | 0.88 | 0.74 | 25 |
| UM | UM |  | S60422-TB | 1 | NEW |  | ** | 2.17 | 0.52 | 1.00 | 0.48 | 27 |
| UM | UM |  | S60440-TB | 2 | NEW |  | * | 1.63 | 0.06 | 0.59 | 0.53 | 28 |
| UM | UM |  | S60446-TB | 2 | NEW |  | ** | 2.80 | 0.51 | 1.00 | 0.49 | 28 |
| UM | UM |  | S60505-TB | 1 | NEW |  | ** | 2.03 | 0.51 | 1.00 | 0.49 | 26 |
| UM | UM |  | S60513-TB | 2 | NEW |  | * | 1.70 | 0.52 | 0.96 | 0.45 | 28 |
| UM | UM |  | S60519-TB | 2 | NEW |  | ** | 3022 | 0.44 | 1.00 | 0.56 | 28 |
| UM | UM |  | S60536-TB | 1 | NEW |  | ** | 2.64 | 0.43 | 1.00 | 0.57 | 28 |
| UM | UM |  | S60552-TB | 2 | NEW |  | * | 1.69 | 0.31 | 0.88 | 0.56 | 28 |
| UM | UM |  | S60585-TB | 4 | NEW |  | * | 1.45 | 0.56 | 0.96 | 0.40 | 27 |
| UM | UM |  | S60630-TB | 3 | NEW |  | * | 1.48 | 0.32 | 0.89 | 0.57 | 26 |
| UM | UM |  | S60728-TB | 3 | NEW |  | * | 1.46 | 0.45 | 0.91 | 0.46 | 28 |
| UM | UM |  | S60812-TB | 1 | NEW |  | * | 1.51 | 0.40 | 0.87 | 0.47 | 27 |
| UM | UM |  | SAC1677 | 3 |  |  | ** | 2.85 | 0.16 | 0.82 | 0.66 | 84 |
| UM | UM |  | SAC1724 | 3 | NEW |  | * | 1.49 | .64 | 1.00 | 0.36 | 27 |
| UM | UM |  | SAG1055 | 5 | NEW |  | * | 1.62 | 0.65 | 1.00 | 0.35 | 28 |
| UM | UM |  | Satt111 | 3 |  |  | ** | 4.00 | .40 | 0.90 | .80 | 83 |
| UM | UM |  | Satt219 | 4 | NEW |  | * | 1.42 | 0.05 | 0.42 | 0.37 | 80 |
| UM | UM |  | Satt299 | 10 | NEW |  | * | 1.38 | 0.65 | 0.35 | 0.30 | 79 |

* 95% significance level
** 99% significance level
†LOD greater than 2.0, increase in frequency less than 25%.

TABLE 13

Favorable Alleles in A3127

| Chromosome | Position | Allele | Parent 1 WILLIAMS | Parent 2 ESSEX | Progeny A3127 | Probability of inheriting "+" allele |
|---|---|---|---|---|---|---|
| A1 | 19.1 | 1 | − | + | + | 0.5 |
| A1 | 27.1 | 3 | + | − | + | 0.5 |
| A2 | 0.0 | 1 | − | + | + | 0.5 |
| A2 | 184.0 | 4 | + | − | + | 0.5 |
| B2 | 45.0 | 2 | + | − | + | 0.5 |
| C1 | 99.0 | 4 | − | + | + | 0.5 |
| C2 | 140.9 | 5 | + | − | + | 0.5 |
| D1a | 129.2 | 5 | + | − | + | 0.5 |
| D2 | 93.8 | 6 | − |  | + | 0.5 |
| D2 | 110.4 | 1 | − | + | + | 0.5 |
| E | 98.0 | 1 | − | + | + | 0.5 |
| F | 1.7 | 3 | + | − | + | 0.5 |
| F | 85.0 | 1 | + | − | + | 0.5 |
| G | 100.8 | 1 | − | + | + | 0.5 |
| H | 125.3 | 5 | + | − | + | 0.5 |
| J | 68.0 | 2 | not segregating |  |  |  |
| K | 17.9 | 4 | + | − | + | 0.5 |
| L | 34.6 | 4 | not segregating |  |  |  |
| L | 77.1 | 3 | + | − | + | 0.5 |
| L | 124.5 | 2 | not segregating |  |  |  |
| M | 87.6 | 4 | − | + | + | 0.5 |
| N | 20.0 | 3 | not segregating |  |  |  |
| O | 6.3 | 4 | not segregating |  |  |  |
| O | 37.7 | 4 | not segregating |  |  |  |
| O | 60.5 | 2 | not segregating |  |  |  |
| O | 125.0 | 2 | + | − | + | 0.5 |
| O | 153.3 | 3 | + | − | + | 0.5 |
| UM | # | 2 | + | − | + | 0.5 |
| UM | # | 3 | − | + | + | 0.5 |
| UM | # | 3 | − | + | + | 0.5 |
|  |  | # of "+" alleles → | 13 | 10 | all 23 | 0.000000119 |
|  |  |  | chance of this happening by chance = |  | 1 in 8,388,608 |  |

TABLE 14

| | SATT591 | SATT429 | SATT144 | SATT270 | SATT529 | SATT166 | # of sublines |
|---|---|---|---|---|---|---|---|
| Elite line | | | segregating alleles at the above marker loci | | | | |
| ***91B91 | | | | | 1 and 2 | 3 and 5 | 4 |
| 92M70 | | | 1 and 2 | 2 and 5 | | | 4 |
| 92B05 | | 3 and 4 | | | | | 2 |
| 93B01 | 1 and 3 | | | | | | 2 |
| 93M80 | | | | 5 and 12 | | | 2 |
| 93M90 | 1 and 3 | | | | | | 2 |

TABLE 15

Isoline seed yield means from field tests

| Original Elite Line | Subline Name | Genotype (allele) at indicated marker locus | | # of plants bulked to form Isoline | # of reps (locations) | Mean Seed Yield (bu/ac) | Statistical grouping | Yield advantage of better subline (bu/ac and %) |
|---|---|---|---|---|---|---|---|---|
| | | SATT529 | SATT166 | | | LSD (0.05) = 2.30 | | |
| 91B91 | 91B91-13 | 1 | 3 | 42 | 7 | 37.5 | A | |
| 91B91 | 91B91-15 | 1 | 5 | 24 | 7 | 38.0 | A | |
| 91B91 | 91B91-23 | 2 | 3 | 14 | 7 | 38.8 | A | |
| 91B91 | 91B91-25 | 2 | 5 | 7 | 7 | 37.2 | A | |
| | | SATT144 | SATT270 | | | LSD (0.05) = 3.48 | | |
| 92M70 | 92M70-12 | 1 | 2 | 14 | 10 | 43.4 | A | |
| 92M70 | 92M70-15 | 1 | 5 | 46 | 10 | 44.4 | A | |
| 92M70 | 92M70-22 | 2 | 2 | 13 | 10 | 43.0 | A | |
| 92M70 | 92M70-25 | 2 | 5 | 15 | 10 | 43.8 | A | |
| | | SATT429 | | | | LSD (0.05) = 2.01 | | |
| 92B05 | 92B05-3 | 3 | | 175 | 5 | 37.0 | A | |
| 92B05 | 92B05-4 | 4 | | 116 | 5 | 37.0 | A | |
| | | SATT591 | | | | LSD (0.05) = 1.71 | | |
| 93B01 | 93B01-1 | 1 | | 51 | 13 | 38.0 | B | |
| 93B01 | 93B01-3 | 3 | | 28 | 13 | 40.1 | A | 2.1 bu = 5.4% |
| | | SATT270 | | | | LSD (0.05) = 2.54 | | |
| 93M80 | 93M80-12 | 12 | | 5 | 14 | 48.5 | B | |
| 93M80 | 93M80-5 | 5 | | 4 | 14 | 51.3 | A | 2.8 bu = 5.6% |
| | | SATT591 | | | | LSD (0.05) = 2.16 | | |
| 93M90 | 93M90-1 | 1 | | 38 | 14 | 50.2 | A | 3.0 bu = 6.2% |
| 93M90 | 93M90-3 | 3 | | 47 | 14 | 47.2 | B | |

APPENDIX I

Allele Definition Table
23 pages

| Marker | Allele | Size | Range bp |
|---|---|---|---|
| Sac1006 | 1 | 91.54 | 92.48 |
| Sac1006 | 2 | 93.67 | 94.41 |
| Sac1006 | 3 | 105.49 | 106.22 |
| Sac1677 | 1 | 191.96 | 192.46 |
| Sac1677 | 2 | 193.94 | 194.93 |
| Sac1677 | 3 | 205.90 | 206.91 |
| Sac1677 | 4 | 332.86 | 333.35 |
| Sac1677 | 5 | 190.20 | 190.40 |
| Sac1677 | 6 | 204.40 | 204.60 |
| Sat_084 | 1 | 151.69 | 152.30 |
| Sat_084 | 2 | 153.28 | 154.30 |
| Sat_084 | 3 | 157.85 | 158.85 |
| Sat_084 | 4 | 163.84 | 164.82 |
| Sat_084 | 5 | 172.09 | 172.56 |
| Sat_084 | 6 | 160.26 | 160.46 |
| Sat_090 | 1 | 336.52 | 337.36 |
| Sat_090 | 2 | 349.84 | 350.92 |
| Sat_090 | 3 | 355.55 | 356.29 |
| Sat_090 | 4 | 338.64 | 339.23 |
| Sat_090 | 5 | 340.79 | 340.09 |
| Sat_090 | 6 | 348.04 | 348.57 |
| Sat_090 | 7 | 351.54 | 352.37 |
| Sat_090 | 8 | 353.79 | 354.12 |
| Sat_090 | 9 | 357.22 | 357.86 |
| Sat_104 | 1 | 266.36 | 267.50 |
| Sat_104 | 2 | 284.72 | 285.73 |
| Sat_110 | 1 | 165.79 | 166.96 |
| Sat_110 | 2 | 179.85 | 180.32 |
| Sat_110 | 3 | 181.88 | 183.02 |
| Sat_110 | 4 | 183.72 | 184.58 |
| Sat_110 | 5 | 185.65 | 186.71 |
| Sat_110 | 6 | 187.88 | 188.05 |
| Sat_117 | 1 | 210.34 | 211.45 |
| Sat_117 | 2 | 218.15 | 219.41 |
| Sat_117 | 3 | 220.13 | 221.05 |
| Sat_117 | 4 | 226.19 | 226.96 |
| Sat_117 | 5 | 232.64 | 232.99 |
| Sat_117 | 6 | 212.76 | 213.12 |
| Sat_117 | 7 | 216.86 | 217.25 |
| Sat_117 | 8 | 222.62 | 222.99 |
| Sat_117 | 9 | 224.83 | 224.93 |
| Sat_117 | 10 | 242.75 | 242.85 |
| Sat_117 | 11 | 252.02 | 252.23 |
| Sat_117 | 12 | 255.97 | 256.17 |
| Sat_117 | 13 | 203.20 | 203.35 |
| Sat_117 | 14 | 208.93 | 209.13 |
| Sat_117 | 15 | 234.70 | 234.90 |
| Satt020 | 1 | 147.56 | 148.62 |
| Satt020 | 2 | 160.10 | 160.87 |
| Satt040 | 1 | 317.25 | 318.26 |
| Satt040 | 2 | 323.30 | 324.31 |
| Satt040 | 3 | 326.83 | 327.81 |
| Satt040 | 4 | 329.75 | 330.66 |
| Satt040 | 5 | 332.71 | 333.35 |
| Satt040 | 6 | 320.28 | 321.05 |
| Satt040 | 7 | 335.83 | 336.33 |
| Satt040 | 8 | 308.03 | 308.53 |
| Satt040 | 9 | 338.89 | 339.09 |
| Satt040 | 10 | 314.39 | 314.69 |
| Satt042 | 1 | 148.26 | 149.12 |
| Satt042 | 2 | 157.59 | 158.45 |
| Satt042 | 3 | 160.69 | 161.67 |
| Satt042 | 4 | 163.71 | 164.64 |
| Satt042 | 5 | 154.82 | 155.22 |
| Satt042 | 6 | 160.26 | 160.46 |
| Satt042 | 7 | 166.96 | 167.56 |
| Satt042 | 8 | 135.78 | 135.98 |
| Satt042 | 9 | 145.41 | 145.61 |
| Satt050 | 1 | 221.60 | 222.79 |
| Satt050 | 2 | 224.66 | 225.89 |
| Satt050 | 3 | 239.80 | 240.68 |
| Satt050 | 4 | 252.17 | 253.84 |
| Satt050 | 5 | 255.27 | 255.57 |
| Satt066 | 1 | 160.87 | 161.87 |
| Satt066 | 2 | 105.74 | 106.69 |
| Satt066 | 3 | 166.76 | 167.07 |
| Satt066 | 4 | 169.95 | 171.12 |
| Satt066 | 5 | 110.96 | 112.11 |
| Satt066 | 6 | 151.75 | 152.78 |
| Satt066 | 7 | 155.32 | 155.84 |
| Satt066 | 8 | 158.20 | 158.86 |
| Satt066 | 9 | 164.34 | 164.82 |
| Satt066 | 10 | 168.42 | 169.19 |
| Satt066 | 11 | 173.11 | 174.03 |
| Satt066 | 12 | 176.16 | 176.93 |
| Satt066 | 13 | 148.64 | 149.67 |
| Satt066 | 14 | 117.63 | 118.13 |
| Satt092 | 1 | 340.69 | 341.13 |
| Satt092 | 2 | 349.07 | 350.92 |
| Satt092 | 3 | 332.36 | 333.35 |
| Satt092 | 4 | 338.79 | 339.25 |
| Satt092 | 5 | 341.43 | 342.56 |
| Satt092 | 6 | 353.17 | 353.29 |
| Satt102 | 1 | 160.36 | 161.37 |
| Satt102 | 2 | 175.43 | 176.43 |
| Satt102 | 3 | 172.56 | 173.53 |
| Satt102 | 4 | 178.87 | 179.35 |
| Satt102 | 5 | 181.79 | 182.25 |
| Satt102 | 6 | 184.58 | 185.65 |
| Satt108 | 1 | 169.96 | 171.12 |
| Satt108 | 2 | 173.06 | 174.00 |
| Satt108 | 3 | 175.96 | 177.00 |
| Satt108 | 4 | 167.15 | 167.92 |
| Satt108 | 5 | 161.77 | 161.97 |
| Satt108 | 6 | 149.12 | 149.22 |
| Satt109 | 1 | 146.99 | 148.06 |
| Satt109 | 2 | 164.62 | 165.54 |
| Satt109 | 3 | 167.65 | 168.42 |
| Satt109 | 4 | 162.27 | 162.47 |
| Satt109 | 5 | 144.05 | 144.33 |
| Satt111 | 1 | 254.76 | 255.57 |
| Satt111 | 2 | 257.79 | 258.83 |
| Satt111 | 3 | 260.76 | 261.78 |
| Satt111 | 4 | 263.82 | 264.54 |
| Satt111 | 5 | 278.98 | 280.09 |
| Satt111 | 6 | 285.22 | 285.73 |
| Satt111 | 7 | 288.24 | 288.75 |
| Satt111 | 8 | 266.88 | 267.90 |
| Satt111 | 9 | 270.13 | 270.33 |
| Satt111 | 10 | 276.28 | 276.85 |
| Satt111 | 11 | 248.80 | 249.00 |
| Satt115 | 1 | 218.67 | 219.88 |
| Satt115 | 2 | 236.35 | 237.83 |
| Satt115 | 3 | 239.29 | 240.78 |
| Satt115 | 4 | 242.65 | 243.20 |
| Satt115 | 5 | 221.82 | 222.22 |
| Satt115 | 6 | 238.31 | 238.51 |
| Satt122 | 1 | 234.40 | 235.37 |
| Satt122 | 2 | 282.65 | 283.26 |
| Satt122 | 3 | 291.75 | 292.40 |
| Satt127 | 1 | 241.61 | 242.25 |
| Satt127 | 2 | 244.22 | 245.31 |
| Satt127 | 3 | 232.44 | 233.10 |
| Satt127 | 4 | 238.81 | 239.29 |
| Satt127 | 5 | 247.60 | 248.20 |
| Satt127 | 6 | 250.71 | 251.22 |
| Satt129 | 1 | 120.97 | 122.06 |
| Satt129 | 2 | 133.16 | 134.38 |
| Satt129 | 3 | 136.28 | 137.33 |
| Satt129 | 4 | 149.22 | 150.17 |
| Satt129 | 5 | 152.23 | 153.28 |
| Satt129 | 6 | 155.84 | 156.34 |
| Satt129 | 8 | 127.42 | 128.08 |
| Satt129 | 9 | 140.02 | 140.52 |
| Satt129 | 10 | 143.25 | 143.75 |
| Satt129 | 11 | 132.05 | 132.25 |
| Satt130 | 1 | 142.17 | 143.25 |
| Satt130 | 2 | 147.44 | 148.62 |
| Satt130 | 3 | 150.62 | 151.75 |
| Satt130 | 4 | 154.30 | 154.82 |

APPENDIX I-continued

Allele Definition Table
23 pages

| Marker | Allele | Size | Range bp |
|---|---|---|---|
| Satt131 | 1 | 157.85 | 159.25 |
| Satt131 | 2 | 173.06 | 174.03 |
| Satt131 | 3 | 175.96 | 176.93 |
| Satt131 | 4 | 179.35 | 179.85 |
| Satt131 | 5 | 182.16 | 182.75 |
| Satt131 | 6 | 148.62 | 149.67 |
| Satt133 | 1 | 163.80 | 164.82 |
| Satt133 | 2 | 181.99 | 182.85 |
| Satt133 | 3 | 167.36 | 167.56 |
| Satt133 | 4 | 176.06 | 176.26 |
| Satt133 | 5 | 172.96 | 173.41 |
| Satt138 | 1 | 226.66 | 227.82 |
| Satt138 | 2 | 229.84 | 230.75 |
| Satt138 | 3 | 232.85 | 233.82 |
| Satt138 | 4 | 235.30 | 236.56 |
| Satt138 | 5 | 241.66 | 242.45 |
| Satt138 | 6 | 231.47 | 231.87 |
| Satt138 | 7 | 238.91 | 239.11 |
| Satt138 | 8 | 214.97 | 215.17 |
| Satt142 | 1 | 122.55 | 123.25 |
| Satt142 | 2 | 137.89 | 138.69 |
| Satt142 | 3 | 141.10 | 142.17 |
| Satt142 | 4 | 144.33 | 145.41 |
| Satt142 | 5 | 156.34 | 156.94 |
| Satt142 | 6 | 148.06 | 148.16 |
| Satt142 | 7 | 108.04 | 108.20 |
| Satt142 | 8 | 129.00 | 129.20 |
| Satt144 | 1 | 210.72 | 212.56 |
| Satt144 | 2 | 227.62 | 228.58 |
| Satt144 | 3 | 231.25 | 231.40 |
| Satt146 | 1 | 291.11 | 292.36 |
| Satt146 | 2 | 294.26 | 295.32 |
| Satt146 | 3 | 309.55 | 310.57 |
| Satt146 | 4 | 313.02 | 314.06 |
| Satt146 | 5 | 316.11 | 317.50 |
| Satt146 | 7 | 306.71 | 307.71 |
| Satt146 | 8 | 298.10 | 298.30 |
| Satt146 | 9 | 319.97 | 320.38 |
| Satt146 | 10 | 322.80 | 323.30 |
| Satt146 | 11 | 329.37 | 329.87 |
| Satt146 | 12 | 331.75 | 332.66 |
| Satt146 | 13 | 334.84 | 335.83 |
| Satt147 | 1 | 176.73 | 177.70 |
| Satt147 | 2 | 182.75 | 183.52 |
| Satt147 | 3 | 193.45 | 195.03 |
| Satt147 | 4 | 179.95 | 180.52 |
| Satt147 | 5 | 207.01 | 208.72 |
| Satt147 | 6 | 211.35 | 211.55 |
| Satt147 | 7 | 213.90 | 214.77 |
| Satt147 | 8 | 216.95 | 217.55 |
| Satt147 | 9 | 199.29 | 199.49 |
| Satt150 | 1 | 246.11 | 248.00 |
| Satt150 | 2 | 249.20 | 249.70 |
| Satt150 | 3 | 267.70 | 267.90 |
| Satt150 | 4 | 270.95 | 271.05 |
| Satt150 | 5 | 282.55 | 283.21 |
| Satt150 | 6 | 234.18 | 234.60 |
| Satt150 | 7 | 237.33 | 237.63 |
| Satt151 | 1 | 169.04 | 170.15 |
| Satt151 | 2 | 178.06 | 179.35 |
| Satt151 | 3 | 184.04 | 185.15 |
| Satt151 | 4 | 187.08 | 188.05 |
| Satt151 | 5 | 205.40 | 206.40 |
| Satt151 | 6 | 166.29 | 166.76 |
| Satt151 | 7 | 175.46 | 175.96 |
| Satt151 | 8 | 198.89 | 199.39 |
| Satt153 | 1 | 198.39 | 199.49 |
| Satt153 | 2 | 201.39 | 202.09 |
| Satt153 | 3 | 213.47 | 214.57 |
| Satt153 | 4 | 231.30 | 232.17 |
| Satt153 | 5 | 220.13 | 220.53 |
| Satt155 | 1 | 151.75 | 152.78 |
| Satt155 | 2 | 160.87 | 162.37 |
| Satt155 | 3 | 163.84 | 165.02 |
| Satt155 | 4 | 167.11 | 167.72 |
| Satt155 | 5 | 158.35 | 158.45 |
| Satt155 | 6 | 148.82 | 149.12 |
| Satt155 | 7 | 197.50 | 197.90 |
| Satt156 | 1 | 326.12 | 326.84 |
| Satt156 | 2 | 329.20 | 330.02 |
| Satt156 | 3 | 343.89 | 344.85 |
| Satt156 | 4 | 349.65 | 350.00 |
| Satt156 | 5 | 346.68 | 347.11 |
| Satt159 | 1 | 268.90 | 269.53 |
| Satt159 | 2 | 269.73 | 270.33 |
| Satt159 | 3 | 271.94 | 272.78 |
| Satt159 | 4 | 287.23 | 287.74 |
| Satt159 | 5 | 290.25 | 290.95 |
| Satt165 | 1 | 210.44 | 211.45 |
| Satt165 | 2 | 213.37 | 214.63 |
| Satt165 | 3 | 219.41 | 220.48 |
| Satt165 | 4 | 216.55 | 216.95 |
| Satt165 | 5 | 204.70 | 204.90 |
| Satt165 | 6 | 225.69 | 225.99 |
| Satt166 | 1 | 187.08 | 188.10 |
| Satt166 | 2 | 220.48 | 221.35 |
| Satt166 | 3 | 226.44 | 227.62 |
| Satt166 | 4 | 229.48 | 230.24 |
| Satt166 | 5 | 232.37 | 233.67 |
| Satt166 | 6 | 223.39 | 223.76 |
| Satt166 | 7 | 217.35 | 217.75 |
| Satt168 | 1 | 345.94 | 346.71 |
| Satt168 | 2 | 359.98 | 360.77 |
| Satt168 | 3 | 362.95 | 363.65 |
| Satt168 | 4 | 365.87 | 367.16 |
| Satt168 | 5 | 368.83 | 369.34 |
| Satt168 | 6 | 335.26 | 336.00 |
| Satt168 | 7 | 311.10 | 311.30 |
| Satt168 | 8 | 329.57 | 329.77 |
| Satt172 | 1 | 155.84 | 156.89 |
| Satt172 | 2 | 167.72 | 168.52 |
| Satt172 | 3 | 170.62 | 171.52 |
| Satt172 | 4 | 179.35 | 180.32 |
| Satt172 | 5 | 182.25 | 183.22 |
| Satt175 | 1 | 160.21 | 161.37 |
| Satt175 | 2 | 163.31 | 164.54 |
| Satt175 | 3 | 166.29 | 166.96 |
| Satt175 | 4 | 169.19 | 170.50 |
| Satt175 | 5 | 178.30 | 179.55 |
| Satt175 | 6 | 193.45 | 194.74 |
| Satt175 | 7 | 172.76 | 173.26 |
| Satt175 | 8 | 175.61 | 176.26 |
| Satt175 | 9 | 188.05 | 188.60 |
| Satt175 | 10 | 190.98 | 191.96 |
| Satt175 | 11 | 181.69 | 181.89 |
| Satt176 | 1 | 138.39 | 139.15 |
| Satt176 | 2 | 141.60 | 142.77 |
| Satt176 | 3 | 160.36 | 162.37 |
| Satt176 | 4 | 169.68 | 170.77 |
| Satt176 | 5 | 172.49 | 173.68 |
| Satt176 | 6 | 187.65 | 188.85 |
| Satt176 | 7 | 148.16 | 149.02 |
| Satt176 | 8 | 163.55 | 164.67 |
| Satt176 | 9 | 175.56 | 176.63 |
| Satt176 | 10 | 181.62 | 182.75 |
| Satt181 | 1 | 324.31 | 325.37 |
| Satt181 | 2 | 346.28 | 347.16 |
| Satt181 | 3 | 354.62 | 355.60 |
| Satt181 | 4 | 357.67 | 358.46 |
| Satt181 | 5 | 363.01 | 364.30 |
| Satt181 | 6 | 351.94 | 352.47 |
| Satt181 | 7 | 360.53 | 361.17 |
| Satt181 | 8 | 366.01 | 367.16 |
| Satt181 | 9 | 349.07 | 349.55 |
| Satt183 | 1 | 122.04 | 123.05 |
| Satt183 | 2 | 128.08 | 129.10 |
| Satt183 | 3 | 144.83 | 145.91 |
| Satt183 | 4 | 148.16 | 148.62 |
| Satt183 | 5 | 131.43 | 131.85 |
| Satt183 | 6 | 135.26 | 135.78 |

APPENDIX I-continued

Allele Definition Table
23 pages

| Marker | Allele | Size | Range bp |
|---|---|---|---|
| Satt183 | 7 | 138.49 | 138.95 |
| Satt183 | 8 | 141.70 | 141.90 |
| Satt186 | 1 | 361.81 | 363.07 |
| Satt186 | 2 | 364.72 | 365.94 |
| Satt186 | 3 | 367.87 | 368.83 |
| Satt186 | 4 | 339.25 | 341.09 |
| Satt186 | 5 | 359.30 | 359.73 |
| Satt186 | 6 | 371.22 | 371.72 |
| Satt186 | 7 | 373.74 | 374.61 |
| Satt186 | 8 | 376.96 | 377.46 |
| Satt186 | 9 | 353.39 | 353.59 |
| Satt190 | 1 | 187.01 | 188.06 |
| Satt190 | 2 | 193.35 | 194.10 |
| Satt190 | 3 | 196.42 | 197.40 |
| Satt190 | 4 | 225.99 | 227.06 |
| Satt190 | 5 | 181.17 | 182.03 |
| Satt190 | 6 | 184.18 | 184.68 |
| Satt190 | 7 | 190.50 | 190.98 |
| Satt190 | 8 | 220.38 | 220.85 |
| Satt190 | 9 | 214.07 | 214.57 |
| Satt191 | 1 | 319.67 | 320.28 |
| Satt191 | 2 | 334.84 | 336.02 |
| Satt191 | 3 | 337.81 | 339.02 |
| Satt191 | 4 | 349.07 | 350.00 |
| Satt191 | 5 | 352.14 | 352.77 |
| Satt191 | 6 | 354.62 | 355.65 |
| Satt191 | 7 | 360.69 | 361.17 |
| Satt191 | 8 | 346.68 | 346.71 |
| Satt193 | 1 | 165.79 | 166.76 |
| Satt193 | 2 | 168.94 | 169.65 |
| Satt193 | 3 | 174.59 | 175.96 |
| Satt193 | 4 | 180.77 | 181.79 |
| Satt193 | 5 | 186.61 | 187.75 |
| Satt193 | 6 | 189.97 | 190.60 |
| Satt193 | 7 | 192.95 | 193.75 |
| Satt193 | 8 | 198.89 | 199.89 |
| Satt193 | 9 | 202.19 | 203.40 |
| Satt193 | 10 | 183.72 | 185.15 |
| Satt193 | 11 | 171.79 | 173.06 |
| Satt193 | 12 | 160.11 | 161.37 |
| Satt193 | 13 | 177.85 | 179.08 |
| Satt193 | 14 | 163.36 | 163.84 |
| Satt195 | 1 | 214.77 | 216.11 |
| Satt195 | 2 | 217.93 | 218.91 |
| Satt195 | 3 | 221.65 | 222.22 |
| Satt196 | 1 | 230.04 | 230.50 |
| Satt196 | 2 | 232.94 | 233.52 |
| Satt196 | 3 | 239.29 | 239.79 |
| Satt196 | 4 | 241.76 | 243.00 |
| Satt196 | 5 | 253.84 | 255.27 |
| Satt196 | 6 | 236.17 | 236.45 |
| Satt196 | 7 | 257.51 | 257.81 |
| Satt196 | 8 | 263.52 | 263.92 |
| Satt197 | 1 | 177.50 | 179.35 |
| Satt197 | 2 | 184.18 | 185.15 |
| Satt197 | 3 | 187.08 | 188.55 |
| Satt197 | 4 | 190.00 | 191.48 |
| Satt197 | 5 | 192.95 | 194.44 |
| Satt197 | 6 | 205.65 | 206.00 |
| Satt197 | 7 | 170.35 | 170.72 |
| Satt197 | 8 | 175.44 | 175.96 |
| Satt197 | 9 | 166.96 | 167.71 |
| Satt197 | 10 | 181.59 | 181.79 |
| Satt199 | 1 | 161.84 | 162.86 |
| Satt199 | 2 | 202.22 | 204.40 |
| Satt199 | 3 | 166.29 | 166.76 |
| Satt199 | 4 | 168.22 | 168.69 |
| Satt199 | 5 | 174.03 | 174.99 |
| Satt199 | 6 | 178.37 | 178.87 |
| Satt199 | 7 | 220.85 | 221.35 |
| Satt199 | 8 | 176.01 | 176.16 |
| Satt199 | 9 | 170.20 | 170.60 |
| Satt202 | 1 | 306.48 | 307.51 |
| Satt202 | 2 | 309.55 | 310.72 |
| Satt202 | 3 | 287.33 | 287.79 |
| Satt202 | 4 | 313.03 | 313.66 |
| Satt202 | 5 | 285.22 | 285.93 |
| Satt203 | 1 | 223.29 | 224.06 |
| Satt203 | 2 | 229.53 | 230.04 |
| Satt203 | 3 | 249.20 | 250.00 |
| Satt203 | 4 | 258.33 | 259.34 |
| Satt203 | 5 | 205.40 | 205.90 |
| Satt203 | 6 | 212.56 | 212.76 |
| Satt203 | 7 | 219.61 | 219.81 |
| Satt203 | 8 | 226.51 | 227.82 |
| Satt203 | 9 | 231.30 | 231.67 |
| Satt204 | 1 | 234.88 | 235.87 |
| Satt204 | 2 | 240.78 | 241.76 |
| Satt204 | 3 | 247.00 | 248.20 |
| Satt204 | 4 | 250.00 | 250.76 |
| Satt204 | 5 | 253.03 | 253.79 |
| Satt204 | 6 | 238.13 | 238.31 |
| Satt204 | 7 | 256.59 | 256.79 |
| Satt209 | 1 | 311.80 | 312.63 |
| Satt209 | 2 | 329.37 | 330.48 |
| Satt209 | 3 | 310.77 | 311.10 |
| Satt212 | 1 | 347.13 | 348.73 |
| Satt212 | 2 | 355.42 | 356.49 |
| Satt212 | 3 | 358.66 | 358.80 |
| Satt213 | 1 | 326.34 | 327.35 |
| Satt213 | 2 | 318.46 | 318.66 |
| Satt216 | 1 | 195.43 | 196.42 |
| Satt216 | 2 | 198.79 | 199.39 |
| Satt216 | 3 | 222.79 | 223.29 |
| Satt216 | 4 | 225.69 | 226.66 |
| Satt216 | 5 | 210.95 | 211.45 |
| Satt216 | 6 | 216.95 | 217.45 |
| Satt216 | 7 | 220.18 | 220.38 |
| Satt218 | 1 | 341.13 | 342.16 |
| Satt218 | 2 | 344.12 | 344.85 |
| Satt219 | 1 | 126.38 | 127.07 |
| Satt219 | 2 | 141.95 | 142.67 |
| Satt219 | 3 | 157.69 | 158.55 |
| Satt219 | 4 | 175.46 | 176.58 |
| Satt219 | 5 | 120.38 | 120.77 |
| Satt219 | 6 | 154.82 | 155.12 |
| Satt219 | 7 | 160.97 | 161.37 |
| Satt219 | 8 | 172.80 | 173.46 |
| Satt219 | 9 | 178.78 | 179.55 |
| Satt219 | 10 | 182.09 | 182.45 |
| Satt220 | 1 | 337.71 | 338.29 |
| Satt220 | 2 | 340.39 | 341.23 |
| Satt220 | 3 | 343.24 | 344.42 |
| Satt220 | 4 | 346.28 | 346.71 |
| Satt220 | 5 | 334.54 | 334.94 |
| Satt220 | 6 | 354.62 | 355.02 |
| Satt220 | 7 | 360.23 | 360.63 |
| Satt220 | 8 | 352.52 | 352.57 |
| Satt221 | 1 | 228.12 | 229.08 |
| Satt221 | 2 | 234.12 | 234.90 |
| Satt221 | 3 | 237.33 | 238.31 |
| Satt221 | 4 | 246.50 | 247.50 |
| Satt221 | 5 | 231.20 | 231.47 |
| Satt225 | 1 | 99.95 | 101.41 |
| Satt225 | 2 | 102.87 | 103.93 |
| Satt225 | 3 | 109.05 | 110.01 |
| Satt227 | 1 | 327.28 | 328.73 |
| Satt227 | 2 | 333.35 | 334.55 |
| Satt228 | 1 | 293.26 | 294.26 |
| Satt228 | 2 | 298.30 | 299.06 |
| Satt228 | 3 | 310.00 | 310.57 |
| Satt228 | 4 | 323.40 | 324.31 |
| Satt228 | 5 | 326.44 | 327.35 |
| Satt228 | 6 | 329.61 | 330.88 |
| Satt228 | 7 | 317.45 | 317.65 |
| Satt228 | 8 | 341.53 | 341.73 |
| Satt230 | 1 | 226.14 | 227.26 |
| Satt230 | 2 | 229.33 | 230.50 |
| Satt230 | 3 | 231.97 | 232.99 |
| Satt230 | 4 | 214.97 | 215.47 |

APPENDIX I-continued

Allele Definition Table
23 pages

| Marker | Allele | Size | Range bp |
|---|---|---|---|
| Satt230 | 5 | 223.39 | 224.26 |
| Satt233 | 1 | 90.83 | 91.34 |
| Satt233 | 4 | 91.64 | 92.40 |
| Satt233 | 5 | 97.75 | 98.46 |
| Satt233 | 6 | 103.73 | 105.25 |
| Satt233 | 7 | 112.77 | 113.66 |
| Satt234 | 1 | 175.32 | 176.21 |
| Satt234 | 2 | 178.35 | 179.35 |
| Satt234 | 3 | 172.96 | 173.06 |
| Satt236 | 1 | 250.00 | 250.81 |
| Satt236 | 2 | 255.77 | 256.79 |
| Satt236 | 3 | 259.08 | 259.84 |
| Satt236 | 4 | 262.16 | 262.95 |
| Satt236 | 5 | 265.46 | 265.66 |
| Satt236 | 6 | 271.35 | 271.56 |
| Satt236 | 7 | 253.39 | 253.84 |
| Satt240 | 1 | 310.07 | 311.30 |
| Satt240 | 2 | 313.16 | 314.63 |
| Satt240 | 3 | 316.44 | 317.86 |
| Satt240 | 4 | 319.60 | 320.48 |
| Satt240 | 5 | 326.34 | 326.54 |
| Satt242 | 1 | 182.25 | 183.22 |
| Satt242 | 2 | 191.48 | 192.46 |
| Satt242 | 3 | 197.40 | 198.39 |
| Satt242 | 4 | 200.39 | 201.52 |
| Satt242 | 5 | 203.25 | 204.40 |
| Satt242 | 6 | 209.43 | 210.44 |
| Satt242 | 7 | 212.91 | 213.47 |
| Satt242 | 8 | 167.72 | 168.22 |
| Satt242 | 9 | 179.85 | 180.32 |
| Satt242 | 10 | 188.55 | 189.02 |
| Satt242 | 11 | 194.93 | 195.43 |
| Satt242 | 12 | 206.91 | 207.41 |
| Satt242 | 13 | 185.65 | 186.11 |
| Satt242 | 14 | 171.94 | 172.29 |
| Satt242 | 15 | 175.09 | 175.34 |
| Satt242 | 16 | 181.17 | 181.22 |
| Satt242 | 17 | 196.12 | 196.27 |
| Satt243 | 1 | 334.69 | 335.83 |
| Satt243 | 2 | 343.48 | 344.47 |
| Satt243 | 3 | 363.37 | 364.48 |
| Satt243 | 4 | 366.24 | 366.91 |
| Satt243 | 5 | 357.96 | 358.16 |
| Satt243 | 6 | 337.76 | 338.69 |
| Satt243 | 7 | 346.58 | 347.06 |
| Satt243 | 8 | 349.47 | 349.60 |
| Satt247 | 1 | 363.62 | 365.08 |
| Satt247 | 2 | 369.29 | 370.70 |
| Satt247 | 3 | 375.25 | 376.51 |
| Satt247 | 4 | 366.63 | 367.67 |
| Satt247 | 5 | 373.15 | 373.35 |
| Satt247 | 6 | 381.11 | 382.25 |
| Satt247 | 7 | 378.30 | 378.50 |
| Satt247 | 8 | 355.25 | 355.45 |
| Satt249 | 1 | 217.90 | 218.73 |
| Satt249 | 2 | 220.85 | 221.65 |
| Satt249 | 3 | 251.19 | 252.23 |
| Satt249 | 4 | 257.31 | 258.33 |
| Satt249 | 5 | 254.61 | 255.06 |
| Satt249 | 6 | 260.96 | 261.38 |
| Satt249 | 7 | 236.75 | 236.95 |
| Satt250 | 1 | 189.02 | 190.00 |
| Satt250 | 2 | 207.16 | 208.02 |
| Satt250 | 3 | 228.68 | 228.98 |
| Satt250 | 4 | 213.87 | 213.97 |
| Satt250 | 5 | 219.41 | 219.61 |
| Satt251 | 1 | 215.92 | 216.95 |
| Satt251 | 2 | 218.91 | 219.41 |
| Satt251 | 3 | 254.26 | 255.27 |
| Satt251 | 4 | 257.81 | 259.08 |
| Satt251 | 5 | 266.48 | 267.50 |
| Satt251 | 6 | 209.77 | 210.95 |
| Satt251 | 7 | 260.86 | 261.38 |
| Satt251 | 8 | 212.97 | 213.97 |
| Satt251 | 9 | 272.98 | 273.18 |
| Satt255 | 1 | 236.85 | 237.43 |
| Satt255 | 2 | 242.75 | 243.33 |
| Satt255 | 3 | 245.71 | 246.70 |
| Satt255 | 4 | 248.70 | 249.30 |
| Satt256 | 1 | 338.99 | 340.19 |
| Satt256 | 2 | 348.27 | 349.50 |
| Satt256 | 3 | 351.28 | 352.27 |
| Satt257 | 1 | 255.20 | 256.29 |
| Satt257 | 2 | 267.33 | 268.52 |
| Satt257 | 3 | 242.25 | 243.15 |
| Satt257 | 4 | 249.20 | 250.41 |
| Satt257 | 5 | 258.48 | 259.74 |
| Satt257 | 6 | 261.78 | 262.18 |
| Satt258 | 1 | 156.62 | 157.69 |
| Satt258 | 2 | 159.71 | 160.71 |
| Satt258 | 3 | 161.37 | 161.87 |
| Satt258 | 4 | 162.82 | 163.84 |
| Satt258 | 5 | 165.79 | 166.76 |
| Satt258 | 6 | 168.22 | 168.42 |
| Satt259 | 1 | 187.08 | 188.15 |
| Satt259 | 2 | 193.45 | 194.44 |
| Satt259 | 3 | 205.40 | 206.50 |
| Satt259 | 4 | 207.65 | 209.58 |
| Satt259 | 5 | 211.82 | 212.64 |
| Satt262 | 1 | 231.97 | 232.94 |
| Satt262 | 2 | 244.38 | 245.21 |
| Satt262 | 3 | 247.20 | 248.20 |
| Satt262 | 4 | 250.21 | 251.22 |
| Satt262 | 5 | 256.29 | 257.31 |
| Satt262 | 6 | 241.41 | 242.06 |
| Satt262 | 7 | 253.42 | 254.04 |
| Satt262 | 8 | 235.67 | 235.87 |
| Satt263 | 1 | 249.53 | 250.21 |
| Satt263 | 2 | 252.43 | 253.44 |
| Satt263 | 3 | 267.70 | 268.72 |
| Satt263 | 4 | 276.75 | 278.02 |
| Satt263 | 5 | 289.18 | 290.10 |
| Satt263 | 6 | 255.72 | 256.29 |
| Satt263 | 7 | 265.04 | 265.46 |
| Satt263 | 8 | 271.56 | 271.76 |
| Satt263 | 9 | 246.44 | 247.20 |
| Satt264 | 1 | 216.38 | 217.45 |
| Satt264 | 2 | 219.35 | 220.38 |
| Satt264 | 3 | 228.41 | 229.54 |
| Satt264 | 4 | 237.33 | 238.46 |
| Satt264 | 5 | 246.65 | 247.70 |
| Satt264 | 6 | 243.63 | 244.72 |
| Satt265 | 1 | 264.64 | 265.96 |
| Satt265 | 2 | 267.88 | 268.52 |
| Satt265 | 3 | 285.98 | 286.93 |
| Satt265 | 4 | 289.35 | 289.55 |
| Satt265 | 5 | 258.93 | 259.54 |
| Satt265 | 6 | 262.18 | 262.40 |
| Satt265 | 7 | 283.11 | 283.41 |
| Satt266 | 1 | 321.79 | 323.05 |
| Satt266 | 2 | 330.98 | 332.32 |
| Satt266 | 3 | 303.20 | 303.93 |
| Satt267 | 1 | 232.44 | 233.42 |
| Satt267 | 2 | 241.46 | 242.25 |
| Satt267 | 3 | 250.61 | 251.32 |
| Satt267 | 4 | 244.82 | 245.21 |
| Satt267 | 5 | 247.80 | 248.00 |
| Satt270 | 1 | 110.46 | 110.96 |
| Satt270 | 2 | 119.10 | 119.98 |
| Satt270 | 3 | 140.97 | 141.60 |
| Satt270 | 4 | 141.86 | 142.67 |
| Satt270 | 5 | 144.05 | 144.98 |
| Satt270 | 6 | 150.65 | 151.28 |
| Satt270 | 7 | 116.20 | 116.71 |
| Satt270 | 8 | 125.06 | 125.56 |
| Satt270 | 9 | 128.60 | 129.10 |
| Satt270 | 10 | 147.56 | 148.06 |
| Satt270 | 11 | 154.31 | 155.32 |
| Satt270 | 12 | 156.61 | 157.34 |
| Satt272 | 1 | 223.76 | 225.23 |

APPENDIX I-continued

Allele Definition Table
23 pages

| Marker | Allele | Size | Range bp |
|---|---|---|---|
| Satt272 | 2 | 229.94 | 231.00 |
| Satt272 | 3 | 226.94 | 228.12 |
| Satt272 | 4 | 233.42 | 233.92 |
| Satt272 | 5 | 242.25 | 242.75 |
| Satt272 | 6 | 247.20 | 247.70 |
| Satt274 | 1 | 195.33 | 196.32 |
| Satt274 | 2 | 198.38 | 199.44 |
| Satt274 | 3 | 201.34 | 202.44 |
| Satt274 | 4 | 204.40 | 205.40 |
| Satt274 | 5 | 180.25 | 180.52 |
| Satt274 | 6 | 189.42 | 189.62 |
| Satt274 | 7 | 207.45 | 208.72 |
| Satt279 | 1 | 174.83 | 175.76 |
| Satt280 | 1 | 230.04 | 231.05 |
| Satt280 | 2 | 180.92 | 181.79 |
| Satt280 | 2 | 233.19 | 233.92 |
| Satt280 | 3 | 236.17 | 236.90 |
| Satt280 | 4 | 202.69 | 203.00 |
| Satt280 | 5 | 224.29 | 224.98 |
| Satt282 | 1 | 314.04 | 314.79 |
| Satt282 | 2 | 317.12 | 318.31 |
| Satt282 | 3 | 326.34 | 327.85 |
| Satt282 | 4 | 192.95 | 193.65 |
| Satt282 | 4 | 332.51 | 334.05 |
| Satt282 | 5 | 335.68 | 336.92 |
| Satt282 | 6 | 347.84 | 348.04 |
| Satt282 | 7 | 323.45 | 324.31 |
| Satt282 | 8 | 329.67 | 330.58 |
| Satt282 | 9 | 338.88 | 339.75 |
| Satt282 | 10 | 310.67 | 311.70 |
| Satt284 | 1 | 115.70 | 116.66 |
| Satt284 | 2 | 124.56 | 125.61 |
| Satt284 | 3 | 127.95 | 128.70 |
| Satt284 | 4 | 119.20 | 119.30 |
| Satt284 | 5 | 112.86 | 113.06 |
| Satt284 | 6 | 198.89 | 199.89 |
| Satt284 | 6 | 129.40 | 129.61 |
| Satt285 | 1 | 208.93 | 210.19 |
| Satt285 | 2 | 231.97 | 232.95 |
| Satt285 | 3 | 235.51 | 236.36 |
| Satt285 | 4 | 241.26 | 242.50 |
| Satt285 | 5 | 243.73 | 245.41 |
| Satt285 | 6 | 206.40 | 206.80 |
| Satt285 | 7 | 187.28 | 187.48 |
| Satt285 | 7 | 229.32 | 230.34 |
| Satt287 | 1 | 203.38 | 204.40 |
| Satt287 | 2 | 233.55 | 234.40 |
| Satt287 | 3 | 197.70 | 198.09 |
| Satt287 | 4 | 243.15 | 243.53 |
| Satt287 | 9 | 205.60 | 205.70 |
| Satt292 | 1 | 221.35 | 221.82 |
| Satt292 | 2 | 224.26 | 225.23 |
| Satt292 | 3 | 239.29 | 240.28 |
| Satt292 | 4 | 242.66 | 243.23 |
| Satt292 | 5 | 251.70 | 252.23 |
| Satt292 | 6 | 229.18 | 229.48 |
| Satt292 | 7 | 232.24 | 232.44 |
| Satt292 | 8 | 211.25 | 211.55 |
| Satt292 | 9 | 254.76 | 255.06 |
| Satt292 | 10 | 257.91 | 258.21 |
| Satt295 | 1 | 220.38 | 221.25 |
| Satt295 | 2 | 223.29 | 224.26 |
| Satt295 | 3 | 226.57 | 227.16 |
| Satt295 | 4 | 232.44 | 233.14 |
| Satt295 | 5 | 244.62 | 245.21 |
| Satt295 | 6 | 256.73 | 257.41 |
| Satt295 | 7 | 264.94 | 265.96 |
| Satt295 | 8 | 208.82 | 209.03 |
| Satt295 | 9 | 217.15 | 217.75 |
| Satt295 | 11 | 235.62 | 236.02 |
| Satt295 | 12 | 238.81 | 239.01 |
| Satt295 | 13 | 241.66 | 241.91 |
| Satt295 | 14 | 253.84 | 254.04 |
| Satt299 | 1 | 258.01 | 258.21 |
| Satt299 | 2 | 283.51 | 283.61 |
| Satt299 | 3 | 284.01 | 284.97 |
| Satt299 | 4 | 285.12 | 286.27 |
| Satt299 | 5 | 291.25 | 292.30 |
| Satt299 | 6 | 303.70 | 304.30 |
| Satt299 | 7 | 306.88 | 307.51 |
| Satt299 | 8 | 313.66 | 314.69 |
| Satt299 | 9 | 318.76 | 319.47 |
| Satt299 | 10 | 328.65 | 329.87 |
| Satt299 | 11 | 331.87 | 332.81 |
| Satt299 | 12 | 342.56 | 343.49 |
| Satt299 | 13 | 293.26 | 293.36 |
| Satt300 | 1 | 238.81 | 239.79 |
| Satt300 | 2 | 245.20 | 245.81 |
| Satt300 | 3 | 254.26 | 255.27 |
| Satt300 | 4 | 266.48 | 267.23 |
| Satt300 | 5 | 269.53 | 270.55 |
| Satt300 | 6 | 242.25 | 242.85 |
| Satt300 | 7 | 257.81 | 258.11 |
| Satt300 | 8 | 263.57 | 263.82 |
| Satt303 | 1 | 128.60 | 129.10 |
| Satt303 | 2 | 131.59 | 132.15 |
| Satt303 | 3 | 134.68 | 135.34 |
| Satt303 | 4 | 137.82 | 138.39 |
| Satt303 | 5 | 140.96 | 141.70 |
| Satt303 | 6 | 144.13 | 144.88 |
| Satt303 | 7 | 153.65 | 154.41 |
| Satt303 | 8 | 156.67 | 157.49 |
| Satt303 | 9 | 119.59 | 120.08 |
| Satt303 | 10 | 122.75 | 123.05 |
| Satt303 | 11 | 147.66 | 147.86 |
| Satt303 | 12 | 159.96 | 160.16 |
| Satt304 | 1 | 98.35 | 99.16 |
| Satt304 | 2 | 162.75 | 163.84 |
| Satt304 | 3 | 165.99 | 166.59 |
| Satt304 | 4 | 168.81 | 169.65 |
| Satt307 | 1 | 336.32 | 337.51 |
| Satt307 | 2 | 350.42 | 351.44 |
| Satt307 | 3 | 355.99 | 356.92 |
| Satt307 | 4 | 358.93 | 360.82 |
| Satt307 | 5 | 362.00 | 362.67 |
| Satt307 | 6 | 365.33 | 365.84 |
| Satt307 | 7 | 367.97 | 368.48 |
| Satt311 | 1 | 152.78 | 153.81 |
| Satt311 | 2 | 164.82 | 165.79 |
| Satt311 | 3 | 175.96 | 176.43 |
| Satt311 | 4 | 156.24 | 156.34 |
| Satt311 | 5 | 192.37 | 192.47 |
| Satt311 | 6 | 207.41 | 207.51 |
| Satt311 | 7 | 201.44 | 201.89 |
| Satt311 | 8 | 210.14 | 210.85 |
| Satt311 | 9 | 181.29 | 181.69 |
| Satt314 | 1 | 241.26 | 242.25 |
| Satt314 | 2 | 244.22 | 245.21 |
| Satt314 | 3 | 247.50 | 247.80 |
| Satt319 | 1 | 173.31 | 174.59 |
| Satt319 | 2 | 176.48 | 177.50 |
| Satt319 | 3 | 179.47 | 180.52 |
| Satt319 | 4 | 218.91 | 219.88 |
| Satt319 | 5 | 237.16 | 238.13 |
| Satt319 | 6 | 240.78 | 241.26 |
| Satt319 | 7 | 183.22 | 183.32 |
| Satt319 | 8 | 192.27 | 192.47 |
| Satt319 | 9 | 210.44 | 210.95 |
| Satt319 | 10 | 234.90 | 235.00 |
| Satt321 | 1 | 231.97 | 233.25 |
| Satt321 | 2 | 235.25 | 236.23 |
| Satt321 | 3 | 238.31 | 239.26 |
| Satt321 | 4 | 244.22 | 244.72 |
| Satt322 | 1 | 313.03 | 313.81 |
| Satt322 | 2 | 312.13 | 312.78 |
| Satt326 | 1 | 323.68 | 324.81 |
| Satt326 | 2 | 326.69 | 327.85 |
| Satt326 | 3 | 329.87 | 330.88 |
| Satt326 | 4 | 342.06 | 342.76 |
| Satt326 | 5 | 320.83 | 321.39 |

APPENDIX I-continued

Allele Definition Table
23 pages

| Marker | Allele | Size | Range bp |
|---|---|---|---|
| Satt327 | 1 | 251.22 | 252.23 |
| Satt327 | 2 | 254.26 | 255.28 |
| Satt327 | 3 | 245.41 | 245.81 |
| Satt327 | 4 | 248.55 | 248.80 |
| Satt327 | 5 | 233.62 | 234.02 |
| Satt327 | 6 | 263.72 | 263.92 |
| Satt327 | 7 | 242.42 | 242.80 |
| Satt327 | 8 | 257.51 | 257.66 |
| Satt328 | 1 | 248.20 | 249.20 |
| Satt328 | 2 | 251.22 | 252.23 |
| Satt329 | 1 | 238.31 | 238.81 |
| Satt329 | 2 | 268.52 | 269.53 |
| Satt329 | 3 | 272.58 | 273.38 |
| Satt329 | 4 | 275.63 | 276.65 |
| Satt329 | 5 | 279.69 | 280.70 |
| Satt329 | 6 | 247.20 | 247.70 |
| Satt329 | 7 | 254.26 | 254.76 |
| Satt329 | 8 | 257.31 | 258.33 |
| Satt329 | 9 | 267.50 | 268.00 |
| Satt329 | 10 | 277.25 | 277.45 |
| Satt329 | 11 | 279.28 | 279.48 |
| Satt329 | 12 | 274.00 | 274.10 |
| Satt329 | 13 | 270.13 | 270.23 |
| Satt330 | 1 | 308.03 | 308.78 |
| Satt330 | 2 | 342.41 | 343.49 |
| Satt330 | 3 | 348.04 | 348.72 |
| Satt330 | 4 | 355.55 | 355.99 |
| Satt330 | 5 | 364.02 | 364.78 |
| Satt330 | 6 | 344.72 | 344.85 |
| Satt330 | 7 | 345.50 | 345.98 |
| Satt330 | 8 | 346.71 | 346.91 |
| Satt330 | 9 | 316.53 | 316.93 |
| Satt331 | 1 | 233.42 | 234.40 |
| Satt331 | 2 | 239.67 | 240.28 |
| Satt331 | 3 | 251.56 | 252.43 |
| Satt331 | 4 | 236.95 | 237.15 |
| Satt332 | 1 | 161.69 | 162.37 |
| Satt332 | 2 | 176.57 | 177.90 |
| Satt332 | 3 | 179.65 | 180.32 |
| Satt332 | 4 | 182.85 | 183.20 |
| Satt332 | 5 | 173.78 | 174.13 |
| Satt333 | 1 | 180.32 | 180.82 |
| Satt333 | 2 | 195.43 | 196.47 |
| Satt333 | 3 | 198.89 | 199.39 |
| Satt333 | 4 | 201.89 | 202.39 |
| Satt333 | 5 | 204.74 | 205.40 |
| Satt333 | 6 | 171.79 | 171.99 |
| Satt333 | 7 | 189.82 | 190.00 |
| Satt333 | 8 | 177.75 | 178.20 |
| Satt333 | 9 | 192.76 | 193.10 |
| Satt334 | 1 | 202.39 | 202.90 |
| Satt334 | 2 | 207.92 | 208.93 |
| Satt334 | 3 | 210.95 | 211.96 |
| Satt334 | 4 | 214.33 | 215.77 |
| Satt334 | 5 | 215.96 | 216.76 |
| Satt334 | 6 | 217.93 | 218.70 |
| Satt334 | 7 | 220.38 | 221.35 |
| Satt334 | 8 | 196.12 | 196.32 |
| Satt334 | 9 | 230.34 | 230.50 |
| Satt335 | 1 | 145.31 | 146.49 |
| Satt335 | 2 | 154.82 | 156.09 |
| Satt335 | 3 | 164.34 | 165.27 |
| Satt335 | 4 | 167.51 | 168.22 |
| Satt335 | 5 | 170.55 | 171.27 |
| Satt336 | 1 | 176.43 | 177.40 |
| Satt336 | 2 | 182.53 | 183.22 |
| Satt336 | 3 | 185.50 | 186.61 |
| Satt336 | 4 | 191.48 | 192.46 |
| Satt338 | 1 | 229.08 | 230.04 |
| Satt338 | 2 | 232.54 | 233.92 |
| Satt338 | 3 | 253.24 | 254.37 |
| Satt338 | 4 | 265.46 | 266.68 |
| Satt338 | 5 | 274.62 | 275.57 |
| Satt338 | 6 | 277.67 | 278.68 |
| Satt338 | 7 | 238.31 | 238.71 |
| Satt338 | 8 | 280.90 | 281.90 |
| Satt339 | 1 | 234.90 | 235.38 |
| Satt339 | 2 | 240.47 | 241.97 |
| Satt339 | 3 | 243.73 | 244.72 |
| Satt339 | 4 | 255.91 | 257.31 |
| Satt339 | 5 | 264.88 | 266.26 |
| Satt339 | 6 | 268.14 | 269.07 |
| Satt339 | 7 | 206.70 | 206.91 |
| Satt339 | 8 | 252.83 | 253.92 |
| Satt339 | 9 | 271.45 | 271.56 |
| Satt339 | 10 | 250.21 | 250.61 |
| Satt339 | 11 | 262.28 | 262.40 |
| Satt339 | 12 | 259.13 | 259.35 |
| Satt343 | 1 | 138.39 | 138.95 |
| Satt343 | 2 | 141.50 | 142.37 |
| Satt343 | 3 | 160.14 | 161.87 |
| Satt343 | 4 | 169.19 | 169.87 |
| Satt343 | 5 | 172.09 | 173.06 |
| Satt343 | 6 | 187.08 | 188.05 |
| Satt343 | 7 | 148.16 | 148.62 |
| Satt343 | 8 | 181.12 | 181.99 |
| Satt343 | 9 | 163.26 | 164.00 |
| Satt343 | 10 | 175.46 | 175.86 |
| Satt343 | 11 | 154.51 | 154.71 |
| Satt346 | 1 | 321.29 | 322.30 |
| Satt346 | 2 | 327.35 | 328.36 |
| Satt346 | 3 | 336.32 | 337.41 |
| Satt346 | 4 | 339.25 | 340.29 |
| Satt346 | 5 | 318.20 | 319.27 |
| Satt346 | 6 | 324.40 | 325.32 |
| Satt347 | 1 | 345.25 | 346.28 |
| Satt347 | 2 | 347.94 | 349.07 |
| Satt347 | 3 | 351.02 | 351.84 |
| Satt348 | 1 | 308.03 | 308.72 |
| Satt348 | 2 | 333.01 | 333.85 |
| Satt348 | 3 | 341.83 | 342.66 |
| Satt348 | 4 | 344.67 | 345.35 |
| Satt348 | 5 | 330.27 | 330.58 |
| Satt348 | 6 | 326.84 | 327.35 |
| Satt348 | 7 | 339.55 | 339.85 |
| Satt352 | 1 | 334.54 | 335.83 |
| Satt352 | 2 | 341.13 | 341.63 |
| Satt352 | 3 | 346.15 | 347.21 |
| Satt352 | 4 | 351.72 | 352.87 |
| Satt352 | 5 | 354.62 | 355.55 |
| Satt352 | 6 | 340.59 | 340.89 |
| Satt352 | 7 | 343.79 | 343.92 |
| Satt352 | 8 | 369.49 | 369.69 |
| Satt352 | 9 | 349.17 | 349.80 |
| Satt352 | 10 | 337.41 | 338.54 |
| Satt352 | 11 | 360.53 | 360.63 |
| Satt353 | 1 | 144.20 | 145.03 |
| Satt353 | 2 | 159.86 | 160.87 |
| Satt353 | 3 | 169.19 | 169.75 |
| Satt353 | 4 | 174.94 | 175.96 |
| Satt353 | 5 | 184.18 | 185.08 |
| Satt353 | 6 | 178.37 | 178.97 |
| Satt353 | 7 | 165.84 | 166.96 |
| Satt353 | 8 | 154.30 | 154.50 |
| Satt355 | 1 | 248.20 | 249.20 |
| Satt355 | 2 | 257.22 | 258.33 |
| Satt355 | 3 | 272.58 | 273.43 |
| Satt355 | 4 | 236.35 | 237.33 |
| Satt355 | 5 | 254.26 | 254.86 |
| Satt355 | 6 | 269.53 | 270.03 |
| Satt355 | 7 | 275.88 | 276.33 |
| Satt355 | 8 | 278.88 | 279.28 |
| Satt355 | 9 | 260.76 | 260.96 |
| Satt356 | 1 | 322.24 | 323.30 |
| Satt356 | 2 | 325.15 | 326.72 |
| Satt357 | 1 | 171.69 | 173.06 |
| Satt357 | 2 | 275.63 | 277.15 |
| Satt357 | 3 | 278.60 | 280.19 |
| Satt357 | 4 | 183.22 | 184.18 |
| Satt357 | 5 | 198.70 | 199.39 |

APPENDIX I-continued

Allele Definition Table
23 pages

| Marker | Allele | Size | Range bp |
|---|---|---|---|
| Satt357 | 6 | 262.40 | 262.90 |
| Satt357 | 7 | 269.53 | 270.03 |
| Satt357 | 8 | 286.73 | 287.23 |
| Satt358 | 1 | 194.93 | 196.42 |
| Satt358 | 2 | 206.91 | 208.17 |
| Satt358 | 3 | 209.94 | 210.95 |
| Satt358 | 4 | 203.90 | 205.10 |
| Satt358 | 5 | 164.82 | 166.29 |
| Satt358 | 6 | 198.39 | 199.39 |
| Satt358 | 7 | 162.85 | 163.84 |
| Satt359 | 1 | 182.58 | 183.65 |
| Satt359 | 2 | 184.68 | 186.00 |
| Satt359 | 3 | 197.75 | 198.64 |
| Satt359 | 4 | 200.89 | 201.39 |
| Satt359 | 5 | 189.12 | 189.42 |
| Satt359 | 6 | 203.80 | 204.50 |
| Satt359 | 7 | 206.75 | 207.36 |
| Satt359 | 8 | 164.82 | 165.27 |
| Satt361 | 1 | 271.81 | 273.08 |
| Satt361 | 2 | 274.95 | 275.93 |
| Satt361 | 3 | 269.02 | 269.93 |
| Satt361 | 4 | 278.07 | 278.78 |
| Satt364 | 1 | 232.45 | 233.40 |
| Satt364 | 2 | 235.38 | 236.18 |
| Satt364 | 3 | 241.26 | 242.55 |
| Satt364 | 4 | 244.22 | 245.41 |
| Satt364 | 5 | 238.61 | 238.91 |
| Satt364 | 6 | 229.54 | 229.74 |
| Satt367 | 1 | 191.96 | 193.00 |
| Satt367 | 2 | 212.97 | 214.07 |
| Satt367 | 3 | 215.96 | 217.15 |
| Satt367 | 4 | 221.82 | 223.09 |
| Satt367 | 5 | 225.13 | 226.19 |
| Satt367 | 6 | 228.12 | 229.18 |
| Satt367 | 7 | 231.25 | 232.07 |
| Satt367 | 8 | 195.58 | 195.83 |
| Satt367 | 9 | 189.07 | 189.47 |
| Satt367 | 10 | 234.70 | 234.80 |
| Satt367 | 11 | 196.72 | 197.10 |
| Satt367 | 12 | 210.34 | 210.64 |
| Satt369 | 1 | 234.60 | 236.18 |
| Satt369 | 2 | 236.65 | 237.33 |
| Satt369 | 3 | 239.55 | 240.78 |
| Satt369 | 4 | 242.51 | 243.73 |
| Satt369 | 5 | 218.43 | 219.06 |
| Satt369 | 6 | 227.53 | 228.02 |
| Satt369 | 7 | 231.00 | 231.20 |
| Satt369 | 8 | 245.63 | 246.11 |
| Satt372 | 1 | 336.98 | 338.29 |
| Satt372 | 2 | 340.05 | 341.13 |
| Satt372 | 3 | 345.78 | 346.28 |
| Satt372 | 4 | 348.57 | 349.17 |
| Satt372 | 5 | 351.34 | 352.27 |
| Satt372 | 6 | 334.15 | 334.54 |
| Satt372 | 7 | 350.52 | 350.62 |
| Satt372 | 8 | 306.08 | 306.58 |
| Satt373 | 1 | 143.25 | 143.75 |
| Satt373 | 2 | 146.49 | 147.09 |
| Satt373 | 3 | 149.52 | 150.27 |
| Satt373 | 4 | 158.75 | 159.51 |
| Satt373 | 5 | 179.85 | 180.32 |
| Satt373 | 6 | 182.70 | 183.72 |
| Satt373 | 7 | 212.97 | 213.47 |
| Satt373 | 8 | 152.78 | 153.28 |
| Satt373 | 9 | 155.72 | 156.54 |
| Satt373 | 10 | 173.73 | 174.43 |
| Satt373 | 11 | 178.20 | 178.58 |
| Satt373 | 12 | 185.85 | 186.11 |
| Satt373 | 13 | 191.97 | 192.37 |
| Satt373 | 14 | 194.93 | 195.33 |
| Satt373 | 15 | 198.10 | 198.40 |
| Satt373 | 16 | 215.96 | 216.71 |
| Satt373 | 17 | 218.80 | 219.66 |
| Satt373 | 18 | 207.11 | 207.31 |
| Satt378 | 1 | 138.70 | 139.45 |
| Satt378 | 2 | 151.75 | 152.78 |
| Satt378 | 3 | 145.61 | 145.81 |
| Satt378 | 4 | 148.82 | 149.22 |
| Satt378 | 5 | 159.86 | 160.26 |
| Satt380 | 1 | 147.94 | 148.82 |
| Satt380 | 2 | 149.22 | 149.82 |
| Satt380 | 3 | 151.31 | 152.15 |
| Satt380 | 4 | 152.35 | 152.78 |
| Satt383 | 1 | 341.04 | 341.89 |
| Satt383 | 2 | 345.72 | 346.86 |
| Satt383 | 3 | 348.45 | 349.60 |
| Satt383 | 4 | 351.32 | 352.42 |
| Satt383 | 5 | 340.29 | 340.49 |
| Satt383 | 6 | 344.22 | 344.42 |
| Satt384 | 1 | 125.06 | 125.76 |
| Satt384 | 2 | 153.68 | 154.45 |
| Satt384 | 3 | 156.80 | 157.34 |
| Satt385 | 1 | 100.37 | 101.41 |
| Satt385 | 2 | 115.70 | 116.30 |
| Satt385 | 3 | 128.08 | 128.60 |
| Satt385 | 4 | 140.32 | 141.60 |
| Satt385 | 5 | 143.45 | 144.53 |
| Satt385 | 6 | 149.91 | 151.11 |
| Satt385 | 7 | 146.97 | 148.06 |
| Satt385 | 8 | 156.29 | 157.34 |
| Satt385 | 9 | 160.87 | 161.37 |
| Satt385 | 10 | 163.84 | 164.34 |
| Satt385 | 11 | 173.06 | 174.29 |
| Satt385 | 12 | 153.18 | 153.38 |
| Satt387 | 1 | 171.12 | 171.59 |
| Satt387 | 2 | 177.90 | 178.37 |
| Satt387 | 3 | 200.35 | 201.14 |
| Satt387 | 4 | 204.90 | 206.40 |
| Satt387 | 5 | 212.97 | 213.97 |
| Satt387 | 6 | 216.16 | 216.36 |
| Satt389 | 1 | 145.91 | 146.49 |
| Satt389 | 2 | 148.87 | 149.67 |
| Satt389 | 3 | 153.28 | 154.21 |
| Satt389 | 4 | 173.49 | 174.62 |
| Satt389 | 5 | 176.43 | 177.45 |
| Satt389 | 6 | 179.45 | 180.94 |
| Satt389 | 7 | 147.96 | 148.26 |
| Satt389 | 8 | 156.44 | 156.84 |
| Satt389 | 9 | 182.45 | 183.15 |
| Satt389 | 10 | 140.52 | 140.82 |
| Satt389 | 11 | 168.22 | 168.42 |
| Satt390 | 1 | 358.94 | 359.73 |
| Satt390 | 2 | 361.62 | 362.77 |
| Satt390 | 3 | 356.49 | 356.92 |
| Satt390 | 4 | 364.73 | 365.44 |
| Satt390 | 5 | 350.67 | 350.87 |
| Satt391 | 1 | 168.69 | 169.65 |
| Satt391 | 2 | 183.67 | 184.68 |
| Satt391 | 3 | 181.12 | 181.29 |
| Satt391 | 4 | 187.28 | 187.48 |
| Satt393 | 1 | 325.13 | 326.20 |
| Satt393 | 2 | 328.15 | 329.16 |
| Satt393 | 3 | 322.09 | 322.50 |
| Satt393 | 4 | 331.47 | 331.67 |
| Satt398 | 1 | 151.61 | 152.78 |
| Satt398 | 2 | 154.70 | 155.84 |
| Satt398 | 3 | 157.71 | 158.86 |
| Satt398 | 4 | 166.76 | 167.92 |
| Satt398 | 5 | 169.85 | 171.12 |
| Satt398 | 6 | 160.79 | 161.87 |
| Satt398 | 7 | 163.89 | 164.82 |
| Satt398 | 8 | 176.43 | 176.93 |
| Satt398 | 9 | 179.85 | 180.32 |
| Satt398 | 10 | 182.25 | 183.72 |
| Satt398 | 11 | 148.62 | 148.82 |
| Satt399 | 1 | 312.51 | 313.76 |
| Satt399 | 2 | 325.00 | 326.12 |
| Satt399 | 3 | 328.05 | 329.37 |
| Satt399 | 4 | 331.31 | 332.12 |
| Satt406 | 1 | 161.57 | 162.57 |

APPENDIX I-continued

Allele Definition Table
23 pages

| Marker | Allele | Size | Range bp |
|---|---|---|---|
| Satt406 | 2 | 239.21 | 240.38 |
| Satt406 | 3 | 242.25 | 243.33 |
| Satt406 | 4 | 245.41 | 246.20 |
| Satt406 | 5 | 158.73 | 159.46 |
| Satt406 | 6 | 233.42 | 233.82 |
| Satt406 | 7 | 230.34 | 230.44 |
| Satt406 | 8 | 215.47 | 215.57 |
| Satt406 | 9 | 236.28 | 237.26 |
| Satt406 | 10 | 227.26 | 227.46 |
| Satt409 | 1 | 166.29 | 166.76 |
| Satt409 | 2 | 169.19 | 170.15 |
| Satt409 | 3 | 174.99 | 176.16 |
| Satt409 | 4 | 184.18 | 185.20 |
| Satt409 | 5 | 187.08 | 188.35 |
| Satt409 | 6 | 193.68 | 194.44 |
| Satt409 | 7 | 199.69 | 200.39 |
| Satt409 | 8 | 196.72 | 196.90 |
| Satt409 | 9 | 157.24 | 157.54 |
| Satt409 | 10 | 163.56 | 163.66 |
| Satt409 | 11 | 202.79 | 202.90 |
| Satt409 | 12 | 190.51 | 191.28 |
| Satt409 | 13 | 172.29 | 172.39 |
| Satt411 | 1 | 97.95 | 99.06 |
| Satt411 | 2 | 100.93 | 102.21 |
| Satt411 | 3 | 93.77 | 94.17 |
| Satt412 | 1 | 248.70 | 249.57 |
| Satt412 | 2 | 254.76 | 255.78 |
| Satt412 | 3 | 257.79 | 258.83 |
| Satt412 | 4 | 260.81 | 261.88 |
| Satt412 | 5 | 263.87 | 264.94 |
| Satt412 | 6 | 251.91 | 252.73 |
| Satt412 | 7 | 267.23 | 268.00 |
| Satt413 | 1 | 333.87 | 334.84 |
| Satt413 | 2 | 356.86 | 357.96 |
| Satt413 | 3 | 359.66 | 360.72 |
| Satt413 | 4 | 369.64 | 370.75 |
| Satt413 | 5 | 342.16 | 342.36 |
| Satt413 | 6 | 342.96 | 342.99 |
| Satt413 | 7 | 366.61 | 366.81 |
| Satt413 | 8 | 368.63 | 369.49 |
| Satt414 | 1 | 277.87 | 279.18 |
| Satt414 | 2 | 317.75 | 319.16 |
| Satt414 | 3 | 321.22 | 322.30 |
| Satt414 | 4 | 324.15 | 325.32 |
| Satt414 | 5 | 327.35 | 328.36 |
| Satt414 | 7 | 336.62 | 337.31 |
| Satt414 | 8 | 302.69 | 303.40 |
| Satt414 | 9 | 315.21 | 316.23 |
| Satt414 | 10 | 339.70 | 340.19 |
| Satt414 | 11 | 342.66 | 342.86 |
| Satt414 | 12 | 330.78 | 331.28 |
| Satt415 | 1 | 290.25 | 291.40 |
| Satt415 | 2 | 297.19 | 298.60 |
| Satt415 | 3 | 300.33 | 301.87 |
| Satt415 | 4 | 303.75 | 304.96 |
| Satt415 | 5 | 310.07 | 310.97 |
| Satt415 | 6 | 323.10 | 323.50 |
| Satt415 | 7 | 292.05 | 292.35 |
| Satt415 | 8 | 307.61 | 307.96 |
| Satt415 | 9 | 288.66 | 289.45 |
| Satt416 | 1 | 241.96 | 242.16 |
| Satt416 | 2 | 253.32 | 254.26 |
| Satt416 | 3 | 256.56 | 257.91 |
| Satt416 | 4 | 262.64 | 263.42 |
| Satt416 | 5 | 265.86 | 266.48 |
| Satt416 | 6 | 280.82 | 282.30 |
| Satt416 | 7 | 244.34 | 244.77 |
| Satt416 | 8 | 259.66 | 260.05 |
| Satt417 | 1 | 299.06 | 300.33 |
| Satt417 | 2 | 318.26 | 319.27 |
| Satt417 | 3 | 321.44 | 322.30 |
| Satt417 | 4 | 339.40 | 341.13 |
| Satt417 | 5 | 342.44 | 343.92 |
| Satt417 | 6 | 336.96 | 337.51 |
| Satt418 | 1 | 207.40 | 208.42 |
| Satt418 | 2 | 210.36 | 211.45 |
| Satt418 | 3 | 213.40 | 214.47 |
| Satt418 | 4 | 216.35 | 217.45 |
| Satt418 | 5 | 219.41 | 219.88 |
| Satt418 | 6 | 189.53 | 190.00 |
| Satt418 | 7 | 192.47 | 193.45 |
| Satt418 | 8 | 198.60 | 199.39 |
| Satt418 | 9 | 204.50 | 204.85 |
| Satt420 | 1 | 249.67 | 250.71 |
| Satt420 | 2 | 260.72 | 261.97 |
| Satt420 | 3 | 266.98 | 268.00 |
| Satt420 | 4 | 274.62 | 275.12 |
| Satt420 | 5 | 252.88 | 253.74 |
| Satt420 | 6 | 256.08 | 256.29 |
| Satt420 | 7 | 264.22 | 264.44 |
| Satt421 | 1 | 135.14 | 136.43 |
| Satt421 | 2 | 144.83 | 146.49 |
| Satt421 | 3 | 148.55 | 149.22 |
| Satt422 | 1 | 311.60 | 312.77 |
| Satt422 | 2 | 321.29 | 321.79 |
| Satt422 | 3 | 330.38 | 331.74 |
| Satt422 | 4 | 333.35 | 334.34 |
| Satt422 | 5 | 315.31 | 315.61 |
| Satt422 | 6 | 318.36 | 319.30 |
| Satt422 | 7 | 336.92 | 337.12 |
| Satt422 | 8 | 327.85 | 328.05 |
| Satt423 | 1 | 241.76 | 242.75 |
| Satt423 | 2 | 262.90 | 263.92 |
| Satt423 | 3 | 266.06 | 266.98 |
| Satt423 | 4 | 340.05 | 340.69 |
| Satt423 | 6 | 321.79 | 321.89 |
| Satt423 | 7 | 248.60 | 248.80 |
| Satt426 | 1 | 198.39 | 199.59 |
| Satt426 | 2 | 200.39 | 200.89 |
| Satt426 | 3 | 202.39 | 203.40 |
| Satt426 | 4 | 203.90 | 204.40 |
| Satt426 | 5 | 205.34 | 206.40 |
| Satt426 | 6 | 217.55 | 218.03 |
| Satt426 | 7 | 192.46 | 192.66 |
| Satt426 | 8 | 223.59 | 223.76 |
| Satt426 | 9 | 196.90 | 197.00 |
| Satt429 | 1 | 263.42 | 264.22 |
| Satt429 | 2 | 266.48 | 267.50 |
| Satt429 | 3 | 269.53 | 270.65 |
| Satt429 | 4 | 272.54 | 273.65 |
| Satt429 | 5 | 245.21 | 246.11 |
| Satt429 | 6 | 248.20 | 248.85 |
| Satt429 | 7 | 254.46 | 254.76 |
| Satt429 | 8 | 275.83 | 276.43 |
| Satt429 | 9 | 257.31 | 257.71 |
| Satt430 | 1 | 241.76 | 242.75 |
| Satt430 | 2 | 244.72 | 245.41 |
| Satt430 | 3 | 248.10 | 248.70 |
| Satt430 | 4 | 254.26 | 254.46 |
| Satt430 | 5 | 257.31 | 257.51 |
| Satt430 | 6 | 239.21 | 239.30 |
| Satt431 | 1 | 305.46 | 306.38 |
| Satt431 | 2 | 318.20 | 318.96 |
| Satt431 | 3 | 321.29 | 322.30 |
| Satt431 | 4 | 324.31 | 324.81 |
| Satt431 | 5 | 342.51 | 343.29 |
| Satt431 | 6 | 348.11 | 349.07 |
| Satt431 | 7 | 315.41 | 315.51 |
| Satt431 | 8 | 331.37 | 331.57 |
| Satt431 | 9 | 328.05 | 328.25 |
| Satt431 | 10 | 340.15 | 340.29 |
| Satt431 | 11 | 345.50 | 345.88 |
| Satt431 | 12 | 351.44 | 351.54 |
| Satt432 | 1 | 255.78 | 256.29 |
| Satt432 | 2 | 258.53 | 259.50 |
| Satt432 | 3 | 261.72 | 262.40 |
| Satt432 | 4 | 264.89 | 265.46 |
| Satt433 | 1 | 125.56 | 126.50 |
| Satt433 | 2 | 134.74 | 135.78 |
| Satt433 | 3 | 144.33 | 145.41 |

APPENDIX I-continued

Allele Definition Table
23 pages

| Marker | Allele | Size | Range bp |
|---|---|---|---|
| Satt433 | 4 | 153.80 | 154.98 |
| Satt433 | 5 | 166.14 | 167.20 |
| Satt433 | 6 | 156.64 | 156.94 |
| Satt433 | 7 | 138.19 | 138.49 |
| Satt433 | 8 | 159.55 | 159.86 |
| Satt436 | 1 | 187.58 | 188.75 |
| Satt436 | 2 | 208.93 | 209.94 |
| Satt436 | 3 | 244.72 | 245.76 |
| Satt436 | 4 | 226.96 | 227.26 |
| Satt436 | 5 | 247.70 | 248.85 |
| Satt436 | 6 | 250.71 | 251.92 |
| Satt436 | 7 | 203.30 | 203.60 |
| Satt436 | 8 | 254.11 | 254.76 |
| Satt440 | 1 | 286.23 | 287.23 |
| Satt440 | 2 | 307.74 | 308.88 |
| Satt440 | 3 | 320.28 | 320.98 |
| Satt440 | 4 | 338.74 | 339.58 |
| Satt440 | 5 | 287.33 | 288.04 |
| Satt440 | 6 | 323.70 | 324.36 |
| Satt440 | 7 | 335.80 | 336.32 |
| Satt440 | 8 | 317.45 | 317.65 |
| Satt441 | 1 | 161.80 | 162.77 |
| Satt441 | 2 | 164.82 | 165.79 |
| Satt441 | 3 | 173.68 | 174.69 |
| Satt441 | 4 | 176.69 | 177.70 |
| Satt441 | 5 | 179.78 | 180.62 |
| Satt441 | 6 | 191.90 | 192.86 |
| Satt441 | 7 | 207.02 | 207.92 |
| Satt441 | 8 | 171.07 | 171.59 |
| Satt441 | 10 | 168.42 | 168.52 |
| Satt441 | 11 | 136.72 | 137.43 |
| Satt441 | 12 | 152.88 | 153.48 |
| Satt441 | 13 | 158.95 | 159.75 |
| Satt441 | 14 | 155.84 | 156.44 |
| Satt441 | 15 | 195.03 | 195.70 |
| Satt441 | 16 | 185.85 | 186.39 |
| Satt441 | 17 | 189.52 | 189.72 |
| Satt442 | 1 | 240.28 | 240.78 |
| Satt442 | 2 | 246.20 | 247.30 |
| Satt442 | 3 | 249.20 | 250.21 |
| Satt442 | 4 | 252.23 | 253.24 |
| Satt442 | 5 | 261.68 | 262.40 |
| Satt442 | 6 | 264.44 | 265.46 |
| Satt442 | 7 | 258.63 | 259.03 |
| Satt442 | 8 | 243.66 | 244.13 |
| Satt442 | 9 | 267.80 | 268.20 |
| Satt442 | 10 | 237.63 | 238.03 |
| Satt442 | 11 | 255.72 | 256.29 |
| Satt442 | 12 | 283.01 | 283.31 |
| Satt442 | 13 | 270.75 | 271.00 |
| Satt444 | 1 | 134.84 | 136.28 |
| Satt444 | 2 | 137.94 | 138.95 |
| Satt445 | 1 | 166.18 | 166.96 |
| Satt445 | 2 | 169.02 | 169.85 |
| Satt445 | 3 | 184.28 | 185.15 |
| Satt445 | 4 | 193.35 | 194.54 |
| Satt445 | 5 | 196.52 | 197.40 |
| Satt445 | 6 | 215.17 | 215.47 |
| Satt445 | 7 | 163.11 | 163.76 |
| Satt445 | 8 | 190.20 | 190.80 |
| Satt445 | 9 | 178.78 | 179.08 |
| Satt445 | 10 | 187.38 | 187.83 |
| Satt445 | 11 | 217.45 | 217.90 |
| Satt448 | 1 | 340.69 | 341.63 |
| Satt448 | 2 | 347.47 | 348.19 |
| Satt448 | 3 | 350.42 | 350.92 |
| Satt448 | 4 | 355.86 | 356.92 |
| Satt448 | 5 | 361.62 | 362.12 |
| Satt448 | 6 | 358.66 | 359.34 |
| Satt448 | 7 | 364.68 | 365.08 |
| Satt448 | 8 | 343.59 | 343.92 |
| Satt448 | 9 | 332.07 | 332.27 |
| Satt448 | 10 | 324.81 | 325.01 |
| Satt451 | 1 | 325.32 | 326.49 |
| Satt451 | 2 | 351.84 | 352.37 |
| Satt451 | 3 | 354.42 | 355.25 |
| Satt451 | 4 | 357.52 | 357.72 |
| Satt451 | 5 | 319.67 | 319.92 |
| Satt452 | 1 | 256.74 | 257.81 |
| Satt452 | 2 | 259.68 | 260.86 |
| Satt452 | 3 | 263.42 | 263.92 |
| Satt452 | 4 | 265.81 | 266.98 |
| Satt452 | 5 | 274.98 | 275.83 |
| Satt452 | 6 | 296.79 | 296.99 |
| Satt452 | 7 | 254.14 | 254.36 |
| Satt452 | 8 | 302.57 | 303.40 |
| Satt452 | 9 | 272.46 | 272.78 |
| Satt452 | 10 | 309.45 | 309.55 |
| Satt454 | 1 | 158.70 | 159.60 |
| Satt454 | 2 | 170.40 | 171.59 |
| Satt454 | 3 | 173.53 | 174.49 |
| Satt454 | 4 | 176.63 | 177.50 |
| Satt454 | 5 | 161.87 | 162.37 |
| Satt454 | 6 | 182.95 | 183.15 |
| Satt455 | 1 | 273.08 | 274.10 |
| Satt455 | 2 | 276.03 | 277.15 |
| Satt455 | 3 | 279.31 | 280.19 |
| Satt457 | 1 | 356.79 | 357.42 |
| Satt457 | 2 | 368.33 | 369.29 |
| Satt457 | 3 | 324.81 | 325.11 |
| Satt457 | 4 | 336.67 | 337.12 |
| Satt457 | 5 | 354.12 | 354.32 |
| Satt457 | 6 | 365.44 | 366.09 |
| Satt457 | 7 | 371.42 | 371.82 |
| Satt460 | 1 | 113.80 | 114.50 |
| Satt460 | 2 | 116.66 | 117.63 |
| Satt460 | 3 | 135.24 | 136.08 |
| Satt460 | 4 | 144.83 | 145.61 |
| Satt460 | 5 | 160.36 | 161.17 |
| Satt460 | 6 | 163.46 | 164.24 |
| Satt460 | 7 | 129.40 | 129.61 |
| Satt461 | 1 | 128.60 | 129.61 |
| Satt461 | 2 | 131.65 | 132.67 |
| Satt461 | 3 | 138.39 | 138.95 |
| Satt461 | 4 | 144.83 | 145.41 |
| Satt461 | 5 | 154.30 | 154.82 |
| Satt461 | 6 | 122.95 | 124.05 |
| Satt461 | 7 | 153.28 | 153.80 |
| Satt461 | 8 | 134.94 | 135.24 |
| Satt464 | 1 | 144.77 | 146.31 |
| Satt464 | 2 | 164.65 | 165.79 |
| Satt464 | 3 | 174.13 | 175.55 |
| Satt464 | 4 | 168.02 | 168.42 |
| Satt464 | 5 | 177.90 | 178.10 |
| Satt466 | 1 | 165.27 | 166.29 |
| Satt466 | 2 | 168.32 | 169.19 |
| Satt466 | 3 | 177.80 | 178.77 |
| Satt467 | 1 | 274.79 | 275.52 |
| Satt467 | 2 | 294.84 | 295.98 |
| Satt469 | 1 | 245.81 | 246.90 |
| Satt469 | 2 | 276.65 | 277.20 |
| Satt469 | 3 | 279.69 | 280.24 |
| Satt469 | 4 | 225.63 | 225.89 |
| Satt469 | 5 | 249.50 | 249.80 |
| Satt470 | 1 | 263.62 | 264.94 |
| Satt470 | 2 | 266.48 | 268.00 |
| Satt471 | 1 | 233.92 | 234.60 |
| Satt471 | 2 | 245.71 | 246.70 |
| Satt471 | 3 | 248.70 | 249.70 |
| Satt473 | 1 | 307.51 | 308.53 |
| Satt473 | 2 | 310.57 | 311.60 |
| Satt473 | 3 | 313.86 | 314.69 |
| Satt473 | 4 | 317.25 | 317.75 |
| Satt473 | 5 | 295.27 | 295.78 |
| Satt473 | 6 | 298.30 | 298.81 |
| Satt473 | 7 | 301.35 | 302.37 |
| Satt473 | 8 | 304.43 | 305.46 |
| Satt473 | 9 | 292.20 | 292.35 |
| Satt475 | 1 | 150.47 | 151.46 |
| Satt475 | 2 | 159.86 | 160.87 |

APPENDIX I-continued

Allele Definition Table
23 pages

| Marker | Allele | Size | Range bp |
|---|---|---|---|
| Satt475 | 3 | 171.92 | 173.06 |
| Satt475 | 4 | 175.46 | 175.66 |
| Satt475 | 5 | 178.10 | 178.30 |
| Satt476 | 1 | 343.49 | 344.02 |
| Satt476 | 2 | 346.43 | 347.21 |
| Satt476 | 3 | 354.62 | 355.55 |
| Satt476 | 4 | 357.52 | 358.36 |
| Satt476 | 5 | 365.94 | 366.91 |
| Satt476 | 6 | 349.17 | 349.37 |
| Satt476 | 7 | 351.94 | 352.27 |
| Satt476 | 8 | 360.53 | 360.67 |
| Satt476 | 9 | 363.37 | 363.72 |
| Satt476 | 10 | 325.62 | 325.92 |
| Satt477 | 1 | 141.60 | 142.67 |
| Satt477 | 2 | 157.34 | 158.35 |
| Satt477 | 3 | 163.62 | 164.44 |
| Satt477 | 4 | 154.71 | 155.42 |
| Satt477 | 5 | 161.07 | 161.27 |
| Satt478 | 1 | 194.36 | 195.23 |
| Satt478 | 2 | 227.16 | 227.82 |
| Satt478 | 3 | 232.95 | 234.12 |
| Satt478 | 4 | 236.28 | 236.86 |
| Satt478 | 5 | 239.30 | 240.15 |
| Satt478 | 6 | 242.25 | 243.03 |
| Satt478 | 7 | 254.26 | 255.11 |
| Satt478 | 8 | 257.31 | 258.06 |
| Satt478 | 9 | 224.41 | 224.73 |
| Satt478 | 10 | 230.40 | 230.70 |
| Satt478 | 11 | 251.42 | 251.82 |
| Satt478 | 12 | 248.40 | 248.75 |
| Satt478 | 13 | 221.56 | 221.66 |
| Satt478 | 14 | 221.26 | 221.46 |
| Satt479 | 1 | 114.30 | 115.40 |
| Satt479 | 2 | 117.63 | 118.50 |
| Satt479 | 3 | 142.52 | 143.25 |
| Satt479 | 4 | 145.41 | 146.49 |
| Satt479 | 5 | 151.75 | 152.83 |
| Satt479 | 6 | 111.76 | 112.01 |
| Satt480 | 1 | 137.81 | 138.95 |
| Satt480 | 2 | 140.99 | 142.17 |
| Satt480 | 3 | 144.33 | 145.41 |
| Satt487 | 1 | 114.30 | 114.90 |
| Satt487 | 2 | 117.16 | 118.13 |
| Satt487 | 3 | 120.28 | 121.07 |
| Satt487 | 4 | 123.05 | 124.20 |
| Satt487 | 5 | 126.31 | 127.07 |
| Satt487 | 6 | 111.36 | 111.91 |
| Satt487 | 7 | 132.67 | 132.87 |
| Satt487 | 8 | 135.78 | 135.98 |
| Satt487 | 9 | 129.61 | 129.91 |
| Satt488 | 1 | 295.57 | 295.78 |
| Satt488 | 2 | 311.35 | 312.33 |
| Satt488 | 3 | 314.61 | 315.41 |
| Satt488 | 4 | 323.85 | 324.71 |
| Satt488 | 5 | 327.29 | 327.75 |
| Satt491 | 1 | 195.86 | 196.52 |
| Satt491 | 2 | 201.78 | 202.49 |
| Satt491 | 3 | 207.41 | 208.42 |
| Satt491 | 4 | 216.95 | 217.35 |
| Satt491 | 5 | 219.98 | 220.28 |
| Satt492 | 1 | 235.72 | 237.13 |
| Satt492 | 2 | 238.81 | 239.97 |
| Satt492 | 3 | 227.46 | 227.62 |
| Satt493 | 1 | 266.41 | 267.50 |
| Satt493 | 2 | 269.83 | 270.55 |
| Satt493 | 3 | 281.93 | 282.71 |
| Satt493 | 4 | 279.23 | 279.38 |
| Satt495 | 1 | 231.00 | 231.97 |
| Satt495 | 2 | 243.11 | 244.22 |
| Satt495 | 3 | 237.33 | 237.83 |
| Satt497 | 1 | 268.82 | 269.53 |
| Satt497 | 2 | 271.96 | 272.58 |
| Satt497 | 3 | 274.62 | 276.23 |
| Satt497 | 4 | 277.67 | 279.03 |
| Satt497 | 5 | 296.18 | 297.49 |
| Satt497 | 6 | 299.31 | 300.43 |
| Satt497 | 7 | 281.10 | 281.90 |
| Satt497 | 8 | 265.86 | 266.06 |
| Satt497 | 9 | 262.80 | 263.20 |
| Satt503 | 1 | 226.19 | 227.00 |
| Satt503 | 2 | 228.90 | 230.09 |
| Satt503 | 3 | 231.92 | 233.15 |
| Satt503 | 4 | 221.83 | 222.55 |
| Satt503 | 5 | 211.15 | 211.65 |
| Satt503 | 6 | 224.93 | 225.23 |
| Satt503 | 7 | 234.95 | 235.59 |
| Satt503 | 8 | 223.00 | 223.10 |
| Satt506 | 1 | 280.19 | 281.35 |
| Satt506 | 2 | 283.21 | 284.01 |
| Satt506 | 3 | 292.26 | 293.61 |
| Satt506 | 4 | 289.75 | 290.15 |
| Satt507 | 1 | 230.60 | 231.47 |
| Satt507 | 2 | 233.42 | 234.40 |
| Satt507 | 3 | 236.36 | 237.43 |
| Satt507 | 4 | 227.62 | 228.02 |
| Satt507 | 5 | 239.70 | 239.90 |
| Satt508 | 1 | 333.06 | 334.15 |
| Satt508 | 2 | 336.15 | 337.31 |
| Satt508 | 3 | 339.25 | 339.65 |
| Satt509 | 1 | 192.47 | 193.55 |
| Satt509 | 2 | 195.43 | 196.52 |
| Satt509 | 3 | 198.40 | 199.39 |
| Satt509 | 4 | 201.39 | 202.59 |
| Satt509 | 5 | 204.78 | 205.40 |
| Satt509 | 6 | 236.86 | 238.41 |
| Satt509 | 7 | 249.20 | 250.41 |
| Satt509 | 8 | 240.68 | 241.18 |
| Satt509 | 9 | 243.79 | 244.22 |
| Satt509 | 10 | 184.18 | 184.48 |
| Satt509 | 11 | 252.83 | 253.13 |
| Satt510 | 1 | 109.05 | 109.55 |
| Satt510 | 2 | 127.07 | 127.58 |
| Satt510 | 3 | 136.08 | 137.33 |
| Satt510 | 4 | 139.35 | 140.52 |
| Satt510 | 5 | 96.44 | 97.45 |
| Satt510 | 6 | 121.07 | 122.06 |
| Satt510 | 7 | 111.91 | 112.86 |
| Satt510 | 8 | 130.11 | 130.31 |
| Satt511 | 1 | 255.83 | 256.79 |
| Satt511 | 2 | 262.02 | 262.90 |
| Satt511 | 3 | 265.03 | 266.01 |
| Satt511 | 4 | 268.06 | 269.07 |
| Satt511 | 5 | 277.87 | 278.07 |
| Satt511 | 6 | 259.23 | 259.55 |
| Satt512 | 1 | 316.16 | 317.25 |
| Satt512 | 2 | 319.37 | 320.28 |
| Satt512 | 3 | 325.53 | 326.44 |
| Satt512 | 4 | 328.71 | 329.57 |
| Satt512 | 5 | 331.77 | 332.86 |
| Satt512 | 6 | 310.07 | 310.62 |
| Satt512 | 7 | 313.03 | 313.68 |
| Satt513 | 1 | 117.63 | 118.13 |
| Satt513 | 2 | 130.11 | 130.63 |
| Satt513 | 3 | 142.17 | 143.25 |
| Satt513 | 4 | 173.06 | 173.83 |
| Satt513 | 5 | 181.79 | 182.75 |
| Satt513 | 6 | 185.05 | 185.65 |
| Satt513 | 7 | 170.15 | 170.62 |
| Satt513 | 8 | 164.34 | 164.44 |
| Satt513 | 9 | 167.26 | 167.63 |
| Satt513 | 10 | 133.07 | 133.37 |
| Satt513 | 11 | 139.14 | 139.65 |
| Satt513 | 12 | 148.77 | 148.92 |
| Satt513 | 13 | 153.38 | 153.58 |
| Satt513 | 14 | 145.81 | 146.11 |
| Satt514 | 1 | 314.34 | 315.21 |
| Satt514 | 2 | 316.63 | 317.25 |
| Satt514 | 3 | 325.76 | 326.34 |
| Satt514 | 4 | 351.18 | 351.94 |
| Satt514 | 5 | 328.96 | 329.26 |

APPENDIX I-continued

Allele Definition Table
23 pages

| Marker | Allele | Size | Range bp |
|---|---|---|---|
| Satt514 | 6 | 329.77 | 330.38 |
| Satt514 | 7 | 331.97 | 332.36 |
| Satt514 | 8 | 337.12 | 337.71 |
| Satt514 | 9 | 340.15 | 340.39 |
| Satt514 | 10 | 328.25 | 328.56 |
| Satt514 | 11 | 345.78 | 346.18 |
| Satt514 | 12 | 359.93 | 360.13 |
| Satt514 | 13 | 362.87 | 363.17 |
| Satt514 | 14 | 354.22 | 354.62 |
| Satt514 | 15 | 334.25 | 334.34 |
| Satt515 | 1 | 341.13 | 342.06 |
| Satt515 | 2 | 352.77 | 353.69 |
| Satt515 | 3 | 355.05 | 356.44 |
| Satt517 | 1 | 159.30 | 160.36 |
| Satt517 | 2 | 162.12 | 163.56 |
| Satt517 | 3 | 165.13 | 166.49 |
| Satt517 | 4 | 173.15 | 174.50 |
| Satt517 | 5 | 176.21 | 177.23 |
| Satt517 | 6 | 179.45 | 180.15 |
| Satt517 | 7 | 149.89 | 150.91 |
| Satt517 | 8 | 170.05 | 171.02 |
| Satt519 | 1 | 354.60 | 355.55 |
| Satt519 | 2 | 357.42 | 358.36 |
| Satt519 | 3 | 360.33 | 361.17 |
| Satt519 | 4 | 363.27 | 363.47 |
| Satt519 | 5 | 372.02 | 372.18 |
| Satt522 | 1 | 231.47 | 232.34 |
| Satt522 | 2 | 240.78 | 241.26 |
| Satt522 | 3 | 255.78 | 256.89 |
| Satt522 | 4 | 258.83 | 259.90 |
| Satt522 | 5 | 283.31 | 284.36 |
| Satt522 | 6 | 237.53 | 238.13 |
| Satt522 | 7 | 252.83 | 253.39 |
| Satt522 | 8 | 280.29 | 280.70 |
| Satt523 | 1 | 171.58 | 172.39 |
| Satt523 | 2 | 174.43 | 175.34 |
| Satt523 | 3 | 189.52 | 190.40 |
| Satt523 | 4 | 192.76 | 193.45 |
| Satt523 | 5 | 184.02 | 184.18 |
| Satt523 | 6 | 199.04 | 199.39 |
| Satt524 | 1 | 168.22 | 168.94 |
| Satt524 | 2 | 171.12 | 172.29 |
| Satt524 | 3 | 177.40 | 177.60 |
| Satt524 | 4 | 174.59 | 174.89 |
| Satt526 | 1 | 322.80 | 324.22 |
| Satt526 | 2 | 332.02 | 333.44 |
| Satt529 | 1 | 214.47 | 215.47 |
| Satt529 | 2 | 220.38 | 221.35 |
| Satt529 | 3 | 217.85 | 218.08 |
| Satt529 | 4 | 229.67 | 230.24 |
| Satt529 | 5 | 223.96 | 224.06 |
| Satt532 | 1 | 170.15 | 171.37 |
| Satt532 | 2 | 172.86 | 174.48 |
| Satt532 | 3 | 179.35 | 180.37 |
| Satt532 | 4 | 182.50 | 183.32 |
| Satt532 | 5 | 154.40 | 154.82 |
| Satt532 | 6 | 175.31 | 176.55 |
| Satt532 | 7 | 176.58 | 177.40 |
| Satt532 | 8 | 167.48 | 168.17 |
| Satt533 | 1 | 169.19 | 170.15 |
| Satt533 | 2 | 174.99 | 175.96 |
| Satt533 | 3 | 193.94 | 194.44 |
| Satt533 | 4 | 196.72 | 196.90 |
| Satt533 | 5 | 172.23 | 172.96 |
| Satt533 | 6 | 178.37 | 178.57 |
| Satt533 | 7 | 193.15 | 193.55 |
| Satt534 | 1 | 165.79 | 166.90 |
| Satt534 | 2 | 172.01 | 173.06 |
| Satt534 | 3 | 177.90 | 178.87 |
| Satt534 | 4 | 180.82 | 181.84 |
| Satt534 | 5 | 183.72 | 185.15 |
| Satt534 | 6 | 187.08 | 188.55 |
| Satt534 | 7 | 190.00 | 191.28 |
| Satt534 | 8 | 192.95 | 194.44 |
| Satt534 | 9 | 195.92 | 197.05 |
| Satt534 | 10 | 163.36 | 163.84 |
| Satt534 | 11 | 160.36 | 160.76 |
| Satt534 | 12 | 169.18 | 169.85 |
| Satt534 | 13 | 157.34 | 157.74 |
| Satt534 | 14 | 175.04 | 175.96 |
| Satt534 | 15 | 199.89 | 200.19 |
| Satt534 | 16 | 150.71 | 151.11 |
| Satt536 | 1 | 220.76 | 221.83 |
| Satt536 | 2 | 223.76 | 224.26 |
| Satt536 | 3 | 226.66 | 227.72 |
| Satt536 | 4 | 229.38 | 230.70 |
| Satt536 | 5 | 197.20 | 197.50 |
| Satt536 | 6 | 232.95 | 234.22 |
| Satt536 | 7 | 236.18 | 236.61 |
| Satt537 | 1 | 292.58 | 293.76 |
| Satt537 | 2 | 295.78 | 296.79 |
| Satt537 | 3 | 311.28 | 312.63 |
| Satt537 | 4 | 317.75 | 318.36 |
| Satt537 | 5 | 320.67 | 321.79 |
| Satt537 | 6 | 323.80 | 324.81 |
| Satt537 | 7 | 301.35 | 302.62 |
| Satt537 | 8 | 308.03 | 309.10 |
| Satt537 | 9 | 280.43 | 281.20 |
| Satt537 | 10 | 289.75 | 290.25 |
| Satt537 | 11 | 299.31 | 299.83 |
| Satt537 | 12 | 305.46 | 305.98 |
| Satt537 | 13 | 314.69 | 315.21 |
| Satt537 | 14 | 333.35 | 333.85 |
| Satt537 | 15 | 283.61 | 283.91 |
| Satt540 | 1 | 175.14 | 176.06 |
| Satt540 | 2 | 181.17 | 182.25 |
| Satt540 | 3 | 190.28 | 191.48 |
| Satt540 | 4 | 192.71 | 194.19 |
| Satt540 | 5 | 199.39 | 200.39 |
| Satt540 | 6 | 210.59 | 211.96 |
| Satt540 | 7 | 213.37 | 213.85 |
| Satt540 | 8 | 169.65 | 170.15 |
| Satt540 | 9 | 184.68 | 185.15 |
| Satt540 | 10 | 187.58 | 188.05 |
| Satt540 | 12 | 195.73 | 196.12 |
| Satt540 | 13 | 196.56 | 197.20 |
| Satt540 | 14 | 204.70 | 204.90 |
| Satt543 | 1 | 171.12 | 172.39 |
| Satt543 | 2 | 174.39 | 175.09 |
| Satt543 | 3 | 175.29 | 176.26 |
| Satt543 | 4 | 195.43 | 196.52 |
| Satt543 | 5 | 198.83 | 199.49 |
| Satt543 | 6 | 207.41 | 208.42 |
| Satt543 | 7 | 210.95 | 211.45 |
| Satt543 | 8 | 213.65 | 214.47 |
| Satt543 | 9 | 210.34 | 210.54 |
| Satt543 | 10 | 216.56 | 217.05 |
| Satt543 | 11 | 178.15 | 178.78 |
| Satt544 | 1 | 116.66 | 117.63 |
| Satt544 | 2 | 147.56 | 149.12 |
| Satt544 | 3 | 154.30 | 155.84 |
| Satt544 | 4 | 160.56 | 161.37 |
| Satt544 | 5 | 163.56 | 164.34 |
| Satt544 | 6 | 166.54 | 167.72 |
| Satt544 | 7 | 169.59 | 170.62 |
| Satt544 | 8 | 132.15 | 132.45 |
| Satt544 | 9 | 151.41 | 151.61 |
| Satt544 | 10 | 157.54 | 157.79 |
| Satt544 | 11 | 172.44 | 173.53 |
| Satt545 | 1 | 242.25 | 242.85 |
| Satt545 | 2 | 254.11 | 254.66 |
| Satt545 | 3 | 260.29 | 260.86 |
| Satt545 | 4 | 275.32 | 276.23 |
| Satt545 | 5 | 278.35 | 279.48 |
| Satt545 | 6 | 281.59 | 282.30 |
| Satt545 | 7 | 284.46 | 285.32 |
| Satt545 | 8 | 290.55 | 292.10 |
| Satt545 | 9 | 293.64 | 294.56 |
| Satt545 | 10 | 266.36 | 266.78 |
| Satt545 | 11 | 272.58 | 272.98 |

APPENDIX I-continued

Allele Definition Table
23 pages

| Marker | Allele | Size | Range bp |
|---|---|---|---|
| Satt545 | 12 | 287.84 | 288.04 |
| Satt545 | 13 | 296.79 | 297.29 |
| Satt545 | 14 | 269.53 | 269.98 |
| Satt546 | 1 | 332.22 | 333.26 |
| Satt546 | 2 | 341.33 | 342.06 |
| Satt546 | 3 | 344.12 | 344.85 |
| Satt546 | 4 | 355.29 | 356.49 |
| Satt546 | 5 | 358.46 | 358.66 |
| Satt548 | 1 | 352.27 | 352.77 |
| Satt548 | 2 | 359.73 | 361.17 |
| Satt548 | 3 | 362.57 | 364.12 |
| Satt548 | 4 | 365.63 | 366.41 |
| Satt548 | 5 | 348.57 | 348.97 |
| Satt548 | 6 | 351.34 | 351.54 |
| Satt548 | 7 | 368.83 | 368.93 |
| Satt549 | 1 | 225.08 | 225.33 |
| Satt549 | 2 | 233.92 | 234.80 |
| Satt549 | 3 | 240.10 | 240.38 |
| Satt549 | 4 | 243.05 | 243.23 |
| Satt549 | 5 | 245.94 | 246.80 |
| Satt549 | 6 | 249.00 | 250.00 |
| Satt549 | 7 | 255.38 | 255.88 |
| Satt550 | 1 | 223.78 | 224.73 |
| Satt550 | 2 | 226.66 | 227.46 |
| Satt550 | 3 | 241.76 | 242.85 |
| Satt550 | 4 | 244.72 | 245.71 |
| Satt550 | 5 | 229.84 | 230.24 |
| Satt550 | 6 | 220.91 | 221.36 |
| Satt550 | 7 | 232.80 | 233.35 |
| Satt550 | 8 | 238.96 | 239.16 |
| Satt551 | 1 | 230.50 | 231.57 |
| Satt551 | 2 | 236.85 | 237.63 |
| Satt551 | 3 | 242.75 | 243.73 |
| Satt552 | 1 | 160.66 | 161.67 |
| Satt552 | 2 | 175.66 | 176.68 |
| Satt552 | 3 | 181.73 | 182.80 |
| Satt552 | 4 | 184.98 | 185.75 |
| Satt552 | 5 | 169.80 | 170.62 |
| Satt555 | 1 | 249.45 | 250.30 |
| Satt555 | 2 | 271.56 | 272.75 |
| Satt555 | 3 | 274.87 | 275.78 |
| Satt555 | 4 | 277.96 | 278.68 |
| Satt556 | 1 | 135.95 | 136.83 |
| Satt556 | 2 | 148.62 | 149.94 |
| Satt556 | 3 | 151.96 | 152.78 |
| Satt556 | 4 | 184.68 | 186.12 |
| Satt556 | 5 | 197.30 | 197.99 |
| Satt556 | 6 | 155.32 | 155.84 |
| Satt556 | 7 | 164.34 | 164.82 |
| Satt556 | 8 | 168.22 | 168.69 |
| Satt556 | 9 | 176.93 | 177.90 |
| Satt556 | 10 | 188.45 | 188.65 |
| Satt557 | 1 | 201.89 | 202.90 |
| Satt557 | 2 | 204.90 | 205.90 |
| Satt557 | 3 | 211.20 | 212.01 |
| Satt557 | 4 | 214.17 | 214.97 |
| Satt557 | 5 | 220.29 | 221.36 |
| Satt557 | 6 | 208.42 | 208.93 |
| Satt557 | 7 | 193.45 | 193.75 |
| Satt558 | 1 | 220.38 | 221.46 |
| Satt558 | 2 | 229.54 | 230.55 |
| Satt558 | 3 | 235.38 | 236.66 |
| Satt558 | 4 | 238.68 | 239.70 |
| Satt558 | 6 | 233.05 | 233.42 |
| Satt558 | 7 | 241.86 | 242.45 |
| Satt558 | 8 | 245.21 | 245.41 |
| Satt560 | 1 | 231.06 | 231.97 |
| Satt560 | 2 | 237.11 | 238.91 |
| Satt560 | 3 | 243.15 | 244.52 |
| Satt560 | 4 | 246.20 | 247.40 |
| Satt560 | 5 | 276.80 | 277.67 |
| Satt560 | 6 | 286.02 | 286.83 |
| Satt560 | 7 | 273.70 | 274.30 |
| Satt560 | 8 | 271.25 | 271.56 |
| Satt560 | 9 | 283.06 | 283.41 |
| Satt560 | 10 | 250.10 | 250.21 |
| Satt560 | 11 | 253.13 | 253.24 |
| Satt563 | 1 | 166.45 | 167.82 |
| Satt563 | 2 | 169.65 | 170.82 |
| Satt563 | 3 | 236.85 | 237.83 |
| Satt563 | 4 | 173.53 | 174.49 |
| Satt563 | 5 | 181.49 | 182.95 |
| Satt563 | 6 | 212.36 | 213.47 |
| Satt563 | 8 | 160.42 | 160.99 |
| Satt563 | 9 | 164.34 | 164.54 |
| Satt563 | 10 | 206.30 | 207.41 |
| Satt563 | 11 | 185.15 | 185.55 |
| Satt563 | 12 | 209.63 | 209.83 |
| Satt565 | 1 | 299.47 | 300.33 |
| Satt565 | 2 | 302.62 | 304.63 |
| Satt565 | 3 | 327.31 | 328.46 |
| Satt565 | 4 | 351.34 | 351.84 |
| Satt565 | 5 | 330.48 | 331.06 |
| Satt566 | 1 | 356.49 | 357.42 |
| Satt566 | 2 | 359.44 | 360.23 |
| Satt566 | 3 | 362.12 | 363.07 |
| Satt566 | 4 | 365.18 | 365.94 |
| Satt566 | 5 | 374.11 | 375.06 |
| Satt566 | 6 | 376.96 | 377.90 |
| Satt566 | 7 | 367.97 | 368.33 |
| Satt566 | 8 | 379.97 | 380.17 |
| Satt566 | 9 | 385.90 | 386.30 |
| Satt567 | 1 | 97.45 | 97.95 |
| Satt567 | 2 | 112.41 | 113.36 |
| Satt567 | 3 | 115.25 | 116.20 |
| Satt567 | 4 | 118.56 | 119.10 |
| Satt567 | 5 | 110.01 | 110.51 |
| Satt567 | 6 | 98.05 | 98.15 |
| Satt568 | 1 | 345.38 | 346.08 |
| Satt568 | 2 | 350.62 | 351.84 |
| Satt568 | 3 | 357.02 | 357.22 |
| Satt568 | 4 | 354.12 | 354.42 |
| Satt569 | 1 | 103.33 | 104.23 |
| Satt569 | 2 | 115.60 | 116.30 |
| Satt569 | 3 | 121.47 | 122.55 |
| Satt569 | 4 | 124.56 | 125.31 |
| Satt569 | 5 | 127.58 | 128.38 |
| Satt569 | 6 | 130.63 | 131.38 |
| Satt569 | 7 | 133.70 | 134.10 |
| Satt569 | 8 | 106.59 | 106.99 |
| Satt570 | 1 | 108.50 | 109.05 |
| Satt570 | 2 | 111.41 | 112.41 |
| Satt570 | 3 | 114.48 | 115.25 |
| Satt570 | 4 | 126.57 | 127.58 |
| Satt570 | 5 | 120.72 | 120.97 |
| Satt570 | 6 | 130.01 | 130.21 |
| Satt570 | 7 | 132.94 | 133.17 |
| Satt572 | 1 | 172.56 | 174.08 |
| Satt572 | 2 | 175.86 | 176.53 |
| Satt572 | 3 | 178.87 | 179.50 |
| Satt572 | 4 | 169.89 | 170.45 |
| Satt573 | 1 | 167.36 | 167.56 |
| Satt573 | 2 | 163.84 | 164.82 |
| Satt573 | 3 | 175.96 | 176.53 |
| Satt576 | 1 | 261.38 | 261.88 |
| Satt576 | 2 | 288.75 | 290.25 |
| Satt576 | 3 | 342.10 | 342.99 |
| Satt576 | 4 | 350.48 | 351.84 |
| Satt576 | 5 | 361.83 | 363.07 |
| Satt576 | 6 | 365.11 | 365.94 |
| Satt576 | 7 | 353.64 | 354.12 |
| Satt576 | 8 | 356.69 | 356.89 |
| Satt576 | 9 | 359.09 | 359.59 |
| Satt577 | 1 | 312.82 | 313.96 |
| Satt577 | 2 | 316.01 | 317.25 |
| Satt578 | 1 | 178.37 | 179.35 |
| Satt578 | 2 | 181.29 | 182.25 |
| Satt578 | 3 | 199.89 | 200.39 |
| Satt578 | 4 | 202.39 | 203.00 |
| Satt578 | 5 | 199.49 | 199.79 |

APPENDIX I-continued

Allele Definition Table
23 pages

| Marker | Allele | Size | Range bp |
|---|---|---|---|
| Satt578 | 6 | 184.78 | 184.98 |
| Satt581 | 1 | 138.39 | 139.45 |
| Satt581 | 2 | 148.06 | 149.22 |
| Satt581 | 3 | 151.21 | 152.43 |
| Satt581 | 4 | 161.07 | 161.27 |
| Satt582 | 1 | 333.83 | 334.34 |
| Satt582 | 2 | 336.72 | 337.31 |
| Satt582 | 3 | 339.75 | 340.19 |
| Satt582 | 4 | 318.76 | 319.16 |
| Satt583 | 1 | 122.06 | 123.05 |
| Satt583 | 2 | 146.99 | 147.86 |
| Satt583 | 3 | 150.17 | 151.21 |
| Satt583 | 4 | 180.82 | 181.64 |
| Satt583 | 5 | 125.56 | 125.76 |
| Satt583 | 6 | 131.58 | 131.95 |
| Satt583 | 7 | 137.89 | 138.09 |
| Satt583 | 8 | 141.10 | 141.30 |
| Satt583 | 9 | 144.15 | 144.60 |
| Satt583 | 10 | 113.46 | 113.66 |
| Satt583 | 11 | 116.50 | 116.66 |
| Satt583 | 12 | 153.80 | 154.00 |
| Satt583 | 13 | 156.84 | 157.04 |
| Satt583 | 14 | 159.96 | 160.16 |
| Satt583 | 15 | 168.99 | 169.19 |
| Satt583 | 16 | 198.89 | 199.19 |
| Satt583 | 17 | 202.09 | 202.39 |
| Satt583 | 18 | 222.89 | 223.39 |
| Satt584 | 1 | 171.59 | 172.56 |
| Satt584 | 2 | 174.49 | 175.46 |
| Satt584 | 3 | 180.77 | 181.32 |
| Satt584 | 4 | 195.43 | 196.42 |
| Satt584 | 5 | 183.72 | 184.68 |
| Satt584 | 6 | 186.91 | 188.85 |
| Satt584 | 7 | 198.89 | 199.89 |
| Satt586 | 1 | 318.76 | 319.77 |
| Satt586 | 2 | 337.12 | 338.01 |
| Satt586 | 3 | 342.99 | 343.79 |
| Satt586 | 4 | 348.57 | 349.50 |
| Satt586 | 5 | 354.14 | 355.05 |
| Satt586 | 6 | 331.18 | 331.77 |
| Satt586 | 7 | 334.15 | 334.54 |
| Satt586 | 8 | 340.05 | 340.84 |
| Satt586 | 9 | 351.34 | 351.94 |
| Satt587 | 1 | 168.02 | 169.19 |
| Satt587 | 2 | 170.97 | 172.20 |
| Satt587 | 3 | 173.93 | 175.05 |
| Satt587 | 4 | 176.93 | 177.90 |
| Satt587 | 5 | 129.10 | 129.61 |
| Satt587 | 6 | 155.84 | 156.34 |
| Satt590 | 1 | 317.18 | 318.26 |
| Satt590 | 2 | 323.30 | 324.81 |
| Satt590 | 3 | 332.86 | 333.55 |
| Satt590 | 4 | 335.78 | 336.87 |
| Satt590 | 6 | 339.25 | 339.75 |
| Satt590 | 7 | 266.88 | 268.52 |
| Satt590 | 8 | 272.88 | 274.62 |
| Satt590 | 9 | 264.22 | 264.44 |
| Satt590 | 12 | 314.28 | 315.21 |
| Satt590 | 13 | 304.83 | 305.16 |
| Satt590 | 14 | 320.48 | 321.06 |
| Satt590 | 15 | 300.73 | 301.25 |
| Satt590 | 16 | 311.10 | 312.00 |
| Satt590 | 17 | 326.64 | 327.60 |
| Satt590 | 18 | 329.87 | 330.88 |
| Satt591 | 1 | 137.43 | 138.44 |
| Satt591 | 2 | 140.52 | 141.60 |
| Satt591 | 3 | 150.27 | 151.59 |
| Satt591 | 4 | 144.63 | 144.83 |
| Satt591 | 5 | 119.20 | 119.50 |
| Satt592 | 1 | 236.85 | 237.43 |
| Satt592 | 2 | 242.75 | 243.53 |
| Satt592 | 3 | 245.71 | 246.85 |
| Satt592 | 4 | 254.76 | 255.87 |
| Satt594 | 1 | 122.50 | 123.25 |
| Satt594 | 2 | 134.74 | 135.44 |
| Satt594 | 3 | 141.10 | 141.60 |
| Satt594 | 4 | 144.33 | 145.61 |
| Satt594 | 5 | 147.56 | 148.82 |
| Satt594 | 6 | 166.22 | 167.36 |
| Satt594 | 7 | 172.56 | 173.63 |
| Satt594 | 8 | 157.04 | 157.64 |
| Satt594 | 9 | 160.06 | 160.46 |
| Satt594 | 10 | 178.20 | 179.13 |
| Satt594 | 11 | 138.09 | 138.29 |
| Satt594 | 12 | 169.19 | 169.59 |
| Satt595 | 1 | 340.05 | 341.13 |
| Satt595 | 2 | 342.99 | 344.85 |
| Satt595 | 4 | 345.98 | 346.38 |
| Satt596 | 1 | 257.73 | 258.83 |
| Satt596 | 2 | 260.72 | 261.88 |
| Satt596 | 3 | 266.68 | 267.70 |
| Satt596 | 4 | 272.86 | 273.90 |
| Satt596 | 5 | 275.88 | 277.15 |
| Satt596 | 6 | 281.80 | 282.91 |
| Satt596 | 7 | 264.17 | 264.64 |
| Satt596 | 8 | 270.10 | 270.65 |
| Satt596 | 9 | 279.43 | 279.58 |
| Satt596 | 10 | 251.92 | 252.12 |
| Satt597 | 1 | 144.68 | 145.51 |
| Satt597 | 2 | 147.86 | 148.82 |
| Satt597 | 3 | 160.26 | 161.37 |
| Satt597 | 4 | 157.34 | 157.90 |
| Satt598 | 1 | 163.36 | 164.37 |
| Satt598 | 2 | 175.46 | 176.43 |
| Satt601 | 1 | 344.86 | 345.93 |
| Satt601 | 2 | 347.84 | 348.57 |
| Satt601 | 3 | 342.36 | 342.66 |
| Satt601 | 4 | 351.02 | 351.22 |
| Satt601 | 5 | 356.39 | 356.59 |
| Satt601 | 6 | 336.72 | 336.92 |
| Satt602 | 1 | 336.21 | 336.82 |
| Satt602 | 2 | 339.14 | 341.14 |
| Satt602 | 4 | 342.86 | 343.92 |
| Sct_010 | 1 | 107.29 | 108.10 |
| Sct_010 | 2 | 99.45 | 99.95 |
| Sct_010 | 3 | 105.44 | 105.64 |
| Sct_026 | 1 | 328.36 | 329.37 |
| Sct_026 | 2 | 330.38 | 331.37 |
| Sct_026 | 3 | 326.64 | 326.84 |
| Sct_026 | 4 | 333.80 | 334.25 |
| Sct_026 | 5 | 317.50 | 317.65 |
| Sct_028 | 1 | 236.07 | 237.33 |
| Sct_028 | 2 | 244.12 | 245.21 |
| Sct_028 | 3 | 248.10 | 249.20 |
| Sct_028 | 4 | 242.10 | 243.23 |
| Sct_034 | 1 | 126.67 | 127.58 |
| Sct_034 | 2 | 128.83 | 129.61 |
| Sct_034 | 3 | 130.63 | 131.65 |
| Sct_046 | 1 | 260.66 | 262.28 |
| Sct_046 | 2 | 267.69 | 268.52 |
| Sct_046 | 3 | 275.88 | 276.65 |
| Sct_046 | 4 | 277.89 | 278.68 |
| Sct_046 | 5 | 284.15 | 285.73 |
| Sct_046 | 6 | 286.23 | 287.83 |
| Sct_046 | 7 | 288.24 | 288.75 |
| Sct_046 | 8 | 292.89 | 293.76 |
| Sct_046 | 9 | 298.60 | 299.83 |
| Sct_046 | 10 | 290.05 | 290.75 |
| Sct_046 | 11 | 270.03 | 270.55 |
| Sct_046 | 12 | 274.10 | 274.62 |
| Sct_046 | 13 | 282.71 | 283.71 |
| Sct_065 | 1 | 163.26 | 164.40 |
| Sct_065 | 2 | 165.27 | 166.40 |
| Sct_065 | 3 | 171.12 | 172.18 |
| Sct_137 | 1 | 269.32 | 270.03 |
| Sct_137 | 2 | 273.08 | 274.10 |
| Sct_147 | 1 | 130.11 | 131.03 |
| Sct_147 | 2 | 136.28 | 136.93 |
| Sct_186 | 1 | 97.45 | 97.95 |
| Sct_186 | 2 | 105.24 | 105.74 |

APPENDIX I-continued

Allele Definition Table
23 pages

| Marker | Allele | Size | Range bp |
|---|---|---|---|
| Sct_186 | 3 | 111.36 | 111.91 |
| Sct_186 | 4 | 113.36 | 113.80 |
| Sct_186 | 5 | 115.35 | 115.70 |
| Sct_186 | 6 | 117.36 | 117.63 |
| Sct_187 | 1 | 313.34 | 314.19 |
| Sct_187 | 2 | 311.40 | 311.90 |
| Sct_187 | 3 | 315.21 | 317.35 |
| Sct_188 | 1 | 242.25 | 243.23 |
| Sct_188 | 2 | 252.23 | 253.24 |
| Sct_188 | 3 | 254.76 | 254.96 |
| Sctt008 | 1 | 159.36 | 159.86 |
| Sctt008 | 2 | 162.36 | 163.36 |
| Sctt008 | 3 | 165.42 | 165.62 |
| Sctt008 | 4 | 147.56 | 147.76 |
| Sctt009 | 1 | 213.93 | 214.97 |
| Sctt009 | 2 | 219.71 | 220.86 |
| Sctt012 | 1 | 343.92 | 344.72 |
| Sctt012 | 2 | 351.84 | 353.02 |
| Sctt012 | 3 | 355.05 | 355.55 |

APPENDIX II

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Sac1006 | CAATCAGGTTAGTGGTCCTACC | 1 | CAAAAGGTTTTCAGTGGTGG | 285 | GTTTCTT | 2 |
| Sac1677 | AAGTTCACAGCACCTGGACCAT | 2 | CCAATCCCTACCCTGATTGCAC | 286 | GTTTCTT | 2 |
| Sat_084 | GAAACAAACACCCCCAAGGTGA | 3 | GGAAGTGGATTTGGAGTTGGGA | 287 | GTTTCTT | 2 |
| Sat_090 | CCAATCGTGTCTTATCCTCGGG | 4 | AACCCATAACCTGCTCGTCTCA | 288 | GTTTCTT | 2 |
| Sat_104 | TTCCAGACAGAACCCAAGTAGCC | 5 | AGGCGGGTTTGGAGCTGTTTAC | 289 | GTTTCTT | 2 |
| Sat_110 | AACATTTTTCATCGCTTTTCTTAG | 6 | TCTTCTCAGGAACTTGAATTACTCA | 290 | GTTTCTT | 2 |
| Sat_117 | AAAGCATTTTTGGCAGTTTCTTGT | 7 | GGAATGTCCCAAGTGTCAGCAA | 291 | GTTTCTT | 2 |
| Satt020 | TGGACAGAATGGAGAAAGAAATGTG | 8 | TGAAAATAAGTGGAAAGAAAAGGAAAA | 292 | GTTTCTT | 3 |
| Satt040 | CCAAGCCAAACAAAGAATCACA | 9 | GTCCCCGTTCCTCAAACACCTT | 293 | GTTTCTT | 3 |
| Satt042 | GCTTGCTATGATTGATTGATTGATTGA | 10 | TGCACACTCACTTGGTCTTACACA | 294 | GTTTCTT | 3 |
| Satt050 | AGAACGGTGTTAAGATAGAATAGTT | 11 | CTGTTGGAAAATGATGCGTGGC | 295 | GTTTCTT | 3 |
| Satt066 | GGGAAGCTTAATAATGAAAATGACAC | 12 | TTGATCACTTCTGTAACATTC | 296 | GTTTCTT | 3 |
| Satt092 | AACCGATGCTTTTTTCGCCTTT | 13 | CTTTGTTGTTTGGTCAAGGCCC | 297 | GTTTCTT | 3 |
| Satt102 | GAAGAAGGCTCAGCAACACCTTG | 14 | TGCCGAAATAAGTGAGAGCATAGAA | 298 | GTTTCTT | 3 |
| Satt108 | CACCCAATCTTGCCTTTGAAACA | 15 | TGTTAGGTATGGGATTTAGGGTTTTGA | 299 | GTTTCTT | 3 |
| Satt109 | TAGACACTTTCAGGTTAAAATATAAC | 16 | TCCACTCACTGTATGTCTTCCCTTG | 300 | GTTTCTT | 3 |
| Satt111 | CAACTTGTCACTTACACATAGTTTAG | 17 | TTGAGTGCTCTTGGTGTTTTCCT | 301 | GTTTCTT | 3 |
| Satt115 | ATTTCGCTCGCAAACACAAGGT | 18 | CCAAACACCCCAGTATAAAAAATGGA | 302 | GTTTCTT | 3 |
| Satt122 | TCAAGAAATACAAGTGCAAGAAAGACC | 19 | GGATTTTGAGTTGCTCCAAGGC | 303 | GTTTCTT | 3 |
| Satt127 | AATTTTCGCTTGTGAACCCTGC | 20 | TGTATGATCCATCCTCTGAAACCG | 304 | GTTTCTT | 3 |
| Satt129 | TTCAGTACAAGTCGGGTGAATAATAATA | 21 | TCACATGTTCGGGACTTAAGGTAT | 305 | GTTTCTT | 3 |
| Satt130 | TGGGACTCTCACACACGGAAAA | 22 | TGAATGGCTAAAAACGTGATTTGGA | 306 | GTTTCTT | 3 |
| Satt131 | TGGGAGTCAATTTCCCATTATCA | 23 | GGACCTTCCCTTTCCCATGACT | 307 | GTTTCTT | 3 |
| Satt133 | TGGATTTGAAACCACAAATAACAACAAC | 24 | AGCGATGGTTGAAGAAAGGGTC | 308 | GTTTCTT | 3 |
| Satt138 | AAAAGGGGGACATTTTTCCACG | 25 | AGAGAACGGGCGATTTATGGCT | 309 | GTTTCTT | 3 |
| Satt142 | CATTAGGGACAACAACAGCGTTT | 26 | ATGTCGCCACTAGGCCAATCAG | 310 | GTTTCTT | 3 |
| Satt144 | CGTCGCCATCACTATGAGAA | 27 | CCATCTTGAGCAGAGTTTGAAGTT | 311 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt146 | AAGGGATCCCTCAACTGACTG | 28 | GTGGTGGTGGTGAAAACTATTAGAA | 312 | GTTTCTT | 3 |
| Satt147 | CCATCCCTTCCTCCAAATAGAT | 29 | CTTCCACACCCTAGTTTAGTGACAA | 313 | GTTTCTT | 3 |
| Satt150 | TGACGAAGCTTGAGGTTATTCG | 30 | TCAAGCTTATGCTCTATAGGCT | 314 | GTTTCTT | 3 |
| Satt151 | GCCAAGAAGATAACAAGCTCGGC | 31 | GACCAAAATTCAAGGCAGTGACAA | 315 | GTTTCTT | 3 |
| Satt153 | GGGTTATATCAGTTTTTCTTTTTGTT | 32 | CCATCCTCGTTAGCATCTAT | 316 | GTTTCTT | 3 |
| Satt155 | AGATCCAACACCTGGCCTAAT | 33 | GCTGCACAATTCATTCCATTT | 317 | GTTTCTT | 3 |
| Satt156 | AACAAAACTAGCCCATAGAAACATTGA | 34 | CCCAGGGACTTACTTTTTTCAGTTT | 318 | GTTTCTT | 3 |
| Satt159 | GAAATGCCCAGAAAAACCTAATAAC | 35 | TGAAGCAACAAAATAGAGGAATAGAG | 319 | GTTTCTT | 3 |
| Satt165 | GCCGTGAAGACAGTTGATCGTT | 36 | CATTACTAGGCGTGTGTTGTTTCAA | 320 | GTTTCTT | 3 |
| Satt166 | CAGTTGATTTTGTTTTTCGGCA | 37 | CACGCGCATCAGCTTTGTAGAG | 321 | GTTTCTT | 3 |
| Satt168 | TTGTCCAAACTTGCAGGGAACA | 38 | TCTTTTCACCATTCTCCAACCTCA | 322 | GTTTCTT | 3 |
| Satt172 | TGGATGAGTTCTATTGGGGTAGTCG | 39 | TCCTTTCTCCCATTTTTTTGGG | 323 | GTTTCTT | 3 |
| Satt175 | GACCTCGCTCTCTGTTTCTCAT | 40 | GGTGACCACCCCTATTCCTTAT | 324 | GTTTCTT | 3 |
| Satt176 | CGCAATCCCAATTCACCTCTTC | 41 | AATTGTTAGGGCGCGAGAAACA | 325 | GTTTCTT | 3 |
| Satt181 | GAACCCCGTTTCAACATTTTATGA | 42 | CTAGCCAAGGGAGAGAGGAGCA | 326 | GTTTCTT | 3 |
| Satt183 | GGTCGTTAAGCCCACTTTGAGA | 43 | CCTCACACCAACCAGCACAAAA | 327 | GTTTCTT | 3 |
| Satt186 | TGCAGCTTTCACTAATCGTCAGAA | 44 | CAATTTTATGATTTGCTTTTGAAGGGA | 328 | GTTTCTT | 3 |
| Satt190 | GGGAGTGTGAACTTACATTGTCT | 45 | GGGCCTTGAATTTTGTGCTAT | 329 | GTTTCTT | 3 |
| Satt191 | GCGATCATGTCTCTGCCATCAG | 46 | CCTCTTGAAACCGTGAAACCGT | 330 | GTTTCTT | 3 |
| Satt193 | GAAGGGATATGGAGAGTGAGAAATTAGA | 47 | TCTTTTTCTTCATTTTTGTTCGCA | 331 | GTTTCTT | 3 |
| Satt195 | AAAAATTGTGTAAACGAAAGATGGGA | 48 | AAACTGCTCTGAAGTGCGACACA | 332 | GTTTCTT | 3 |
| Satt196 | TGAGCCCAACCTCCACATCTTT | 49 | TGTGAATAAAAGAAATCCCCATTGA | 333 | GTTTCTT | 3 |
| Satt197 | CACTGCTTTTTCCCCTCTCT | 50 | AAGATACCCCCAACATTATTTGTAA | 334 | GTTTCTT | 3 |
| Satt199 | GCGGTAAATGGTGAAAATCATTTATGGTT | 51 | GCGTTTTCATACGGTGTTTTGCCTAT | 335 | GTTTCTT | 3 |
| Satt202 | GGAATGCATGAGTATTAACCTCTTAT | 52 | GGGCTAACGAACATGTAACTTATCAAC | 336 | GTTTCTT | 3 |
| Satt203 | TGTCTTCCCAATCCATCTAATCTAATCA | 53 | GCACTACAATATGTGCATGAATTTTTCT | 337 | GTTTCTT | 3 |
| Satt204 | CCAATTATGTTTCTATGCCATCTTGTT | 54 | TCTCCTTACTCACTCCATTGGCA | 338 | GTTTCTT | 3 |
| Satt209 | TGTGGATAAAAGCCATCTCTAACAAA | 55 | TCCATGTCACCAACCACAAAAA | 339 | GTTTCTT | 3 |
| Satt212 | TCGATACCAATCATCCAATCCAAA | 56 | CGTATCCCTTTCCCATACGTGG | 340 | GTTTCTT | 3 |
| Satt213 | TCCTTAGACCTCTCGCGCAAAC | 57 | ATGACGGGATGAAAGAGCCAAA | 341 | GTTTCTT | 3 |
| Satt216 | TACCCTTAATCACCGGACAA | 58 | AGGGAACTAACACATTTAATCATCA | 342 | GTTTCTT | 3 |
| Satt218 | ACGTATGCGAAGGAGGGAGATG | 59 | CGGAAAAGATATACCGAGTGAGAAAA | 343 | GTTTCTT | 3 |
| Satt219 | TTGGCTCTTGTGTAAGTGGCCC | 60 | TTCTAAGGATTTGTGGTAATCGGC | 344 | GTTTCTT | 3 |
| Satt220 | TTCAGTCCCTTGGTGGTTCCAA | 61 | CATGGAGAAAGAAGAGGAGGGA | 345 | GTTTCTT | 3 |
| Satt221 | CATGGTCCTTGGGTGCAATTTA | 62 | AAGCAAACCATTATCTTCATTGGTG | 346 | GTTTCTT | 3 |
| Satt225 | AAAAATGTGTTAGAGCTTGTGTTGTTA | 63 | GCCCACACTATTCCAGCCACTAC | 347 | GTTTCTT | 3 |
| Satt227 | ATGGTGCAGTGTTGCAGGTTGT | 64 | AGTAGTCCAAACCGAAACGCCA | 348 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt228 | GACCACAACTTCTTTTTTGTGAATGG | 65 | TCAATTCGGTCAAAAGGCTTGA | 349 | GTTTCTT | 3 |
| Satt230 | CCGTCACCGTTAATAAAATAGCAT | 66 | CTCCCCCAAATTTAACCTTAAAGA | 350 | GTTTCTT | 3 |
| Satt233 | AGAAGCATACTCGTCGTAACACTATCC | 67 | AATGGATGGACCTGTCAGTCTGC | 351 | GTTTCTT | 3 |
| Satt234 | GAGCAGGACATTTTTTTATCCTTGA | 68 | TGCTTCCATTAGTCTCTCATCCTCC | 352 | GTTTCTT | 3 |
| Satt236 | TGCTTGAGGTTGAAGGAAATGC | 69 | TGGAAAAGATAACGTGTGTTTGCAG | 353 | GTTTCTT | 3 |
| Satt240 | TCCTTGGGGTGAATTGTTTTTCA | 70 | CCTTCTTTTGACATGGGGCCTA | 354 | GTTTCTT | 3 |
| Satt242 | GCGTTGATCAGGTCGATTTTTATTGT | 71 | GCGAGTGCCAACTAACTACTTTTATGA | 355 | GTTTCTT | 3 |
| Satt243 | AATGCTTTGGTCGTTGCATTG | 72 | TGGTATCGGGAGATTTTTTCAGC | 356 | GTTTCTT | 3 |
| Satt247 | CAGCGTCTGCATGATAGCGTTT | 73 | TTTTTCGTCAGCACATTATTACACATTT | 357 | GTTTCTT | 3 |
| Satt249 | TGCAAATTGTTATTGTGAGACTGAATGA | 74 | GGCCAGTGTTGAGGGATTTAGAA | 358 | GTTTCTT | 3 |
| Satt250 | CGCCAGCTAGCTAGTCTCAT | 75 | AATTTGCTCCAGTGTTTTAAGTTT | 359 | GTTTCTT | 3 |
| Satt251 | CCTCCACCCCCTTCCCACCCAAAA | 76 | GGTGATATCGCGCTAAAATTA | 360 | GTTTCTT | 3 |
| Satt255 | AGCGTCGTCTGGCTAGGTCTGT | 77 | GGAAACCCTGTCATTTTCGTGC | 361 | GTTTCTT | 3 |
| Satt256 | GTCATTGGTCTCAAACAATCTTCAT | 78 | AGAGTTCTCAGTCCGCCAGCTC | 362 | GTTTCTT | 3 |
| Satt257 | GCGACTTTCTTTTCAATTTCACTCC | 79 | GCGCAATTGTCACCAACACAT | 363 | GTTTCTT | 3 |
| Satt258 | CACTTTTTCACTGTCTCCCCCC | 80 | CCCAAACCAACAAGCAACAACA | 364 | GTTTCTT | 3 |
| Satt259 | TGGGCCATTTGGGCAGCTCGACT | 81 | ATTCACACGCATCTGGAATAATA | 365 | GTTTCTT | 3 |
| Satt262 | GCGCCCCATTAATGTTAACACA | 82 | GCGGAGTTCAACGCATTCACCTT | 366 | GTTTCTT | 3 |
| Satt263 | GGAGAGAATCCATATATATTGAATTGC | 83 | TGAAAGCAAACGAGACTCATGGA | 367 | GTTTCTT | 3 |
| Satt264 | CCTTTTGACAATTATGGCATATA | 84 | GCATAGAAGGGCATCATTCAGAT | 368 | GTTTCTT | 3 |
| Satt265 | CCTGTCAAATTGGCTGATGCAA | 85 | GCTAGATGAGCAGACCATTGCACTT | 369 | GTTTCTT | 3 |
| Satt266 | TTTTACCAAACAAATTAAACTGCGTCT | 86 | CAAGAGGTTGTTGTAAGAGTGATCTCG | 370 | GTTTCTT | 3 |
| Satt267 | CCGGTCTGACCTATTCTCAT | 87 | CACGGCGTATTTTATTTTG | 371 | GTTTCTT | 3 |
| Satt270 | GGTGTTTCAAGTTTCAACACCAT | 88 | CAGTGCATGGTTTTCTCATGTACC | 372 | GTTTCTT | 3 |
| Satt272 | ATGACAAGGAAAAATCAATCAAC | 89 | GCTGCTGTTAAGAGTGTTTG | 373 | GTTTCTT | 3 |
| Satt274 | GCGGGGTCAATTAGTTTTCGTCAGTT | 90 | GCGCACGGTATATAATCGAACCTAT | 374 | GTTTCTT | 3 |
| Satt279 | GCGCAAAAGGACGCCCACCAATAG | 91 | GCGGTGATCGGATGTTATAGTTTCAG | 375 | GTTTCTT | 3 |
| Satt280 | TCTGCTTATTCATTGTGTGCGTG | 92 | TGTCTCCATGCTGTAACACGTCAA | 376 | GTTTCTT | 3 |
| Satt282 | TGGTATATGTTTTTGCGGGACAA | 93 | CGCCAAAGATGCAACACACTTG | 377 | GTTTCTT | 3 |
| Satt284 | AGGTGGGCTAGGAGTGACCACA | 94 | TGTAATTGCTGTTTTGGTTTCATTTC | 378 | GTTTCTT | 3 |
| Satt285 | GCGACATATTGCATTAAAAACATACTT | 95 | GCGGACTAATTCTATTTTACACCAACAAC | 379 | GTTTCTT | 3 |
| Satt287 | GGGGTGAATGAATGTCAAGATGA | 96 | GCGCGAGGTATCAACACAATTACT | 380 | GTTTCTT | 3 |
| Satt292 | GCGGAATTAGAACTCCAGTAAAGA | 97 | GCGAGGCCAACATTGAAAAGT | 381 | GTTTCTT | 3 |
| Satt295 | TTAGTGGATCTACACTAAACTAATCCG | 98 | CGTACCATTGGACAACTCTGTAATTCAA | 382 | GTTTCTT | 3 |
| Satt299 | AGGCATTTCTGGCAAGGGTATG | 99 | TGGTGAATCAATCTCCTCTAAGTGC | 383 | GTTTCTT | 3 |
| Satt300 | GCGCCCACACAACCTTTAATCTT | 100 | GCGGCGACTGTTAACGTGTC | 384 | GTTTCTT | 3 |
| Satt303 | ATGGGCTATGGGAGGAGGTGTT | 101 | CCACACGGGACTTTCCATTTTC | 385 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt304 | CCAGTGCAGTTTTACATGAACTT | 102 | TATATGTAATGACCCCCATCATG | 386 | GTTTCTT | 3 |
| Satt307 | GCTGGCCTTTAGAACGTCTGACT | 103 | CGTTGGATTCGACTTTTTGGGA | 387 | GTTTCTT | 3 |
| Satt311 | CCACAAAAAGATGAAACAAAATAG | 104 | TTGAAGCTCAGGCTGTGATGAAT | 388 | GTTTCTT | 3 |
| Satt314 | GCGGAGATTCGAACCTACTCATTC | 105 | GCGGGGACCAAAAATTCAAAA | 389 | GTTTCTT | 3 |
| Satt319 | AACAATTTGATGGTCGGGGTTG | 106 | TAGGGGAACCGATTTGGTGAAA | 390 | GTTTCTT | 3 |
| Satt321 | CACCGTCGTAAAAACTGTGTCGT | 107 | GCGTGTCAAAGAGTTTTAGACATC | 391 | GTTTCTT | 3 |
| Satt327 | GAAGTGCTAGTTCTCACGGTGTGG | 108 | TTGGAGGGAGGTTTTGGAAGGT | 392 | CTTTCTT | 3 |
| Satt326 | TTCGCTGCATAATTTTTAGCATCA | 109 | CCAATCTTTTGTTAGTTCACCTTCCA | 393 | GTTTCTT | 3 |
| Satt327 | AAAGAGACACCCAAAAGATAACAAACA | 110 | TTCGTAGCAATGTCACCACCTTGT | 394 | GTTTCTT | 3 |
| Satt328 | TGACCACCATGAGTTCATT | 111 | GGGGGTGGCTTTTAGATTC | 395 | GTTTCTT | 3 |
| Satt329 | GCGGGACGCAAAATTGGATTTAGT | 112 | GCGCCGAATAAAACGTGAGAACTG | 386 | GTTTCTT | 3 |
| Satt330 | GTGACCCTCCATTCCACAACAA | 113 | TCCTTGCCTTTTAGTTGTTCGGT | 397 | GTTTCTT | 3 |
| Satt331 | GCAGAGTCCCCCCTAAATATAG | 114 | CGGGAACAACCACACTCTCCATT | 398 | GTTTCTT | 3 |
| Satt332 | GTGAATCATCCAGGGCTTGC | 115 | TCCTTCACTTTCAAAAACAAAAACAA | 399 | CTTTCTT | 3 |
| Satt333 | GCGAATGGTTTTTGCTGGAAAGTA | 116 | GCGCAACGACATTTTCACGAAGTT | 400 | GTTTCTT | 3 |
| Satt334 | GCGTTAAGAATGCATTTATGTTTAGTC | 117 | GCGAGTTTTTGGTTGGATTGAGTTG | 401 | GTTTCTT | 3 |
| Satt335 | CAAGCTCAAGCCTCACACAT | 118 | TGACCAGAGTCCAAAGTTCATC | 402 | GTTTCTT | 3 |
| Satt336 | AATTGGAGTGGGTCACAC | 119 | TTCCCGGAAAGAAAGAAA | 403 | GTTTCTT | 3 |
| Satt338 | GCGCCCAAGTATTATGAGATATTTGAT | 120 | GCGATAATTTTAAAACTGGACCA | 404 | GTTTCTT | 3 |
| Satt339 | CTTTGTTTGGTTGGTGATAAGTTTCTA | 121 | AAGCAGTTCCTCTCATCACGTAACA | 405 | GTTTCTT | 3 |
| Satt343 | AATTGTTAGGGCGCGAGAAACA | 122 | CGCAATCCCAATTCACCTCTTC | 406 | GTTTCTT | 3 |
| Satt346 | GTTCGGAGGGAGGAAAGTGTTG | 123 | CCATAAAACATAGCAACTGTCGTCTC | 407 | GTTTCTT | 3 |
| Satt347 | TGTTCAATCGACAAATAAGGGTGC | 124 | TCCCAGGGTAAAAGTTCAAGTTCA | 408 | GTTTCTT | 3 |
| Satt348 | CTTTACTTAGTAATGGTTCCCACAG | 125 | TCGATGTTTCTCCCTCCCTTAGA | 409 | GTTTCTT | 3 |
| Satt352 | CCAGATTTTACGTTAATGTTTTAGTTTTA | 126 | TTGCACATGGTCCTTGGTTGAT | 410 | GTTTCTT | 3 |
| Satt353 | CATACACGCATTGCCTTTCCTGAA | 127 | GCGAATGGGAATGCCTTCTTATTCTA | 411 | GTTTCTT | 3 |
| Satt355 | GCGTCCCAGGACATCATCATCATC | 128 | GCGTAGCGTGTTATTTTGTGTTTG | 412 | GTTTCTT | 3 |
| Satt356 | TGCTGCTTGTGTTTGGTTGATCT | 129 | CATATCCTGCCCCCCCAATTAT | 413 | GTTTCTT | 3 |
| Satt357 | AATCCCCAAACAAACGCACAGT | 130 | TGACATCTAAGTCCAGAAATCAAAGCA | 414 | GTTTCTT | 3 |
| Satt358 | GCGGCGCTTTATGTAACAATACGATTT | 131 | GCGAGTAAAAGCAGAGTGCGGAGTA | 415 | GTTTCTT | 3 |
| Satt359 | GCGAGAAAATAATCCTGCTCAAG | 132 | GCGTTTAAGTCCAATAACAAAGATAAC | 416 | GTTTCTT | 3 |
| Satt361 | TCGGGAGACACTAAAGGCACTG | 133 | TCGTTGACACACAAAAAAAGCGA | 417 | GTTTCTT | 3 |
| Satt364 | GCGGCATAAGTTTTCATCCCATC | 134 | ATCGGGTCATGACTTTTGAAGA | 418 | GTTTCTT | 3 |
| Satt367 | GCGGATATGCCACTTCTCTCGTGAC | 135 | GCGGAATAGTTGCCAAACAATAATC | 419 | GTTTCTT | 3 |
| Satt369 | GGAGAAAACATCCAAAGAAATGTG | 136 | CAAGTGGATTGACACACTAAGGTTTGA | 420 | GTTTCTT | 3 |
| Satt372 | GGATAATTTTTTCATCATCACAATTTATC | 137 | CACAAAAGACAGGAGATGTGAGCAA | 421 | GTTTCTT | 3 |
| Satt373 | TGGAAATACTGAATGAAAGCATATTGG | 138 | TTGTAGACGACTTGTGGTTCGATTC | 422 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt378 | CCATTGGGATCGAGAATAATTGATG | 139 | AATGAAGAAAATGTGAATTTGAAACCA | 423 | GTTTCTT | 3 |
| Satt380 | AGAGTAATGGCTCCTGCTCCGA | 140 | TTCCCTTTTTCTAACTCTCCTTTTTCA | 424 | GTTTCTT | 3 |
| Satt383 | CGATCTAACACGCATATTTCCTCTGA | 141 | TGTCTTGGTGCAATACCTGACATTT | 425 | GTTTCTT | 3 |
| Satt384 | TGGGGGTCAATTTTAATTTGTGC | 142 | ATTTCCCTTTCACCCACCTCTGTTT | 426 | GTTTCTT | 3 |
| Satt385 | GATTCTCTTCATTCTAATACTCGTTT | 143 | CAACGATCCCAGCTCACAGTTT | 427 | GTTTCTT | 3 |
| Satt387 | GCGTTACGTTTCACTATTTATTTAACAT | 144 | GCGGCAGGCTAGCTACATCAAGAG | 428 | GTTTCTT | 3 |
| Satt389 | GCTGGTGTATGGTGAAATCAAATTACT | 145 | TTTCAAACAAGGAAGAAACCTCTTTTT | 429 | GTTTCTT | 3 |
| Satt390 | TGATATTGTTTTGTGTGAAAGATGCAC | 146 | AAGTAACACTGTGGCGGCATCC | 430 | GTTTCTT | 3 |
| Satt391 | TGCTCAAAGGGTCAATTTCTTTCC | 147 | TGTGTAATTTCTATCACCTTATTGTGCC | 431 | GTTTCTT | 3 |
| Satt393 | CCAAGCCCATAAACGAAATAAAACA | 148 | TCCTTTGGCTCGGCCTATGTAA | 432 | GTTTCTT | 3 |
| Satt398 | CAGTGCTCATATCAAATTAAAGTGG | 149 | CGCGGACTCAGTTAAACCGTAT | 433 | GTTTCTT | 3 |
| Satt399 | TTTCAACCACCAAGCCAACCTT | 150 | CGTTCAATAGTTCCTATGATGGACGA | 434 | GTTTCTT | 3 |
| Satt406 | TGCAGCATGTGTTTTAGGCTTTC | 151 | GCATTGCACGTCGATTTTAGGG | 435 | GTTTCTT | 3 |
| Satt409 | CCTTAGACCATGAATGTCTCGAAGATA | 152 | CTTAAGGACACGTGGAAGATGACTAC | 436 | GTTTCTT | 3 |
| Satt411 | TGGCCATGTCAAACCATAACAACA | 153 | GCGTTGAAGCCGCCTACAAATATAAT | 437 | GTTTCTT | 3 |
| Satt412 | ACTGGCGCTGACCTTAAATTGC | 154 | TCCTTTTAATTCTAACATTGAGACAGCA | 438 | GTTTCTT | 3 |
| Satt413 | TGTTTTTAAGTAATCCGGTGAAATAGCA | 155 | TCTGTCCCAAAAAAGAAAGAAGATATG | 439 | GTTTCTT | 3 |
| Satt414 | TCACATCACAAGTTTCATAAATGCTG | 156 | CAATCTTTAATGCTCTGGAGTTTGAGA | 440 | GTTTCTT | 3 |
| Satt415 | GCGTCTCCCTTAATCTTCAAGC | 157 | GCGTGTGACGGTTCAAAATGATAGTT | 441 | GTTTCTT | 3 |
| Satt416 | AGATTAAGAGAAGACGAGAGTTTTA | 158 | GGGTAATTTATCTGTGTGATTGTTC | 442 | GTTTCTT | 3 |
| Satt417 | GCCAGGTGCTCACTTCTTGCTA | 159 | TTGCTTGGGATTTTCATTTTATTATAGG | 443 | GTTTCTT | 3 |
| Satt418 | CAGGAGAAAAAAGGAAAAGAAAAGCA | 160 | GGTCAAAGAATAAGGGATTTGCCTC | 444 | GTTTCTT | 3 |
| Satt420 | AGGTTTTGCTTCTTGAAAGTGAAGAG | 161 | TGGGACTTTGATTTTTGGAATACCC | 445 | GTTTCTT | 3 |
| Satt421 | GTCTCCGTTCAAAGCTTCTTCTTC | 162 | CCAGAGAAATTATTGGAGTGGCAA | 446 | GTTTCTT | 3 |
| Satt422 | GAGGGGAGGTAAAAAGTCGGGA | 163 | GCGCAAAGAAATTCCCATCCTA | 447 | GTTTCTT | 3 |
| Satt423 | CGCTTGGGTTCAGTTACTTGGTG | 164 | GGGAGAGGTTCAGTTGGGGAAT | 448 | GTTTCTT | 3 |
| Satt426 | GCGCCCATTATTATTTTCCTTGAATTGT | 165 | GCGAATGCCTAATGTGATGATAAAAAAATA | 449 | GTTTCTT | 3 |
| Satt429 | GCGACCATCATCTAATCACAATCTACTA | 166 | TCCCCATCATTTATCGAAAATAATAATT | 450 | GTTTCTT | 3 |
| Satt430 | AATGCAAGAAGCAATCAGCAAGA | 167 | AATAATGGAGTGACCCGCTGCT | 451 | GTTTCTT | 3 |
| Satt431 | TGGCACCCTTGATAAATAAGAGAAGG | 168 | TGGTACGAGTGGCACGAAATGT | 452 | GTTTCTT | 3 |
| Satt432 | AATTGAACCACTCAGCCAAGCC | 169 | GCCATCCTTTCCTTTCAACCAA | 453 | GTTTCTT | 3 |
| Satt433 | GTCTAACATTTTAATTAGGGTGATTC | 170 | TGTAGGCTATTGGAAGGGTGCG | 454 | GTTTCTT | 3 |
| Satt436 | GCGTATAAAGAAAAACGAGCATATCAT | 171 | GCGCTTATAAAGGCTTGTGAAAGACACT | 455 | GTTTCTT | 3 |
| Satt440 | CAAATTGAAAAACACAAGAAAACACAA | 172 | TGGTTAGTGCAATCTTGGCGGT | 456 | GTTTCTT | 3 |
| Satt441 | AGCAACTAACCTTGGGCTTCAGTAA | 173 | TGCACCCATCAATCACATTTTTG | 457 | GTTTCTT | 3 |
| Satt442 | CCTGGACTTGTTTGCTCATCAA | 174 | GCGGTTCAAGGCTTCAAGTAGTCAC | 458 | GTTTCTT | 3 |
| Satt444 | AATTCCTTTGGCATTTTTGTTGC | 175 | TTTTTTCTCACACCCATGCCGT | 459 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt445 | TTTCACTTTTGAATCATTGCATCG | 176 | CCGGTTGGCGTAATGTGTCTTT | 460 | GTTTCTT | 3 |
| Satt448 | CACCACTCGTATCCTTCACAAGAGC | 177 | GCCAGCAGCCTGTTCAGTTTTT | 461 | GTTTCTT | 3 |
| Satt451 | GCGCAATTAAAAGGATAACTTATATC | 178 | CCCCTCTTTGGCCCTCACACCTTCTC | 462 | GTTTCTT | 3 |
| Satt452 | AAAATTCATGTCGCTGCGTTCA | 179 | ATTTGAAGCTCTTGGTATCTTGGC | 463 | GTTTCTT | 3 |
| Satt454 | TGAAAACCATGTCAAAGTAATGGCA | 180 | CAACCATGATAAATGTGACTGAGCTTG | 464 | GTTTCTT | 3 |
| Satt455 | GGAAAGTTTTGTTACATGCCGGA | 181 | GTCACAATTTCACGATCCCAAA | 465 | GTTTCTT | 3 |
| Satt457 | TTTTAACTGGAGAAACCTGAGGGA | 182 | TCCATTTTCCCTTTAGTCCAACG | 466 | GTTTCTT | 3 |
| Satt460 | GCGCGATGGGCTGTTGGTTTTTAT | 183 | GCGCATACGATTTGGCATTTTTCTATTG | 467 | GTTTCTT | 3 |
| Satt461 | TTGCTTGCTGCACATGACTGAG | 184 | AATTTCTTACGTTTCCATAGATTTCTCG | 468 | GTTTCTT | 3 |
| Satt464 | TTGAAATAGTGGTGGGGTTGGG | 185 | TGCCCTCTTCCCAAACTAGGGT | 469 | GTTTCTT | 3 |
| Satt466 | TGTGTTGTGTGGTGGTGGTC | 186 | CAACCACTGATTCAAGCCAACAA | 470 | GTTTCTT | 3 |
| Satt467 | CAAAGTCCCCTTTCACACCTTTT | 187 | CAATTTAAGCACGGTCATATTTTCTCA | 471 | GTTTCTT | 3 |
| Satt469 | AAAGGGAAAGGAAGAATAAACCGA | 188 | CGTGATGCAGTGAATTTTTTCG | 472 | GTTTCTT | 3 |
| Satt470 | TGCTTTTTCTCTTTGGCAACCC | 189 | GGGTTACTTTTCTTTATCCTCCTCCA | 473 | GTTTCTT | 3 |
| Satt471 | GCGCCCAAAACTATCTAGTAATTCTT | 190 | GGGCTATCAAATTGACTAAAGCCAAA | 474 | GTTTCTT | 3 |
| Satt473 | CCAACAACCAAATCAATCACTGC | 191 | ACACTTGAATCATCGAGAGTTGCTAA | 475 | GTTTCTT | 3 |
| Satt475 | GCTCCGGTCCTTCAACTGACCT | 192 | TGTGCTGCTTGCTTCAATTTGC | 476 | GTTTCTT | 3 |
| Satt476 | ATGTGGGTATGTTGCAGGCAGA | 193 | TGGCCTGTCTTATATTACCGAACCAA | 477 | GTTTCTT | 3 |
| Satt477 | GTTGGGAAAAGGTTACTACCATATC | 194 | GGTCCGTATGCAATTCTTGACTAATA | 478 | GTTTCTT | 3 |
| Satt478 | CAGCCAAGCAAAAGATAAATAATA | 195 | TCCCCCACAAGAGAACAAGAAGGT | 479 | GTTTCTT | 3 |
| Satt479 | GCGCTTTCAAAAAGTAACAATTAATGAAA | 196 | GCGGGAATTGGTTAATCTCATCGTGAC | 480 | GTTTCTT | 3 |
| Satt480 | GACCTTTCATCATCGTCCCCAC | 197 | TGCGAAAAGCAGAGTGACCAA | 481 | GTTTCTT | 3 |
| Satt487 | TCAATTCATCACGGACCAGTTCA | 198 | TGAGCATATTTTGATCCGATGCC | 482 | GTTTCTT | 3 |
| Satt488 | GTGAGTTTCGGTGCTGTATTCC | 199 | GTTGCTTTGTTATGTAATGGAAGTC | 483 | GTTTCTT | 3 |
| Satt491 | CCTAAATTGATGAAAGGATACAAG | 200 | GCCCCACAAATATTCAGAAGGTAA | 484 | GTTTCTT | 3 |
| Satt492 | GTATCGTTCGCGTCTTGAGTC | 201 | GCAGCGGTGTAGTTCGTTCTTTCT | 485 | GTTTCTT | 3 |
| Satt493 | TTAACGGGAAAAAATTAAACCTACGA | 202 | AAATCGTCTTTTGTGGCTGCCT | 486 | GTTTCTT | 3 |
| Satt495 | TGGAGATTTAATATAGATGCCGCGA | 203 | GCACCATGTTCTTTTTCCATCAAA | 487 | GTTTCTT | 3 |
| Satt497 | GCGGTTTTGGATTGACTTTGTTGA | 204 | GGCTCAATTAGAGCATGCAACATC | 488 | GTTTCTT | 3 |
| Satt503 | CCGTGACTTTTGTTATCCTGAGTTCC | 205 | CATGTTAAACGTCCACCCACCA | 489 | GTTTCTT | 3 |
| Satt506 | GCGAATTGGCATACATAGTACC | 206 | GCGTGAATTCGCCTAAGTTTAT | 490 | GTTTCTT | 3 |
| Satt507 | TGCACCACTAATGTCCTCAGCC | 207 | TCCCTACTCTCGTGTCGTTAGTTATTTT | 491 | GTTTCTT | 3 |
| Satt508 | GCAATGGGTATTGATCGTGTCA | 208 | AGTTACATTATTTTTGTCTTTCTGCCGT | 492 | GTTTCTT | 3 |
| Satt509 | GCGCTACCGTGTGGTGGTGCTACCT | 209 | GCGCAAGTGGCCAGCTCATCTATT | 493 | GTTTCTT | 3 |
| Satt510 | GCGAGTTTCGCCGTTACCACCTCAGCTT | 210 | CCCTCTTATTTCACCCTAAGACCTACAA | 494 | GTTTCTT | 3 |
| Satt511 | TGCGACTTTACTGAAAACCTGGAA | 211 | GGAAATGCTTCAAACCAACAAACA | 495 | GTTTCTT | 3 |
| Satt512 | AACGTCTTCAAGTCAAGTGCCTACA | 212 | GCCCACATAGTTTTCATTTTTCTCCA | 496 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt513 | GCGCATCACAAGTTTTATAGATGCTGA | 213 | GAGGTCTAGTGCTTTGGTAAGGTT | 497 | GTTTCTT | 3 |
| Satt514 | GGGTACATTTTATTAAAAGTAAACACACC | 214 | TGTCACACAACCAGTGTCTCAAAATC | 498 | GTTTCTT | 3 |
| Satt515 | TGAACCTTGTCTGTTGATTTTTTTATGT | 215 | CACACCCCAGGACCCATTAAGA | 499 | GTTTCTT | 3 |
| Satt517 | TCTCCTACTTCTCTTTCTCCCGTTCA | 216 | AAAGCGCACACAATGCAAATACA | 500 | GTTTCTT | 3 |
| Satt519 | CCTGATTATATGTCTAGACAAACAT | 217 | CAAGGTTACGAACTGCTCGAATAAG | 501 | GTTTCTT | 3 |
| Satt522 | GAGATCACATCAAAGTCAAAACTGCC | 218 | TGAGGAGGCAAGATGATCCAAA | 502 | GTTTCTT | 3 |
| Satt523 | GCGATTTCTTCCTTGAAGAATTTTCTG | 219 | GCGTTTTTCGGCTGTTATTTTTAACT | 503 | GTTTCTT | 3 |
| Satt524 | GCGAATTATCCAAAGATACACTTAGTC | 220 | GCGGGTCTTACGAACGTGTCACATTAT | 504 | GTTTCTT | 3 |
| Satt526 | ATATCGAAAATCGCGCATCTGG | 221 | CGAACCCAAACCACAAAGCATA | 505 | GTTTCTT | 3 |
| Satt529 | GCGCATTAAGGCATAAAAAAGGATA | 222 | GCACAATGACAATCACATACA | 506 | GTTTCTT | 3 |
| Satt532 | GCGCCAATATTATCATGCTTTATGT | 223 | GCGTGTAAAAATCTTTGAATCTTGA | 507 | GTTTCTT | 3 |
| Satt533 | AGTGGTCGTCACAACACTATCATAT | 224 | CACCCATTATTGAAAATACAAGGACCA | 508 | GTTTCTT | 3 |
| Satt534 | CTCCTCCTGCGCAACAACAATA | 225 | GGGGGATCTAGGCCATGAC | 509 | GTTTCTT | 3 |
| Satt536 | GCGTGGAATGAGAGGTAACCAA | 226 | GCATAATGGTCTAATAAAAGTGGAGACC | 510 | GTTTCTT | 3 |
| Satt537 | CAAAACTTATGTGCAACACGACTTCA | 227 | TGCTTTTGGAGGAACTTTGTCTCA | 511 | GTTTCTT | 3 |
| Satt540 | AATGTAGCAATTTGACTGGCGAA | 228 | CATTCAACCGTGATTGCGAAGA | 512 | GTTTCTT | 3 |
| Satt543 | GCGGATCTAAGGATAATTCATTAA | 229 | GGGAGCGGATCATTCGGTGAAA | 513 | GTTTCTT | 3 |
| Satt544 | GCTATGGGAAAAGGATGTGTG | 230 | GAGCTACCCGAGATGATACTC | 514 | GTTTCTT | 3 |
| Satt545 | ATGTGATGGCATGTGAAATGGT | 231 | GGATCAAATTGGGAAACACAAAGG | 515 | GTTTCTT | 3 |
| Satt546 | CAGGGTATAGTTCAATTCAGTGAGCG | 232 | CTCACATACATGGCAGCCGTAA | 516 | GTTTCTT | 3 |
| Satt548 | CCTCTTTGTTGGTGGTTAAGTCTCC | 233 | TGCCTTTAGCTGGTGGGAAAAA | 517 | GTTTCTT | 3 |
| Satt549 | GCGGCAAAACTTTGGAGTATTGCAA | 234 | GCGCGCAACAATCACTAGTACG | 518 | GTTTCTT | 3 |
| Satt550 | TCGTCAATTAAGCAAAAATGTGAGA | 235 | TTAGAGGTTTTCGGATGAGCGTG | 519 | GTTTCTT | 3 |
| Satt551 | GAATATCACGCGAGAATTTTAC | 236 | TATATGCGAACCCTCTTACAAT | 520 | GTTTCTT | 3 |
| Satt552 | ACAAAAGAAATCGAACCGGCA | 237 | GTTTTGGTTGATCCGCATTGGT | 521 | GTTTCTT | 3 |
| Satt555 | TGGCTTTGATGATGTTTGAGACAA | 238 | TTTCATTACCGCATGTTCTTGGA | 522 | GTTTCTT | 3 |
| Satt556 | CCCAGATACAGACAATAAAACCCGA | 239 | TTATGTTCGTTCATCTCTGAAGCCT | 523 | GTTTCTT | 3 |
| Satt557 | TCCACCATGTAATATGTGAAGTGGAT | 240 | TTCTGTCCATTCTAGCTCACTAACCC | 524 | GTTTCTT | 3 |
| Satt558 | CTCACACCCTTTCATTATCTA | 241 | AAATCGCGCATCTAAATTTAC | 525 | GTTTCTT | 3 |
| Satt560 | ACTCTATTTTATTATCGTGCAAGAA | 242 | ACAATAACTTGTTTTGCACACTATT | 526 | GTTTCTT | 3 |
| Satt563 | GATGACAACGTAGGCTAAAAA | 243 | GCGCCCACATGATTTTGTACTGAT | 527 | GTTTCTT | 3 |
| Satt565 | GATTCTATATCCATCGTGTTGCT | 244 | TATGGTAAATATTAACCATTGTCCT | 528 | GTTTCTT | 3 |
| 5att566 | CCCACTGTATCCTTAGTGTGCCA | 245 | CCTCGTTTTATTCCGAAAGCCG | 529 | GTTTCTT | 3 |
| Satt567 | GGCTAACCCGCTCTATGT | 246 | GGGCCATGCACCTGCTACT | 530 | GTTTCTT | 3 |
| Satt568 | CATTAACTAATAAGTTGTTGGTAGC | 247 | TTAGATTCGGACACCGGTCTACT | 531 | GTTTCTT | 3 |
| Satt569 | ACCAAATTGCTTCACGCATCC | 248 | TCTTAATTTTTTTAGGAATGGCATCAA | 532 | GTTTCTT | 3 |
| Satt570 | TGCTCATGTGGTCCTACCCAGA | 249 | CGCTATCCCTTTGTATTTTCTTTTGC | 533 | GTTTCTT | 3 |

APPENDIX II-continued

SSR Markers: Table of Primers
9 pages

| Marker Name | Left Primer Sequence | SEQ ID NO | Right Primer Sequence | SEQ ID NO | Pigtail | Repeat |
|---|---|---|---|---|---|---|
| Satt572 | GCGGAGCATGTAAATCCAGCCTATTGA | 250 | GCGGGCTAACTTATGTTACTAAACAAT | 534 | GTTTCTT | 3 |
| 5att573 | GCGGATTTCGATTTGAATATACTTAC | 251 | CCTGTGGCTGTTATACTATGCATATA | 535 | GTTTCTT | 3 |
| Satt576 | TGGACACACACAAACACCTACAGAA | 252 | GGGTGGCGTTGACAATGTTTTA | 536 | GTTTCTT | 3 |
| Satt577 | AGCAAGTCTTGAGTCTTTTGTCT | 253 | TTATTATCTAAACTTATATGTGCAT | 537 | GTTTCTT | 3 |
| Satt578 | TCCCACGTCATATCCACTGCTC | 254 | GCCTCCTAAGTCCGTACACAGCAT | 538 | GTTTCTT | 3 |
| Satt581 | CCAAAGCTGAGCAGCTGATAACT | 255 | CCCTCACTCCTAGATTATTTGTTGT | 539 | GTTTCTT | 3 |
| Satt582 | CCGGTGATACTCCATACCAATAACA | 256 | GGATTTGGTTTCTGTGTGCTGTG | 540 | GTTTCTT | 3 |
| Satt583 | CCGAGCTAACAAAGGCGACCAAAT | 257 | GGGGCACAAGCCACACTT | 541 | GTTTCTT | 3 |
| Satt584 | GCGCCCAAACCTATTAAGGTATGAACA | 258 | GCGGGTCAGAAGATGCTACCAAACTCT | 542 | GTTTCTT | 3 |
| Satt586 | ATGGCCGTCTCAAAAGAACTGG | 259 | TGGGCACTTGCAGTCCAAATAG | 543 | GTTTCTT | 3 |
| Satt587 | GCGAATGGTTGCTCAAATAATC | 260 | GCGCAAACCGCACAAGTTTATGT | 544 | GTTTCTT | 3 |
| Satt590 | GCGCGCATTTTTTAAGTTAATGTTCT | 261 | GCGCGAGTTAGCGAATTATTTGTC | 545 | GTTTCTT | 3 |
| Satt591 | GGCAGACTCGTAGAGCAATTTA | 262 | TGTTGAAATTGACCAAAATTCCCA | 546 | GTTTCTT | 3 |
| Satt592 | GCGAAGATTGGTCTTTTATGTCAAATG | 263 | GCGGAGGAATACAAGTCTCTATTCAA | 547 | GTTTCTT | 3 |
| Satt594 | GCGGTAACTCCTCGAGTCCCTCTCAAT | 264 | GCGCCGCTAACAGACATCCAATA | 548 | GTTTCTT | 3 |
| Satt595 | TGGTGATGGGAAGCAAACAAGA | 265 | TGGATTTCACCCAAGAAAAAAGC | 549 | GTTTCTT | 3 |
| Satt596 | CCATCCCTTCGTCCACCAAATA | 266 | TCGACTACCCGTCGATTCCGTA | 550 | GTTTCTT | 3 |
| Satt597 | TGCTGCAGCGTGTCTGTAGTATAATTT | 267 | GGCACAACCATCACCACCTTATT | 551 | GTTTCTT | 3 |
| Satt598 | CGATTTGAATATACTTACCGTCTATA | 268 | CACAATACCTGTGGCTGTTATACTAT | 552 | GTTTCTT | 3 |
| Satt601 | GTAACATTGGTTGTCATCTTTGTCTA | 269 | ATCGAACTGTGACCGTCCCTTC | 553 | GTTTCTT | 3 |
| Satt602 | GGAGGTTATCTAGTGGTATAGATGGT | 270 | AAGGGAAGAGAGTCGTGCTTCTTT | 554 | GTTTCTT | 3 |
| Sct_010 | CCAAAAGCATTGAGAGTGGGGA | 271 | CCAGCAAACCCCCAGGTAAAG | 555 | GTTTCTT | 2 |
| Sct_026 | GAAACCCGAAACGCAAAATCTC | 272 | GAAGAAAACGCGAATAACCCCA | 556 | GTTTCTT | 2 |
| Sct_028 | CTCTCGCCGGTACAAAACACCT | 273 | GCACGCAGACTCAAGTTCATTCA | 557 | GTTTCTT | 2 |
| Sct_034 | TCACTCTGACAACTTCAATCTCTTTCTC | 274 | AATAGTTGGGTCGTCGAAGGGG | 558 | GTTTCTT | 2 |
| Sct_046 | CACGACTCTTCCTCTTCCTCCG | 275 | TCCAACTTAACACAAGATCAGCAA | 559 | GTTTCTT | 2 |
| Sct_065 | CCCTGTGTTTCCCTCT | 276 | GAAAGTTTTATGTTCTGAGTG | 560 | GTTTCTT | 2 |
| Sct_137 | GTGTTGCTCTTGGGAATCTGCC | 277 | CCACACACACTGACACAGTAAACCA | 561 | GTTTCTT | 2 |
| Sct_147 | TCTCGACTCACGACTCA | 278 | CCAAGGTCTCTCAGAGG | 562 | GTTTCTT | 2 |
| Sct_186 | AAAATGAAAACACACAGAGAGAGAGA | 279 | ACGGAGGCACTTCCCATTGTTA | 563 | GTTTCTT | 2 |
| Sct_187 | AGCGAAATGTGTGGTCCAAGGT | 280 | CAAAACGACATGCAAGGAAACTTCA | 564 | GTTTCTT | 2 |
| Sct_188 | CGTCGAGAAAGGAAGAGAGGCA | 281 | TCCTCCATAAAAATTAAAAACATTGGAA | 565 | GTTTCTT | 2 |
| Sctt008 | GCGGAAACCATTCTGACGGATA | 282 | GCCCCCAGACACAACATAATCA | 566 | GTTTCTT | 3 |
| Sctt009 | GGAGGAACTTGGAAGGCATATCA | 283 | CGAGAGAAGCAGAAGCAGAGGC | 567 | GTTTCTT | 3 |
| Sctt012 | ACGGACAACGCTGGCACTAAG | 284 | GAGAAAGGTGACGATGGACGCT | 568 | GTTTCTT | 3 |

APPENDIX III

ASH marker primer sequences
2 pages

| Marker Name | Primer 1<br>Primer 2<br>Primer 3 | Primer 1 sequence<br>Primer 2 sequence<br>Primer 3 sequence | SEQ ID NO |
|---|---|---|---|
| P10355B-1 | 19392<br>19393<br>25400 | CATGGTTTCTCTTATCTTAT(AG)ACATTGTTGCCAAG<br>CAATTCATGGTTTCTCTTAT(AG)ACATTGTTGCCAAG<br>CACTGTCCCTGCTCCTGTTTCAAGTATC | 569<br>570<br>571 |
| P10598A-1 | 14507<br>14505 | CAATTCTTGTGGGTTGAAGCCTTGTTCTGAC<br>GGAATCAACTTCTTCGTGAGTGGGTTGTTC | 572<br>573 |
| P10615A-1 | 1125<br>4186 | TGGTGGCTATGGAAATCTCATGTGTGGA<br>CTCTCATTTACCAAACTCCAACATTTGATCACC | 574<br>575 |
| P10618A-1 | 14492<br>14490 | CACACTGGTAGATGGGAAGCAAGAATAGG<br>GAAGAAGATTCCACCCAGATCATCATCAGTAG | 576<br>577 |
| P10620A-1 | 12099<br>12101 | GCTTGTGCAGCTCCAATCGGTGTAAC<br>GTGCAATCCAAGACATCTGGTTCGGAC | 578<br>579 |
| P10621B-2 | 12158<br>12159 | CAGCTAAACCTTACAAGGATGATTGGTCAAG<br>CCCTGGACTGAAGTTGCCATAATGTATC | 580<br>581 |
| P10623A-1 | 12153<br>12154 | GCTGGTTGGGAGAAAGCACTTCC<br>GAATCTAACATTACGCTCTGCTGGAGTATC | 582<br>583 |
| P10624A-1 | 14328<br>14330 | GAGGGACTATGTGAAATGGAGAGGAGTG<br>GTATGCTAAAAGAGGAGACTTGACTGGTGAG | 584<br>585 |
| P10632A-1 | 12105<br>12106 | GATGAAGGAACCAACACTTGCATAACAATTTG<br>TGTCAGCACTCCTCACTCATTTGCCGA | 586<br>587 |
| P10633A-1 | 4187<br>1183 | CACTTAACAGGAGTGCTCCTGATCACCAG<br>GAGAACAAGGACAAATCAATAGGTGAGACGAAGAA | 588<br>589 |
| P10634A-1 | 12600<br>12601 | CTCATCTGCTCAGAACCTTCAGTCAGTC<br>CGGATCATGTCTAGTACATTAGAGATGCTTGTG | 590<br>591 |
| P10635A-1 | 12779<br>12780 | CTACACTTCTAATGCCTATTTAGGTGTGCTTG<br>GTCATATCTAGGGAGATTTCTAACCAGTTGTC | 592<br>593 |
| P10636A-1 | 15252<br>15258 | TAGGCAGCGTGACAAACTGAGCATAGG<br>GGGTTGATGTCCGATGGGTAAATGAAGTTG | 594<br>595 |
| P10637A-1 | 14136<br>14138 | GCACTAATACTTTAGTTGACTTTTGAGGTGGTTGAG<br>GCTATGTGGTAGAAGTATATGAAAAGGTAGATGACAG | 596<br>597 |
| P10638B-2 | 15290<br>15040 | GAATATACTAGCTTGATGCCTATTTGTTTCTAAACCC<br>AGCAGTCATACAATGCTCTTTATTGTGGTGAAG | 598<br>599 |
| P10639A-1 | 15345<br>15347 | GCTCATAGCCTGCTTCTTAATCTTGTTATTCTG<br>CTATTTGTTTCAGGAGTTTCACAACCATCTCAAGT | 600<br>601 |
| P10640A-1 | 15280<br>15281 | CATCTTGACCAGTCACCAATCTGAGTACAG<br>GGCTTCAGTGAGAAAGGTGGATCAAATGGA | 602<br>603 |
| P10641A-1 | 15349<br>15350 | CAACGTGTAAAATCAAGAGATTGAGCTTCTGG<br>TCGGTGTGTTCAACTATGACTTTGGTTCTG | 604<br>605 |
| P10646A-1 | 5642<br>6803 | CCCCCAACAAAACTAAAAATAGAACCCTCAACAACC<br>GGTCCAAGAACATTATGATCTTGAACAATCTTCAC | 606<br>607 |
| P10648A-1 | 14436<br>14333 | TGGCTAGAGCATCAACACATCTATACCTTC<br>CATTGGGCATGATTCTTGAATAGCCTTTTTACC | 608<br>609 |
| P10649C-3 | 12171<br>12173 | GAGGGCTATGTTTTCTTCTCCAGATGTGAG<br>AAGGTCGGCTTGGTGGTTAAAGGCAG | 610<br>611 |
| P10651A-1 | 10414<br>10415 | GCCTTTTATGCACATTTTTCCTGGGGATCTAAC<br>CTCAATGTCATGGGATCAATTTGGAAATTCAATGACC | 612<br>613 |
| P10782A-1 | 15294<br>15296 | GATTACATTAATTACCGCTATGACTATATCTTGGGAC<br>GCTACCTTCTCCATTGCTTCTATGTATTGGTC | 614<br>615 |
| P10783A-1 | 15771<br>15772 | GGGCATCACATACATGAAAACAACTACACTTG<br>CAACAGCTCTCTTCCACCACAATCCTG | 616<br>617 |

APPENDIX III-continued

ASH marker primer sequences
2 pages

| Marker Name | Primer 1<br>Primer 2<br>Primer 3 | Primer 1 sequence<br>Primer 2 sequence<br>Primer 3 sequence | SEQ ID<br>NO |
|---|---|---|---|
| P10792A-1 | 15805 | GAGATTGGAAATTGTAGCTCTCTTTACTTGCTG | 618 |
|  | 15807 | CTTTGAGGACTTATTTGGTTGTTATAGGCATTTGG | 619 |
| P10793A-1 | 15621 | GTGTTTCCCTCCATTTTTGCCAAAAGACAG | 620 |
|  | 15814 | TATACACACTAAGAATTCGCTCGCTGTACAA | 621 |
| P11070A-1 | 16188 | GGTCTAGACTTTCACTCAGACAAGGAAC | 622 |
|  | 17490 | CAAAATACTACAGACCTAATTTGTAACTAATTGCTCCC | 623 |
| P11347A-1 | 9642 | GGGAAGAAGAAGAACACTCGGTACAGTAG | 624 |
|  | 7693 | AAGCTAGGAAATCCACACTCAAATTATCGACTTGTGT | 625 |
| P12105A-1 | 23538 | GACCTGAAGCAAAACGCCACCATTTCC | 626 |
|  | 29311 | CGTTCGAGACGACGCCGTTTGATTAC | 627 |
| P12198A-1 | 39113 | CAGTCGACACGTCTTCTACTCC | 628 |
|  | 39114 | TGGAAGGCATGTCGGAACTTG | 629 |
| P12390B-1 | 21397 | CCTTTTTGCCCTCACTTCATGCCTTCTATG | 630 |
|  | 23525 | GCATAACCCAAGAGCTGGACTGACAAG | 631 |
| P12391A-1 | 21215 | CAAGCTCTGCTGCCAGGTTAAGTGTTTC | 632 |
|  | 21216 | GACTAGAACAAATTGGGGCTAGTGTGTTTGAG | 633 |
| P12392A-1 | 21494 | TGGACTTGCGGGACTATGCCTTAGAG | 634 |
|  | 21495 | GCAGGAACACGTTCGTAACCATCAACTG | 635 |
| P12394A-1 | 22161 | GTCCCTTTCTGAACCACTTAAAGAGTCAACAG | 636 |
|  | 22163 | GGCATAGTGAGTTGAATACCAGGAGGAATC | 637 |
| P12396A-1 | 23679 | ATTGAAGGGTGGGCGTTACCAGGTTAC | 638 |
|  | 23680 | GAGTTAATGGGGCTATGCTATTGGCTATTCAC | 639 |
| P13069A-1 | 24588 | GTCACTATATGGAGTCAAGGTAATTATTGTGTTCAC | 640 |
|  | 24590 | GGTCTAGAGTTTGAATATTAGTAATGACTTGTATTGAC | 641 |
|  | 24591 | GCATATTGTGCCATAGAGAGAGAAAATGTAGTAAG | 642 |
| P13070A-1 | 24508 | CGCTACTGCAAGTTATCAGTCAAGAGATTATTCC | 643 |
|  | 24510 | GCCGTGTAAGCGTGTTTACCAATCTAGTTG | 644 |
| P13071A-1 | 24795 | CAAAACTGAGCGAAACTTGTGTTGGGAGAAAG | 645 |
|  | 25395 | GTGGGGACTCTTTATTCGAAGTTTGCTGAAC | 646 |
| P13072A-1 | 24499 | CTCATGTAACCAACTCTCTATGAAGTTTGAGATCCA | 647 |
|  | 24500 | CTCTAATCGGATTTGGTGTTTCACTTCGGTAAG | 648 |
| P13073A-1 | 24503 | GATGGCTGTCATTGCTACAGAGGAGTATC | 649 |
|  | 24505 | GTGACTCCAAAGGAAAGAGAAATGTTTCTTAAATCATC | 650 |
| P13074A-1 | 25287 | GGATAGCAAGTCAATTTCATGCCTTGTGATAG | 651 |
|  | 25288 | GCAGGACATGAAGATGTACTTAGTGAATGTGAAG | 652 |
| P13158A-1 | 24713 | ACTGGAAGAGGGTGCTTAGGGAATCTG | 653 |
|  | 24715 | GAGAATCTAGTCTACCACCATACCACGAAC | 654 |
| P13560A-1 | 25671 | GGGACTCTCTTTATATTGGAAGGTATAACTCAGTG | 655 |
|  | 25672 | GTTGGACCCTTGTAATTAGACCCGAAACAAATG | 656 |
| P13561A-1 | 26537 | ATCTGTCCAACGATCTCTCCATGTTCATTC | 657 |
|  | 27121 | CGAATAAGAAGTTGGGTATCACTTACACGTTGG | 658 |
| P2447B-2 | 8815 | GATGGGGTTCTAGACTGGGATCTGGAT | 659 |
|  | 8616 | CTTTTCCTACAGGATTGTCAGGCTTATCGTCA | 660 |
| P2481A-1 | 10468 | GAAGAGTAACAGAGTCTACGCACCGAC | 661 |
|  | 10470 | GTCAACGAACATACTATGCATGATGATTTCTGATTAG | 662 |
| P2636C-2 | 21190 | CATATGCAGACAGCAGGCTAAGGAACTC | 663 |
|  | 15824 | GCAGCAATATAACCAGGATTCAGAATTAATCTAGTTAG | 664 |
| P3050A-2 | 16940 | CGATGGGGTTGACTTAGAAATGGCATATAC | 665 |
|  | 16860 | GCACCAATTCCTCAAGCATACTCCAAAC | 666 |

APPENDIX III-continued

ASH marker primer sequences
2 pages

| Marker Name | Primer 1<br>Primer 2<br>Primer 3 | Primer 1 sequence<br>Primer 2 sequence<br>Primer 3 sequence | SEQ ID<br>NO |
|---|---|---|---|
| P3436A-1 | 10660 | CTGACAAGGTGTTTTGGTAGGGAGAGATTC | 667 |
|  | 10663 | GCATCCTCCGTTACTCCAATCAGAGTTTCCAT | 668 |
| P3436A-7 | 10660 | CTGACAAGGTGTTTTGGTAGGGAGAGATTC | 669 |
|  | 10663 | GCATCCTCCGTTACTCCAATCAGAGTTTCCAT | 670 |
| P5219A-1 | 11913 | CACACTATCAACACCTATTGGTGACCATTGTA | 671 |
|  | 8395 | GGAGGGTGCTTATGTAAATGATGTAAAGACCAT | 672 |
| P5219A-2 | 11917 | GATGACCATTTTGATTCCCTCATGCTATTAGTACC | 673 |
|  | 8396 | CCAATAAGTTAGCAGCATGTGGATCACAGTGTA | 674 |
| P5467A-1 | 19156 | GTCTCTCGGAGTTGCTTCAATTGCTCATAC | 675 |
|  | 19864 | GAGAGTGTGGAATTGTA(AG)TCATTGATTGAAAACTC | 676 |
| P5467A-2 | 19156 | GTCTCTCGGAGTTGCTTCAATTGCTCATAC | 677 |
|  | 19864 | GAGAGTGTGGAATTGTA(AG)TCATTGATTGAAAACTC | 678 |
| P6181A-2 | 17279 | GCAGAAGGAGCATTGAGGCTTTCCAG | 679 |
|  | 9372 | GAAAAGGTTTGTTATGCTTCGTACTCTGTCTC | 680 |
| P7659A-1 | 7847 | CATGAAGCTCCACCATTTGCTAGTACATGAAAC | 681 |
|  | 10878 | CCAGAGTTACCAAACCATCTGTGAGAAATATCC | 682 |
| P7659A-2 | 7847 | CATGAAGCTCCACCATTTGCTAGTACATGAAAC | 683 |
|  | 10878 | CCAGAGTTACCAAACCATCTGTGAGAAATATCC | 684 |
| P8230A-1 | 13958 | CAAACGCTCCCAACAGCTTCAGAATCTC | 685 |
|  | 13959 | TTGAAGGTTGTAAGAGTCTCGGTCGTCG | 686 |
| P8584A-1 | 15081 | CCCATTCTTCATGTACTCATACACCAAGAG | 687 |
|  | 15086 | GCAGCCACCAATAATTTCTCATTTGACAACAAG | 688 |
| P8584A-2 | 19660 | CTCTGTATATGAYATATGTGCTCAGTGCCTC | 689 |
|  | 19389 | GACTTACCAAATGAGTTTGACCAGGTTTTACC | 690 |
| P9026A-1 | 14494 | AGGATTCAACCTCTAGCCATGATGATGTTG | 691 |
|  | 14493 | CCAAGCTCTTTCCGTGTGTATCAATCTG | 692 |

APPENDIX IV

ASH marker: probes
2 pages

| Marker Name | Allele1 | Probe 1 sequence | SEQ ID NO | Allele2 | Probe 2 sequence | SEQ ID NO | Allele3 | Probe 3 sequence | SEQ ID NO |
|---|---|---|---|---|---|---|---|---|---|
| P10355B-1 | 18119 | GTTTCAGATAAC | 693 | 18118 | GTTTCTGATAAC | 754 | | | |
| P10598A-1 | 13358 | GAATGACTTTGA | 694 | 13360 | GAATGATTTTGAC | 755 | | | |
| P10615A-1 | 1630 | TCATTCTTTCATG | 695 | 1629 | TCATTCTTTCATG | 756 | | | |
| P10618A-1 | 13392 | TCTCCAGAAACA | 696 | 13394 | GTTTCGGGAG | 757 | | | |
| P10620A-1 | 13919 | GTGATCCGTG | 697 | 11141 | ATCACGAATCAC | 758 | | | |
| P10621B-2 | 11150 | ATCTTTTCAGGTT | 698 | 12304 | TATGGAGTAATTG | 759 | | | |
| P10623A-1 | 11360 | GGATTACATACTA | 699 | 11361 | TGGATTTTATACTA | 760 | | | |
| P10624A-1 | 13361 | TTTGAAGCTTTAT | 700 | 13362 | TTTGAATCTTTATC | 761 | | | |
| P10632A-1 | 10697 | AAGAATCTTCGTA | 701 | 10698 | AAAGAATATTCCTA | 762 | | | |
| P10633A-1 | 15132 | AATCTAAAATTTAGT | 702 | 15131 | ATCTAACATTTAGT | 763 | | | |
| P10634A-1 | 11987 | ACTAAATTTATACC | 703 | 11988 | GGTATACATTTAG | 764 | | | |
| P10635A-1 | 12562 | ATTAGGGGCAG | 704 | 12563 | ATTAGGGGGCA | 765 | | | |

APPENDIX IV-continued

ASH marker: probes
2 pages

| Marker Name | Allele1 | Probe 1 sequence | SEQ ID NO | Allele2 | Probe 2 sequence | SEQ ID NO | Allele3 | Probe 3 sequence | SEQ ID NO |
|---|---|---|---|---|---|---|---|---|---|
| P10636A-1 | 13678 | ACTATAGTTCGC | 705 | 13679 | ACTATACTTCGC | 766 | | | |
| P10637A-1 | 13428 | AACCTTTCTGTC | 706 | 13430 | ACCTTGCTGTC | 767 | | | |
| P10638B-2 | 12041 | TTGAGGATTTAG | 707 | 12042 | TTGAGCATTTAG | 768 | | | |
| P10639A-1 | 15144 | TCTCAACTTGGA | 708 | 15145 | TCTCAATTTGGAA | 769 | | | |
| P10640A-1 | 15137 | TTCAGTCAAACC | 709 | 20442 | TTCAGTTAAACC | 770 | | | |
| P10641A-1 | 13673 | TTCTTTTGTGACA | 710 | 13675 | TTCTTTGGTGAC | 771 | | | |
| P10646A-1 | 6223 | TGTGACAACCGA | 711 | 6224 | GTGACACAACC | 772 | | | |
| P10648A-1 | 14935 | AATCTTTTTTAAAG | 712 | 13666 | AATCTTCTTTAAAG | 773 | | | |
| P10649C-3 | 11356 | TCATCTCTGATAA | 713 | 11358 | TCATGTGTGATAA | 774 | 11357 | TCATCTCTGATAA | 815 |
| P10651A-1 | 8002 | AAGAGAAGGCTA | 714 | 8003 | AAGAGATGGCTA | 775 | | | |
| P10782A-1 | 15302 | ATATAAGTAAGGG | 715 | 15301 | AATATAAATAAGGG | 776 | | | |
| P10783A-1 | 15599 | GCATGTCGAC | 716 | 15600 | GCATCTCGAC | 777 | | | |
| P10792A-1 | 16759 | TTGAAGTTATAC | 717 | 15707 | TTGAAGATATAC | 778 | 15706 | TTGAATATATACT | 816 |
| P10793A-1 | 15624 | GGCATGTGAGT | 718 | 15625 | GGCTTGCGAG | 779 | | | |
| P11070A-1 | 14956 | ATTAACAGTAAAGT | 719 | 14957 | TATTAACATTAAAGT | 780 | | | |
| P11347A-1 | 15073 | TATCTATGTATATTA | 720 | 17277 | TATCTATATATATTAA | 781 | | | |
| P12105A-1 | 23530 | TGGGAATGATG | 721 | 21919 | ATCATCCCCAA | 782 | | | |
| P12198A-1 | 23164 | TAAATAAATAAGATG | 722 | 23165 | AAATAAGTAAGATG | 783 | | | |
| P12390B-1 | 21475 | AAAAAAAATGAGG | 723 | 23524 | AAAAAAATATGAGG | 784 | | | |
| P12391A-1 | 23527 | TCAATGTTGGAT | 724 | 21219 | TCAATGATGGATA | 785 | | | |
| P12392A-1 | 21493 | TTGTGACCAATAT | 725 | 23437 | ATATTGATCACAA | 786 | | | |
| P12394A-1 | 23401 | ATCAAGCCCAA | 726 | 23529 | TGGGTTTGATC | 787 | | | |
| P12396A-1 | 23681 | AGAAGCTCGTG | 727 | 24579 | GAAGGTCGTG | 788 | | | |
| P13069A-1 | 24584 | GAAAAGAAAGG | 728 | 24585 | GAAAAAAAAGGA | 789 | 29603 | AGATGTTAGAGTTA | 817 |
| P13070A-1 | 24509 | ACATATAATAGTAG | 729 | 25336 | ACATATAGTAGTA | 790 | | | |
| P13071A-1 | 24796 | TTTTGTATCTGTAT | 730 | 24798 | TTTGTGGCTGTA | 791 | | | |
| P13072A-1 | 25337 | TTAACTTGCCAG | 731 | 25338 | TTAACTAGCCAG | 792 | | | |
| P13073A-1 | 24504 | AATGATAATTTAGT | 732 | 24506 | AATGATCATTTAG | 793 | | | |
| P13074A-1 | 25306 | GAATGAATTTTTC | 733 | 25307 | AATGAACTTTTTC | 794 | | | |
| P13158A-1 | 25339 | ACACTGCTTAC | 734 | 25700 | TTTTTGCTAGAG | 795 | | | |
| P13560A-1 | 25673 | ACAACTAATAAGG | 735 | 25674 | TACAACTAAGGTA | 796 | | | |
| P13561A-1 | 26309 | TTCTGATAAAAAA | 736 | 26310 | TCTGATGAAAAAA | 797 | | | |
| P2447B-2 | 11878 | TGTAATGCGTG | 737 | 8378 | TGTAACGCGTG | 798 | 12003 | TGTAACGCATGT | 818 |
| P2481A-1 | 5486 | GACAATCTAAAAA | 738 | 7441 | GACAATTTAAAAA | 799 | | | |
| P2636C-2 | 14678 | TAATAATAATTGTGT | 739 | 15823 | AATAATGATTGTG | 800 | | | |
| P3050A-2 | 16760 | TTCCTTCTTTTTT | 740 | 16761 | TCCTTCCTTTTTT | 801 | | | |
| P3436A-1 | 10239 | GGAACGTTACC | 741 | 10240 | TGGAACATTACC | 802 | | | |

APPENDIX IV-continued

ASH marker: probes
2 pages

| Marker Name | Allele1 | Probe 1 sequence | SEQ ID NO | Allele2 | Probe 2 sequence | SEQ ID NO | Allele3 | Probe 3 sequence | SEQ ID NO |
|---|---|---|---|---|---|---|---|---|---|
| P3436A-7 | 18078 | AATTTTTTAGTATG | 742 | 14278 | AATTTTTGAGTATG | 803 | 14617 | ATTTTTTGGTATG | 819 |
| P5219A-1 | 7700 | TTATAGACACTTG | 743 | 7699 | TATAGGCACTTG | 804 | | | |
| P5219A-2 | 7944 | ATAAACCATATATG | 744 | 7943 | ATAAACCTTATATG | 805 | | | |
| P5467A-1 | 18980 | TTAATTACCTTAAG | 745 | 18981 | TTAATTATCTTAAG | 806 | | | |
| P5467A-2 | 20239 | ATGCCATTTTG | 746 | 19197 | ATGCCCTTTTGT | 807 | | | |
| P6181A-2 | 9448 | TAATATCTTATGCA | 747 | 9292 | AATATCGTATGCA | 808 | | | |
| P7659A-1 | 7858 | AGTGCGATGAAA | 748 | 7859 | AGTGCACTGAAA | 809 | | | |
| P7659A-2 | 10390 | GAGGAGATGTAG | 749 | 7845 | AGAGGAGATGTA | 810 | | | |
| P8230A-1 | 10586 | TAAAATTGTTGGTT | 750 | 14933 | TAAAATTATTGGTT | 811 | | | |
| P8584A-1 | 14786 | TGAAGAAAATATG | 751 | 14787 | GAACAAAAGATG | 812 | | | |
| P8584A-2 | 20517 | CTGTCCACTAA | 752 | 20358 | ACTGTCAACTAA | 813 | | | |
| P9026A-1 | 14340 | AGAGGCAGTGA | 753 | 14341 | AGAGCCAGTGA | 814 | | | |

What is claimed is:

1. A method of identifying a first soybean plant or germplasm that displays increased yield, the method comprising:

detecting in a genome of the first soybean plant or germplasm at least one allelic form of a set of chromosome segments, each segment in said set comprising a genetic element contributing to increased yield and each segment in said set comprising or proximal to a marker locus selected from the group of marker loci consisting of:

Satt684, Satt165, Satt042, Satt364, Satt454, Satt526, Satt300, Satt591, Satt155, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT__261, Satt197, Satt519, Satt597, SCT__026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT__311-DB, Satt338, Satt227, Satt640-TB, Satt422, Satt457, Satt557, Satt319, SAT__142-DB, Satt460, P13073A-1, Satt307, SCT__028, Satt433, Satt357, Satt321, Satt267, Satt383, Satt295, Satt203, Satt507, SAT__110, P10620A-1, Satt129, Satt147, Satt216, SAT__351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT__273-DB, Satt146, Satt193, Satt569, Satt343, Satt586, Satt040, Satt423, Satt348, Satt595, P10782A-1, P3436A-1, P10598A-1, Satt334, Satt510, Satt144, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT__117, Satt353, Satt442, Satt279, Satt314, Satt142, Satt181, Satt367, Satt127, SCTT012, Satt270, Satt292, Satt440, P10640A-1, Satt249, SCT__065, Satt596, Satt280, Satt406, Satt380, Satt183, Satt529, Satt431, Satt242, Satt102, Satt441, Satt544, Satt617, Satt240, P10618A-1, Satt475, Satt196, SAT__301, Satt523, Satt418, Satt398, Satt497, Satt284, Satt166, Satt448, Satt373, Satt513, P12394A-1, Satt590, Satt567, Satt220, Satt536, Satt175, Satt677, Satt680, P10615A-1, Satt551, Satt250, Satt346, Satt336, SAT__330-DB, P13069A-1, P5467A-1, P5467A-2, Satt584, SAT__084, P3050A-2, SAT__275-DB, Satt387, Satt549, Satt660, Satt339, Satt255, Satt257, Satt358, P12396A-1, Satt487, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P2481A-1, Satt040, Satt108, Satt109, Satt111, Satt176, Satt219, Satt299, and Satt512;

wherein said set of chromosome segments comprises segments that comprise or are proximal to between about 10% and about 100% of said marker loci;

thereby identifying a first soybean plant or germplasm with increased yield.

2. The method of claim 1, wherein the set of chromosome segments comprises segments that comprise or are proximal to between about 50% and about 100% of the marker loci of claim 1.

3. The method of claim 1, comprising determining the favorable allelic form of at least one chromosome segment, wherein the favorable allelic form of at least one chromosome segment is determined by:
a) identifying at least one polymorphic marker locus selected from the marker loci of claim 1 in a plurality of progeny of a progenitor soybean plant;
b) assessing yield in at least two progeny plants, which progeny plants have different allelic forms of the at least one marker locus; and,
c) identifying the progeny plant with increased yield relative to the progenitor soybean.

4. A method of identifying a progeny soybean plant with increased yield, the method comprising:

detecting in a genome of a plurality of progeny of a progenitor soybean a set of chromosome segments, each chromosome segment comprising at least one allele of one or more segregating marker loci, each of which segregating marker loci comprises a first allele and a second allele, which first allele correlates with increased yield and which second allele does not correlate with increased yield relative to the mean yield of the plurality of progeny of the progenitor soybean, wherein the set of chromosome segments comprises between about 10% and about 100% of the marker loci selected from the group consisting of: Satt684, Satt165, Satt042, Satt364, Satt454, Satt526, Satt300, Satt591, Satt155, Satt385, Satt225, Satt236, Satt511, P12390B-1, Satt480, Satt632-TB, Satt233, Satt327, Satt329, Satt508, P10635A-1, Satt409, Satt228, Satt429, Satt426, Satt509, SAT__261, Satt197, Satt519, Satt597, SCT__026, Satt415, Satt583, Satt430, P12198A-1, P8584A-1, Satt359, P10648A-1, P12105A-1, P10641A-1, Satt168, Satt556, Satt272, Satt020, Satt066, Satt534, P10638B-2, Satt399, Satt361, P10639A-1, Satt661-TB, Satt190, SAT__311-DB, Satt338, Satt227, Satt640-TB, Satt422, Satt457, Satt557, Satt319, SAT__142-DB, Satt460, P13073A-1, Satt307, SCT__028, Satt433, Satt357, Satt321, Satt267, Satt383, Satt295, Satt203, Satt507, SAT__110, P10620A-1, Satt129, Satt147, Satt216, SAT__351, P10621B-2, Satt701, Satt634, Satt558, Satt266, Satt282, Satt537, Satt506, Satt546, P13072A-1, Satt582, Satt389, Satt461, Satt311, Satt514, Satt464, Satt662, Satt543, Satt186, Satt413, Satt672, P13074A-1, P10624A-1, Satt573, Satt598, Satt204, Satt263, Satt491, Satt602, Satt151, Satt355, Satt452, SAT__273-DB, Satt146, Satt193, Satt569, Satt343, Satt586, Satt040, Satt423, Satt348, Satt595, P10782A-1, P3436A-1, P10598A-1, Satt334, Satt510, Satt144, Satt522, P9026A-1, P10646A-1, P5219A-1, P7659A-2, Satt570, Satt356, Satt130, Satt115, Satt594, Satt533, Satt303, Satt352, Satt566, Satt199, Satt503, Satt517, Satt191, SAT__117, Satt353, Satt442, Satt279, Satt314, Satt142, Satt181, Satt367, Satt127, SCTT012, Satt270, Satt292, Satt440, P10640A-1, Satt249, SCT__065, Satt596, Satt280, Satt406, Satt380, Satt183, Satt529, Satt431, Satt242, Satt102, Satt441, Satt544, Satt617, Satt240, P10618A-1, Satt475, Satt196, SAT__301, Satt523, Satt418, Satt398, Satt497, Satt284, Satt166, Satt448, Satt373, Satt513, P12394A-1, Satt590, Satt567, Satt220, Satt536, Satt175, Satt677, Satt680, P10615A-1, Satt551, Satt250, Satt346, Satt336, SAT__330-DB, P13069A-1, P5467A-1, P5467A-2, Satt584, SAT__084, P3050A-2, SAT__275-DB, Satt387, Satt549, Satt660, Satt339, Satt255, Satt257, Satt358, P12396A-1, Satt487, Satt259, Satt347, Satt420, Satt576, Satt550, Satt633, Satt262, Satt473, Satt477, Satt581, P11070A-1, Satt153, Satt243, P8230A-1, P10623A-1, P10632A-1, P10793A-1, P12391A-1, P13560A-1, P13561A-1, P2481A-1, Satt040, Satt108, Satt109, Satt111, Satt176, Satt219, Satt299, and Satt512.

5. The method of claim 4, wherein the first allele that correlates with increased yield and the second allele that does not correlate with increased yield are determined by:
a) identifying at least one polymorphic marker locus selected from the marker loci of claim 6, which polymorphic marker locus comprises at least two alleles segregating in a plurality of progeny of a progenitor soybean;

b) assessing yield in at least two progeny plants, which progeny plants have different alleles of the at least one polymorphic marker locus; and, c) identifying the progeny plant with increased yield relative to the mean yield of the plurality of progeny of the progenitor soybean.

6. The method of claim 4, wherein the plurality of progeny are obtained by selfing a progenitor soybean.

7. The method of claim 4, wherein the plurality of progeny are obtained by crossing a first progenitor soybean and a second progenitor soybean 8. The method of claim 7, wherein a first progenitor soybean comprising a strain of elite germplasm is crossed with a second progenitor soybean comprising a different strain of elite germplasm to generate a population of soybean plants from which the progeny is selected 9. The method of claim 7, wherein a first progenitor soybean comprising a strain of elite germplasm is crossed with a second progenitor soybean comprising a strain of exotic germplasm to generate a population of soybean plants from which the progeny is selected.

10. The method of claim 8, wherein one or both of the elite strains of germplasm is selected from the group consisting of: 90A07, 90B11, 90B31, 90B43, 90B72, 90B73, 91B01, 91B12, 91B33, 91B52, 91B53, 91B64, 91B91, 91B92, 92B05, 92B12, 92B23, 92B38, 92B52, 92B63, 92B74, 92B75, 92B84, 92B95, 92M30, 92M31, 92M70, 92M71, 92M72, 92M80, 92M91, 93B01, 93B09, 93B11, 93B15, 93B25, 93B26, 93B36, 93B41, 93B45, 93B46, 93B66, 93B67, 93B68, 93B72, 93B82, 93B84, 93B85, 93B86, 93B87, 93M10, 93M30, 93M40, 93M50, 93M60, 93M80, 93M90, 93M92, 93M93, 94B01, 94B23, 94B24, 94B53, 94B54, 94B73, 95B32, 95B33, 95B34, 95B53, 95B95, 95B96, 95B97, 96B21, 96B51, 97B52, 97B61, BEDFORD, CX105, CX232, CX253, CX289, CX394C, CX469C, ESSEX, FORREST, HS93-4118, HUTCHESON, JIM, KORADA, PHARAOH, S0066, S0880, S1990, 519T9, S20F8, S25J5, S32Z3, S33N1, S38T8, S3911, S4260, S42H1, S43B5, S5960, S6262, ST0653, ST1073, ST1090, ST1570, ST1690, ST1970, ST2250, ST2488, ST2660, ST2686, ST2688, ST2788, ST2870, ST3171, ST3630, ST3660, ST3870, ST3883, TRACY, TRAILL, and YOUNG.

11. A method of identifying a first soybean plant or germplasm that displays increased yield, the method comprising:

detecting in a genome of the first soybean plant or germplasm at least one allelic form of a set of chromosome segments, each segment in said set comprising a genetic element contributing to increased yield and each segment in said set comprising or proximal to a marker locus selected from the group of marker loci consisting of:

Satt642, Satt042, Satt364, Satt454, Satt526, Satt300, Satt591, Satt155, Satt385, Satt511, P12390B-1, Satt632-TB, Satt429, SAT__261, Satt197, P10641A-1, Satt556, Satt534, P10638B-2, Satt399, Satt361, P10639A-1, Satt661-TB, Satt190, SAT__311-DB, Satt338, Satt640-TB, Satt557, Satt319, SAT__142-DB, Satt460, Satt433, Satt357, Satt321, Satt295, Satt203, Satt507, Satt129, Satt147, SAT__351, P10621B-2, Satt558, Satt701, Satt634, Satt582, Satt389, Satt464, Satt662, Satt672, Satt573, Satt598, Satt263, Satt602, Satt151, SAT__273-DB, Satt146, Satt193, Satt569, Satt176, Satt343, Satt586, Satt040, Satt595, P10782A-1, Satt334, Satt144, Satt522, Satt570, Satt356, Satt533, Satt199, Satt517, Satt191, SAT__117, Satt279, Satt181, Satt127, Satt270, Satt292, SAT__065, Satt596, Satt406, Satt380, Satt183, Satt529, Satt242, Satt617, Satt240, SAT__301, Satt418, Satt398, Satt497, Satt166, Satt448, Satt373, Satt513, P12394A-1, Satt536, Satt175, Satt677, Satt680, P10615A-1, Satt551, Satt346, Satt336, SAT__330-DB, P13069A-1, P5467A-1, P5467A-2, SAT__084, SAT__275-DB, Satt660, Satt339, P12396A-1, Satt358, Satt487, Satt259, Satt420, Satt576, Satt633, Satt477, Satt581, Satt153, Satt243, P10793A-1, P12391A-1, P12392A-1, P13560A-1, P13561A-1, Satt040, Satt111, Satt176, Satt219 and Satt299;

wherein said set of chromosome segments comprises segments that comprise or are proximal to between about 10% and about 100% of said marker loci;

thereby identifying a first soybean plant or germplasm with increased yield.

12. A method of identifying a first soybean plant or germplasm that displays increased yield, the method comprising:

detecting in a genome of the first soybean plant or germplasm at least one allelic form of a set of chromosome segments, each segment in said set comprising a genetic element contributing to increased yield and each segment in said set comprising or proximal to a marker locus selected from the group of marker loci consisting of:

Satt684, Satt042, Satt364, Satt454, Satt526, Satt300, Satt591, Satt155, Satt385, Satt632-TB, Satt429, SAT-__261, P10641A-1, Satt556, P10638B-2, Satt399, Satt361, Satt661-TB, Satt190, SAT__311-DB, Satt338, Satt640-TB, Satt557, Satt319, SAT__142-DB, Satt321, Satt203, Satt129, Satt147, SAT__351, P10621B-2, Satt701, Satt634, Satt582, Satt389, Satt464, Satt662, Satt672, Satt573, Satt598, Satt263, Satt151, SAT__273-DB, Satt146, Satt193, Satt569, Satt343, Satt586, Satt040, Satt595, Satt334, Satt144, Satt522, Satt570, Satt356, Satt199, Satt517, Satt191, Sat__117, Satt279, Satt181, Satt127, Satt270, Satt292, Sat__065, Satt596, Satt406, Satt380, Satt183, Satt529, Satt242, Satt617, Satt240, SAT__301, Satt418, Satt398, Satt497, Satt166, Satt448, Satt373, Satt513, P12394A-1, Satt536, Satt175, Satt677, Satt680, P10615A-1, Satt551, SAT__330-DB, P13069A-1, P5467A-1, P5467A-2, SAT__084, SAT__275-DB, Satt660, Satt339, Satt358, Satt487, Satt420, Satt576, Satt633, Satt581, Satt153, Satt243, P10793A-1, P13560A-1, P13561A-1, Satt111, Satt219 and Satt299;

wherein said set of chromosome segments comprises segments that comprise or are proximal to between about 10% and about 100% of said marker loci;

thereby identifying a first soybean plant or germplasm with increased yield.

13. A method of identifying a first soybean plant or germplasm that displays increased yield, the method comprising:

detecting in a genome of the first soybean plant or germplasm at least one allelic form of a set of chromosome segments, each segment in said set comprising a genetic element contributing to increased yield and each segment in said set comprising or proximal to a marker locus selected from the group of marker loci consisting of:

Satt684, Satt526, Satt591, Satt385, Satt632-TB, Satt429, SAT-__261, P10641A-1, Satt556, P10638B-2, Satt190, SAT__311-DB, Satt338, Satt640-TB, Satt557, SAT__142-DB, Satt321, Satt203, Satt129, SAT__351, Satt701, Satt582, Satt389, Satt464, Satt672, Satt598, Satt343, Satt595, Satt334, Satt144, Satt522, Satt570, Satt356, Satt199, Sat_117, Satt279, Satt181, Satt127, Satt270, Satt292, Sat_065, Satt529, Satt242, Satt617, SAT_301, Satt398, Satt497, Satt166, Satt373, Satt680, P10615A-1, SAT_330-DB, P13069A-1, SAT_275-DB, Satt339, Satt487, Satt420, Satt581 and Satt153;

wherein said set of chromosome segments comprises segments that comprise or are proximal to between about 10% and about 100% of said marker loci;

thereby identifying a first soybean plant or germplasm with increased yield.

14. The method of claim 13, wherein the marker loci consist of:

Satt684, Satt526, Satt591, Satt385, Satt632-TB, Satt429, SAT-_261, P10641A-1, Satt556, P10638B-2, Satt190, SAT_311-DB, Satt338, Satt640-TB, Satt557, SAT_142-DB, Satt321, Satt203, Satt129, SAT_351, Satt701, Satt582, Satt389, Satt464, Satt672, Satt598, Satt343, Satt595, Satt334, Satt144, Satt522, Satt570, Satt356, Satt199, Sat_117, Satt279, Satt181, Satt127, Satt270, Satt292, Sat_065, Satt529, Satt242, Satt617, SAT_301, Satt398, Satt497, Satt166, Satt373, Satt680, P10615A-1, SAT_330-DB, P13069A-1, SAT_275-DB, Satt339, Satt487, Satt420, Satt581 and Satt153.

15. A method of identifying a first soybean plant or germplasm that displays increased yield, the method comprising:

detecting in a genome of the first soybean plant or germplasm at least one allelic form of a set of chromosome segments, each segment in said set comprising a genetic element contributing to increased yield and each segment in said set comprising or proximal to a marker locus selected from the group of marker loci consisting of:

Satt526, Satt591, Satt429, SAT-_261, P10641A-1, Satt190, Satt557, SAT_142-DB, Satt129, SAT_351, Satt464, Satt343, Satt595, Satt570, Satt181, Satt127, Satt270, Sat_065, Satt529, Satt242, Satt398, Satt166, Satt373, Satt680, SAT_330-DB, P13069A-1, Satt339, Satt487, Satt581 and Satt153;

wherein said set of chromosome segments comprises segments that comprise or are proximal to between about 10% and about 100% of said marker loci;

thereby identifying a first soybean plant or germplasm with increased yield.

16. The method of claim 15, wherein the marker loci consist of:

Satt526, Satt591, Satt429, SAT-_261, P10641A-1, Satt190, Satt557, SAT_142-DB, Satt129, SAT_351, Satt464, Satt343, Satt595, Satt570, Satt181, Satt127, Satt270, Sat_065, Satt529, Satt242, Satt398, Satt166, Satt373, Satt680, SAT_330-DB, P13069A-1, Satt339, Satt487, Satt581 and Satt153.

17. The method of claim 1, further comprising electronically transmitting or electronically storing data representing the determined allelic forms in a computer readable medium.

18. The method of claim 1, further comprising selecting the identified soybean plant.

19. The method of claim 18, wherein the selected soybean plant comprises a whole plant, a plant organ, a plant seed, a plant cell or a plant tissue culture.

20. The method of claim 18, wherein the selected soybean plant or a progeny thereof is crossed with a second soybean plant, which second soybean plant lacks the determined alleles of marker loci or the determined allelic forms of the plurality of chromosome segments.

21. The method of claim 20, wherein the second soybean plant comprises an elite strain of germplasm.

22. The method of claim 20, wherein the second soybean plant comprises exotic germplasm.

23. The method of claim 1, wherein the allelic form of each of a plurality of marker loci are determined in a first soybean plant genome and at least a second soybean plant genome, wherein the first soybean plant comprises a parent soybean plant and the at least second soybean plant comprises at least one progeny of the first soybean plant.

24. The method of claim 9, wherein the elite strain of germplasm is selected from the group consisting of:

90A07, 90B11, 90B31, 90B43, 90B72, 90B73, 91B01, 94B53, 94B54, 94B73, 95B32, 95B33, 95B34, 95B53, 95B95, 95B96, 95B97, 96B21, 96B51, 97B52, 97B61, BEDFORD, CX105, CX232, CX253, CX289, CX394C, CX469C, ESSEX, FORREST, HS93-4118, HUTCHESON, JIM, KORADA, PHARAOH, S0066, S0880, S1990, S19T9, S20F8, 525J5, S32Z3, S33N1, S38T8, S3911, S4260, S42H1, S43B5, S5960, S6262, ST0653, ST1073, ST1090, ST1570, ST1690, ST1970, ST2250, ST2488, ST2660, ST2686, ST2688, ST2788, ST2870, ST3171, ST3630, ST3660, ST3870, ST3883, TRACY, TRAILL, and YOUNG.

* * * * *

SEQUENCE LISTING

```
<160> NUMBER OF SEQ ID NOS: 819

<210> SEQ ID NO 1
<211> LENGTH: 22
<212> TYPE: DNA
<213> ORGANISM: Artificial
<220> FEATURE:
<223> OTHER INFORMATION: synthetic synthetic oligonucleotide primer

<400> SEQUENCE: 1
caatcaggtt agtggtccta cc                                              22

<210> SEQ ID NO 2
<211> LENGTH: 22
<212> TYPE: DNA
<213> ORGANISM: Artificial
<220> FEATURE:
<223> OTHER INFORMATION: synthetic synthetic oligonucleotide primer

<400> SEQUENCE: 2
aagttcacag cacctggacc at                                              22

<210> SEQ ID NO 3
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 3
gaaacaaaca cccccaaggt ga                                              22

<210> SEQ ID NO 4
<211> LENGTH: 22
<212> TYPE: DNA
<213> ORGANISM: Artificial
```

```
<220> FEATURE:
<223> OTHER INFORMATION: synthetic oligonucleotide primer

<400> SEQUENCE: 4
ccaatcgtgt cttatcctcg gg                                              22

<210> SEQ ID NO 5
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 5
ttccagacag aacccaagta gcc                                             23

<210> SEQ ID NO 6
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 6
aacatttttc atcgcttttc ttag                                            24

<210> SEQ ID NO 7
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 7
aaagcatttt tggcagtttc ttgt                                            24

<210> SEQ ID NO 8
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 8
tggacagaat ggagaaagaa atgtg                                           25

<210> SEQ ID NO 9
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 9
ccaagccaaa caaagaatca ca                                              22

<210> SEQ ID NO 10
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 10
gcttgctatg attgattgat tgattga                                         27
```

<210> SEQ ID NO 11
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 11
agaacggtgt aagatagaa tagtt                                           25

<210> SEQ ID NO 12
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 12
gggaagctta ataatgaaaa tgacac                                         26

<210> SEQ ID NO 13
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 13
aaccgatgct ttttcgcct tt                                              22

<210> SEQ ID NO 14
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 14
gaagaaggct cagcaacacc ttg                                            23

<210> SEQ ID NO 15
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 15
cacccaatct tgcctttgaa aca                                            23

<210> SEQ ID NO 16
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 16
tagacacttt caggttaaaa tataac                                         26

<210> SEQ ID NO 17
<211> LENGTH: 26
<212> TYPE: DNA
<213> ORGANISM: Artificial
<220> FEATURE:
<223> OTHER INFORMATION: synthetic oligonucleotide primer

```
<400> SEQUENCE: 17
caacttgtca cttacacata gtttag                                         26

<210> SEQ ID NO 18
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 18
atttcgctcg caaacacaag gt                                             22

<210> SEQ ID NO 19
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 19
tcaagaaata caagtgcaag aaagacc                                        27

<210> SEQ ID NO 20
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 20
aattttcgct tgtgaaccct gc                                             22

<210> SEQ ID NO 21
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 21
ttcagtacaa gtcgggtgaa taataata                                       28

<210> SEQ ID NO 22
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 22
tgggactctc acacacggaa aa                                             22

<210> SEQ ID NO 23
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 23
tgggagtcaa tttcccatta tca                                            23

<210> SEQ ID NO 24
```

-continued

```
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 24
tggatttgaa accacaaata acaacaac                                          28

<210> SEQ ID NO 25
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 25
aaaaggggga catttttcca cg                                                22

<210> SEQ ID NO 26
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 26
cattagggac aacaacagcg ttt                                               23

<210> SEQ ID NO 27
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 27
cgtcgccatc actatgagaa                                                   20

<210> SEQ ID NO 28
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 28
aagggatccc tcaactgact g                                                 21

<210> SEQ ID NO 29
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 29
ccatcccttc ctccaaatag at                                                22

<210> SEQ ID NO 30
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 30
```
tgacgaagct tgaggttatt cg                                              22

<210> SEQ ID NO 31
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 31
gccaagaaga taacaagctc ggc                                             23

<210> SEQ ID NO 32
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 32
gggttatatc agtttttctt tttgtt                                          26

<210> SEQ ID NO 33
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 33
agatccaaca cctggcctaa t                                               21

<210> SEQ ID NO 34
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 34
aacaaaacta gcccatagaa acattga                                         27

<210> SEQ ID NO 35
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 35
gaaatgccca gaaaaccta ataac                                            25

<210> SEQ ID NO 36
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 36
gccgtgaaga cagttgatcg tt                                              22

<210> SEQ ID NO 37
<211> LENGTH: 23
<212> TYPE: DNA

```
<213> ORGANISM: Artificial
<220> FEATURE:
<223> OTHER INFORMATION: synthetic oligonucleotide primer

<400> SEQUENCE: 37
cagttgattt tgtttttcg gca                                              23

<210> SEQ ID NO 38
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 38
ttgtccaaac ttgcagggaa ca                                              22

<210> SEQ ID NO 39
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 39
tggatgagtt ctattggggt agtcg                                           25

<210> SEQ ID NO 40
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 40
gacctcgctc tctgtttctc at                                              22

<210> SEQ ID NO 41
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 41
cgcaatccca attcacctct tc                                              22

<210> SEQ ID NO 42
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 42
gaaccccgtt tcaacatttt atga                                            24

<210> SEQ ID NO 43
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 43
ggtcgttaag cccactttga ga                                              22
```

<210> SEQ ID NO 44
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 44
tgcagctttc actaatcgtc agaa        24

<210> SEQ ID NO 45
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 45
gggagtgtga acttacattg tct        23

<210> SEQ ID NO 46
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 46
gcgatcatgt ctctgccatc ag        22

<210> SEQ ID NO 47
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 47
gaagggatat ggagagtgag aaattaga        28

<210> SEQ ID NO 48
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 48
aaaaattgtg taaacgaaag atggga        26

<210> SEQ ID NO 49
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 49
tgagcccaac ctccacatct tt        22

<210> SEQ ID NO 50
<211> LENGTH: 20
<212> TYPE: DNA
<213> ORGANISM: Artificial
<220> FEATURE:

```
<223> OTHER INFORMATION: synthetic oligonucleotide primer

<400> SEQUENCE: 50
cactgctttt tccctctct                                              20

<210> SEQ ID NO 51
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 51
gcggtaaatg gtgaaaatca tttatggtt                                   29

<210> SEQ ID NO 52
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 52
ggaatgcatg agtattaacc tcttat                                      26

<210> SEQ ID NO 53
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 53
tgtcttccca atccatctaa tctaatca                                    28

<210> SEQ ID NO 54
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 54
ccaattatgt ttctatgcca tcttgtt                                     27

<210> SEQ ID NO 55
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 55
tgtggataaa agccatctct aacaaa                                      26

<210> SEQ ID NO 56
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 56
tcgataccaa tcatccaatc caaa                                        24
```

```
<210> SEQ ID NO 57
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 57
tccttagacc tctcgcgcaa ac                                                22

<210> SEQ ID NO 58
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 58 taccccttaat caccggacaa                                                  20

<210> SEQ ID NO 59
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 59
acgtatgcga aggagggaga tg                                                22

<210> SEQ ID NO 60
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 60
ttggctcttg tgtaagtggc cc                                                22

<210> SEQ ID NO 61
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 61
ttcagtccct tggtggttcc aa                                                22

<210> SEQ ID NO 62
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 62
catggtcctt gggtgcaatt ta                                                22

<210> SEQ ID NO 63
<211> LENGTH: 27
<212> TYPE: DNA
<213> ORGANISM: Artificial
<220> FEATURE:
<223> OTHER INFORMATION: synthetic oligonucleotide primer
```

```
<400> SEQUENCE: 63
aaaaatgtgt tagagcttgt gttgtta                                27

<210> SEQ ID NO 64
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 64
atggtgcagt gttgcaggtt gt                                     22

<210> SEQ ID NO 65
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 65
gaccacaact tcttttttgt gaatgg                                 26

<210> SEQ ID NO 66
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 66
ccgtcaccgt taataaaata gcat                                   24

<210> SEQ ID NO 67
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 67
agaagcatac tcgtcgtaac actatcc                                27

<210> SEQ ID NO 68
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 68
gagcaggaca tttttttat ccttga                                  26

<210> SEQ ID NO 69
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 69
tgcttgaggt tgaaggaaat gc                                     22

<210> SEQ ID NO 70
<211> LENGTH: 23
```

```
<212> TYPE: DNA
<213> ORGANISM: Artificial
<220> FEATURE:
<223> OTHER INFORMATION: synthetic oligonucleotide primer

<400> SEQUENCE: 70
tccttggggt gaattgtttt tca                                              23

<210> SEQ ID NO 71
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 71
gcgttgatca ggtcgatttt tatttgt                                          27

<210> SEQ ID NO 72
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 72
aatgctttgg tcgttgcatt g                                                21

<210> SEQ ID NO 73
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 73
cagcgtctgc atgatagcgt tt                                               22

<210> SEQ ID NO 74
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 74
tgcaaattgt tattgtgaga ctgaatga                                         28

<210> SEQ ID NO 75
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 75
cgccagctag ctagtctcat                                                  20

<210> SEQ ID NO 76
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 76
```

```
cctccacccc cttcccaccc aaaa                                              24
```

<210> SEQ ID NO 77
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 77

```
agcgtcgtct ggctaggtct gt                                                22
```

<210> SEQ ID NO 78
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 78

```
gtcattggtc tcaaacaatc ttcat                                             25
```

<210> SEQ ID NO 79
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 79

```
gcgactttct tttcaatttc actcc                                             25
```

<210> SEQ ID NO 80
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 80

```
cacttttca ctgtctcccc cc                                                 22
```

<210> SEQ ID NO 81
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 81

```
tgggccattt gggcagctcg act                                               23
```

<210> SEQ ID NO 82
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 82

```
gcgccccatt aatgttaaca ca                                                22
```

<210> SEQ ID NO 83
<211> LENGTH: 27
<212> TYPE: DNA
<213> ORGANISM: Artificial

-continued

```
<220> FEATURE:
<223> OTHER INFORMATION: synthetic oligonucleotide primer

<400> SEQUENCE: 83
ggagagaatc catatatatt gaattgc                                            27

<210> SEQ ID NO 84
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 84 cctttttgaca attatggcat ata                                               23

<210> SEQ ID NO 85
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 85
cctgtcaaat tggctgatgc aa                                                 22

<210> SEQ ID NO 86
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 86
ttttaccaaa caaattaaac tgcgtct                                            27

<210> SEQ ID NO 87
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 87
ccggtctgac ctattctcat                                                    20

<210> SEQ ID NO 88
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 88
ggtgtttcaa gtttcaacac cat                                                23

<210> SEQ ID NO 89
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 89
atgacaagga aaaatcaatc aac                                                23
```

<210> SEQ ID NO 90
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 90
gcggggtcaa ttagttttcg tcagtt                                          26

<210> SEQ ID NO 91
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 91
gcgcaaaagg acgcccacca atag                                            24

<210> SEQ ID NO 92
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 92
tctgcttatt cattgtgtgc gtg                                             23

<210> SEQ ID NO 93
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 93
tggtatatgt ttttgcggga caa                                             23

<210> SEQ ID NO 94
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 94
aggtgggcta ggagtgacca ca                                              22

<210> SEQ ID NO 95
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 95
gcgacatatt gcattaaaaa catactt                                         27

<210> SEQ ID NO 96
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 96
ggggtgaatg aatgtcaaga tga                                    23

<210> SEQ ID NO 97
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 97
gcggaattag aactccagta aaga                                   24

<210> SEQ ID NO 98
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 98
ttagtggatc tacactaaac taatccg                                27

<210> SEQ ID NO 99
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 99
aggcatttct ggcaagggta tg                                     22

<210> SEQ ID NO 100
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 100
gcgcccacac aacctttaat ctt                                    23

<210> SEQ ID NO 101
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 101
atgggctatg ggaggaggtg tt                                     22

<210> SEQ ID NO 102
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 102
ccagtgcagt tttacatgaa ctt                                    23

<210> SEQ ID NO 103

```
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 103
gctggccttt agaacgtctg act                                               23

<210> SEQ ID NO 104
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 104
ccacaaaaag atgaaacaaa atag                                              24

<210> SEQ ID NO 105
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 105
gcggagattg gaacctactc attc                                              24

<210> SEQ ID NO 106
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 106
aacaatttga tggtcggggt tg                                                22

<210> SEQ ID NO 107
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 107
caccgtcgta aaaactgtgt cgt                                               23

<210> SEQ ID NO 108
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 108
gaagtgctag ttctcacggt gtgg                                              24

<210> SEQ ID NO 109
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 109
```
ttcgctgcat aattttttagc atca          24

<210> SEQ ID NO 110
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 110
aaagagacac ccaaaagata acaaaca          27

<210> SEQ ID NO 111
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 111
tgaccaccat gagttcatt          19

<210> SEQ ID NO 112
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 112
gcgggacgca aaattggatt tagt          24

<210> SEQ ID NO 113
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 113
gtgaccctcc attccacaac aa          22

<210> SEQ ID NO 114
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 114
gcagagtccc ccctaaatat ag          22

<210> SEQ ID NO 115
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 115
gtgaatcatc cagggcttgc          20

<210> SEQ ID NO 116
<211> LENGTH: 24
<212> TYPE: DNA

<213> ORGANISM: Artificial
<220> FEATURE:
<223> OTHER INFORMATION: synthetic oligonucleotide primer

<400> SEQUENCE: 116
gcgaatggtt tttgctggaa agta                                  24

<210> SEQ ID NO 117
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 117
gcgttaagaa tgcatttatg tttagtc                               27

<210> SEQ ID NO 118
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 118
caagctcaag cctcacacat                                       20

<210> SEQ ID NO 119
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 119
aattggagtg ggtcacac                                         18

<210> SEQ ID NO 120
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 120
gcgcccaagt attatgagat atttgat                               27

<210> SEQ ID NO 121
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 121
ctttgtttgg ttggtgataa gtttcta                               27

<210> SEQ ID NO 122
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 122
aattgttagg gcgcgagaaa ca                                    22

```
<210> SEQ ID NO 123
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 123
gttcggaggg aggaaagtgt tg                                          22

<210> SEQ ID NO 124
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 124
tgttcaatcg acaaataagg gtgc                                        24

<210> SEQ ID NO 125
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 125
ctttacttag taatggttcc cacag                                       25

<210> SEQ ID NO 126
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 126
ccagatttta cgttaatgtt ttagttttta                                  29

<210> SEQ ID NO 127
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 127
catacacgca ttgcctttcc tgaa                                        24

<210> SEQ ID NO 128
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 128
gcgtcccagg acatcatcat catc                                        24

<210> SEQ ID NO 129
<211> LENGTH: 23
<212> TYPE: DNA
<213> ORGANISM: Artificial
<220> FEATURE:
```

```
<223> OTHER INFORMATION: synthetic oligonucleotide primer

<400> SEQUENCE: 129
tgctgcttgt gtttggttga tct                                       23

<210> SEQ ID NO 130
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 130
aatccccaaa caaacgcaca gt                                        22

<210> SEQ ID NO 131
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 131
gcggcgcttt atgtaacaat acgattt                                   27

<210> SEQ ID NO 132
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 132
gcgagaaaat aatcctgctc aag                                       23

<210> SEQ ID NO 133
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 133
tcgggagaca ctaaaggcac tg                                        22

<210> SEQ ID NO 134
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 134
gcggcataag tttcatccc atc                                        23

<210> SEQ ID NO 135
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 135
gcggatatgc cacttctctc gtgac                                     25
```

```
<210> SEQ ID NO 136
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 136
ggagaaaaac atccaaagaa atgtg                                     25

<210> SEQ ID NO 137
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 137
ggataatttt ttcatcatca caatttatc                                 29

<210> SEQ ID NO 138
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 138
tggaaatact gaatgaaagc atattgg                                   27

<210> SEQ ID NO 139
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 139
ccattgggat cgagaataat tgatg                                     25

<210> SEQ ID NO 140
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 140
agagtaatgg ctcctgctcc ga                                        22

<210> SEQ ID NO 141
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 141
cgatctaaca cgcatatttc ctctga                                    26

<210> SEQ ID NO 142
<211> LENGTH: 23
<212> TYPE: DNA
<213> ORGANISM: Artificial
<220> FEATURE:
<223> OTHER INFORMATION: synthetic oligonucleotide primer
```

```
<400> SEQUENCE: 142
tgggggtcaa ttttaatttg tgc                                          23

<210> SEQ ID NO 143
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 143
gattctcttc attctaatac tcgttt                                       26

<210> SEQ ID NO 144
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 144
gcgttacgtt tcactattta tttaacat                                     28

<210> SEQ ID NO 145
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 145
gctggtgtat ggtgaaatca aattact                                      27

<210> SEQ ID NO 146
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 146
tgatattgtt ttgtgtgaaa gatgcac                                      27

<210> SEQ ID NO 147
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 147
tgctcaaagg gtcaatttct ttcc                                         24

<210> SEQ ID NO 148
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 148
ccaagcccat aaacgaaata aaaca                                        25

<210> SEQ ID NO 149
<211> LENGTH: 25
```

```
<212> TYPE: DNA
<213> ORGANISM: Artificial
<220> FEATURE:
<223> OTHER INFORMATION: synthetic oligonucleotide primer

<400> SEQUENCE: 149
cagtgctcat atcaaattaa agtgg                                          25

<210> SEQ ID NO 150
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 150
tttcaaccac caagccaacc tt                                             22

<210> SEQ ID NO 151
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 151
tgcagcatgt gttttaggct ttc                                            23

<210> SEQ ID NO 152
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 152
ccttagacca tgaatgtctc gaagata                                        27

<210> SEQ ID NO 153
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 153
tggccatgtc aaaccataac aaca                                           24

<210> SEQ ID NO 154
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 154
actggcgctg accttaaatt gc                                             22

<210> SEQ ID NO 155
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 155
``` tgttttttaag taatccggtg aaatagca                                             28

<210> SEQ ID NO 156
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 156
tcacatcaca agtttcataa atgctg                                                26

<210> SEQ ID NO 157
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 157
gcgtctccct taatcttcaa gc                                                    22

<210> SEQ ID NO 158
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 158
agattaagag aagacgagag tttta                                                 25

<210> SEQ ID NO 159
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 159
gccaggtgct cacttcttgc ta                                                    22

<210> SEQ ID NO 160
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 160
caggagaaaa aaggaaaaga aaagca                                                26

<210> SEQ ID NO 161
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 161
aggttttgct tcttgaaagt gaagag                                                26

<210> SEQ ID NO 162
<211> LENGTH: 24
<212> TYPE: DNA
<213> ORGANISM: Artificial

```
<220> FEATURE:
<223> OTHER INFORMATION: synthetic oligonucleotide primer

<400> SEQUENCE: 162
gtctccgttc aaagcttctt cttc                                              24

<210> SEQ ID NO 163
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 163
gaggggaggt aaaaagtcgg ga                                                22

<210> SEQ ID NO 164
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 164
cgcttgggtt cagttacttg gtg                                               23

<210> SEQ ID NO 165
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 165
gcgcccatta ttattttcct tgaattgt                                          28

<210> SEQ ID NO 166
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 166
gcgaccatca tctaatcaca atctacta                                          28

<210> SEQ ID NO 167
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 167
aatgcaagaa gcaatcagca aga                                               23

<210> SEQ ID NO 168
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 168 tggcacccctt gataaataag agaagg                                           26
```

<210> SEQ ID NO 169
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 169
aattgaacca ctcagccaag cc                                          22

<210> SEQ ID NO 170
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 170
gtctaagatt ttaattaggg tgattc                                      26

<210> SEQ ID NO 171
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 171
gcgtataaag aaaaacgagc atatcat                                     27

<210> SEQ ID NO 172
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 172
caaattgaaa aacacaagaa aacacaa                                     27

<210> SEQ ID NO 173
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 173
agcaactaac cttgggcttc agtaa                                       25

<210> SEQ ID NO 174
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 174
cctggacttg tttgctcatc aa                                          22

<210> SEQ ID NO 175
<211> LENGTH: 23
<212> TYPE: DNA
<213> ORGANISM: Artificial
<220> FEATURE:
<223> OTHER INFORMATION: synthetic oligonucleotide primer

```
<400> SEQUENCE: 175
aattcctttg gcattttgt tgc                                              23

<210> SEQ ID NO 176
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 176
tttcactttt gaatcattgc atcg                                            24

<210> SEQ ID NO 177
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 177
caccactcgt atccttcaca agagc                                           25

<210> SEQ ID NO 178
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 178
gcgcaattaa aaggataact tatatc                                          26

<210> SEQ ID NO 179
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 179
aaaattcatg tcgctgcgtt ca                                              22

<210> SEQ ID NO 180
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 180
tgaaaaccat gtcaaagtaa tggca                                           25

<210> SEQ ID NO 181
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 181
ggaaagtttt gttacatgcc gga                                             23

<210> SEQ ID NO 182
```

```
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 182
ttttaactgg agaaacctga ggga                                          24

<210> SEQ ID NO 183
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 183
gcgcgatggg ctgttggttt ttat                                          24

<210> SEQ ID NO 184
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 184
ttgcttgctg cacatgactg ag                                            22

<210> SEQ ID NO 185
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 185
ttgaaatagt ggtggggttg gg                                            22

<210> SEQ ID NO 186
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 186
tgtgttgtgt ggtgtggtgg tc                                            22

<210> SEQ ID NO 187
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 187
caaagtcccc tttcacacct ttt                                           23

<210> SEQ ID NO 188
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 188
```

```
aaagggaaag gaagaataaa ccga                                          24

<210> SEQ ID NO 189
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 189
tgctttttct ctttggcaac cc                                            22

<210> SEQ ID NO 190
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 190
gcgcccaaaa ctatctagta attctt                                        26

<210> SEQ ID NO 191
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 191
ccaacaacca aatcaatcac tgc                                           23

<210> SEQ ID NO 192
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 192
gctccggtcc ttcaactgac ct                                            22

<210> SEQ ID NO 193
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 193
atgtgggtat gttgcaggca ga                                            22

<210> SEQ ID NO 194
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 194
gttgggaaaa ggttactacc atatc                                         25

<210> SEQ ID NO 195
<211> LENGTH: 24
<212> TYPE: DNA
```

-continued

<213> ORGANISM: Artificial
<220> FEATURE:
<223> OTHER INFORMATION: synthetic oligonucleotide primer

<400> SEQUENCE: 195
cagccaagca aaagataaat aata                                              24

<210> SEQ ID NO 196
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 196
gcgctttcaa aaagtaacaa ttaatgaaa                                         29

<210> SEQ ID NO 197
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 197
gacctttcat catcgtcccc ac                                                22

<210> SEQ ID NO 198
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 198
tcaattcatc acggaccagt tca                                               23

<210> SEQ ID NO 199
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 199
gtgagtttcg gtgctgtatt cc                                                22

<210> SEQ ID NO 200
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 200
cctaaattga tgaaaggata caag                                              24

<210> SEQ ID NO 201
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 201
gtatcgttcg cgtcttgagt c                                                 21

<210> SEQ ID NO 202
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 202
ttaacgggaa aaaattaaac ctacga                                        26

<210> SEQ ID NO 203
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 203
tggagattta atatagatgc cgcga                                         25

<210> SEQ ID NO 204
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 204
gcggttttgg attgactttg ttga                                          24

<210> SEQ ID NO 205
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 205
ccgtgacttt tgttatcctg agttcc                                        26

<210> SEQ ID NO 206
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 206
gcgaattggc atacatagta cc                                            22

<210> SEQ ID NO 207
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 207
tgcaccacta atgtcctcag cc                                            22

<210> SEQ ID NO 208
<211> LENGTH: 22
<212> TYPE: DNA
<213> ORGANISM: Artificial
<220> FEATURE:

```
<223> OTHER INFORMATION: synthetic oligonucleotide primer

<400> SEQUENCE: 208
gcaatgggta ttgatcgtgt ca                                              22

<210> SEQ ID NO 209
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 209
gcgctaccgt gtggtggtgt gctacct                                         27

<210> SEQ ID NO 210
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 210
gcgagtttcg ccgttaccac ctcagctt                                        28

<210> SEQ ID NO 211
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 211
tgcgacttta ctgaaaacct ggaa                                            24

<210> SEQ ID NO 212
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 212
aacgtcttca agtcaagtgc ctaca                                           25

<210> SEQ ID NO 213
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 213
gcgcatcaca agttttatag atgctga                                         27

<210> SEQ ID NO 214
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 214
gggtacattt tattaaaagt aaacacacc                                       29
```

```
<210> SEQ ID NO 215
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 215
tgaaccttgt ctgttgattt ttttatgt                                          28

<210> SEQ ID NO 216
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 216
tctcctactt ctctttctcc cgttca                                            26

<210> SEQ ID NO 217
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 217
cctgattata tgtctagaca aacat                                             25

<210> SEQ ID NO 218
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 218
gagatcacat caaagtcaaa actgcc                                            26

<210> SEQ ID NO 219
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 219
gcgatttctt ccttgaagaa ttttctg                                           27

<210> SEQ ID NO 220
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 220
gcgaattatc caaagataca cttagtc                                           27

<210> SEQ ID NO 221
<211> LENGTH: 22
<212> TYPE: DNA
<213> ORGANISM: Artificial
<220> FEATURE:
<223> OTHER INFORMATION: synthetic oligonucleotide primer
```

<400> SEQUENCE: 221
atatcgaaaa tcgcgcatct gg					22

<210> SEQ ID NO 222
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 222
gcgcattaag gcataaaaaa ggata					25

<210> SEQ ID NO 223
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 223
gcgccaatat tatcatgctt tatgt					25

<210> SEQ ID NO 224
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 224
agtggtcgtc acaacactat catat					25

<210> SEQ ID NO 225
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 225
ctcctcctgc gcaacaacaa ta					22

<210> SEQ ID NO 226
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 226
gcgtggaatg agacgtaacc aa					22

<210> SEQ ID NO 227
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 227
caaaacttat gtgcaacacg acttca					26

<210> SEQ ID NO 228
<211> LENGTH: 23

```
<212> TYPE: DNA
<213> ORGANISM: Artificial
<220> FEATURE:
<223> OTHER INFORMATION: synthetic oligonucleotide primer

<400> SEQUENCE: 228
aatgtagcaa tttgactggc gaa                                           23

<210> SEQ ID NO 229
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 229
gcggatctaa ggataattca ttaa                                          24

<210> SEQ ID NO 230
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 230
gctatgggaa aaggatgtgt g                                             21

<210> SEQ ID NO 231
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 231
atgtgatggc atgtgaaatg gt                                            22

<210> SEQ ID NO 232
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 232
cagggtatag ttcaattcag tgagcg                                        26

<210> SEQ ID NO 233
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 233
cctctttgtt ggtggttaag tctcc                                         25

<210> SEQ ID NO 234
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 234
```

```
gcggcaaaac tttggagtat tgcaa                                          25
```

<210> SEQ ID NO 235
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 235

```
tcgtcaatta agcaaaaatg tgaga                                          25
```

<210> SEQ ID NO 236
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 236

```
gaatatcacg cgagaatttt ac                                             22
```

<210> SEQ ID NO 237
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 237

```
acaaaaagaa atcgaaccgg ca                                             22
```

<210> SEQ ID NO 238
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 238

```
tggctttgat gatgtttgag acaa                                           24
```

<210> SEQ ID NO 239
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 239

```
cccagataca gacaataaaa cccga                                          25
```

<210> SEQ ID NO 240
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 240

```
tccaccatgt aatatgtgaa gtggat                                         26
```

<210> SEQ ID NO 241
<211> LENGTH: 21
<212> TYPE: DNA
<213> ORGANISM: Artificial

```
<220> FEATURE:
<223> OTHER INFORMATION: synthetic oligonucleotide primer

<400> SEQUENCE: 241
ctcacaccct ttcattatct a                                          21

<210> SEQ ID NO 242
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 242
actctatttt attatcgtgc aagaa                                      25

<210> SEQ ID NO 243
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 243
gatgacaacg taggctaaaa a                                          21

<210> SEQ ID NO 244
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 244
gattctatat ccatcgtgtt gct                                        23

<210> SEQ ID NO 245
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 245
cccactgtat ccttagtgtg cca                                        23

<210> SEQ ID NO 246
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 246
ggctaacccg ctctatgt                                              18

<210> SEQ ID NO 247
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 247
cattaactaa taagttgttg gtagc                                      25
```

```
<210> SEQ ID NO 248
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 248
accaaattgc ttcacgcatc c                                           21

<210> SEQ ID NO 249
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 249
tgctcatgtg gtcctaccca ga                                          22

<210> SEQ ID NO 250
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 250
gcggagcatg taaatccagc ctattga                                     27

<210> SEQ ID NO 251
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 251
gcggatttcg atttgaatat acttac                                      26

<210> SEQ ID NO 252
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 252
tggacacaca caaacaccta cagaa                                       25

<210> SEQ ID NO 253
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 253
agcaagtctt gagtcttttg tct                                         23

<210> SEQ ID NO 254
<211> LENGTH: 22
<212> TYPE: DNA
<213> ORGANISM: Artificial
<220> FEATURE:
<223> OTHER INFORMATION: synthetic oligonucleotide primer
```

-continued

<400> SEQUENCE: 254
tcccacgtca tatccactgc tc                                        22

<210> SEQ ID NO 255
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 255
ccaaagctga gcagctgata act                                       23

<210> SEQ ID NO 256
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 256
ccggtgatac tccataccaa taaca                                     25

<210> SEQ ID NO 257
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 257
ccgagctaac aaaggcgacc aaat                                      24

<210> SEQ ID NO 258
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 258
gcgcccaaac ctattaaggt atgaaca                                   27

<210> SEQ ID NO 259
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 259
atggccgtct caaaagaact gg                                        22

<210> SEQ ID NO 260
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 260
gcgaatggtt gctcaaataa tc                                        22

<210> SEQ ID NO 261

```
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 261
gcgcgcattt tttaagttaa tgttct                                    26

<210> SEQ ID NO 262
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 262
ggcagactcg tagagcaatt ta                                        22

<210> SEQ ID NO 263
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 263
gcgaagattg gtcttttatg tcaaatg                                   27

<210> SEQ ID NO 264
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 264
gcggtaactc ctcgagtccc tctcaat                                   27

<210> SEQ ID NO 265
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 265
tggtgatggg aagcaaacaa ga                                        22

<210> SEQ ID NO 266
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 266
ccatcccttc gtccaccaaa ta                                        22

<210> SEQ ID NO 267
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 267
```
tgctgcagcg tgtctgtagt ataattt                                              27

<210> SEQ ID NO 268
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 268
cgatttgaat atacttaccg tctata                                               26

<210> SEQ ID NO 269
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 269
gtaacattgg ttgtcatctt tgtcta                                               26

<210> SEQ ID NO 270
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 270
ggaggttatc tagtggtata gatggt                                               26

<210> SEQ ID NO 271
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 271
ccaaaagcat tgagagtggg ga                                                   22

<210> SEQ ID NO 272
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 272
gaaacccgaa acgcaaaatc tc                                                   22

<210> SEQ ID NO 273
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 273
ctctcgccgg tacaaaacac ct                                                   22

<210> SEQ ID NO 274
<211> LENGTH: 28
<212> TYPE: DNA

```
<213> ORGANISM: Artificial
<220> FEATURE:
<223> OTHER INFORMATION: synthetic oligonucleotide primer

<400> SEQUENCE: 274
tcactctcac aacttcaatc tctttctc                                28

<210> SEQ ID NO 275
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 275
cacgactctt cctcttcctc cg                                      22

<210> SEQ ID NO 276
<211> LENGTH: 16
<212> TYPE: DNA
<213> ORGANISM: Artificial
<220> FEATURE:
<223> OTHER INFORMATION: synthetic oligonucleotide primer

<400> SEQUENCE: 276
ccctgtgttt ccctct                                             16

<210> SEQ ID NO 277
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 277
gtgttgctct tgggaatctg gc                                      22

<210> SEQ ID NO 278
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 278
tctcgactca cgactca                                            17

<210> SEQ ID NO 279
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 279
aaaatgaaaa cacacagaga gagagaga                                28

<210> SEQ ID NO 280
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 280
agcgaaatgt gtggtccaag gt                                      22
```

```
<210> SEQ ID NO 281
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 281
cgtcgagaaa ggaagagagg ca                                          22

<210> SEQ ID NO 282
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 282
gcggaaacca ttctgacgga ta                                          22

<210> SEQ ID NO 283
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 283
ggaggaactt ggaaggcata tca                                         23

<210> SEQ ID NO 284
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 284
acggacaacg ctggcactaa g                                           21

<210> SEQ ID NO 285
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 285
caaaaggttt tcagtggtgg                                             20

<210> SEQ ID NO 286
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 286
ccaatcccta ccctgattgc ac                                          22

<210> SEQ ID NO 287
<211> LENGTH: 22
<212> TYPE: DNA
<213> ORGANISM: Artificial
<220> FEATURE:
```

```
<223> OTHER INFORMATION: synthetic oligonucleotide primer

<400> SEQUENCE: 287
ggaagtggat tggagttgg ga                                            22

<210> SEQ ID NO 288
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 288
aacccataac ctgctcgtct ca                                           22

<210> SEQ ID NO 289
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 289
aggcgggttt ggagctgttt ac                                           22

<210> SEQ ID NO 290
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 290
tcttctcagg aacttgaatt actca                                        25

<210> SEQ ID NO 291
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 291
ggaatgtccc aagtgtcagc aa                                           22

<210> SEQ ID NO 292
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 292
tgaaaataag tggaaagaaa aaggaaaa                                     28

<210> SEQ ID NO 293
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 293
gtccccgttc ctcaaacacc tt                                           22
```

```
<210> SEQ ID NO 294
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 294
tgcacactca cttggtctta caca                                          24

<210> SEQ ID NO 295
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 295
ctgttggaaa atgatgcgtg gc                                            22

<210> SEQ ID NO 296
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 296
ttgatcactt ctgtaacatt c                                             21

<210> SEQ ID NO 297
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 297
ctttgttgtt tggtcaaggc cc                                            22

<210> SEQ ID NO 298
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 298
tgccgaaata agtgagagca tagaa                                         25

<210> SEQ ID NO 299
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 299
tgttaggtat gggatttagg gttttga                                       27

<210> SEQ ID NO 300
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 300
tccactcact gtatgtcttc ccttg                                          25

<210> SEQ ID NO 301
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 301
ttgagtgctc ttggtgtttt cct                                            23

<210> SEQ ID NO 302
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 302
ccaaacaccc cagtataaaa aatgga                                         26

<210> SEQ ID NO 303
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 303
ggattttgag ttgctccaag gc                                             22

<210> SEQ ID NO 304
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 304
tgtatgatcc atcctctgaa accg                                           24

<210> SEQ ID NO 305
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 305
tcacatgttc gggacttaag gtat                                           24

<210> SEQ ID NO 306
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 306
tgaatggcta aaaacgtgat ttgga                                          25

<210> SEQ ID NO 307
<211> LENGTH: 22
```

```
<212> TYPE: DNA
<213> ORGANISM: Artificial
<220> FEATURE:
<223> OTHER INFORMATION: synthetic oligonucleotide primer

<400> SEQUENCE: 307
ggaccttccc tttcccatga ct                                              22

<210> SEQ ID NO 308
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 308
agcgatggtt gaagaaaggg tc                                              22

<210> SEQ ID NO 309
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 309
agagaacggg cgatttatgg ct                                              22

<210> SEQ ID NO 310
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 310
atgtcgccac taggccaatc ag                                              22

<210> SEQ ID NO 311
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 311
ccatcttgag cagagtttga agtt                                            24

<210> SEQ ID NO 312
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 312
gtggtggtgg tgaaaactat tagaa                                           25

<210> SEQ ID NO 313
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 313
```

```
cttccacacc ctagtttagt gacaa                                          25
```

<210> SEQ ID NO 314
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 314

```
tcaagcttat gctctatagg ct                                             22
```

<210> SEQ ID NO 315
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 315

```
gaccaaaatt caaggcagtg acaa                                           24
```

<210> SEQ ID NO 316
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 316

```
ccatcctcgt tagcatctat                                                20
```

<210> SEQ ID NO 317
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 317

```
gctgcacaat tcattccatt t                                              21
```

<210> SEQ ID NO 318
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 318

```
cccagggact tactttttc agttt                                           25
```

<210> SEQ ID NO 319
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 319

```
tgaagcaaca aaatagagga atagag                                         26
```

<210> SEQ ID NO 320
<211> LENGTH: 25
<212> TYPE: DNA
<213> ORGANISM: Artificial

-continued

```
<220> FEATURE:
<223> OTHER INFORMATION: synthetic oligonucleotide primer

<400> SEQUENCE: 320
cattactagg cgtgtgttgt ttcaa                                              25

<210> SEQ ID NO 321
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 321
cacgcgcatc agctttgtag ag                                                 22

<210> SEQ ID NO 322
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 322
tcttttcacc attctccaac ctca                                               24

<210> SEQ ID NO 323
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 323
tcctttctcc catttttttt ggg                                                23

<210> SEQ ID NO 324
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 324
ggtgaccacc cctattcctt at                                                 22

<210> SEQ ID NO 325
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 325
aattgttagg gcgcgagaaa ca                                                 22

<210> SEQ ID NO 326
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 326
ctagccaagg gagagaggag ca                                                 22
```

```
<210> SEQ ID NO 327
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 327
cctcacacca accagcacaa aa                                              22

<210> SEQ ID NO 328
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 328
caattttatg atttgctttt gaaggga                                         27

<210> SEQ ID NO 329
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 329
gggccttgaa ttttgtgcta t                                               21

<210> SEQ ID NO 330
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 330
cctcttgaaa ccgtgaaacc gt                                              22

<210> SEQ ID NO 331
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 331
tctttttctt cattttgtt cgca                                             24

<210> SEQ ID NO 332
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 332
aaactgctct gaagtgcgac aca                                             23

<210> SEQ ID NO 333
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 333
tgtgaataaa agaaatcccc attga                                          25

<210> SEQ ID NO 334
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 334
aagatacccc caacattatt tgtaa                                          25

<210> SEQ ID NO 335
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 335
gcgttttcat acggtgtttt gcctat                                         26

<210> SEQ ID NO 336
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 336
gggctaacga acatgtaact tatcaac                                        27

<210> SEQ ID NO 337
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 337
gcactacaat atgtgcatga atttttct                                       28

<210> SEQ ID NO 338
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 338
tctccttact cactccattg gca                                            23

<210> SEQ ID NO 339
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 339
tccatgtcac caaccacaaa aa                                             22

<210> SEQ ID NO 340
```

```
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 340
cgtatccctt tcccatacgt gg                                              22

<210> SEQ ID NO 341
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 341
atgacgggat gaaagagcca aa                                              22

<210> SEQ ID NO 342
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 342
agggaactaa cacatttaat catca                                           25

<210> SEQ ID NO 343
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 343
cggaaaagat ataccgagtg agaaaa                                          26

<210> SEQ ID NO 344
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 344
ttctaaggat ttgtggtaat cggc                                            24

<210> SEQ ID NO 345
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 345
catggagaaa agaagaggag gga                                             23

<210> SEQ ID NO 346
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 346
```

-continued aagcaaaacca ttatcttcat tggtg                                    25

<210> SEQ ID NO 347
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 347
gccacactat tccagccact ac                                        22

<210> SEQ ID NO 348
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 348
agtagtccaa accgaaacgc ca                                        22

<210> SEQ ID NO 349
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 349
tcaattcggt caaaaggctt ga                                        22

<210> SEQ ID NO 350
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 350
ctcccccaaa tttaacctta aaga                                      24

<210> SEQ ID NO 351
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 351
aatggatgga cctgtcagtc tgc                                       23

<210> SEQ ID NO 352
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 352
tgcttccatt agtctctcat cctcc                                     25

<210> SEQ ID NO 353
<211> LENGTH: 26
<212> TYPE: DNA

<213> ORGANISM: Artificial
<220> FEATURE:
<223> OTHER INFORMATION: synthetic oligonucleotide primer

<400> SEQUENCE: 353
tggaaaaaga taacgtgtgt ttgcag    26

<210> SEQ ID NO 354
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 354
ccttcttttg acatggggcc ta    22

<210> SEQ ID NO 355
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 355
gcgagtgcca actaactact tttatga    27

<210> SEQ ID NO 356
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 356
tggtatcggg agattttttc agc    23

<210> SEQ ID NO 357
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 357
tttttcgtca gcacattatt acacattt    28

<210> SEQ ID NO 358
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 358
ggccagtgtt gagggattta gaa    23

<210> SEQ ID NO 359
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 359
aatttgctcc agtgttttaa gttt    24

<210> SEQ ID NO 360
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 360
ggtgatatcg cgctaaaatt a                                              21

<210> SEQ ID NO 361
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 361
ggaaaccctg tcattttcgt gc                                             22

<210> SEQ ID NO 362
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 362
agagttctca gtccgccagc tc                                             22

<210> SEQ ID NO 363
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 363
gcgcaattgt caccaacaca t                                              21

<210> SEQ ID NO 364
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 364
cccaaaccaa caagcaacaa ca                                             22

<210> SEQ ID NO 365
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 365
attcacacgc atctggaata ata                                            23

<210> SEQ ID NO 366
<211> LENGTH: 23
<212> TYPE: DNA
<213> ORGANISM: Artificial
<220> FEATURE:

<223> OTHER INFORMATION: synthetic oligonucleotide primer

<400> SEQUENCE: 366
gcggagttca acgcattcac ctt                                    23

<210> SEQ ID NO 367
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 367
tgaaagcaaa cgagactcat gga                                    23

<210> SEQ ID NO 368
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 368
gcatagaagg gcatcattca gat                                    23

<210> SEQ ID NO 369
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 369
gctagatgag cagaccattg cactt                                  25

<210> SEQ ID NO 370
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 370
caagaggttg ttgtaagagt gatctcg                                27

<210> SEQ ID NO 371
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 371
cacggcgtat ttttattttg                                        20

<210> SEQ ID NO 372
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 372
cagtgcatgg ttttctcatg tacc                                   24

```
<210> SEQ ID NO 373
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 373
gctgctgtta agagtgtttg                                              20

<210> SEQ ID NO 374
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 374
gcgcacggta taatcgaa cctat                                          25

<210> SEQ ID NO 375
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 375
gcggtgatcg gatgttatag tttcag                                       26

<210> SEQ ID NO 376
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 376
tgtctccatg ctgtaacacg tcaa                                         24

<210> SEQ ID NO 377
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 377
cgccaaagat gcaacacact tg                                           22

<210> SEQ ID NO 378
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 378
tgtaattgct gttttggttt catttc                                       26

<210> SEQ ID NO 379
<211> LENGTH: 29
<212> TYPE: DNA
<213> ORGANISM: Artificial
<220> FEATURE:
<223> OTHER INFORMATION: synthetic oligonucleotide primer
```

```
<400> SEQUENCE: 379
gcggactaat tctattttac accaacaac                              29

<210> SEQ ID NO 380
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 380
gcgcgaggta tcaacacaat tact                                   24

<210> SEQ ID NO 381
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 381
gcgaggccaa cattgaaaag t                                      21

<210> SEQ ID NO 382
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 382
cgtaccattg gacaactctg taattcaa                               28

<210> SEQ ID NO 383
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 383
tggtgaatca atctcctcta agtgc                                  25

<210> SEQ ID NO 384
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 384
gcggcgactg ttaacgtgtc                                        20

<210> SEQ ID NO 385
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 385
ccacacggga ctttccattt tc                                     22

<210> SEQ ID NO 386
<211> LENGTH: 23
```

```
<212> TYPE: DNA
<213> ORGANISM: Artificial
<220> FEATURE:
<223> OTHER INFORMATION: synthetic oligonucleotide primer

<400> SEQUENCE: 386
tatatgtaat gacccccatc atg                                              23

<210> SEQ ID NO 387
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 387
cgttggattc gacttttgg ga                                                22

<210> SEQ ID NO 388
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 388
ttgaagctca ggctgtgatg aat                                              23

<210> SEQ ID NO 389
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 389
gcggggacca aaaattcaaa a                                                21

<210> SEQ ID NO 390
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 390 tagggaacc gatttggtga aa                                                22

<210> SEQ ID NO 391
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 391
gcgtgtcaaa gagttttaga catc                                             24

<210> SEQ ID NO 392
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 392
```
ttggagggag gttttggaag gt 22

<210> SEQ ID NO 393
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 393
ccaatctttt tgttagttca ccttcca 27

<210> SEQ ID NO 394
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 394
ttcgtagcaa tgtcaccacc ttgt 24

<210> SEQ ID NO 395
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 395
gggggtggct tttagattc 19

<210> SEQ ID NO 396
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 396
gcgccgaata aaacgtgaga actg 24

<210> SEQ ID NO 397
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 397
tccttgcctt ttagttgttc ggt 23

<210> SEQ ID NO 398
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 398
cgggaacaac cacactctcc att 23

<210> SEQ ID NO 399
<211> LENGTH: 26
<212> TYPE: DNA
<213> ORGANISM: Artificial

```
<220> FEATURE:
<223> OTHER INFORMATION: synthetic oligonucleotide primer

<400> SEQUENCE: 399
tccttcactt tcaaaaacaa aaacaa                                          26

<210> SEQ ID NO 400
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 400
gcgcaacgac attttcacga agtt                                            24

<210> SEQ ID NO 401
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 401
gcgagttttt ggttggattg agttg                                           25

<210> SEQ ID NO 402
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 402
tgaccagagt ccaaagttca tc                                              22

<210> SEQ ID NO 403
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 403
ttcccggaaa gaaagaaa                                                   18

<210> SEQ ID NO 404
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 404
gcgataattt taaaactgga cca                                             23

<210> SEQ ID NO 405
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 405
aagcagttcc tctcatcacg taaca                                           25
```

```
<210> SEQ ID NO 406
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 406
cgcaatccca attcacctct tc                                              22

<210> SEQ ID NO 407
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 407
ccataaaaca tagcaactgt cgtctc                                          26

<210> SEQ ID NO 408
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 408
tcccagggta aaagttcaag ttca                                            24

<210> SEQ ID NO 409
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 409
tcgatgtttc tccctccctt aga                                             23

<210> SEQ ID NO 410
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 410
ttgcacatgg tccttggttg at                                              22

<210> SEQ ID NO 411
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 411
gcgaatggga atgccttctt attcta                                          26

<210> SEQ ID NO 412
<211> LENGTH: 24
<212> TYPE: DNA
<213> ORGANISM: Artificial
<220> FEATURE:
<223> OTHER INFORMATION: synthetic oligonucleotide primer
```

```
<400> SEQUENCE: 412
gcgtagcgtg ttattttgtg tttg                                        24

<210> SEQ ID NO 413
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 413
catatcctgc cccccaatt at                                           22

<210> SEQ ID NO 414
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 414
tgacatctaa gtccagaaat caaagca                                     27

<210> SEQ ID NO 415
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 415
gcgagtaaaa gcagagtgcg gagta                                       25

<210> SEQ ID NO 416
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 416
gcgtttaagt ccaataacaa agataac                                     27

<210> SEQ ID NO 417
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 417
tcgttgacac acaaaaaaag cga                                         23

<210> SEQ ID NO 418
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 418
atcgggtcat gacttttgaa ga                                          22

<210> SEQ ID NO 419
```

```
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 419
gcggaatagt tgccaaacaa taatc                                    25

<210> SEQ ID NO 420
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 420
caagtggatt gacacactaa ggtttga                                  27

<210> SEQ ID NO 421
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 421
cacaaaagac aggagatgtg agcaa                                    25

<210> SEQ ID NO 422
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 422
ttgtagacga cttgtggttc gattc                                    25

<210> SEQ ID NO 423
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 423
aatgaagaaa atgtgaattt gaaacca                                  27

<210> SEQ ID NO 424
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 424 ttccctttttt ctaactctcc tttttca                                 27

<210> SEQ ID NO 425
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 425
```
tgtcttggtg caatacctga cattt         25

<210> SEQ ID NO 426
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 426
atttcccttt cacccacctc tgttt         25

<210> SEQ ID NO 427
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 427
caacgatccc agctcacagt tt            22

<210> SEQ ID NO 428
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 428
gcggcaggct agctacatca agag          24

<210> SEQ ID NO 429
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 429
tttcaaacaa ggaagaaacc tcttttt       27

<210> SEQ ID NO 430
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 430
aagtaacact gtggcggcat cc            22

<210> SEQ ID NO 431
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 431
tgtgtaattt ctatcaccttt attgtgcc     28

<210> SEQ ID NO 432
<211> LENGTH: 22
<212> TYPE: DNA

```
<213> ORGANISM: Artificial
<220> FEATURE:
<223> OTHER INFORMATION: synthetic oligonucleotide primer

<400> SEQUENCE: 432
tcctttggct cggcctatgt aa                                              22

<210> SEQ ID NO 433
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 433
cgcggactca gttaaaccgt at                                              22

<210> SEQ ID NO 434
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 434
cgttcaatag ttcctatgat ggacga                                          26

<210> SEQ ID NO 435
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 435
gcattgcacg tcgattttag gg                                              22

<210> SEQ ID NO 436
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 436
cttaaggaca cgtggaagat gactac                                          26

<210> SEQ ID NO 437
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 437
gcgttgaagc cgcctacaaa tataat                                          26

<210> SEQ ID NO 438
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 438 tcctttaat tctaacattg agacagca                                         28
```

```
<210> SEQ ID NO 439
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 439
tctgtcccaa aaagaaaga agatatg                                          27

<210> SEQ ID NO 440
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 440
caatctttaa tgctctggag tttgaga                                         27

<210> SEQ ID NO 441
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 441
gcgtgtgacg gttcaaaatg atagtt                                          26

<210> SEQ ID NO 442
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 442
gggtaattta tctgtgtgat tgttc                                           25

<210> SEQ ID NO 443
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 443
ttgcttggga ttttcatttt attatagg                                        28

<210> SEQ ID NO 444
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 444
ggtcaaagaa taaggggattt gcctc                                          25

<210> SEQ ID NO 445
<211> LENGTH: 25
<212> TYPE: DNA
<213> ORGANISM: Artificial
<220> FEATURE:
```

<223> OTHER INFORMATION: synthetic oligonucleotide primer

<400> SEQUENCE: 445
tgggactttg attttggaa taccc                                      25

<210> SEQ ID NO 446
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 446
ccagagaaat tattggagtg gcaa                                      24

<210> SEQ ID NO 447
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 447
gcgcaaagaa attcccatcc ta                                        22

<210> SEQ ID NO 448
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 448
gggagaggtt cagttgggga at                                        22

<210> SEQ ID NO 449
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 449
gcgaatgcct aatgtgatga taaaaaaata                                30

<210> SEQ ID NO 450
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 450
tccccatcat ttatcgaaaa taataatt                                  28

<210> SEQ ID NO 451
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 451
aataatggag tgacccgctg ct                                        22

```
<210> SEQ ID NO 452
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 452
tggtacgagt ggcacgaaat gt                                          22

<210> SEQ ID NO 453
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 453
gccatccttt cctttcaacc aa                                          22

<210> SEQ ID NO 454
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 454
tgtaggctat tggaagggtg cg                                          22

<210> SEQ ID NO 455
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 455
gcgcttataa aggcttgtga aagacact                                    28

<210> SEQ ID NO 456
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 456
tggttagtgc aatcttggcg gt                                          22

<210> SEQ ID NO 457
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 457
tgcacccatc aatcacattt ttg                                         23

<210> SEQ ID NO 458
<211> LENGTH: 25
<212> TYPE: DNA
<213> ORGANISM: Artificial
<220> FEATURE:
<223> OTHER INFORMATION: synthetic oligonucleotide primer
```

<400> SEQUENCE: 458
gcggttcaag gcttcaagta gtcac                                    25

<210> SEQ ID NO 459
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 459 tttttctca cacccatgcc gt                                        22

<210> SEQ ID NO 460
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 460
ccggttggcg taatgtgtct tt                                       22

<210> SEQ ID NO 461
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 461
gccagcagcc tgttcagttt tt                                       22

<210> SEQ ID NO 462
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 462
cccctctttg gccctcacac cttctc                                   26

<210> SEQ ID NO 463
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 463
atttgaagct cttggtatct tggc                                     24

<210> SEQ ID NO 464
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 464
caaccatgat aaatgtgagt gagcttg                                  27

<210> SEQ ID NO 465
<211> LENGTH: 22

```
<212> TYPE: DNA
<213> ORGANISM: Artificial
<220> FEATURE:
<223> OTHER INFORMATION: synthetic oligonucleotide primer

<400> SEQUENCE: 465
gtcacaattt cacgatccca aa                                              22

<210> SEQ ID NO 466
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 466
tccattttcc ctttagtcca acg                                             23

<210> SEQ ID NO 467
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 467
gcgcatacga tttggcattt ttctattg                                        28

<210> SEQ ID NO 468
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 468
aatttcttac gtttccatag atttctcg                                        28

<210> SEQ ID NO 469
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 469
tgccctcttc ccaaactagg gt                                              22

<210> SEQ ID NO 470
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 470
caaccactga ttcaagccaa caa                                             23

<210> SEQ ID NO 471
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 471
```

```
caatttaagc acggtcatat tttctca                                        27
```

<210> SEQ ID NO 472
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 472

```
cgtgatgcag tgaattttt tcg                                             23
```

<210> SEQ ID NO 473
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 473

```
gggttacttt tctttatcct cctcca                                         26
```

<210> SEQ ID NO 474
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 474

```
gggctatcaa attgactaaa gccaaa                                         26
```

<210> SEQ ID NO 475
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 475

```
acacttgaat catcgagagt tgctaa                                         26
```

<210> SEQ ID NO 476
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 476

```
tgtgctgctt gcttcaattt gg                                             22
```

<210> SEQ ID NO 477
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 477

```
tggcctgtct tatattaccg aaccaa                                         26
```

<210> SEQ ID NO 478
<211> LENGTH: 26
<212> TYPE: DNA
<213> ORGANISM: Artificial

```
<220> FEATURE:
<223> OTHER INFORMATION: synthetic oligonucleotide primer

<400> SEQUENCE: 478
ggtccgtatg caattcttga ctaata                                          26

<210> SEQ ID NO 479
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 479
tcccccacaa gagaacaaga aggt                                            24

<210> SEQ ID NO 480
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 480
gcgggaattg gttaatctca tcgtgac                                         27

<210> SEQ ID NO 481
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 481
tgcgaaaaag cagagtgacc aa                                              22

<210> SEQ ID NO 482
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 482
tgagcatatt ttgatccgat gcc                                             23

<210> SEQ ID NO 483
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 483
gttgctttgt tatgtaatgg aagtc                                           25

<210> SEQ ID NO 484
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 484
gccccacaaa tattcagaag gtaa                                            24
```

```
<210> SEQ ID NO 485
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 485
gcagcggtgt agttcgttct ttct                                              24

<210> SEQ ID NO 486
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 486
aaatcgtctt ttgtggctgc ct                                                22

<210> SEQ ID NO 487
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 487
gcaccatgtt cttttccat caaa                                               24

<210> SEQ ID NO 488
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 488
ggctcaatta gagcatgcaa catc                                              24

<210> SEQ ID NO 489
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 489
catgttaaac gtccacccac ca                                                22

<210> SEQ ID NO 490
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 490
gcgtgaattc gcctaagttt at                                                22

<210> SEQ ID NO 491
<211> LENGTH: 28
<212> TYPE: DNA
<213> ORGANISM: Artificial
<220> FEATURE:
<223> OTHER INFORMATION: synthetic oligonucleotide primer
```

```
<400> SEQUENCE: 491
tccctactct cgtgtcgtta gttatttt                                              28

<210> SEQ ID NO 492
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 492
agttacatta ttttgtctt tctgccgt                                              28

<210> SEQ ID NO 493
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 493
gcgcaagtgg ccagctcatc tatt                                                 24

<210> SEQ ID NO 494
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 494
ccctcttatt tcaccctaag acctacaa                                             28

<210> SEQ ID NO 495
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 495
ggaaatgctt caaaccaaca aaca                                                 24

<210> SEQ ID NO 496
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 496
gcccacatag ttttcatttt tctcca                                               26

<210> SEQ ID NO 497
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 497
gaggtctagt gctttggtaa ggtt                                                 24

<210> SEQ ID NO 498
```

```
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 498
tgtcacacaa ccagtgtctc aaaatc                                          26

<210> SEQ ID NO 499
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 499
cacaccccag gacccattaa ga                                              22

<210> SEQ ID NO 500
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 500
aaagcgcaca caatgcaaat aca                                             23

<210> SEQ ID NO 501
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 501
caaggttacg aactgctcga ataag                                           25

<210> SEQ ID NO 502
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 502
tgaggaggca agatgatcca aa                                              22

<210> SEQ ID NO 503
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 503 gcgcttttc ggctgttatt tttaact                                          27

<210> SEQ ID NO 504
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 504
```
gcgggtctta cgaacgtgtc acattat                                                27

<210> SEQ ID NO 505
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 505
cgaacccaaa ccacaaagca ta                                                     22

<210> SEQ ID NO 506
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 506
gcacaatgac aatcacatac a                                                      21

<210> SEQ ID NO 507
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 507
gcgtgtaaaa atctttgaat cttga                                                  25

<210> SEQ ID NO 508
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 508
cacccattat tgaaaataca aggacca                                                27

<210> SEQ ID NO 509
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 509
gggggatcta ggccatgac                                                         19

<210> SEQ ID NO 510
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 510
gcataatggt ctaataaaag tggagacc                                               28

<210> SEQ ID NO 511
<211> LENGTH: 24
<212> TYPE: DNA

```
<213> ORGANISM: Artificial
<220> FEATURE:
<223> OTHER INFORMATION: synthetic oligonucleotide primer

<400> SEQUENCE: 511
tgcttttgga ggaactttgt ctca                                            24

<210> SEQ ID NO 512
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 512
cattcaaccg tgattgcgaa ga                                              22

<210> SEQ ID NO 513
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 513
gggagcggat cattcggtga aa                                              22

<210> SEQ ID NO 514
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 514
gagctacccg agatgatact c                                               21

<210> SEQ ID NO 515
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 515
ggatcaaatt gggaaacaca aagg                                            24

<210> SEQ ID NO 516
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 516
ctcacataca tggcagccgt aa                                              22

<210> SEQ ID NO 517
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 517
tgcctttagc tggtgggaaa aa                                              22
```

-continued

<210> SEQ ID NO 518
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 518
gcgcgcaaca atcactagta cg                                              22

<210> SEQ ID NO 519
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 519
ttagaggttt tcggatgagc gtg                                             23

<210> SEQ ID NO 520
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 520
tatatgcgaa ccctcttaca at                                              22

<210> SEQ ID NO 521
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 521
gttttggttg atccgcattg gt                                              22

<210> SEQ ID NO 522
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 522
tttcattacc gcatgttctt gga                                             23

<210> SEQ ID NO 523
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 523
ttatgttcgt tcatctctga agcct                                           25

<210> SEQ ID NO 524
<211> LENGTH: 26
<212> TYPE: DNA
<213> ORGANISM: Artificial
<220> FEATURE:

<223> OTHER INFORMATION: synthetic oligonucleotide primer

<400> SEQUENCE: 524
ttctgtccat tctagctcac taaccc                26

<210> SEQ ID NO 525
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 525
aaatcgcgca tctaaattta c                21

<210> SEQ ID NO 526
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 526
acaataactt gttttgcaca ctatt                25

<210> SEQ ID NO 527
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 527
gcgcccacat gattttgtac tgat                24

<210> SEQ ID NO 528
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 528
tatggtaaat attaaccatt gtcct                25

<210> SEQ ID NO 529
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 529
cctcgtttta ttccgaaagc cg                22

<210> SEQ ID NO 530
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 530
gggccatgca cctgctact                19

```
<210> SEQ ID NO 531
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 531
ttagattcgg acaccggtct act                                              23

<210> SEQ ID NO 532
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 532 tcttaattttt tttaggaatg gcatcaa                                         27

<210> SEQ ID NO 533
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 533
cgctatccct ttgtattttc ttttgc                                           26

<210> SEQ ID NO 534
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 534
gcgggctaac ttatgttact aaacaat                                          27

<210> SEQ ID NO 535
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 535
cctgtggctg ttatactatg catata                                           26

<210> SEQ ID NO 536
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 536
gggtggcgtt gacaatgttt ta                                               22

<210> SEQ ID NO 537
<211> LENGTH: 25
<212> TYPE: DNA
<213> ORGANISM: Artificial
<220> FEATURE:
<223> OTHER INFORMATION: synthetic oligonucleotide primer
```

```
<400> SEQUENCE: 537
ttattatcta aacttatatg tgcat                                              25

<210> SEQ ID NO 538
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 538
gcctcctaag tccgtacaca gcat                                               24

<210> SEQ ID NO 539
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 539
ccctcactcc tagattattt gttgt                                              25

<210> SEQ ID NO 540
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 540
ggatttggtt tctgtgtgct gtg                                                23

<210> SEQ ID NO 541
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 541
ggggcacaag ccacactt                                                      18

<210> SEQ ID NO 542
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 542
gcgggtcaga agatgctacc aaactct                                            27

<210> SEQ ID NO 543
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 543
tgggcacttg cagtccaaat ag                                                 22

<210> SEQ ID NO 544
<211> LENGTH: 23
```

```
<212> TYPE: DNA
<213> ORGANISM: Artificial
<220> FEATURE:
<223> OTHER INFORMATION: synthetic oligonucleotide primer

<400> SEQUENCE: 544
gcgcaaaccg cacaagttta tgt                                             23

<210> SEQ ID NO 545
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 545
gcgcgagtta gcgaattatt tgtc                                            24

<210> SEQ ID NO 546
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 546
tgttgaaatt gaccaaaatt ccca                                            24

<210> SEQ ID NO 547
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 547
gcggaggaat acaagtctct attcaa                                          26

<210> SEQ ID NO 548
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 548
gcgccgctaa cagacatcca ata                                             23

<210> SEQ ID NO 549
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 549
tggatttcac ccaagaaaaa agc                                             23

<210> SEQ ID NO 550
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 550
```
tcgactaccc gtcgattccg ta                                                22

<210> SEQ ID NO 551
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 551
ggcacaacca tcaccacctt att                                               23

<210> SEQ ID NO 552
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 552
cacaatacct gtggctgtta tactat                                            26

<210> SEQ ID NO 553
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 553
atcgaactgt gaccgtccct tc                                                22

<210> SEQ ID NO 554
<211> LENGTH: 24
<212> TYPE: DNA
<213> ORGANISM: Artificial
<220> FEATURE:
<223> OTHER INFORMATION: synthetic oligonucleotide primer

<400> SEQUENCE: 554
aagggaagag agtcgtgctt cttt                                              24

<210> SEQ ID NO 555
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 555
ccagcaaacc cccaggtaaa g                                                 21

<210> SEQ ID NO 556
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 556
gaagaaaacg cgaataaccc ca                                                22

<210> SEQ ID NO 557
<211> LENGTH: 23
<212> TYPE: DNA
<213> ORGANISM: Artificial

```
<220> FEATURE:
<223> OTHER INFORMATION: synthetic oligonucleotide primer

<400> SEQUENCE: 557
gcacgcagac tcaagttcat tca                                              23

<210> SEQ ID NO 558
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 558
aatagttggg tcgtcgaagg gg                                               22

<210> SEQ ID NO 559
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 559
tccaacttaa cacaagatca gcgaa                                            25

<210> SEQ ID NO 560
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 560
gaaaagtttt atgttctgag tg                                               22

<210> SEQ ID NO 561
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 561
ccacacacac tgacacagta aagca                                            25

<210> SEQ ID NO 562
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 562
ccaaggtctc tcagagg                                                     17

<210> SEQ ID NO 563
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 563
acggaggcac ttcccattgt ta                                               22
```

<210> SEQ ID NO 564
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 564
caaaacgaca tgacaaggaa acttca                                          26

<210> SEQ ID NO 565
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 565
tcctccataa aaattaaaaa cattggaa                                        28

<210> SEQ ID NO 566
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 566
gcccccagac acaacataat ca                                              22

<210> SEQ ID NO 567
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 567
cgagagaagc agaagcagag gc                                              22

<210> SEQ ID NO 568
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 568
gagaaaggtg acgatggacg ct                                              22

<210> SEQ ID NO 569
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 569
catggtttct cttatcttat agacattgtt gccaag                               36

<210> SEQ ID NO 570
<211> LENGTH: 36
<212> TYPE: DNA
<213> ORGANISM: Artificial
<220> FEATURE:
<223> OTHER INFORMATION: synthetic oligonucleotide primer

```
<400> SEQUENCE: 570
caattcatgg tttctcttat agacattgtt gccaag                                    36

<210> SEQ ID NO 571
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 571
cactgtccct gctcctgttt caagtatc                                             28

<210> SEQ ID NO 572
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 572
caattcttgt gggttgaagc cttgttctga c                                         31

<210> SEQ ID NO 573
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 573
ggaatcaact tcttcgtgag tgggttgttc                                           30

<210> SEQ ID NO 574
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 574
tggtggctat ggaaatctca tgtgtgga                                             28

<210> SEQ ID NO 575
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 575
ctctcattta ccaaactcca acatttgatc acc                                       33

<210> SEQ ID NO 576
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 576
cacactggta gatgggaagc aagaatagg                                            29

<210> SEQ ID NO 577
```

```
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 577
gaagaagatt ccacccagat catcatcagt ag                                    32

<210> SEQ ID NO 578
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 578
gcttgtgcag ctccaatcgg tgtaac                                           26

<210> SEQ ID NO 579
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 579
gtgcaatcca agacatctgg ttcggac                                          27

<210> SEQ ID NO 580
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 580
cagctaaacc ttacaaggat gattggtcaa g                                     31

<210> SEQ ID NO 581
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 581
ccctggactg aagttgccat aatgtatc                                         28

<210> SEQ ID NO 582
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 582
gctggttggg agaaagcact tcc                                              23

<210> SEQ ID NO 583
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 583
```

-continued gaatctaaca ttacgctctg ctggagtatc    30

<210> SEQ ID NO 584
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 584
gagggactat gtgaaatgga gaggagtg    28

<210> SEQ ID NO 585
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 585
gtatgctaaa agaggagact tgactggtga g    31

<210> SEQ ID NO 586
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 586
gatgaaggaa ccaacacttg cataacaatt tg    32

<210> SEQ ID NO 587
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 587
tgtcagcact cctcactcat ttgccga    27

<210> SEQ ID NO 588
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 588
cacttaacag gagtgctcct gatcaccag    29

<210> SEQ ID NO 589
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 589
gagaacaagg acaaatcaat aggtgagacg aagaaa    36

<210> SEQ ID NO 590
<211> LENGTH: 28
<212> TYPE: DNA

```
<213> ORGANISM: Artificial
<220> FEATURE:
<223> OTHER INFORMATION: synthetic oligonucleotide primer

<400> SEQUENCE: 590
ctcatctgct cagaaccttc agtcagtc                                        28

<210> SEQ ID NO 591
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 591
cggatcatgt ctagtacatt agagatgctt gtg                                  33

<210> SEQ ID NO 592
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 592
ctacacttct aatgcctatt taggtgtgct tg                                   32

<210> SEQ ID NO 593
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 593
gtcatatcta gggagatttc taaccagttg tc                                   32

<210> SEQ ID NO 594
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 594
taggcagcgt gacaaactga gcatagg                                         27

<210> SEQ ID NO 595
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 595
gggttgatgt ccgatgggta aatgaagttg                                      30

<210> SEQ ID NO 596
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 596
gcactaatac tttagttgac ttttgaggtg gttgag                               36
```

```
<210> SEQ ID NO 597
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 597
gctatgtggt agaagtatat gaaaaggtag atgacag                              37

<210> SEQ ID NO 598
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 598
gaatatacta gcttgatgcc tatttgtttc taaaccc                              37

<210> SEQ ID NO 599
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 599
agcagtcata caatgctctt tattgtggtg aag                                  33

<210> SEQ ID NO 600
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 600
gctcatagcc tgcttcttaa tcttgttatt ctg                                  33

<210> SEQ ID NO 601
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 601
ctatttgttt caggagtttc acaaccatct caagt                                35

<210> SEQ ID NO 602
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 602
catcttgacc agtcaccaat ctgagtacag                                      30

<210> SEQ ID NO 603
<211> LENGTH: 30
<212> TYPE: DNA
<213> ORGANISM: Artificial
<220> FEATURE:
```

<223> OTHER INFORMATION: synthetic oligonucleotide primer

<400> SEQUENCE: 603
ggcttcagtg agaaaggtgg atcaaatgga                                   30

<210> SEQ ID NO 604
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 604
caacgtgtaa aatcaagaga ttgagcttct gg                                32

<210> SEQ ID NO 605
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 605
tcggtgtgtt caactatgac tttggttctg                                   30

<210> SEQ ID NO 606
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 606
cccccaacaa aactaaaaat agaaccctca acaacc                             36

<210> SEQ ID NO 607
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 607
ggtccaagaa cattatgatc ttgaacaatc ttcac                              35

<210> SEQ ID NO 608
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 608
tggctagagc atcaacacat ctataccttc                                   30

<210> SEQ ID NO 609
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 609
cattgggcat gattcttgaa tagccttttt acc                               33

```
<210> SEQ ID NO 610
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 610
gagggctatg ttttcttctc cagatgtgag                              30

<210> SEQ ID NO 611
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 611
aaggtcggct tggtggttaa aggcag                                  26

<210> SEQ ID NO 612
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 612 gcctttatg cacatttttc ctggggatct aac                           33

<210> SEQ ID NO 613
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 613
ctcaatgtca tgggatcaat ttggaaattc aatgacc                      37

<210> SEQ ID NO 614
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 614
gattacatta attaccgcta tgactatatc ttgggac                      37

<210> SEQ ID NO 615
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 615
gctaccttct ccattgcttc tatgtattgg tc                           32

<210> SEQ ID NO 616
<211> LENGTH: 32
<212> TYPE: DNA
<213> ORGANISM: Artificial
<220> FEATURE:
<223> OTHER INFORMATION: synthetic oligonucleotide primer
```

```
<400> SEQUENCE: 616
gggcatcaca tacatgaaaa caactacact tg                              32

<210> SEQ ID NO 617
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 617
caacagctct cttccaccac aatcctg                                    27

<210> SEQ ID NO 618
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 618
gagattggaa attgtagctc tctttacttg ctg                             33

<210> SEQ ID NO 619
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 619
ctttgaggac ttatttggtt gttataggca tttgg                           35

<210> SEQ ID NO 620
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 620
gtgtttccct ccattttgc caaaagacag                                  30

<210> SEQ ID NO 621
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 621
tatacacact aagaattcgc tcgctgtaca a                               31

<210> SEQ ID NO 622
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 622
ggtctagact ttcactcaga caaggaac                                   28

<210> SEQ ID NO 623
<211> LENGTH: 38
```

```
<212> TYPE: DNA
<213> ORGANISM: Artificial
<220> FEATURE:
<223> OTHER INFORMATION: synthetic oligonucleotide primer

<400> SEQUENCE: 623
caaaatacta cagacctaat ttgtaactaa ttgctccc                              38

<210> SEQ ID NO 624
<211> LENGTH: 29
<212> TYPE: DNA
<213> ORGANISM: Artificial
<220> FEATURE:
<223> OTHER INFORMATION: synthetic oligonucleotide primer

<400> SEQUENCE: 624
gggaagaaga agaacactcg gtacagtag                                       29

<210> SEQ ID NO 625
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 625
aagctaggaa atccacactc aaattatcga cttgtgt                              37

<210> SEQ ID NO 626
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 626
gacctgaagc aaaacgccac catttcc                                         27

<210> SEQ ID NO 627
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 627
cgttggagac gacgccgttt gattac                                          26

<210> SEQ ID NO 628
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 628
cagtcgacac gtcttctact cc                                              22

<210> SEQ ID NO 629
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 629
```
tggaaggcat gtcggaactt g                                              21

<210> SEQ ID NO 630
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 630 ccttttttgcc ctcacttcat gccttctatg                                    30

<210> SEQ ID NO 631
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 631
gcataaccca agagctggac tgacaag                                        27

<210> SEQ ID NO 632
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 632
caagctctgc tgccaggtta agtgtttc                                       28

<210> SEQ ID NO 633
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 633
gactagaaca aattggggct agtgtgtttg ag                                  32

<210> SEQ ID NO 634
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 634
tggacttgcg ggactatgcc ttagag                                         26

<210> SEQ ID NO 635
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 635
gcaggaacac gttcgtaacc atcaactg                                       28

<210> SEQ ID NO 636
<211> LENGTH: 32
<212> TYPE: DNA
<213> ORGANISM: Artificial

```
<220> FEATURE:
<223> OTHER INFORMATION: synthetic oligonucleotide primer

<400> SEQUENCE: 636
gtccctttct gaaccactta aagagtcaac ag                                    32

<210> SEQ ID NO 637
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 637
ggcatagtga gttgaatacc aggaggaatc                                       30

<210> SEQ ID NO 638
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 638
attgaagggt gggcgttacc aggttac                                          27

<210> SEQ ID NO 639
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 639
gagttaatgg ggctatgcta ttggctattc ac                                    32

<210> SEQ ID NO 640
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 640
gtcactatat ggagtcaagg taattattgt gttcac                                36

<210> SEQ ID NO 641
<211> LENGTH: 38
<212> TYPE: DNA
<213> ORGANISM: Artificial
<220> FEATURE:
<223> OTHER INFORMATION: synthetic oligonucleotide primer

<400> SEQUENCE: 641
ggtctagagt ttgaatatta gtaatgactt gtattgac                              38

<210> SEQ ID NO 642
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 642
gcatattgtg ccatagagag agaaaatgta gtaag                                 35
```

<210> SEQ ID NO 643
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 643
cgctactgca agttatcagt caagagatta ttcc                              34

<210> SEQ ID NO 644
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 644
gccgtgtaag cgtgtttacc aatctagttg                                   30

<210> SEQ ID NO 645
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 645
caaaactgag cgaaacttgt gttgggagaa ag                                32

<210> SEQ ID NO 646
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 646
gtggggactc tttattcgaa gtttgctgaa c                                 31

<210> SEQ ID NO 647
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 647
ctcatgtaac caactctcta tgaagtttga gatcca                            36

<210> SEQ ID NO 648
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 648
ctctaatcgg atttggtgtt tcacttcggt aag                               33

<210> SEQ ID NO 649
<211> LENGTH: 29
<212> TYPE: DNA
<213> ORGANISM: Artificial
<220> FEATURE:
<223> OTHER INFORMATION: synthetic oligonucleotide primer

```
<400> SEQUENCE: 649
gatggctgtc attgctacag aggagtatc                                     29

<210> SEQ ID NO 650
<211> LENGTH: 38
<212> TYPE: DNA
<213> ORGANISM: Artificial
<220> FEATURE:
<223> OTHER INFORMATION: synthetic oligonucleotide primer

<400> SEQUENCE: 650
gtgactccaa aggaaagaga atgtttctt aaatcatc                            38

<210> SEQ ID NO 651
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 651
ggatagcaag tcaatttcat gccttgtgat ag                                 32

<210> SEQ ID NO 652
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 652
gcaggacatg aagatgtact tagtgaatgt gaag                               34

<210> SEQ ID NO 653
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 653
actggaagag ggtgcttagg gaatctg                                       27

<210> SEQ ID NO 654
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 654
gagaatctag tctaccacca taccacgaac                                    30

<210> SEQ ID NO 655
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 655
gggactctct ttatattgga aggtataact cagtg                              35

<210> SEQ ID NO 656
```

<211> LENGTH: 33
<212> TYPE: DNA
<213> ORGANISM: Artificial
<220> FEATURE:
<223> OTHER INFORMATION: synthetic oligonucleotide primer

<400> SEQUENCE: 656
gttggaccct tgtaattaga cccgaaacaa atg                              33

<210> SEQ ID NO 657
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 657
atctgtccaa cgatctctcc atgttcattc                                  30

<210> SEQ ID NO 658
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 658
cgaataagaa gttgggtatc acttacacgt tgg                              33

<210> SEQ ID NO 659
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 659
gatggggttc tagactggga tctggat                                     27

<210> SEQ ID NO 660
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 660
cttttcctac aggattgtca ggcttatcgt ca                               32

<210> SEQ ID NO 661
<211> LENGTH: 27
<212> TYPE: DNA
<213> ORGANISM: Artificial
<220> FEATURE:
<223> OTHER INFORMATION: synthetic oligonucleotide primer

<400> SEQUENCE: 661
gaagagtaac agagtctacg caccgac                                     27

<210> SEQ ID NO 662
<211> LENGTH: 37
<212> TYPE: DNA
<213> ORGANISM: Artificial
<220> FEATURE:
<223> OTHER INFORMATION: synthetic oligonucleotide primer

<400> SEQUENCE: 662

```
gtcaacgaac atactatgca tgatgatttc tgattag                                37
```

<210> SEQ ID NO 663
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 663

```
catatgcaga cagcaggcta aggaactc                                          28
```

<210> SEQ ID NO 664
<211> LENGTH: 38
<212> TYPE: DNA
<213> ORGANISM: Artificial
<220> FEATURE:
<223> OTHER INFORMATION: synthetic oligonucleotide primer

<400> SEQUENCE: 664

```
gcagcaatat aaccaggatt cagaattaat ctagttag                               38
```

<210> SEQ ID NO 665
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 665

```
cgatggggtt gacttagaaa tggcatatac                                        30
```

<210> SEQ ID NO 666
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 666

```
gcaccaattc ctcaagcata ctccaaac                                          28
```

<210> SEQ ID NO 667
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 667

```
ctgacaaggt gttttggtag ggagagattc                                        30
```

<210> SEQ ID NO 668
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 668

```
gcatcctccg ttactccaat cagagtttcc at                                     32
```

<210> SEQ ID NO 669
<211> LENGTH: 30
<212> TYPE: DNA

-continued

<213> ORGANISM: Artificial
<220> FEATURE:
<223> OTHER INFORMATION: synthetic oligonucleotide primer

<400> SEQUENCE: 669
ctgacaaggt gttttggtag ggagagattc                                30

<210> SEQ ID NO 670
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 670
gcatcctccg ttactccaat cagagtttcc at                             32

<210> SEQ ID NO 671
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 671
cacactatca acacctattg gtgaccattg ta                             32

<210> SEQ ID NO 672
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 672
ggagggtgct tatgtaaatg atgtaaagac cat                            33

<210> SEQ ID NO 673
<211> LENGTH: 35
<212> TYPE: DNA
<213> ORGANISM: Artificial
<220> FEATURE:
<223> OTHER INFORMATION: synthetic oligonucleotide primer

<400> SEQUENCE: 673
gatgaccatt ttgattccct catgctatta gtacc                          35

<210> SEQ ID NO 674
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 674
ccaataagtt agcagcatgt ggatcacagt gta                            33

<210> SEQ ID NO 675
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 675
gtctctcgga gttgcttcaa ttgctcatac                                30

<210> SEQ ID NO 676
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 676
gagagtgtgg aattgtaagt cattgattga aaactc                    36

<210> SEQ ID NO 677
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 677
gtctctcgga gttgcttcaa ttgctcatac                           30

<210> SEQ ID NO 678
<211> LENGTH: 36
<212> TYPE: DNA
<213> ORGANISM: Artificial
<220> FEATURE:
<223> OTHER INFORMATION: synthetic oligonucleotide primer

<400> SEQUENCE: 678
gagagtgtgg aattgtaagt cattgattga aaactc                    36

<210> SEQ ID NO 679
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 679
gcagaaggag cattgaggct ttccag                               26

<210> SEQ ID NO 680
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 680
gaaaaggttt gttatgcttc gtactctgtc tc                        32

<210> SEQ ID NO 681
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 681
catgaagctc caccatttgc tagtacatga aac                       33

<210> SEQ ID NO 682
<211> LENGTH: 33
<212> TYPE: DNA
<213> ORGANISM: Artificial
<220> FEATURE:

<223> OTHER INFORMATION: synthetic oligonucleotide primer

<400> SEQUENCE: 682
ccagagttac caaaccatct gtgagaaata tcc						33

<210> SEQ ID NO 683
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 683
catgaagctc caccatttgc tagtacatga aac						33

<210> SEQ ID NO 684
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 684
ccagagttac caaaccatct gtgagaaata tcc						33

<210> SEQ ID NO 685
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 685
caaacgctcc caacagcttc agaatctc							28

<210> SEQ ID NO 686
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 686
ttgaaggttg taagagtctc ggtcgtcg							28

<210> SEQ ID NO 687
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 687
cccattcttc atgtactcat acaccaagag						30

<210> SEQ ID NO 688
<211> LENGTH: 33
<212> TYPE: DNA
<213> ORGANISM: Artificial
<220> FEATURE:
<223> OTHER INFORMATION: synthetic oligonucleotide primer

<400> SEQUENCE: 688
gcagccacca ataatttctc atttgacaac aag						33

```
<210> SEQ ID NO 689
<211> LENGTH: 31
<212> TYPE: DNA
<213> ORGANISM: Artificial
<220> FEATURE:
<223> OTHER INFORMATION: synthetic oligonucleotide primer

<400> SEQUENCE: 689
ctctgtatat gayatatgtg ctcagtgcct c                           31

<210> SEQ ID NO 690
<211> LENGTH: 32
<212> TYPE: DNA
<213> ORGANISM: Artificial
<220> FEATURE:
<223> OTHER INFORMATION: synthetic oligonucleotide primer

<400> SEQUENCE: 690
gacttaccaa atgagtttga ccaggtttta cc                          32

<210> SEQ ID NO 691
<211> LENGTH: 30
<212> TYPE: DNA
<213> ORGANISM: Artificial
<220> FEATURE:
<223> OTHER INFORMATION: synthetic oligonucleotide primer

<400> SEQUENCE: 691
aggattcaac ctctagccat gatgatgttg                             30

<210> SEQ ID NO 692
<211> LENGTH: 28
<212> TYPE: DNA
<213> ORGANISM: Artificial
<220> FEATURE:
<223> OTHER INFORMATION: synthetic oligonucleotide primer

<400> SEQUENCE: 692
ccaagctctt tccgtgtgta tcaatctg                               28

<210> SEQ ID NO 693
<211> LENGTH: 12
<212> TYPE: DNA
<213> ORGANISM: Artificial
<220> FEATURE:
<223> OTHER INFORMATION: oligonucleotide probe

<400> SEQUENCE: 693
gtttcagata ac                                                12

<210> SEQ ID NO 694
<211> LENGTH: 12
<212> TYPE: DNA
<213> ORGANISM: Artificial
<220> FEATURE:
<223> OTHER INFORMATION: oligonucleotide probe

<400> SEQUENCE: 694
gaatgacttt ga                                                12

<210> SEQ ID NO 695
<211> LENGTH: 13
<212> TYPE: DNA
<213> ORGANISM: Artificial
<220> FEATURE:
<223> OTHER INFORMATION: oligonucleotide probe
```

<400> SEQUENCE: 695
tcattctttc atg                                                13

<210> SEQ ID NO 696
<211> LENGTH: 12
<212> TYPE: DNA
<213> ORGANISM: Artificial
<220> FEATURE:
<223> OTHER INFORMATION: oligonucleotide probe

<400> SEQUENCE: 696
tctccagaaa ca                                                 12

<210> SEQ ID NO 697
<211> LENGTH: 10
<212> TYPE: DNA
<213> ORGANISM: Artificial
<220> FEATURE:
<223> OTHER INFORMATION: oligonucleotide probe

<400> SEQUENCE: 697
gtgatccgtg                                                    10

<210> SEQ ID NO 698
<211> LENGTH: 13
<212> TYPE: DNA
<213> ORGANISM: Artificial
<220> FEATURE:
<223> OTHER INFORMATION: oligonucleotide probe

<400> SEQUENCE: 698
atcttttcag gtt                                                13

<210> SEQ ID NO 699
<211> LENGTH: 13
<212> TYPE: DNA
<213> ORGANISM: Artificial
<220> FEATURE:
<223> OTHER INFORMATION: oligonucleotide probe

<400> SEQUENCE: 699
ggattacata cta                                                13

<210> SEQ ID NO 700
<211> LENGTH: 13
<212> TYPE: DNA
<213> ORGANISM: Artificial
<220> FEATURE:
<223> OTHER INFORMATION: oligonucleotide probe

<400> SEQUENCE: 700
tttgaagctt tat                                                13

<210> SEQ ID NO 701
<211> LENGTH: 13
<212> TYPE: DNA
<213> ORGANISM: Artificial
<220> FEATURE:
<223> OTHER INFORMATION: oligonucleotide probe

<400> SEQUENCE: 701
aagaatcttc cta                                                13

<210> SEQ ID NO 702
<211> LENGTH: 15

-continued

```
<212> TYPE: DNA
<213> ORGANISM: Artificial
<220> FEATURE:
<223> OTHER INFORMATION: oligonucleotide probe

<400> SEQUENCE: 702
aatctaaaat ttagt                                                      15

<210> SEQ ID NO 703
<211> LENGTH: 14
<212> TYPE: DNA
<213> ORGANISM: Artificial
<220> FEATURE:
<223> OTHER INFORMATION: oligonucleotide probe

<400> SEQUENCE: 703
actaaattta tacc                                                       14

<210> SEQ ID NO 704
<211> LENGTH: 11
<212> TYPE: DNA
<213> ORGANISM: Artificial
<220> FEATURE:
<223> OTHER INFORMATION: oligonucleotide probe

<400> SEQUENCE: 704
attaggggca g                                                          11

<210> SEQ ID NO 705
<211> LENGTH: 12
<212> TYPE: DNA
<213> ORGANISM: Artificial
<220> FEATURE:
<223> OTHER INFORMATION: oligonucleotide probe

<400> SEQUENCE: 705
actatagttc gc                                                         12

<210> SEQ ID NO 706
<211> LENGTH: 12
<212> TYPE: DNA
<213> ORGANISM: Artificial
<220> FEATURE:
<223> OTHER INFORMATION: oligonucleotide probe

<400> SEQUENCE: 706
aacctttctg tc                                                         12

<210> SEQ ID NO 707
<211> LENGTH: 12
<212> TYPE: DNA
<213> ORGANISM: Artificial
<220> FEATURE:
<223> OTHER INFORMATION: oligonucleotide probe

<400> SEQUENCE: 707
ttgaggattt ag                                                         12

<210> SEQ ID NO 708
<211> LENGTH: 12
<212> TYPE: DNA
<213> ORGANISM: Artificial
<220> FEATURE:
<223> OTHER INFORMATION: oligonucleotide probe

<400> SEQUENCE: 708
```
tctcaacttg ga                                                       12

<210> SEQ ID NO 709
<211> LENGTH: 12
<212> TYPE: DNA
<213> ORGANISM: Artificial
<220> FEATURE:
<223> OTHER INFORMATION: oligonucleotide probe

<400> SEQUENCE: 709
ttcagtcaaa cc                                                       12

<210> SEQ ID NO 710
<211> LENGTH: 13
<212> TYPE: DNA
<213> ORGANISM: Artificial
<220> FEATURE:
<223> OTHER INFORMATION: oligonucleotide probe

<400> SEQUENCE: 710
ttcttttgtg aca                                                      13

<210> SEQ ID NO 711
<211> LENGTH: 12
<212> TYPE: DNA
<213> ORGANISM: Artificial
<220> FEATURE:
<223> OTHER INFORMATION: oligonucleotide probe

<400> SEQUENCE: 711
tgtgacaacc ga                                                       12

<210> SEQ ID NO 712
<211> LENGTH: 14
<212> TYPE: DNA
<213> ORGANISM: Artificial
<220> FEATURE:
<223> OTHER INFORMATION: oligonucleotide probe

<400> SEQUENCE: 712
aatctttttt aaag                                                     14

<210> SEQ ID NO 713
<211> LENGTH: 13
<212> TYPE: DNA
<213> ORGANISM: Artificial
<220> FEATURE:
<223> OTHER INFORMATION: oligonucleotide probe

<400> SEQUENCE: 713
tcatctgtga taa                                                      13

<210> SEQ ID NO 714
<211> LENGTH: 12
<212> TYPE: DNA
<213> ORGANISM: Artificial
<220> FEATURE:
<223> OTHER INFORMATION: oligonucleotide probe

<400> SEQUENCE: 714
aagagaaggc ta                                                       12

<210> SEQ ID NO 715
<211> LENGTH: 13
<212> TYPE: DNA
<213> ORGANISM: Artificial

```
<220> FEATURE:
<223> OTHER INFORMATION: oligonucleotide probe

<400> SEQUENCE: 715
atataagtaa ggg                                                          13

<210> SEQ ID NO 716
<211> LENGTH: 10
<212> TYPE: DNA
<213> ORGANISM: Artificial
<220> FEATURE:
<223> OTHER INFORMATION: oligonucleotide probe

<400> SEQUENCE: 716
gcatgtcgac                                                              10

<210> SEQ ID NO 717
<211> LENGTH: 13
<212> TYPE: DNA
<213> ORGANISM: Artificial
<220> FEATURE:
<223> OTHER INFORMATION: oligonucleotide probe

<400> SEQUENCE: 717
ttggaagtta tac                                                          13

<210> SEQ ID NO 718
<211> LENGTH: 11
<212> TYPE: DNA
<213> ORGANISM: Artificial
<220> FEATURE:
<223> OTHER INFORMATION: oligonucleotide probe

<400> SEQUENCE: 718
ggcatgtgag t                                                            11

<210> SEQ ID NO 719
<211> LENGTH: 14
<212> TYPE: DNA
<213> ORGANISM: Artificial
<220> FEATURE:
<223> OTHER INFORMATION: oligonucleotide probe

<400> SEQUENCE: 719
attaacagta aagt                                                         14

<210> SEQ ID NO 720
<211> LENGTH: 15
<212> TYPE: DNA
<213> ORGANISM: Artificial
<220> FEATURE:
<223> OTHER INFORMATION: oligonucleotide probe

<400> SEQUENCE: 720
tatctatgta tatta                                                        15

<210> SEQ ID NO 721
<211> LENGTH: 11
<212> TYPE: DNA
<213> ORGANISM: Artificial
<220> FEATURE:
<223> OTHER INFORMATION: oligonucleotide probe

<400> SEQUENCE: 721
tgggaatgat g                                                            11
```

<210> SEQ ID NO 722
<211> LENGTH: 15
<212> TYPE: DNA
<213> ORGANISM: Artificial
<220> FEATURE:
<223> OTHER INFORMATION: oligonucleotide probe

<400> SEQUENCE: 722
taaataaata agatg                                                        15

<210> SEQ ID NO 723
<211> LENGTH: 13
<212> TYPE: DNA
<213> ORGANISM: Artificial
<220> FEATURE:
<223> OTHER INFORMATION: oligonucleotide probe

<400> SEQUENCE: 723
aaaaaaaatg agg                                                          13

<210> SEQ ID NO 724
<211> LENGTH: 12
<212> TYPE: DNA
<213> ORGANISM: Artificial
<220> FEATURE:
<223> OTHER INFORMATION: oligonucleotide probe

<400> SEQUENCE: 724
tcaatgttgg at                                                           12

<210> SEQ ID NO 725
<211> LENGTH: 13
<212> TYPE: DNA
<213> ORGANISM: Artificial
<220> FEATURE:
<223> OTHER INFORMATION: oligonucleotide probe

<400> SEQUENCE: 725
ttgtgaccaa tat                                                          13

<210> SEQ ID NO 726
<211> LENGTH: 11
<212> TYPE: DNA
<213> ORGANISM: Artificial
<220> FEATURE:
<223> OTHER INFORMATION: oligonucleotide probe

<400> SEQUENCE: 726
atcaagccca a                                                            11

<210> SEQ ID NO 727
<211> LENGTH: 11
<212> TYPE: DNA
<213> ORGANISM: Artificial
<220> FEATURE:
<223> OTHER INFORMATION: oligonucleotide probe

<400> SEQUENCE: 727
agaagctcgt g                                                            11

<210> SEQ ID NO 728
<211> LENGTH: 12
<212> TYPE: DNA
<213> ORGANISM: Artificial
<220> FEATURE:
<223> OTHER INFORMATION: oligonucleotide probe

```
<400> SEQUENCE: 728
gaaaaagaaa gg                                                    12

<210> SEQ ID NO 729
<211> LENGTH: 14
<212> TYPE: DNA
<213> ORGANISM: Artificial
<220> FEATURE:
<223> OTHER INFORMATION: oligonucleotide probe

<400> SEQUENCE: 729
acatataata gtag                                                  14

<210> SEQ ID NO 730
<211> LENGTH: 14
<212> TYPE: DNA
<213> ORGANISM: Artificial
<220> FEATURE:
<223> OTHER INFORMATION: oligonucleotide probe

<400> SEQUENCE: 730
ttttgtatct gtat                                                  14

<210> SEQ ID NO 731
<211> LENGTH: 12
<212> TYPE: DNA
<213> ORGANISM: Artificial
<220> FEATURE:
<223> OTHER INFORMATION: oligonucleotide probe

<400> SEQUENCE: 731
ttaacttgcc ag                                                    12

<210> SEQ ID NO 732
<211> LENGTH: 14
<212> TYPE: DNA
<213> ORGANISM: Artificial
<220> FEATURE:
<223> OTHER INFORMATION: oligonucleotide probe

<400> SEQUENCE: 732
aatgataatt tagt                                                  14

<210> SEQ ID NO 733
<211> LENGTH: 13
<212> TYPE: DNA
<213> ORGANISM: Artificial
<220> FEATURE:
<223> OTHER INFORMATION: oligonucleotide probe

<400> SEQUENCE: 733
gaatgaattt ttc                                                   13

<210> SEQ ID NO 734
<211> LENGTH: 11
<212> TYPE: DNA
<213> ORGANISM: Artificial
<220> FEATURE:
<223> OTHER INFORMATION: oligonucleotide probe

<400> SEQUENCE: 734
acactgctta c                                                     11

<210> SEQ ID NO 735
```

<211> LENGTH: 13
<212> TYPE: DNA
<213> ORGANISM: Artificial
<220> FEATURE:
<223> OTHER INFORMATION: oligonucleotide probe

<400> SEQUENCE: 735
acaactaata agg                                                      13

<210> SEQ ID NO 736
<211> LENGTH: 14
<212> TYPE: DNA
<213> ORGANISM: Artificial
<220> FEATURE:
<223> OTHER INFORMATION: oligonucleotide probe

<400> SEQUENCE: 736
ttctgataaa aaaa                                                     14

<210> SEQ ID NO 737
<211> LENGTH: 11
<212> TYPE: DNA
<213> ORGANISM: Artificial
<220> FEATURE:
<223> OTHER INFORMATION: oligonucleotide probe

<400> SEQUENCE: 737
tgtaatgcgt g                                                        11

<210> SEQ ID NO 738
<211> LENGTH: 13
<212> TYPE: DNA
<213> ORGANISM: Artificial
<220> FEATURE:
<223> OTHER INFORMATION: oligonucleotide probe

<400> SEQUENCE: 738
gacaatctaa aaa                                                      13

<210> SEQ ID NO 739
<211> LENGTH: 15
<212> TYPE: DNA
<213> ORGANISM: Artificial
<220> FEATURE:
<223> OTHER INFORMATION: oligonucleotide probe

<400> SEQUENCE: 739
taataataat tgtgt                                                    15

<210> SEQ ID NO 740
<211> LENGTH: 14
<212> TYPE: DNA
<213> ORGANISM: Artificial
<220> FEATURE:
<223> OTHER INFORMATION: oligonucleotide probe

<400> SEQUENCE: 740
ttccttcttt tttt                                                     14

<210> SEQ ID NO 741
<211> LENGTH: 11
<212> TYPE: DNA
<213> ORGANISM: Artificial
<220> FEATURE:
<223> OTHER INFORMATION: oligonucleotide probe

<400> SEQUENCE: 741
ggaacgttac c					11

<210> SEQ ID NO 742
<211> LENGTH: 14
<212> TYPE: DNA
<213> ORGANISM: Artificial
<220> FEATURE:
<223> OTHER INFORMATION: oligonucleotide probe

<400> SEQUENCE: 742 aatttttag tatg					14

<210> SEQ ID NO 743
<211> LENGTH: 13
<212> TYPE: DNA
<213> ORGANISM: Artificial
<220> FEATURE:
<223> OTHER INFORMATION: oligonucleotide probe

<400> SEQUENCE: 743
ttatagacac ttg					13

<210> SEQ ID NO 744
<211> LENGTH: 14
<212> TYPE: DNA
<213> ORGANISM: Artificial
<220> FEATURE:
<223> OTHER INFORMATION: oligonucleotide probe

<400> SEQUENCE: 744
ataaaccata tatg					14

<210> SEQ ID NO 745
<211> LENGTH: 14
<212> TYPE: DNA
<213> ORGANISM: Artificial
<220> FEATURE:
<223> OTHER INFORMATION: oligonucleotide probe

<400> SEQUENCE: 745
ttaattacct taag					14

<210> SEQ ID NO 746
<211> LENGTH: 11
<212> TYPE: DNA
<213> ORGANISM: Artificial
<220> FEATURE:
<223> OTHER INFORMATION: oligonucleotide probe

<400> SEQUENCE: 746
atgccatttt g					11

<210> SEQ ID NO 747
<211> LENGTH: 14
<212> TYPE: DNA
<213> ORGANISM: Artificial
<220> FEATURE:
<223> OTHER INFORMATION: oligonucleotide probe

<400> SEQUENCE: 747
taatatctta tgca					14

<210> SEQ ID NO 748
<211> LENGTH: 12
<212> TYPE: DNA

```
<213> ORGANISM: Artificial
<220> FEATURE:
<223> OTHER INFORMATION: oligonucleotide probe

<400> SEQUENCE: 748
agtgcgatga aa                                                              12

<210> SEQ ID NO 749
<211> LENGTH: 12
<212> TYPE: DNA
<213> ORGANISM: Artificial
<220> FEATURE:
<223> OTHER INFORMATION: oligonucleotide probe

<400> SEQUENCE: 749
gaggagatgt ag                                                              12

<210> SEQ ID NO 750
<211> LENGTH: 14
<212> TYPE: DNA
<213> ORGANISM: Artificial
<220> FEATURE:
<223> OTHER INFORMATION: oligonucleotide probe

<400> SEQUENCE: 750
taaaattgtt ggtt                                                            14

<210> SEQ ID NO 751
<211> LENGTH: 14
<212> TYPE: DNA
<213> ORGANISM: Artificial
<220> FEATURE:
<223> OTHER INFORMATION: oligonucleotide probe

<400> SEQUENCE: 751
tgaagaaaaa tatg                                                            14

<210> SEQ ID NO 752
<211> LENGTH: 11
<212> TYPE: DNA
<213> ORGANISM: Artificial
<220> FEATURE:
<223> OTHER INFORMATION: oligonucleotide probe

<400> SEQUENCE: 752
ctgtccacta a                                                               11

<210> SEQ ID NO 753
<211> LENGTH: 11
<212> TYPE: DNA
<213> ORGANISM: Artificial
<220> FEATURE:
<223> OTHER INFORMATION: oligonucleotide probe

<400> SEQUENCE: 753
agaggcagtg a                                                               11

<210> SEQ ID NO 754
<211> LENGTH: 12
<212> TYPE: DNA
<213> ORGANISM: Artificial
<220> FEATURE:
<223> OTHER INFORMATION: oligonucleotide probe

<400> SEQUENCE: 754
gtttctgata ac                                                              12
```

```
<210> SEQ ID NO 755
<211> LENGTH: 13
<212> TYPE: DNA
<213> ORGANISM: Artificial
<220> FEATURE:
<223> OTHER INFORMATION: oligonucleotide probe

<400> SEQUENCE: 755
gaatgatttt gac                                                        13

<210> SEQ ID NO 756
<211> LENGTH: 13
<212> TYPE: DNA
<213> ORGANISM: Artificial
<220> FEATURE:
<223> OTHER INFORMATION: oligonucleotide probe

<400> SEQUENCE: 756
tcattcattc atg                                                        13

<210> SEQ ID NO 757
<211> LENGTH: 10
<212> TYPE: DNA
<213> ORGANISM: Artificial
<220> FEATURE:
<223> OTHER INFORMATION: oligonucleotide probe

<400> SEQUENCE: 757
gtttcgggag                                                            10

<210> SEQ ID NO 758
<211> LENGTH: 12
<212> TYPE: DNA
<213> ORGANISM: Artificial
<220> FEATURE:
<223> OTHER INFORMATION: oligonucleotide probe

<400> SEQUENCE: 758
atcacgaatc ac                                                         12

<210> SEQ ID NO 759
<211> LENGTH: 13
<212> TYPE: DNA
<213> ORGANISM: Artificial
<220> FEATURE:
<223> OTHER INFORMATION: oligonucleotide probe

<400> SEQUENCE: 759
tatggagtaa ttg                                                        13

<210> SEQ ID NO 760
<211> LENGTH: 14
<212> TYPE: DNA
<213> ORGANISM: Artificial
<220> FEATURE:
<223> OTHER INFORMATION: oligonucleotide probe

<400> SEQUENCE: 760
tggattttat acta                                                       14

<210> SEQ ID NO 761
<211> LENGTH: 14
<212> TYPE: DNA
<213> ORGANISM: Artificial
<220> FEATURE:
```

```
<223> OTHER INFORMATION: oligonucleotide probe

<400> SEQUENCE: 761
tttgaatctt tatc                                                        14

<210> SEQ ID NO 762
<211> LENGTH: 14
<212> TYPE: DNA
<213> ORGANISM: Artificial
<220> FEATURE:
<223> OTHER INFORMATION: oligonucleotide probe

<400> SEQUENCE: 762
aaagaatatt ccta                                                        14

<210> SEQ ID NO 763
<211> LENGTH: 14
<212> TYPE: DNA
<213> ORGANISM: Artificial
<220> FEATURE:
<223> OTHER INFORMATION: oligonucleotide probe

<400> SEQUENCE: 763
atctaacatt tagt                                                        14

<210> SEQ ID NO 764
<211> LENGTH: 13
<212> TYPE: DNA
<213> ORGANISM: Artificial
<220> FEATURE:
<223> OTHER INFORMATION: oligonucleotide probe

<400> SEQUENCE: 764
ggtatacatt tag                                                         13

<210> SEQ ID NO 765
<211> LENGTH: 11
<212> TYPE: DNA
<213> ORGANISM: Artificial
<220> FEATURE:
<223> OTHER INFORMATION: oligonucleotide probe

<400> SEQUENCE: 765 attaggggc a                                                            11

<210> SEQ ID NO 766
<211> LENGTH: 12
<212> TYPE: DNA
<213> ORGANISM: Artificial
<220> FEATURE:
<223> OTHER INFORMATION: oligonucleotide probe

<400> SEQUENCE: 766
actatacttc gc                                                          12

<210> SEQ ID NO 767
<211> LENGTH: 11
<212> TYPE: DNA
<213> ORGANISM: Artificial
<220> FEATURE:
<223> OTHER INFORMATION: oligonucleotide probe

<400> SEQUENCE: 767
accttgctgt c                                                           11
```

<210> SEQ ID NO 768
<211> LENGTH: 12
<212> TYPE: DNA
<213> ORGANISM: Artificial
<220> FEATURE:
<223> OTHER INFORMATION: oligonucleotide probe

<400> SEQUENCE: 768
ttgagcattt ag                                                         12

<210> SEQ ID NO 769
<211> LENGTH: 13
<212> TYPE: DNA
<213> ORGANISM: Artificial
<220> FEATURE:
<223> OTHER INFORMATION: oligonucleotide probe

<400> SEQUENCE: 769
tctcaatttg gaa                                                        13

<210> SEQ ID NO 770
<211> LENGTH: 12
<212> TYPE: DNA
<213> ORGANISM: Artificial
<220> FEATURE:
<223> OTHER INFORMATION: oligonucleotide probe

<400> SEQUENCE: 770
ttcagttaaa cc                                                         12

<210> SEQ ID NO 771
<211> LENGTH: 12
<212> TYPE: DNA
<213> ORGANISM: Artificial
<220> FEATURE:
<223> OTHER INFORMATION: oligonucleotide probe

<400> SEQUENCE: 771
ttctttggtg ac                                                         12

<210> SEQ ID NO 772
<211> LENGTH: 11
<212> TYPE: DNA
<213> ORGANISM: Artificial
<220> FEATURE:
<223> OTHER INFORMATION: oligonucleotide probe

<400> SEQUENCE: 772
gtgacacaac c                                                          11

<210> SEQ ID NO 773
<211> LENGTH: 14
<212> TYPE: DNA
<213> ORGANISM: Artificial
<220> FEATURE:
<223> OTHER INFORMATION: oligonucleotide probe

<400> SEQUENCE: 773
aatcttcttt aaag                                                       14

<210> SEQ ID NO 774
<211> LENGTH: 13
<212> TYPE: DNA
<213> ORGANISM: Artificial
<220> FEATURE:
<223> OTHER INFORMATION: oligonucleotide probe -continued

<400> SEQUENCE: 774
tcatgtgtga taa                                                    13

<210> SEQ ID NO 775
<211> LENGTH: 12
<212> TYPE: DNA
<213> ORGANISM: Artificial
<220> FEATURE:
<223> OTHER INFORMATION: oligonucleotide probe

<400> SEQUENCE: 775
aagagatggc ta                                                     12

<210> SEQ ID NO 776
<211> LENGTH: 14
<212> TYPE: DNA
<213> ORGANISM: Artificial
<220> FEATURE:
<223> OTHER INFORMATION: oligonucleotide probe

<400> SEQUENCE: 776
aatataaata aggg                                                   14

<210> SEQ ID NO 777
<211> LENGTH: 10
<212> TYPE: DNA
<213> ORGANISM: Artificial
<220> FEATURE:
<223> OTHER INFORMATION: oligonucleotide probe

<400> SEQUENCE: 777
gcatctcgac                                                        10

<210> SEQ ID NO 778
<211> LENGTH: 13
<212> TYPE: DNA
<213> ORGANISM: Artificial
<220> FEATURE:
<223> OTHER INFORMATION: oligonucleotide probe

<400> SEQUENCE: 778
ttggaagata tac                                                    13

<210> SEQ ID NO 779
<211> LENGTH: 10
<212> TYPE: DNA
<213> ORGANISM: Artificial
<220> FEATURE:
<223> OTHER INFORMATION: oligonucleotide probe

<400> SEQUENCE: 779
ggcttgcgag                                                        10

<210> SEQ ID NO 780
<211> LENGTH: 15
<212> TYPE: DNA
<213> ORGANISM: Artificial
<220> FEATURE:
<223> OTHER INFORMATION: oligonucleotide probe

<400> SEQUENCE: 780
tattaacatt aaagt                                                  15

<210> SEQ ID NO 781
<211> LENGTH: 16

```
<212> TYPE: DNA
<213> ORGANISM: Artificial
<220> FEATURE:
<223> OTHER INFORMATION: oligonucleotide probe

<400> SEQUENCE: 781
tatctatata tattaa                                                      16

<210> SEQ ID NO 782
<211> LENGTH: 11
<212> TYPE: DNA
<213> ORGANISM: Artificial
<220> FEATURE:
<223> OTHER INFORMATION: oligonucleotide probe

<400> SEQUENCE: 782
atcatcccca a                                                           11

<210> SEQ ID NO 783
<211> LENGTH: 14
<212> TYPE: DNA
<213> ORGANISM: Artificial
<220> FEATURE:
<223> OTHER INFORMATION: oligonucleotide probe

<400> SEQUENCE: 783
aaataagtaa gatg                                                        14

<210> SEQ ID NO 784
<211> LENGTH: 13
<212> TYPE: DNA
<213> ORGANISM: Artificial
<220> FEATURE:
<223> OTHER INFORMATION: oligonucleotide probe

<400> SEQUENCE: 784
aaaaaatatg agg                                                         13

<210> SEQ ID NO 785
<211> LENGTH: 13
<212> TYPE: DNA
<213> ORGANISM: Artificial
<220> FEATURE:
<223> OTHER INFORMATION: oligonucleotide probe

<400> SEQUENCE: 785
tcaatgatgg ata                                                         13

<210> SEQ ID NO 786
<211> LENGTH: 13
<212> TYPE: DNA
<213> ORGANISM: Artificial
<220> FEATURE:
<223> OTHER INFORMATION: oligonucleotide probe

<400> SEQUENCE: 786
atattgatca caa                                                         13

<210> SEQ ID NO 787
<211> LENGTH: 11
<212> TYPE: DNA
<213> ORGANISM: Artificial
<220> FEATURE:
<223> OTHER INFORMATION: oligonucleotide probe

<400> SEQUENCE: 787
```

```
tgggtttgat c                                                    11
```

<210> SEQ ID NO 788
<211> LENGTH: 10
<212> TYPE: DNA
<213> ORGANISM: Artificial
<220> FEATURE:
<223> OTHER INFORMATION: oligonucleotide probe

<400> SEQUENCE: 788

```
gaaggtcgtg                                                      10
```

<210> SEQ ID NO 789
<211> LENGTH: 13
<212> TYPE: DNA
<213> ORGANISM: Artificial
<220> FEATURE:
<223> OTHER INFORMATION: oligonucleotide probe

<400> SEQUENCE: 789

```
gaaaaaaaaa gga                                                  13
```

<210> SEQ ID NO 790
<211> LENGTH: 13
<212> TYPE: DNA
<213> ORGANISM: Artificial
<220> FEATURE:
<223> OTHER INFORMATION: oligonucleotide probe

<400> SEQUENCE: 790

```
acatatagta gta                                                  13
```

<210> SEQ ID NO 791
<211> LENGTH: 12
<212> TYPE: DNA
<213> ORGANISM: Artificial
<220> FEATURE:
<223> OTHER INFORMATION: oligonucleotide probe

<400> SEQUENCE: 791

```
tttgtggctg ta                                                   12
```

<210> SEQ ID NO 792
<211> LENGTH: 12
<212> TYPE: DNA
<213> ORGANISM: Artificial
<220> FEATURE:
<223> OTHER INFORMATION: oligonucleotide probe

<400> SEQUENCE: 792

```
ttaactagcc ag                                                   12
```

<210> SEQ ID NO 793
<211> LENGTH: 13
<212> TYPE: DNA
<213> ORGANISM: Artificial
<220> FEATURE:
<223> OTHER INFORMATION: oligonucleotide probe

<400> SEQUENCE: 793

```
aatgatcatt tag                                                  13
```

<210> SEQ ID NO 794
<211> LENGTH: 13
<212> TYPE: DNA
<213> ORGANISM: Artificial

```
<220> FEATURE:
<223> OTHER INFORMATION: oligonucleotide probe

<400> SEQUENCE: 794
aatgaacttt ttc                                                        13

<210> SEQ ID NO 795
<211> LENGTH: 12
<212> TYPE: DNA
<213> ORGANISM: Artificial
<220> FEATURE:
<223> OTHER INFORMATION: oligonucleotide probe

<400> SEQUENCE: 795
tttttgctag ag                                                         12

<210> SEQ ID NO 796
<211> LENGTH: 13
<212> TYPE: DNA
<213> ORGANISM: Artificial
<220> FEATURE:
<223> OTHER INFORMATION: oligonucleotide probe

<400> SEQUENCE: 796
tacaactaag gta                                                        13

<210> SEQ ID NO 797
<211> LENGTH: 13
<212> TYPE: DNA
<213> ORGANISM: Artificial
<220> FEATURE:
<223> OTHER INFORMATION: oligonucleotide probe

<400> SEQUENCE: 797
tctgatgaaa aaa                                                        13

<210> SEQ ID NO 798
<211> LENGTH: 11
<212> TYPE: DNA
<213> ORGANISM: Artificial
<220> FEATURE:
<223> OTHER INFORMATION: oligonucleotide probe

<400> SEQUENCE: 798
tgtaacgcgt g                                                          11

<210> SEQ ID NO 799
<211> LENGTH: 13
<212> TYPE: DNA
<213> ORGANISM: Artificial
<220> FEATURE:
<223> OTHER INFORMATION: oligonucleotide probe

<400> SEQUENCE: 799
gacaatttaa aaa                                                        13

<210> SEQ ID NO 800
<211> LENGTH: 13
<212> TYPE: DNA
<213> ORGANISM: Artificial
<220> FEATURE:
<223> OTHER INFORMATION: oligonucleotide probe

<400> SEQUENCE: 800
aataatgatt gtg                                                        13
```

```
<210> SEQ ID NO 801
<211> LENGTH: 13
<212> TYPE: DNA
<213> ORGANISM: Artificial
<220> FEATURE:
<223> OTHER INFORMATION: oligonucleotide probe

<400> SEQUENCE: 801 tccttcctttt ttt                                                        13

<210> SEQ ID NO 802
<211> LENGTH: 12
<212> TYPE: DNA
<213> ORGANISM: Artificial
<220> FEATURE:
<223> OTHER INFORMATION: oligonucleotide probe

<400> SEQUENCE: 802
tggaacatta cc                                                          12

<210> SEQ ID NO 803
<211> LENGTH: 14
<212> TYPE: DNA
<213> ORGANISM: Artificial
<220> FEATURE:
<223> OTHER INFORMATION: oligonucleotide probe

<400> SEQUENCE: 803
aatttttgag tatg                                                        14

<210> SEQ ID NO 804
<211> LENGTH: 12
<212> TYPE: DNA
<213> ORGANISM: Artificial
<220> FEATURE:
<223> OTHER INFORMATION: oligonucleotide probe

<400> SEQUENCE: 804
tataggcact tg                                                          12

<210> SEQ ID NO 805
<211> LENGTH: 14
<212> TYPE: DNA
<213> ORGANISM: Artificial
<220> FEATURE:
<223> OTHER INFORMATION: oligonucleotide probe

<400> SEQUENCE: 805
ataaacctta tatg                                                        14

<210> SEQ ID NO 806
<211> LENGTH: 14
<212> TYPE: DNA
<213> ORGANISM: Artificial
<220> FEATURE:
<223> OTHER INFORMATION: oligonucleotide probe

<400> SEQUENCE: 806
ttaattatct taag                                                        14

<210> SEQ ID NO 807
<211> LENGTH: 12
<212> TYPE: DNA
<213> ORGANISM: Artificial
<220> FEATURE:
<223> OTHER INFORMATION: oligonucleotide probe
```

-continued

<400> SEQUENCE: 807 atgcccttttt gt                                                      12

<210> SEQ ID NO 808
<211> LENGTH: 13
<212> TYPE: DNA
<213> ORGANISM: Artificial
<220> FEATURE:
<223> OTHER INFORMATION: oligonucleotide probe

<400> SEQUENCE: 808
aatatcgtat gca                                                      13

<210> SEQ ID NO 809
<211> LENGTH: 12
<212> TYPE: DNA
<213> ORGANISM: Artificial
<220> FEATURE:
<223> OTHER INFORMATION: oligonucleotide probe

<400> SEQUENCE: 809
agtgcactga aa                                                       12

<210> SEQ ID NO 810
<211> LENGTH: 12
<212> TYPE: DNA
<213> ORGANISM: Artificial
<220> FEATURE:
<223> OTHER INFORMATION: oligonucleotide probe

<400> SEQUENCE: 810
agaggagatg ta                                                       12

<210> SEQ ID NO 811
<211> LENGTH: 14
<212> TYPE: DNA
<213> ORGANISM: Artificial
<220> FEATURE:
<223> OTHER INFORMATION: oligonucleotide probe

<400> SEQUENCE: 811
taaaattatt ggtt                                                     14

<210> SEQ ID NO 812
<211> LENGTH: 13
<212> TYPE: DNA
<213> ORGANISM: Artificial
<220> FEATURE:
<223> OTHER INFORMATION: oligonucleotide probe

<400> SEQUENCE: 812
gaacaaaaag atg                                                      13

<210> SEQ ID NO 813
<211> LENGTH: 12
<212> TYPE: DNA
<213> ORGANISM: Artificial
<220> FEATURE:
<223> OTHER INFORMATION: oligonucleotide probe

<400> SEQUENCE: 813
actgtcaact aa                                                       12

<210> SEQ ID NO 814

```
<211> LENGTH: 11
<212> TYPE: DNA
<213> ORGANISM: Artificial
<220> FEATURE:
<223> OTHER INFORMATION: oligonucleotide probe

<400> SEQUENCE: 814
agagccagtg a                                                    11

<210> SEQ ID NO 815
<211> LENGTH: 13
<212> TYPE: DNA
<213> ORGANISM: Artificial
<220> FEATURE:
<223> OTHER INFORMATION: oligonucleotide probe

<400> SEQUENCE: 815
tcatctctga taa                                                  13

<210> SEQ ID NO 816
<211> LENGTH: 14
<212> TYPE: DNA
<213> ORGANISM: Artificial
<220> FEATURE:
<223> OTHER INFORMATION: oligonucleotide probe

<400> SEQUENCE: 816
ttggaatata tact                                                 14

<210> SEQ ID NO 817
<211> LENGTH: 14
<212> TYPE: DNA
<213> ORGANISM: Artificial
<220> FEATURE:
<223> OTHER INFORMATION: oligonucleotide probe

<400> SEQUENCE: 817
agatgttaga gtta                                                 14

<210> SEQ ID NO 818
<211> LENGTH: 12
<212> TYPE: DNA
<213> ORGANISM: Artificial
<220> FEATURE:
<223> OTHER INFORMATION: oligonucleotide probe

<400> SEQUENCE: 818
tgtaacgcat gt                                                   12

<210> SEQ ID NO 819
<211> LENGTH: 13
<212> TYPE: DNA
<213> ORGANISM: Artificial
<220> FEATURE:
<223> OTHER INFORMATION: oligonucleotide probe

<400> SEQUENCE: 819
attttttggt atg                                                  13
```